United States Patent
Maddux et al.

(10) Patent No.: US 11,771,738 B2
(45) Date of Patent: *Oct. 3, 2023

(54) ENDOPARASITIC DEPSIPEPTIDES

(71) Applicant: Zoetis Services LLC, Parsippany, NJ (US)

(72) Inventors: Todd Maddux, Kalamazoo, MI (US); Matthew W. Bedore, Portage, MI (US); Paul D. Johnson, Kalamazoo, MI (US); Tomasz Respondek, Kalamazoo, MI (US); Susan M. K. Sheehan, Galesburg, MI (US); Graham M. Kyne, Portage, MI (US); Richard A. Ewin, Kalamazoo, MI (US); Rajendran Vairagoundar, Kalamazoo, MI (US); Michael P. Curtis, Portage, MI (US)

(73) Assignee: Zoetis Services LLC, Parsippany, NJ (US)

( * ) Notice: Subject to any disclaimer, the term of this patent is extended or adjusted under 35 U.S.C. 154(b) by 462 days.

This patent is subject to a terminal disclaimer.

(21) Appl. No.: 17/052,571

(22) PCT Filed: May 7, 2019

(86) PCT No.: PCT/US2019/031158
§ 371 (c)(1),
(2) Date: Nov. 3, 2020

(87) PCT Pub. No.: WO2019/217449
PCT Pub. Date: Nov. 14, 2019

(65) Prior Publication Data
US 2022/0323540 A1    Oct. 13, 2022

Related U.S. Application Data

(60) Provisional application No. 62/669,623, filed on May 10, 2018.

(51) Int. Cl.
| | | |
|---|---|---|
| *A61K 38/15* | (2006.01) | |
| *A61P 33/00* | (2006.01) | |
| *C07D 273/00* | (2006.01) | |
| *C07D 413/10* | (2006.01) | |
| *C07D 413/14* | (2006.01) | |
| *C07D 417/14* | (2006.01) | |

(52) U.S. Cl.
CPC ............ *A61K 38/15* (2013.01); *A61P 33/00* (2018.01); *C07D 273/00* (2013.01); *C07D 413/10* (2013.01); *C07D 413/14* (2013.01); *C07D 417/14* (2013.01)

(58) Field of Classification Search
CPC ....... A61K 38/15; A61P 33/00; C07D 273/00; C07D 413/10; C07D 413/14; C07D 417/14
See application file for complete search history.

(56) References Cited

U.S. PATENT DOCUMENTS

| | | |
|---|---|---|
| 5,514,773 A | 5/1996 | Nishiyama |
| 5,646,244 A | 7/1997 | Nishiyama |
| 5,747,448 A | 5/1998 | Ohyama |
| 5,874,530 A | 2/1999 | Scherkenbeck |
| 6,355,615 B1 | 3/2002 | Dyker |
| 6,630,569 B1 | 10/2003 | Jeschke |
| 2020/0282016 A1 | 9/2020 | Curtis |

FOREIGN PATENT DOCUMENTS

| | | | |
|---|---|---|---|
| WO | WO 2016/187534 A1 | 11/2016 | |
| WO | WO-2019108591 A1 * | 6/2019 | ............. A01N 37/46 |

OTHER PUBLICATIONS

M. Ohyama, et al., "Structure-Activity Relationship of Anthelmintic Cyclooctadepsipeptides," Biosci. Biotechnol. Biochem., 75 (7), pp. 1354-1363, 2011.

* cited by examiner

*Primary Examiner* — Li N Komatsu
(74) *Attorney, Agent, or Firm* — Paul M. Misiak

(57) ABSTRACT

The present invention provides cyclic depsipeptides of Formula (1), stereoisomers thereof, and veterinary acceptable salts thereof (1)

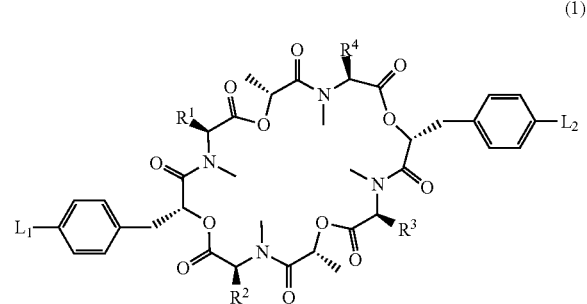

wherein each of $R^1$, $R^2$, $R^3$, $R^4$, $L_1$, and $L_2$ are as defined herein. The present invention also contemplates compositions, methods of treatment, and uses as a medicament to treat an animal for an endoparasitic infection with a Formula (1) compound.

13 Claims, No Drawings

ENDOPARASITIC DEPSIPEPTIDES

FIELD OF THE INVENTION

The present invention is directed to new endoparasitic depsipeptide compounds with improved activity against endoparasites. The invention is also directed to compositions comprising the compounds, methods and uses of the compounds for eradicating, controlling, treating and preventing a parasite infestation and/or infection in animals. The compounds of the invention may be administered to animals, particularly non-human animals, to prevent or treat parasitic infections.

BACKGROUND

Animals, such as non-human mammals, for example, companion animals and livestock, are often susceptible to parasite infestations. These parasites may be endoparasites including for example, helminthiasis which is most frequently caused by a group of parasitic worms described as nematodes or roundworms. These parasites cause severe economic losses in pigs, sheep, horses, and cattle as well as affecting companion animals (e.g. cats and dogs). Other parasites include those which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*.

One type of endoparasite which seriously harms animals is *Dirofilaria immitis*, also known as heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go through several life stages before they become adults infecting the pulmonary artery of the host mammal, particularly canine. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period". L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4's) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection. The macrocyclic lactones (MLs, e.g. ivermectin, eprinomectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (*Vet. Parasitol.* 2005 Oct. 24 133(2-3) 197-206).

In recent years, an increased number of lack of efficacy cases have been reported, in which dogs develop mature heartworm infections despite receiving monthly prophylactic doses of macrocyclic lactone drugs. For example, Atkins et al., (*Vet. Parasitol.* 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (American Heartworm Society, 2010. Heartworm Preventive Resistance. Is it Possible, vol. 37. Bulletin of the American Heartworm Society, pp. 5.). Thus, there is an ongoing need to develop new anthelmintic agents with improved activity against *Dirofilaria immitis* and other endoparasites.

Various parasiticides exist in the art for treating endoparasites infections in animals. In addition to the macrocyclic lactones, cyclic depsipeptides with antiparasitic activity are known. PF1022a, a 24-membered cyclooctadepsipeptide isolated from the fungus *Mycelia sterilia* by Sasaki et al (*J Antibiotics* 45: 692-697 (1992)), has been found to exhibit broad anthelmintic activity against a variety of endoparasites in vivo with low toxicity. These compounds are described, for example, in U.S. Pat. Nos. 5,514,773; 5,747,448; 5,646,244; 5,874,530; among others, which are incorporated herein by reference. Emodepside is a semi-synthetic analog of PF1022a containing a morpholine group at the para position of the aryl ring in the phenyl lactate groups. Emodepside is a potent anthelmintic used in combination with praziquantel in the product PROFENDER® for the treatment of parasitic worms in cats and dogs.

However, the antiparasitic activity of PF 1022a and emodepside is not satisfactory for the treatment of certain parasites, especially for the control of *Dirofilaria immitis* in mammals to prevent the establishment of heartworm disease. Thus, there is a need in the art for more effective antiparasitic agents for treatment and protection of animals against internal parasites including nematodes and filarial worms such as heartworm.

SUMMARY OF THE INVENTION

The invention provides novel and inventive cyclic depsipeptide compounds with selective anthelmintic activity against L3 and L4 staged endoparasites, particularly, *Dirofilaria immitis* L4 (DiL4). In addition, the invention provides compositions comprising the depsipeptide compounds and methods and uses for the treatment and prevention of parasitic infection and possibly infestation of animals using the compounds.

In one aspect, the present invention provides symmetrical (i.e., $L_1$ and $L_2$ are the same; bis) and asymmetric (i.e., $L_1$ is absent) cyclic depsipeptides of Formula (1)

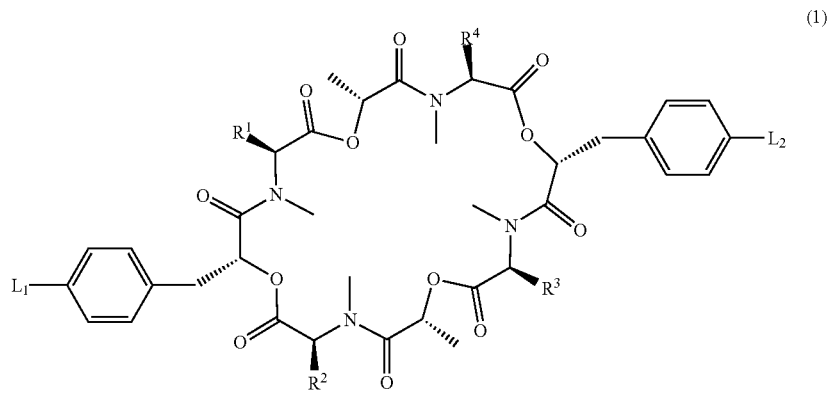

(1)

wherein

L₁ and L₂ are the same and are $C_1$-$C_4$alkyC₃-$C_6$cycloalkyl, $C_1$-$C_4$alkylaryl, $C_1$-$C_4$alkylheteroaryl or $C_1$-$C_4$alkylheterocycle; or L₁ is absent; and wherein the cycloalkyl is a 3- to 6-membered carbocyclic ring; the aryl is a 6-membered monocyclic aromatic ring or a 9- to 10-membered fused aromatic ring;

the heteroaryl is a 5- or 6-member monocyclic aromatic ring or a 9- to 10-member fused aromatic ring wherein each mono- or fused-heteroaryl ring contains at least one heteroatom selected from N, O, and S; and the heterocycle is a 4- to 6-member monocyclic saturated or partially saturated ring or a 9- to 10-member fused saturated or partially saturated ring, each mono- or fused-heterocyclic ring contains at least one heteroatom selected from N, O and S; and wherein the heteroaryl and heterocycle rings are linked to the L₁ and L₂ $C_1$-$C_4$alkyl or L₂ $C_1$-$C_4$alkyl by a ring carbon atom;

and wherein the L₁ and L₂ alkyl group of the alkylcycloalkyl, alkylaryl, alkylheteroaryl and alkylheterocycle can be substituted with an $R^c$ and $R^d$ substituent each individually and separately selected from the group consisting of hydroxyl, halo, $C_1$-$C_6$alkyl, $C_3$-$C_6$cycloalkyl, $C_1$-$C_6$alkoxy, $C_1$-$C_4$haloalkyl, —$NR^aR^b$, pyrazolyl, imidazolyl, pyrrolidinyl, and morpholinyl; and when L₁ is not absent, then each $R^c$ is the same and each $R^d$ is the same;

and wherein the L₁ and L₂ cycloalkyl, aryl, heteroaryl, and heterocycle group can be substituted with $(R)_n$; and when L₁ is not absent, then each $(R)_n$ is the same; and each R substituent is independently selected from the group consisting of $C_1$-$C_6$alkyl optionally substituted with at least one substituent selected from hydroxyl, $C_3$-$C_6$cycloalkyl and —$OR^a$; halo, oxo, cyano, hydroxyl, —$OR^5$, —$NR^aR^b$, $C_1$-$C_4$haloalkyl, $C_1$-$C_4$haloalkoxy, —$S(O)_pR^a$, $C_1$-$C_6$alkoxy, $C_3$-$C_6$cycloalkyl, —$C(O)NR^aR^b$, —$C(O)R^a$, —$C(O)OR^a$, —$NR^aC(O)R^b$, pyrazolyl, imidazolyl, pyridinyl, pyrimidinyl, piperidinyl, morpholinyl, pyrrolidinyl, dihydropyrimidinyl, and phenyl; and wherein the phenyl is optionally substituted with at least one substituent selected from $C_1$-$C_3$alkyl, —$CF_3$, halo, and hydroxyl; and wherein n is the integer 0, 1, 2, or 3;

$R^1$, $R^2$, $R^3$, and $R^4$ are each separately and independently H and $C_1$-$C_6$alkyl;

$R^a$ and $R^b$ are each separately H and $C_1$-$C_6$alkyl; and $R^5$ is $C_3$-$C_6$cycloalkyl and $C_1$-$C_3$alkyl$C_3$-$C_6$cycloalkyl;

p is the integer 0, 1, or 2;

stereoisomers thereof, and veterinary acceptable salts thereof.

In another aspect of the invention, is a composition comprising a Formula (1) compound. In yet another aspect, the Formula (1) composition further comprises a veterinary acceptable excipient. In another aspect of the invention, is a method of treating a parasitic infection in an animal by administering a therapeutic amount of a Formula (1) compound to the animal in need thereof. In yet another aspect, is the use of a Formula (1) compound for treating a parasitic infection in an animal by administering a therapeutic amount of a Formula (1) compound to the animal in need thereof. In yet another aspect, is the use of a Formula (1) compound for preparing a medicament for the use in treating a parasitic infection in an animal.

In one aspect of the invention, $R^1$, $R^2$, $R^3$, and $R^4$ are the same and are each $C_1$-$C_6$alkyl. In another aspect, $R^1$, $R^2$, $R^3$, and $R^4$ are the same and are each methyl, ethyl, propyl, isopropyl, isobutyl, and n-butyl. Preferrably, each of $R^1$, $R^2$, $R^3$, and $R^4$ are the same and are each ethyl, isopropyl or isobutyl. More preferred, $R^1$, $R^2$, $R^3$, and $R^4$ are the same and are each isopropyl or isobutyl. Most preferred, $R^1$, $R^2$, $R^3$, and $R^4$ are the same and are each isobutyl.

In one aspect of the invention, is a Formula (1) compound that is a Formula (1A) compound

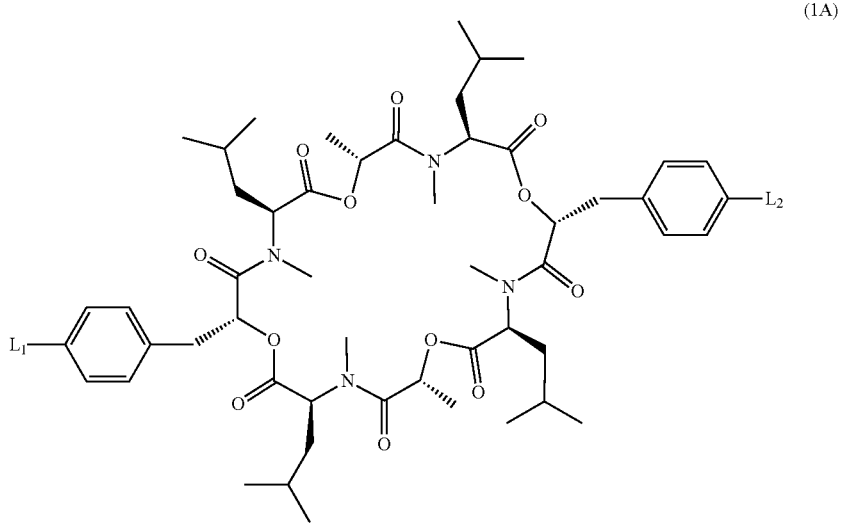

(1A)

stereoisomers thereof, and veterinary acceptable salts thereof.

In another aspect of the invention, is a composition comprising a Formula (1A) compound. In yet another aspect, the Formula (1A) composition further comprises a veterinary acceptable excipient. In another aspect of the invention, is a method of treating a parasitic infection in an animal by administering a therapeutic amount of a Formula (1A) compound to the animal in need thereof. In yet another aspect, is the use of a Formula (1A) compound for treating a parasitic infection in an animal by administering a therapeutic amount of a Formula (1A) compound to the animal in need thereof. In yet another aspect, is the use of a Formula (1A) compound for preparing a medicament for the use in treating a parasitic infection in an animal.

In another aspect of the invention, is a Formula (1) compound that is a Formula (2A) compound, (2A)

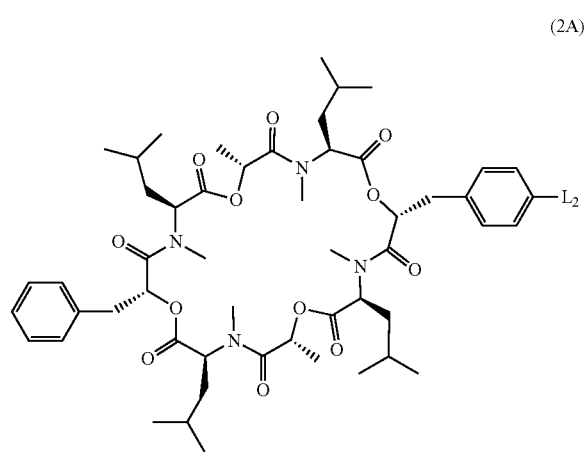

stereoisomers thereof, and veterinary acceptable salts thereof.

In another aspect of the invention, is a composition comprising a Formula (2A) compound. In yet another aspect, the Formula (2A) composition further comprises a veterinary acceptable excipient. In another aspect of the invention, is a method of treating a parasitic infection in an animal by administering a therapeutic amount of a Formula (2A) compound to the animal in need thereof. In yet another aspect, is the use of a Formula (2A) compound for treating a parasitic infection in an animal by administering a therapeutic amount of a Formula (2A) compound to the animal in need thereof. In yet another aspect, is the use of a Formula (2A) compound for preparing a medicament for the use in treating a parasitic infection in an animal.

In one aspect of the invention, when $L_1$ and $L_2$ are present, they are the same, i.e., a symmetrical bis depsipeptide compound of Formula (1). In another aspect, $L_1$ is absent, i.e., a non-symmetrical depsipeptide compound of Formula (1).

In one aspect of the invention, $L_1$ and $L_2$ are the same and are each a $C_1$alkyl$C_3$-$C_6$cycloalkyl (—C—$C_3$-$C_6$cycloalkyl); a $C_1$alkylaryl (—C-aryl); a —$C_1$alkylheterocycle (—C-heterocycle); or a —$C_1$alkylheteroaryl (—C-heteroaryl); or $L_1$ is absent; and wherein each cycloalkyl, aryl, heterocycle, or heteroaryl group can be substituted with $(R)_n$ as described herein; and each —C— of the alkyl group can be substituted with $R^c$ and $R^d$, as described herein.

In one aspect of the invention, $L_1$ and $L_2$ are the same and are each a $C_1$alkyl$C_3$-$C_6$cycloalkyl (—C—$C_3$-$C_6$cycloalkyl); or $L_1$ is absent. In another aspect, the $L_1$ and $L_2$ cycloalkyls are the same and are —C-cyclopropyl, —C-cyclobutyl, —C— cyclopentyl, or —C-cyclohexyl; or $L_1$ is absent. The cycloalkyl groups of $L_1$ and $L_2$ or $L_2$ can be substituted with $(R)_n$ as described herein; and each alkyl group of $L_1$ and $L_2$ or $L_2$ can be substituted with $R^c$ and $R^d$, as described herein. In Formula (3A), Ring A and Ring B is the $L_1$ and $L_2$ cycloalkyl group, respectively. In Formula (4A), Ring B is the $L_2$ cycloalkyl group.

In one aspect of the invention, $L_1$ and $L_2$ are the same and are each a $C_1$alkylaryl (—C-aryl); or $L_1$ is absent. In another aspect, the $L_1$ and $L_2$ aryls are the same and are each —C-phenyl or —C-naphthyl; or $L_1$ is absent. In yet another aspect, the $L_1$ and $L_2$ aryls are each —C-phenyl; or $L_1$ is absent. The aryl groups of $L_1$ and $L_2$ or $L_2$ can be substituted with $(R)_n$ as described herein; and each alkyl group of $L_1$ and $L_2$ or $L_2$ can be substituted with $R^c$ and $R^d$, as described herein.

In one aspect of the invention, L$_1$ and L$_2$ are the same and are each a C$_1$alkylheterocycle (—C-heterocycle); or L$_1$ is absent. In another aspect, the L$_1$ and L$_2$ heterocycles are the same and are each oxetanyl, thietanyl, azetidinyl, tetrahydrofuranyl, tetrahydrothiophenyl, pyrrolidinyl, tetrahydropyranyl, tetrahydropyridinyl, tetrahydrothiopyranyl, piperidinyl, 1,4-dioxanyl, morpholinyl, piperazinyl, azathianyl, or 3,4-dihydro-2H-pyranyl; or L$_1$ is absent. In yet another aspect, the L$_1$ and L$_2$ heterocycles are the same and are each oxetanyl, cyclohexyl, azetidinyl, pyrrolidinyl, tetrahydropyranyl, piperidinyl, or morpholinyl; or L$_1$ is absent. In yet another aspect, the L$_1$ and L$_2$ heterocycles are the same and are each pyrrolidinyl, tetrahydropyranyl, piperidinyl, or morpholinyl; or L$_1$ is absent. In yet another aspect, the L$_1$ and L$_2$ heterocycles are the same and are each morpholinyl; or L$_1$ is absent. The heterocycle groups of L$_1$ and L$_2$ or L$_2$ can be substituted with (R)$_n$ as described herein; and each alkyl group of L$_1$ and L$_2$ or L$_2$ can be substituted with R$^c$ and R$^d$, as described herein. In Formula (3A), Ring A and Ring B is the L$_1$ and L$_2$ heterocycle group, respectively. In Formula (4A), Ring B is the L$_2$ heterocycle group.

In one aspect of the invention, L$_1$ and L$_2$ are the same and are each a C$_1$alkylheteroaryl (—C-heteroaryl); or L$_1$ is absent. In another aspect, the L$_1$ and L$_2$ heteroaryls are the same and are each pyrrolyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, dihydropyridinyl, pyridinyl, pyridazinyl, pyrimidinyl, pyrazinyl, triazinyl, quinolinyl, isoquinolinyl, benzofuranyl, indazolyl, benzothiophenyl, indolyl, benzimidazolyl, pyrazolo[1,5-a]pyridinyl, pyrazolo[1,5-a]pyrimidinyl, 1H-pyrrolo[3,2-b]pyridinyl, indazolebenzo[d][1,3]diazolyl, benzo[d]thiazolyl, furo[2,3-b]pyridinyl, 2,3-dihydrothieno[3,4-b][1,4]dioxinyl, 3,4-dihydro-2H-pyrano[2,3-b]pyridinyl, dihydro-1H-pyrrolo[3,2-b]pyridine, dihydro-1H-pyrrolo[3,2-b]pyridinyl, oxazolo[5,4-b]pyridinyl, or benzo[d]1,3 diaxolyl; or L$_1$ is absent. In yet another aspect, the L$_1$ and L$_2$ heteroaryls are the same and are each thiophenyl, thiazolyl, pyrazolyl, pyridinyl, pyrimidinyl, pyridazinyl, pyrazinyl, oxazolyl, isoxazolyl, isothiazolyl, or furanyl; or L$_1$ is absent. In yet another aspect, the L$_1$ and L$_2$ heteroaryls are the same and are each thiophenyl, thiazolyl, pyrazolyl, pyridinyl, pyridazinyl, pyrazinyl, or pyrimidinyl; or L$_1$ is absent. In yet another aspect, the L$_1$ and L$_2$ heteroaryls are the same and are each pyrazolyl, pyridinyl, pyridazinyl, pyrazinyl, and pyrimidyl; or L$_1$ is absent. In yet another aspect, the L$_1$ and L$_2$ heteroaryls are the same and are each pyrazolyl, pyridinyl, or pyrimidinyl; or L$_1$ is absent. In yet another aspect, the L$_1$ and L$_2$ heteroaryls are the same and are each pyridazinyl; or L$_1$ is absent. In yet another aspect, the L$_1$ and L$_2$ heteroaryls are the same and are each thiazole; or L$_1$ is absent. In yet another aspect of the invention, the L$_1$ and L$_2$ heteroaryls are the same and are each pyrazole, or L$_1$ is absent. In yet another aspect, the L$_1$ and L$_2$ heteroaryls are the same and are each pyridine; or L$_1$ is absent. In yet another aspect, the L$_1$ and L$_2$ heteroaryls are the same and are each pyrimidine; or L$_1$ is absent. In yet another aspect, the L$_1$ and L$_2$ heteroaryls are the same and are each pyrazinyl; or L$_1$ is absent. The heteroaryl groups of L$_1$ and L$_2$ or L$_2$ can be substituted with (R)$_n$ as described herein; and each alkyl group of L$_1$ and L$_2$ or L$_2$ can be substituted with R$^c$ and R$^d$, as described herein. In Formula (3A), Ring A and Ring B is the L$_1$ and L$_2$ heteroaryl group, respectively. In Formula (4A), Ring B is the L$_2$ heteroaryl group.

In one aspect of the invention, is a Formula (1A) compound that is a Formula (1A1) compound

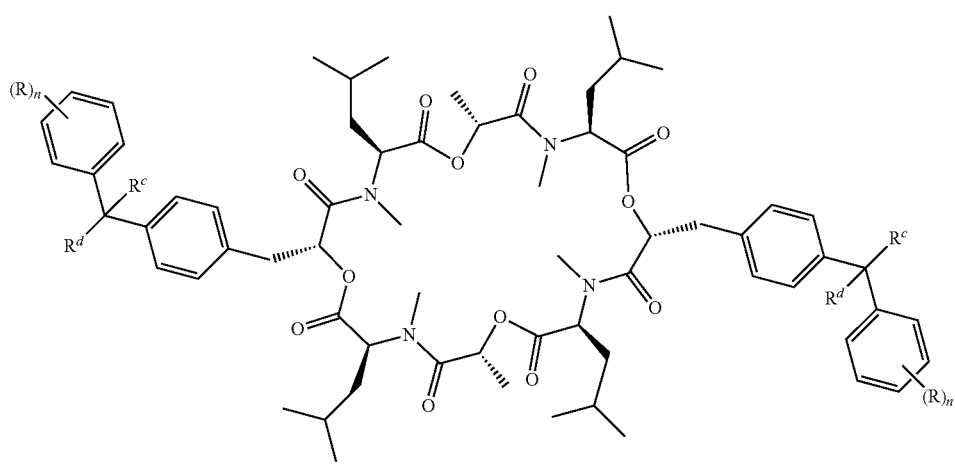

(1A1)

stereoisomers thereof, and veterinary acceptable salts thereof. Each of $(R)_n$, $R^c$, and $R^d$ are as described herein; and each $(R)_n$ is the same, each $R^c$ is the same, and each $R^d$ is the same; stereoisomers thereof, and veterinary acceptable salts thereof.

In one aspect of the invention, is a Formula (2A) compound that is a Formula (2A1) compound,

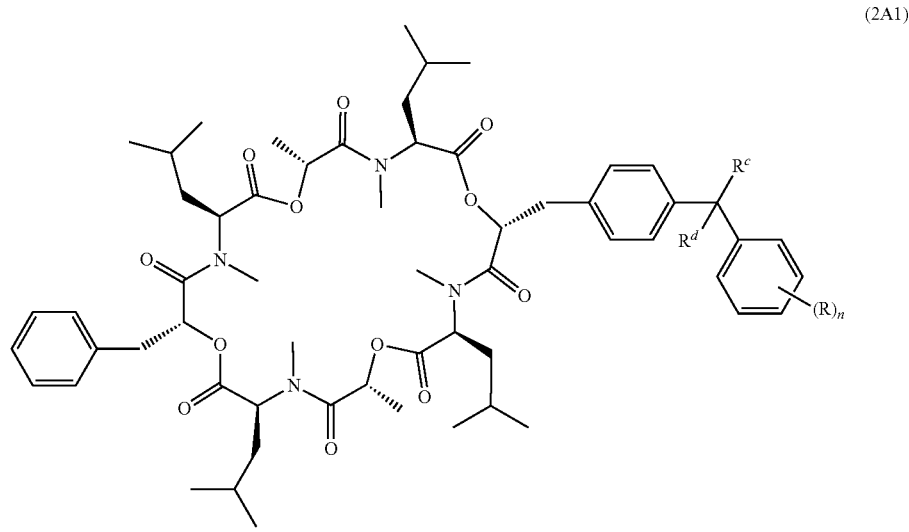

(2A1)

Each of $(R)_n$, $R^c$, and $R^d$ are as described herein; stereoisomers thereof, and veterinary acceptable salts thereof.

In another aspect of the invention, is a composition comprising a Formula (1A1) or (2A1) compound. In yet another aspect, the Formula (1A1) or (2A1) composition further comprises a veterinary acceptable excipient. In another aspect of the invention, is a method of treating a parasitic infection in an animal by administering a therapeutic amount of a Formula (1A1) or (2A1) compound to the animal in need thereof. In yet another aspect, is the use of a Formula (1A1) or (2A1) compound for treating a parasitic infection in an animal by administering a therapeutic amount of a Formula (1A1) or (2A1) compound to the animal in need thereof. In yet another aspect, is the use of a Formula (1A1) or (2A1) compound for preparing a medicament for the use in treating a parasitic infection in an animal.

In another aspect of the invention are Formula (1A) compounds that are Formula (3A) compounds,

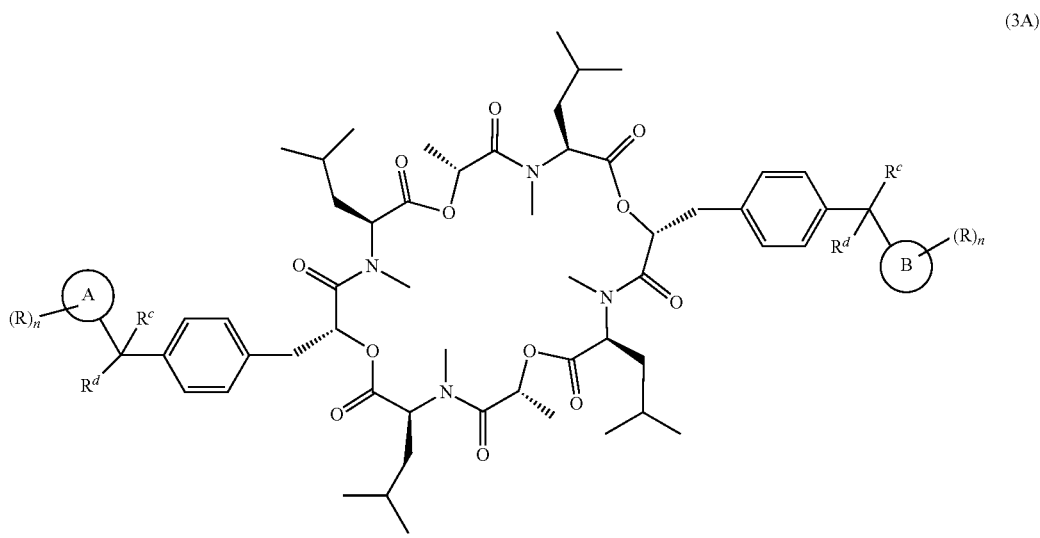

(3A)

Each of Ring A, Ring B, $(R)_n$, $R^c$, and $R^d$ are as described herein. Ring A and Ring B are the same, and each $(R)_n$ is the same, each $R^c$ is the same, and each $R^d$ is the same; stereoisomers thereof, and veterinary acceptable salts thereof.

In yet another aspect of the invention, is a Formula (2A) compound that is a Formula (4A) compound

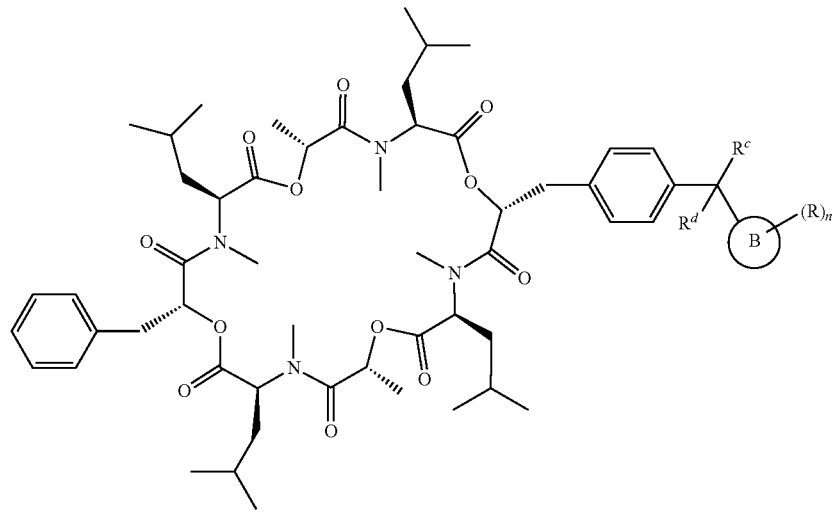

(4A)

Each of Ring B, $(R)_n$, $R^c$, and $R^d$ are as described herein; stereoisomers thereof, and veterinary acceptable salts thereof.

In another aspect of the invention, is a composition comprising a Formula (3A) or (4A) compound. In yet another aspect, the Formula (3A) or (4A) composition further comprises a veterinary acceptable excipient. In another aspect of the invention, is a method of treating a parasitic infection in an animal by administering a therapeutic amount of a Formula (3A) or (4A) compound to the animal in need thereof. In yet another aspect, is the use of a Formula (3A) or (4A) compound for treating a parasitic infection in an animal by administering a therapeutic amount of a Formula (3A) or (4A) compound to the animal in need thereof. In yet another aspect, is the use of a Formula (3A) or (4A) compound for preparing a medicament for the use in treating a parasitic infection in an animal.

As described herein, Ring A and Ring B are the $L_1$ and $L_2$ cycloalkyl, heterocycle, or heteroaryl groups of Formula (1), respectively; or $L_1$ is absent. Ring A and Ring B of Formula (3A) are the same; and Ring B of Formula (4A); are each cyclopropyl, cyclobutyl, cyclopentyl, cyclohexyl, oxetanyl, thietanyl, azetidinyl, tetrahydrofuranyl, tetrahydrothiophenyl, pyrrolidinyl, tetrahydropyranyl, tetrahydrothiopyranyl, piperidinyl, dioxanyl, morpholinyl, piperazinyl, azathianyl, 3,4-dihydro-2H-pyranyl, 4,5,6,7-tetrahydropyrazolo[1,5-a]pyridinyl, 4,5-tetrahydropyrazolo[1,5-a]pyrimidine, pyrrolyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, dihydropyridinyl, pyridinyl, pyridazinyl, pyrimidinyl, pyrazinyl, triazinyl, quinolonyl, isoquinolinyl, benzofuranyl, indazolyl, benzothiophenyl, indolyl, triazinyl, benzimidazolyl, tetrahydropyranyl, pyrazolo[1,5-a]pyridinyl, pyrazolo[1,5-a]pyrimidinyl, 1H-pyrrolo[3,2-b]pyridinyl, indazolebenzo[d][1,3]diazolyl, benzo[d]thiazolyl, furo[2,3-b]pyridinyl, 2,3-dihydrothieno[3,4-b][1,4]dioxinyl, 3,4-dihydro-2H-pyrano[2,3-b]pyridinyl, oxazolo[5,4-b]pyridinyl, or benzo[d]1,3 diaxolyl. In another aspect, Ring A and Ring B of Formula (3A) are the same; and Ring B of Formula (4A); are each pyrrolidinyl, tetrahydropyranyl, piperidinyl, morpholinyl, thiadiazolyl, thiophenyl, thiazolyl, pyrazolyl, pyridinyl, pyrimidinyl, pyridazinyl, pyrazinyl, oxazolyl, isoxazolyl, isothiazolyl, or furanyl. In yet another aspect, Ring A and B are the same and are each morpholinyl, thiophenyl, thiazolyl, pyrazolyl, pyridinyl, pyridazinyl, pyrazinyl, or pyrimidinyl. In yet another aspect, Ring A and B of Formula (3A) are the same; and Ring B of Formula (4A); are each pyrazolyl, thiazolyl, thiadiazolyl, isothiazolyl, pyridinyl, pyridazinyl, pyrazinyl, and pyrimidyl. In yet another aspect, Ring A and B of Formula (3A) are the same; and Ring B of Formula (4A); are each pyrazolyl, pyrazinyl, isothiazolyl, thiazolyl, pyridinyl, pyridazinyl, and pyrimidinyl. In yet another aspect, Ring A and B of Formula (3A) are the same; and Ring B of Formula (4A); are each pyrazolyl, isothiazolyl, thiazolyl, pyridinyl, pyrazinyl, or pyrimidinyl. In yet another aspect, Ring A and B of Formula (3A) are the same; and Ring B of Formula (4A); are each isothiazolyl, thiazolyl, pyridinyl, pyrazinyl, or pyrimidinyl. In yet another aspect, Ring A and B of Formula (3A) are the same; and Ring B of Formula (4A); are pyrazolyl. In yet another aspect, Ring A and B of Formula (3A) are the same; and Ring B of Formula (4A); are isothiazolyl. In yet another aspect, Ring A and B of Formula (3A) are the same; and Ring B of Formula (4A); are thiazolyl. In yet another aspect, Ring A and B of Formula (3A) are the same; and Ring B of Formula (4A); are pyridinyl. In yet another aspect, Ring A and B of Formula (3A) are the same; and Ring B of Formula (4A); are pyrazinyl. In yet another aspect, Ring A and B of Formula (3A) are the same; and Ring B of Formula (4A); are pyrimidinyl.

In one aspect of the invention, R of $(R)_n$ is independently selected from the group consisting of $C_1$-$C_6$alkyl optionally substituted with at least one substituent selected from hydroxyl, $C_3$-$C_6$cycloalkyl, and —$OR^a$; halo, oxo, cyano, hydroxyl, —$OR^5$, —$NR^aR^b$, $C_1$-$C_4$haloalkyl, $C_1$-$C_4$haloalkoxy, —$S(O)_pR^a$, $C_1$-$C_6$alkoxy, $C_3$-$C_6$cycloalkyl, —$C(O)NR^aR^b$, —$C(O)R^a$, —$C(O)OR^a$, —$NR^aC(O)R^b$, pyrazolyl, imidazolyl, pyridinyl, pyrimidinyl, piperidinyl, morpholinyl, pyrrolidinyl, dihydropyrimidinyl, and phenyl; and wherein the phenyl is optionally substituted with at least one substituent selected from $C_1$-$C_3$alkyl, —$CF_3$, halo, and hydroxyl; and wherein n of $(R)_n$ is the integer 0, 1, 2, or 3; and wherein each $(R)_n$ of Formula (1A1) and Formula (3A) are the same. In another aspect, R of $(R)_n$ is independently selected from the group consisting of $C_1$-$C_6$alkyl optionally substituted with at least one substituent selected from hydroxyl, $OR^a$, and $C_3$-$C_6$cycloalkyl; halo, cyano, hydroxyl, —$NR^aR^b$, $C_1$-$C_4$haloalkyl, $C_1$-$C_4$haloalkoxy, —$S(O)_pR^a$, $C_1$-$C_6$alkoxy, —$OR^5$, $C_3$-$C_6$cycloalkyl, morpholinyl, and phenyl optionally substituted with methyl, —$CF_3$, halo, and hydroxyl; and wherein n is the integer 0, 1, 2, or 3; and wherein each $(R)_n$ of Formula (1A1) and Formula (3A) are the same. In yet another aspect, R of $(R)_n$ is independently selected from the group consisting of $C_1$-$C_6$alkyl optionally substituted with at least one substituent selected from hydroxyl and $C_3$-$C_6$cycloalkyl; halo, cyano, hydroxyl, —$NR^aR^b$, $C_1$-$C_4$haloalkyl, $C_1$-$C_4$haloalkoxy, —$S(O)_pR^a$, $C_1$-$C_6$alkoxy, $C_3$-$C_6$cycloalkyl, morpholinyl, and phenyl optionally substituted with methyl, —$CF_3$, halo, and hydroxyl; and wherein n is the integer 0, 1, 2, or 3; and wherein each $(R)_n$ of Formula (1A1) and Formula (3A) are the same. In yet another aspect, R of $(R)_n$ is independently selected from the group consisting of methyl, ethyl, propyl, isopropyl, isobutyl, cyclopropyl, cyclobutyl, —C-cyclopropyl, halo, —$SCH_3$, —$S(O)_2CH_3$, cyano, hydroxyl, —C— $CF_3$, —$CF_3$, —C—$CF_2$, —$NR^aR^b$, methoxy, ethoxy, isopropoxy, —O—C—$CF_3$, —O—$CF_2$, —COH, morpholinyl, and phenyl; and wherein the phenyl can be further substituted with methyl; and wherein n of $(R)_n$ is the integer 0, 1, 2, or 3; and wherein each $(R)_n$ of Formula (1A1) and Formula (3A) are the same. In yet another aspect, R of $(R)_n$ is independently selected from the group consisting of methyl, ethyl, isopropyl, cyclopropyl, —C-cyclopropyl, halo, —$SCH_3$, cyano, hydroxyl, —C—CF, —$CF_2$, —$CF_3$, —$N(CH_3)_2$, methoxy, ethoxy, —$OCF_3$, —$OCF_2$, and morpholinyl; and wherein n of $(R)_n$ is the integer 0, 1, 2, or 3; and wherein each $(R)_n$ of Formula (1A1) and Formula (3A) are the same.

In one aspect of the invention, n of $(R)_n$ of Formula (1A1) and (3A) is the same integer; and n of $(R)_n$ of Formula (2A) and (4A); is the integer 0, 1, 2, or 3. In another aspect, n is the integer 0. In yet another aspect, n is the integer 1. In yet another aspect, n is the integer 2. In yet another aspect, n is the integer 3.

In one aspect of the invention, p is the integer 0, 1, or 2. In another aspect, p is the integer 0. In yet another aspect, p is the integer 1. In yet another aspect, p is the integer 2.

In one aspect of the invention, $R^a$ and $R^b$ are each separately selected from H, methyl, ethyl, propyl, isopropyl, and iso-butyl. In another aspect of the invention, $R^a$ and $R^b$ are each separately H, methyl, ethyl, and isopropyl. In another aspect, $R^a$ and $R^b$ are each separately H, methyl, and ethyl.

In one aspect of the invention, $R^c$ and $R^d$ are each independently and separately selected from the group consisting of H, hydroxyl, halo, $C_1$-$C_6$alkyl, $C_1$-$C_6$alkoxy, —$CF_3$, cyclopropyl, —$NR^aR^b$, pyrazolyl, pyrrolidinyl, and morpholinyl; and wherein each $R^c$ of Formula (1A1) and Formula (3A) are the same and each $R^d$ of Formula (1A1) and Formula (3A) are the same. In another aspect of the invention, $R^c$ and $R^d$ are each independently and separately selected from the group consisting of H, hydroxyl, halo, $C_1$-$C_6$alkyl, $C_1$-$C_6$alkoxy, —$NR^aR^b$, —$CF_3$, cyclopropyl, pyrazolyl, pyrrolidinyl, and morpholinyl; and wherein each $R^c$ of Formula (1A1) and Formula (3A) are the same and each $R^d$ of Formula (1A1) and Formula (3A) are the same.

In yet another aspect of the invention, $R^c$ and $R^d$ are each independently and separately selected from H, F, Cl, $C_1$-$C_6$alkyl, methoxy, ethoxy, isopropoxy, —$CF_3$, hydroxyl, —$N(CH_3)_2$, —$N(CH_2CH_3)_2$, cyclopropyl, pyrazolyl, and morpholine; and wherein each $R^c$ of Formula (1A1) and Formula (3A) are the same and each $R^d$ of Formula (1A1) and Formula (3A) are the same. In another aspect, $R^c$ and $R^d$ are each independently and separately selected from H, F, Cl, methyl, ethyl, isopropyl, hydroxyl, —$CF_3$, methoxy, ethoxy, isopropoxy, cyclopropyl, and —$N(CH_2CH_3)_2$; and wherein each $R^c$ of Formula (1A1) and Formula (3A) are the same and each $R^d$ of Formula (1A1) and Formula (3A) are the same. In yet another aspect, $R^c$ and $R^d$ are each independently and separately selected from H, F, methyl, ethyl, hydroxyl, —$CF_3$, methoxy, ethoxy, and —$N(CH_2CH_3)_2$; and wherein each $R^c$ of Formula (1A1) and Formula (3A) are the same and each $R^d$ of Formula (1A1) and Formula (3A) are the same. In yet another aspect, $R^c$ and $R^d$ are each independently and separately selected from H, F, methyl, ethyl, hydroxyl, methoxy, and ethoxy; and wherein each $R^c$ of Formula (1A1) and Formula (3A) are the same and each $R^d$ of Formula (1A1) and Formula (3A) are the same. In yet another aspect, $R^c$ and $R^d$ are each independently and separately selected from H, F, methyl, hydroxyl, and methoxy; and wherein each $R^c$ of Formula (1A1) and Formula (3A) are the same and each $R^d$ of Formula (1A1) and Formula (3A) are the same. In yet another aspect, $R^c$ and $R^d$ are each independently and separately selected from H, hydroxyl, and methoxy; and wherein each $R^c$ of Formula (1A1) and Formula (3A) are the same and each $R^d$ of Formula (1A1) and Formula (3A) are the same.

In one aspect of the invention, $R^5$ is cyclopropyl, cyclobutyl, cyclopentyl, cyclohexyl, $C_1$-cyclopropyl, $C_2$-cyclopropyl, $C_1$-cyclobutyl, $C_2$-cyclobutyl, $C_2$-cyclopentyl, $C_2$-cyclohexyl, $C_3$-cyclopropyl, or $C_3$-cyclobutyl. In another aspect, $R^5$ is cyclopropyl, cyclobutyl, $C_1$-cyclopropyl, $C_2$-cyclopropyl, $C_1$-cyclobutyl, or $C_2$-cyclobutyl. In yet another aspect, $R^5$ is cyclopropyl, cyclobutyl, $C_1$-cyclopropyl, or $C_1$-cyclobutyl. In yet another aspect, $R^5$ is cyclopropyl, cyclobutyl, or $C_1$-cyclopropyl. In yet another aspect, $R^5$ is cyclopropyl. In yet another aspect, $R^5$ is cyclobutyl. In yet another aspect, $R^5$ is $C_1$-cyclopropyl.

In yet another aspect of the invention are Formula (1A1) compounds selected from the group consisting of those compounds described in Table 1, stereoisomers thereof, and veterinary acceptable salts thereof. In another aspect, is a composition comprising a compound described in Table 1. In another aspect, is a method of treating a parasitic infection in an animal in need thereof by administering a therapeutically effective amount of a Table 1 compound to the animal. In another aspect, is the use of a compound described in Table 1 to prepare a medicament for the treatment of a parasitic infection in an animal.

In another aspect of the invention are Formula (1A1) compounds selected from the group consisting of Examples: (1-5), (1-11), and (1-18), stereoisomers thereof, and veterinary acceptable salts. Preferred (1A1) compounds are Examples (1-5) and (1-11), stereoisomers thereof, and veterinary acceptable salts thereof. In another aspect, is a composition comprising one of these Formula (1A1) compounds, stereoisomers thereof, and veterinary acceptable salts thereof. In another aspect, the composition further comprises a veterinary acceptable excipient. In another aspect, is a method of treating a parasitic infection in an animal in need thereof by administering a therapeutically effective amount of one of these Formula (1A1) compounds to the animal. In another aspect, is the use of one of these Formula (1A1) compounds to prepare a medicament for the treatment of a parasitic infection in an animal.

In yet another aspect of the invention are Formula (2A1) compounds selected from the group consisting of those compounds described in Table 2, stereoisomers thereof, and veterinary acceptable salts thereof. In another aspect, is a composition comprising a compound described in Table 2. In another aspect, is a method of treating a parasitic infection in an animal in need thereof by administering a therapeutically effective amount of a Table 2 compound to the animal. In another aspect, is the use of a compound described in Table 2 to prepare a medicament for the treatment of a parasitic infection in an animal.

In another aspect of the invention are Formula (2A1) compounds selected from the group consisting of Examples: (2-1), (2-4), (2-36), (2-37), (2-38), and (2-42), stereoisomers thereof, and veterinary acceptable salts thereof; and veterinary acceptable salts thereof. Preferred (2A1) compounds are Examples (2-4), (2-36), and (2-42), stereoisomers thereof, and veterinary acceptable salts thereof. In another aspect, is a composition comprising one of these Formula (2A1) compounds, stereoisomers thereof, and veterinary acceptable salts thereof. In another aspect, the composition further comprises a veterinary acceptable excipient. In another aspect, is a method of treating a parasitic infection in an animal in need thereof by administering a therapeutically effective amount of one of these Formula (2A1) compounds to the animal. In another aspect, is the use of one of these Formula (2A1) compounds to prepare a medicament for the treatment of a parasitic infection in an animal.

In yet another aspect of the invention are Formula (3A) compounds selected from the group consisting of those compounds described in Table 3, stereoisomers thereof, and veterinary acceptable salts thereof. In another aspect, is a composition comprising a compound described in Table 3. In another aspect, is a method of treating a parasitic infection in an animal in need thereof by administering a therapeutically effective amount of a Table 3 compound to the animal. In another aspect, is the use of a compound described in Table 3 to prepare a medicament for the treatment of a parasitic infection in an animal.

In yet another aspect of the invention is a Formula (3A) compound selected from the group consisting of Examples: (3-4), (3-8), (3-12), (3-17), (3-18), (3-21), (3-24), (3-31), (3-44), (3-49), (3-50), (3-56), (3-57), (3-60), (3-69), (3-87), (3-110), (3-112), (3-118), (3-120), (3-121), (3-124), (3-125), (3-132), (3-133), (3-148), (3-155), (3-156), (3-157), (3-165), (3-173), (3-176), (3-178), (3-193), (3-194), (3-207), (3-209), (3-215), (3-217), (3-218), (3-220), (3-223), (3-225), (3-228), (3-238), (3-240), (3-243), (3-252), (3-253), (3-254), (3-259), (3-261), (3-268), (3-273), (3-274), (3-275), (3-282), (3-283), (3-284), (3-285), (3-286), (3-287), (3-288), (3-289), (3-290), (3-291), (3-292), (3-293), (3-294), (3-295), (3-296), (3-297), (3-307), (3-308), (3-309), (3-310), (3-313), (3-318), (3-319), (3-321), (3-322), (3-323), (3-324), (3-326), (3-329), (3-332), (3-333), and (3-334), stereoisomers thereof, and veterinary acceptable salts thereof. Preferred (3A) compounds are Examples (3-4), (3-44), (3-56), (3-69), (3-87), (3-110), (3-118), (3-121), (3-124), (3-125), (3-133), (3-157), (3-165), (3-173), (3-207), (3-225), (3-261), (3-284), (3-286), (3-287), (3-293), (3-296), (3-324), (3-326), and (3-332), stereoisomers thereof, and veterinary acceptable salts thereof. In yet another aspect of the invention is a composition comprising one of these Formula (3A) compounds. In yet another aspect, the composition further comprises a veterinary acceptable excipient. In another aspect, is a method of treating a parasitic infection in an animal in need thereof by administering a therapeutically effective amount of one of these Formula (3A) compounds to the animal. In another aspect, is the use of one of these Formula (3A) compounds to prepare a medicament for the treatment of a parasitic infection in an animal.

In yet another aspect of the invention are Formula (4A) compounds selected from the group consisting of those compounds described in Table 4, stereoisomers thereof, and veterinary acceptable salts thereof. In another aspect, is a composition comprising a compound described in Table 4. In another aspect, is a method of treating a parasitic infection in an animal in need thereof by administering a therapeutically effective amount of a Table 4 compound to the animal. In another aspect, is the use of a compound described in Table 4 to prepare a medicament for the treatment of a parasitic infection in an animal.

In yet another aspect of the invention, is a Formula (4A) compound selected from the group consisting of Examples: (4-18), (4-19), (4-21), (4-30), (4-32), (4-34), (4-40), (4-50), (4-63), (4-75), (4-105), (4-107), (4-109), (4-118), (4-126), (4-139), and (4-141), stereoisomers thereof, and veterinary acceptable salts thereof. Preferred Formula (4A) compounds are selected from the group of Examples: (4-18), (4-19), and n (4-21), stereoisomers thereof, and veterinary acceptable salts thereof. In yet another aspect of the invention is a composition comprising one of the Formula (4A) compounds. In yet another aspect, the composition further comprises a veterinary acceptable excipient. In another aspect, is a method of treating a parasitic infection in an animal in need thereof by administering a therapeutically effective amount of one of these Formula (4A) compounds to the animal. In another aspect, is the use of one of these Formula (4A) compounds to prepare a medicament for the treatment of a parasitic infection in an animal.

In yet another aspect, is a Formula (1) compound that is at least 10× selective against $D.$ $immitis$ L4 (i.e., DiMf/DiL4). In yet another aspect of the invention is a composition comprising a Formula (1) compound that is at least 10× selective against $D.$ $immitis$ L4 and a veterinary acceptable excipient. In yet another aspect of the invention is a composition comprising a therapeutically effective amount of a Formula (1) compound that is at least 10× selective over $D.$ $immitis$ L4. In yet another aspect of the invention is a composition comprising a therapeutically effective amount of a Formula (1) compound that is at least 10× selective over $D.$ $immitis$ L4 and a veterinary acceptable excipient. In another aspect, the Formula (1) compounds that are at least 10× selective include Example #'s: (1-18), (2-1), (2-4), (2-37), (2-38), (3-8), (3-31), (3-50), (3-58), (3-60), (3-69), (3-112), (3-121), (3-132), (3-133), (3-173), (3-176), (3-207), (3-209), (3-218), (3-228), (3-238), (3-240), (3-252), (3-259), (3-274), (3-275), (3-286), (3-288), (3-295), (3-296), (3-297), (3-308), (3-318), (3-319), (3-322), (3-323), (3-329), (3-333), (3-334), (4-18), (4-21), (4-34), (4-50), (4-75), (4-105), (4-107), (4-118), and (4-126).

In yet another aspect, is a Formula (1) compound that is at least 100× selective against *D. immitis* L4 (i.e., DiMf/DiL4). In yet another aspect of the invention is a composition comprising a Formula (1) compound that is at least 100× selective against *D. immitis* L4 and a veterinary acceptable excipient. In yet another aspect of the invention is a composition comprising a therapeutically effective amount of a Formula (1) compound that is at least 100× selective over *D. immitis* L4. In yet another aspect of the invention is a composition comprising a therapeutically effective amount of a Formula (1) compound that is at least 100× selective over *D. immitis* L4 and a veterinary acceptable excipient. In another aspect, the Formula (1) compounds that are at least 100× selective include Formula (1A1) compounds: (3S,6R,9S,12R,15S,18R,21S,24R)-3,9,15,21-tetraisobutyl-6,18-bis(4-(3-methoxybenzyl)benzyl)-4,10,12,16,22,24-hexamethyl-1,7,13,19-tetraoxa-4,10,16,22-tetraazacyclotetracosan-2,5,8,11,14,17,20,23-octaone (1-5) and (3S,6R,9S,12R,15S,18R,21S,24R)-3,9,15,21-tetraisobutyl-6,18-bis(4-(2-methoxybenzyl)benzyl)-4,10,12,16,22,24-hexamethyl-1,7,13,19-tetraoxa-4,10,16,22-tetraazacyclotetracosan-2,5,8,11,14,17,20,23-octaone (1-11); and Formula (2A1) compounds: (3S,6R,9S,12R,15S,18R,21S,24R)-6-benzyl-18-(4-(((diethylamino)(3,4-difluorophenyl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (2-36) and (3S,6R,9S,12R,15S,18R,21S,24S)-6-benzyl-3,9,15,21-tetraisobutyl-4,10,12,16,22,24-hexamethyl-18-[[4-[(S)-morpholino-[4-(trifluoromethoxy)phenyl]-methyl]phenyl]methyl]-1,7,13,19-tetraoxa-4,10,16,22-tetrazacyclotetracosane-2,5,8,11,14,17,20,23-octaone (2-42); and Formula (3A) compounds: (3S,6R,9S,12R,15S,18R,21S,24R)-3,9,15,21-tetraisobutyl-4,6,10,16,18,22-hexamethyl-12,24-bis(4-(thiophen-2-ylmethyl)benzyl)-1,7,13,19-tetraoxa-4,10,16,22-tetraazacyclotetracosan-2,5,8,11,14,17,20,23-octaone (3-4), (3S,6R,9S,12R,15S,18R,21S,24R)-3,9,15,21-tetraisobutyl-4,6,10,16,18,22-hexamethyl-12,24-bis(4-((3-methylthiophen-2-yl)methyl)benzyl)-1,7,13,19-tetraoxa-4,10,16,22-tetraazacyclotetracosan-2,5,8,11,14,17,20,23-octaone (3-44), (3S,6R,9S,12R,15S,18R,21S,24R)-3,9,15,21-tetraisobutyl-4,6,10,16,18,22-hexamethyl-12,24-bis(4-(thiophen-3-ylmethyl)benzyl)-1,7,13,19-tetraoxa-4,10,16,22-tetraazacyclotetracosan-2,5,8,11,14,17,20,23-octaone (3-56), (3S,6R,9S,12R,15S,18R,21S,24R)-6,18-bis(4-((3-chlorothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-87), (3S,6R,9S,12R,15S,18R,21S,24R)-3,9,15,21-tetraisobutyl-6,18-bis(4-((3-methoxythiophen-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone (3-110), (3S,6R,9S,12R,15S,18R,21S,24R)-6,18-bis(4-((5-fluoro-6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-118), (3S,6R,9S,12R,15S,18R,21S,24R)-3,9,15,21-tetraisobutyl-4,6,10,16,18,22-hexamethyl-12,24-bis(4-((4-methylthiophen-2-yl)methyl)benzyl)-1,7,13,19-tetraoxa-4,10,16,22-tetraazacyclotetracosan-2,5,8,11,14,17,20,23-octaone (3-124), (3S,6R,9S,12R,15S,18R,21S,24R)-6,18-bis(4-((3-bromothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-125), (3S,6R,9S,12R,15S,18R,21S,24R)-3,9,15,21-tetraisobutyl-4,6,10,16,18,22-hexamethyl-12,24-bis(4-((5-methylfuran-2-yl)methyl)benzyl)-1,7,13,19-tetraoxa-4,10,16,22-tetraazacyclotetracosan-2,5,8,11,14,17,20,23-octaone (3-157), (3-165). (3S,6R,9S,12R,15S,18R,21S,24R)-6,18-bis(4-((2-ethoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-165), (3S,6R,9S,12R,15S,18R,21S,24R)-6,18-bis(4-(1-fluoro-1-(6-methoxypyridin-2-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-225), (3S,6R,9S,12R,15S,18R,21S,24R)-3,9,15,21-tetraisobutyl-6,18-bis(4-(1-(2-methoxypyridin-3-yl)ethyl)benzyl)-4,10,12,16,22,24-hexamethyl-1,7,13,19-tetraoxa-4,10,16,22-tetraazacyclotetracosan-2,5,8,11,14,17,20,23-octaone (3-261), (3S,6R,9S,12R,15S,18R,21S,24R)-6,18-bis(4-((3-cyclopropylisoxazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-284), (3S,6R,9S,12R,15S,18R,21S,24R)-6,18-bis(4-((6-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-287), (3S,6R,9S,12R,15S,18R,21S,24R)-6,18-bis(4-((5-fluoro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-293), (3S,6R,9S,12R,15S,18R,21S,24R)-6,18-bis(4-((2,5-difluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-324), and (3S,6R,9S,12R,15S,18R,21S,24R)-6,18-bis(4-((2,3-difluoropyridin-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-326); (3S,6R,9S,12R,15S,18R,21S,24R)-6,18-bis(4-((5-chloro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone (3-332); and a Formula (4A) compound: (3S,6R,9S,12R,15S,18R,21S,24R)-6-benzyl-18-(4-((2,4-dimethyl-1H-pyrrol-3-yl)methyl)benzyl)-3,9,15,21-tetraisobutyl-4,10,12,16,22,24-hexamethyl-1,7,13,19-tetraoxa-4,10,16,22-tetraazacyclo-tetracosan-2,5,8,11,14,17,20,23-octaone; stereoisomers thereof, and veterinary acceptable salts thereof.

In yet another aspect of the invention, are Formula (2A1) compounds (2-1), (2-9), and (2-38); or Formula (3A) compounds (3-4), (3-8), (3-14), (3-17), (3-18), (3-21), (3-24), (3-36), (3-45), (3-50), (3-52), (3-56), (3-57), (3-58), (3-69), (3-73), (3-87), (3-112), (3-119), (3-120), (3-124), (3-126), (3-155), (3-193), (3-215), (3-253), (3-268), (3-273), (3-274), (3-283), (3-288), (3-290), (3-291), (3-294), (3-299), (3-303), (3-305), (3-306), (3-307), (3-310), (3-319), (3-321), (3-323), (3-324), (3-329), (3-333), and (3-334); or Formula (4A) compounds (4-30), (4-31), (4-32), (4-34), (4-40), (4-52), (4-63), (4-75), (4-105), (4-107), (4-109), (4-118), and (4-139); stereoisomers thereof, and veterinary acceptable salts thereof; all of which have HcL3 MED values≤1 µM.

The compounds of the invention are intended to encompass racemic mixtures, specific stereoisomers, regio-isomers, and tautomeric forms of the Formula (1) compounds.

DETAILED DESCRIPTION

Definitions

For purposes of the present invention, as described and claimed herein, the following terms and phrases are defined as follows:

"Additional veterinary agent(s)" as used herein, refers to other veterinary or veterinary compounds or products that provide a therapeutically effective amount of said agents that are useful for the treatment of a parasitic infection in an animal, as described herein.

"Alkoxy", as used herein, refers to —O-alkyl, wherein the term alkyl is defined below. Non-limiting alkoxy examples include: methoxy, ethoxy, propoxy, isopropoxy, n-butoxy, n-pentoxy, 1-methylbutoxy, 1-ethylpropoxy, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "$C_1$-$C_6$alkyl" refers to a monovalent, straight or branched aliphatic group containing 1 to 6 carbon atoms. In addition, the term "$C_1$-$C_4$alkyl" refers to a monovalent, straight or branched aliphatic group containing 1 to 4 carbon atoms, and is also described as $C_1$ (—C—), $C_2$ (—C—C—), $C_3$ (—C—C—C—), and $C_4$ (—C—C—C—C—) for the straight aliphatic group. Terms like —C—C—, —C—C—C— and the like, are synonymous with —$CH_2CH_2$—, —$CH_2CH_2CH_2$—, and the like, respectively. Non-exclusive examples of $C_1$-$C_6$ alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl group may be attached to the chemical moiety by any one of the carbon atoms of the aliphatic chain. Alkyl groups can be substituted as described herein. Further when used in compound words such as alkylphenyl, said alkyl group has the same meaning as herein defined and may be attached to the chemical moiety by any one of the carbon atoms of the aliphatic chain. Non-limiting examples include: $C_1$alkylaryl which is —$CH_2$aryl (e.g., —$CH_2$phenyl); $C_1$alkyl$C_3$cycloalkyl which is —$CH_2$cyclopropyl; $C_1$alkylheteroaryl which can be —$CH_2$pyrazole, —$CH_2$pyridine, —$CH_2$pyrimidine, and the like.

"Animal(s)", as used herein, unless otherwise indicated, refers to an individual animal that is a mammal or bird. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl.

"Aryl", as described herein, refers to a monovalent aromatic carbocyclic group of from 6 to 10 carbon atoms having a single ring or multiple fused rings. Aryl groups include, but are not limited to, phenyl, biphenyl, and naphthyl. Further when used in compound words such as alkylaryl, said alkyl and aryl groups have the same meaning as herein defined and may be attached to the chemical moiety by any one of the carbon atoms of the aliphatic chain. For example, $C_0$alkylaryl is aryl, (e.g., $C_0$alkylphenyl is phenyl), $C_1$alkylaryl is —$CH_2$aryl (e.g., —$CH_2$phenyl), $C_2$alkylaryl is —$CH_2CH_2$aryl (e.g., —$CH_2CH_2$phenyl), and the like. Aryls can be substituted as described herein.

"Chiral", as used herein, unless otherwise indicated, refers to the structural characteristic of a molecule that makes it impossible to superimpose it on its mirror image, (e.g., "R" and "S" enantiomers).

"Comprise(s)", as used herein, refers to an inclusive meaning, i.e., that it will be taken to mean an inclusion of not only the listed components it directly references, but also other non-specified components or elements. This rationale will also be used when the term "comprised" or "comprising" is used in relation to one or more steps in a method or process. Contains is herein construed as being synonymous to comprise. The term "consisting of", and/or "consisting essentially of" has a non-inclusive meaning.

"Compounds of the present invention", as used herein, unless otherwise indicated, refers to compounds of Formula (1), stereoisomers thereof, and veterinary acceptable salts thereof. The phrase also refers to the sub-genus formulas of Formula (1) including: Formula (1A), (1A1), (2A), (2A1), (3A), and (4A), stereoisomers thereof, and veterinary acceptable salts thereof. Preferred compounds are Formula (3A) compounds.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups can be substituted with at least one substituent, as described herein. Further when used in compound words such as alkylcycloalkyl, said alkyl and cycloalkyl groups have the same meaning as herein defined and may be attached to the chemical moiety by any one of the carbon atoms of the aliphatic chain. Examples of $C_1$-$C_6$alkyl$C_3$-$C_6$cycloalkyl include, methyl-cyclopropane ($C_1$alkyl$C_3$cycloalkyl or —$CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or —$CH_2$cyclobutane), ethylcyclobutane ($C_2$alkyl$C_4$cycloalkyl or —$CH_2CH_2$cyclobutane), methylcyclohexane ($C_1$alkyl$C_6$cycloalkyl or —$CH_2$cyclohexane), and the like. Cycloalkyl moieties can be substituted as described herein.

"Halogen" or "halo", as used herein, unless otherwise indicated, refers to fluorine (F), chlorine (Cl), bromine (Br) and iodine (I). Preferred halo are fluorine, chlorine, and bromine. Further, when used in compound words such as "haloalkyl" or "haloalkoxy", said alkyl and alkoxy may be partially or fully substituted with halogen atoms which may be the same or different and said alkyl and alkoxy groups have the same meaning as above and may be attached to the chemical moiety by any one of the carbon atoms of the aliphatic chain. Examples of haloalkyl include $F_3C$—, $F_2CH$— $ClCH_2$—, $CF_3CH_2$— and $CF_2CCl_2$—, and the like. The term "haloalkoxy" is defined analogously to the term "haloalkyl". Examples of haloalkoxy include $CF_3O$—, $Cl_3CH_2O$—, $HCF_2CH_2CH_2O$— and $CF_3CH_2O$—, and the like.

"Heteroaryl", as used herein, unless otherwise indicated, refers to a 5- to 6-membered aromatic monocyclic ring or an 9- to 10-membered fused aromatic ring where said monocyclic- and fused-ring contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, triazinyl, tetrazolyl, thiazolyl, isoxazolyl, isothiazolyl, oxazolyl, oxadiazolyl, thiadiazolyl, pyridinyl, pyridazinyl, pyrimidinyl, pyrazinyl, dihydropyridinyl, and the like. Non-exclusive examples of fused heteroaryls include: benzofuranyl, oxazolo[5,4-b]pyridine, indolyl, 3,4-dihydro-2H-pyrrano[2,3-b]pyridine, 2,3-dihydrothieno[3,4-b]dioxine, benzo[d][1,3]dioxole, furo[2,3-b]pyridine, benzothiophenyl, benzimidazolyl, indazolyl, quinolinyl, isoquinolinyl, cinnolinyl, quinazolinyl, benzotriazolyl, quinoxaline, benzo[d]thiazolyl, thieno[2,3-c]pyridine, thieno[3,2-b]pyridine, benzo[1,2,5]thiadiazole, pyrazolo[1,5-a]pyridine, pyrazolo[1,5-a]pyrimidine, dihydro-1H-pyrrolo[3,2-b]pyridine, oxazolo[5,5-b]pyridine, and the like. The heteroaryl ring is attached to the chemical moiety by any one of the carbon atoms within the monocyclic or fused ring. Further when used in compound words such as alkylheteroaryl, said alkyl and heteroaryl groups have the same meaning as herein defined and may be attached to the chemical moiety by any one of the carbon atoms of the aliphatic chain. For example, $C_1$alkylheteroaryl is —$CH_2$heteroaryl, $C_2$alkylheteroaryl is —$CH_2CH_2$heteroaryl, and the like. Heteroaryls can be substituted as described herein.

"Heterocycle", as used herein, unless otherwise indicated, refers to a partially saturated or saturated 4- to 6-membered monocyclic ring or a 9- to 10-membered fused ring, each containing one or more heteroatoms independently selected from N, O, or S, preferably from one to four heteroatoms. Non-exclusive examples of heterocycle include oxetane, azetidine, thiatane, tetrahydrofuran, tetrahydrothiophene, pyrrolidine, morpholine, thiomorpholine, tetrahydropyran, piperidine, piperazine, tetrahydropyridine, 2H-azirine, 2,3-dihydro-azete, tetrahydrocyclopentapyrazole, 3,4-dihydro-2H-pyrrole, imidazolidine, oxazolidine, isoxazolidine, tetrahydropyrimidinyl, tetrahydropyridinyl, and the like. The heterocyclic ring is attached to the chemical moiety by any one of the carbon atoms within the ring. Further when used in compound words such as alkylheterocycle, said alkyl and heterocycle groups have the same meaning as herein defined and may be attached to the chemical moiety by any one of the carbon atoms of the aliphatic chain. For example, $C_1$alkylheterocycle is —$CH_2$heterocycle, $C_2$alkylheterocycle is —$CH_2CH_2$heterocycle, and the like. Heterocycles can be substituted as described herein.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., treatment of a parasitic infection or infestation. A preferred parasite is an endoparasite. A preferred endoparasite is heart worm (*D. immitis*).

"Percent" (%), as used herein, refers to individual percent values. When referring to % in liquids (volume/volume % or v/v %) like an aqueous organic solvent, the % is the volume % of the solvent in the total volume of the solution. When referring to % for solids in liquids (weight/volume % or w/v %), the % value is construed to be the weight of the solid in the total volume of the solution and refers to the number of grams of solute in 100 mL of solution. When referring to solids (weight % or w/w %) refers to the weight (mass) of one component relative to the total weight (mass) of the solid composition.

"Protecting group" or "Pg", as used herein, unless otherwise indicated, refers to a substituent that is commonly employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like), acyloxy groups (e.g., 1-tert-butyloxycarbonyl (Boc), methoxycarbonyl, 9-fluorenyl-methoxycarbonyl, 2,2,2-trifluoroethoxycarbonyl, 2-trimethylsilylethoxycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like), diphenylmethane, and benzylcarbamates.

"Substituted", as used herein, refers to a substituent that is bonded to the chemical moiety in place of a hydrogen atom. Common substituents of the invention for alkyl, cycloalkyl, aryl, heterocyle, heteroaryl moieties, an d the like, are as described herein, and include, for example, —$NO_2$, —CN, alkyl, halo, alkoxy, haloalkyl, haloalkoxy, cycloalkyl, hydroxy, amino, alkylamino, dialkylamino, and the like. Substituents can be bonded to any carbon in the aliphatic chain or carbocyclic, aryl, heterocyclic, or heteroaryl ring system. The substituent can also be bonded to any accepting nitrogen and/or sulfur atom.

"Therapeutically effective amount", as used herein, refers to an amount of the active agent (i.e., Formula (1) compound) that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein. The active agent may be in a composition sufficient to elicit the desired biological response to the target parasite(s) after administration of the composition to the animal, as measured by methods known in the art and/or described in the examples herein. In some instances, an "effective amount" of the active agent in the composition will provide an efficacy of at least 70% against the target parasite compared to an untreated control. In other instances, "an effective amount" of the active agent will provide an efficacy of at least 80%, or at least 85% compared to untreated controls. More typically, "an effective amount" of the active agent will provide an efficacy of at least 90%, at least 93%, at least 95% or at least 97% against the target parasite. In certain instances, including the prevention of *Dirofilaria immitis*, the term "effective amount" may provide efficacy as high as 100%. As is understood in the art, a therapeutically effective amount may be in one or more doses, i.e., a single dose or multiple doses may be required to achieve the desired treatment endpoint, for example, (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein. The therapeutically effective amount will vary depending on the compound, the disease and its severity and the age, weight, etc., of the mammal to be treated.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation or after said infection or infestation. As such, compounds of the invention prevent heartworm in an animal by killing the L3 and L4 D. immitis before it can morph into an adult worm. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term "veterinary" acceptable has the same meaning as that recited for "pharmaceutical" acceptable.

The Formula (1) compounds of the invention are 24-membered cyclic depsipeptide compounds which have potent activity against endoparasites such as nematodes and filarial worms (microfilarial and larval stages) and also in some cases against ectoparasites such as fleas and ticks. In one aspect of the invention is a cyclic depsipeptide of Formula (1), or a veterinarily acceptable salt thereof. Surprisingly, it has been found that addition of a methylene linker between the aryl ring in one or both of the phenyl lactate groups in the molecule versus the parent cyclic depsipeptide PF1022 and emodepside, improves the selectivity and activity of the compounds against parasites, particularly, endoparasites. This improvement provides selectivity against the L3 and L4 larvae and the actual microfilaria by killing the L3 and L4 larvae before metamorphosis into the next lifecycle change, the animal is healthier and does not need to succumb to the killing of microfilaria or adult worms which can cause emboli and ultimately death to the host animal. Furthermore, it has been surprisingly found that substitution of the compounds of Formula (1) with certain $L_1$ and $L_2$ groups also significantly improves the in vitro metabolic stability of the compounds of the invention compared with PF1022 and emodepside. Thus, the compounds of the invention have been found to have significantly improved metabolic stability and equal or significantly improved efficacy against endoparasites including Dirofilaria immitis microfilaria and/or L3 and L4 larvae and/or Haemonchus contortus larvae. In some aspects, the compounds of Formula (1) with certain substituents will also exhibit improved activity against ectoparasites.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or Beilsteins Handbuch der organischen Chemie, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction Steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

The depsipeptides of the present invention described herein, include one or more chiral centers which results in a theoretical number of optically active isomers. Where compounds of the invention include n chiral centers, the compounds may comprise up to 2n optical isomers. The present invention encompasses the specific enantiomers or diastereomers, and mixtures thereof, of each compound. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-9 outline the general procedures useful for the preparation and isolation of compounds of the present invention. It is to be understood, however, that the invention, as fully described herein and as recited in the claims, is not intended to be limited by the details of the following schemes or modes of preparation. In the preparation of compounds of the present invention, protection of remote functionality of intermediates from undesired reactions can be accomplished with a protecting group.

In the preparation of compounds of the present invention, protection of remote functionality of intermediates from undesired reactions can be accomplished with a protecting group. The term "protecting group" or "Pg" refers to a substituent that is commonly employed to block or protect a particular functionality while reacting other functional groups on the compound. For example, an amine-protecting group is a substituent attached to an amine that blocks or protects the amine-functionality of the compound or intermediate. Suitable amine protecting groups include: 1-tert-butyloxycarbonyl (Boc), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, amino-caproyl, benzoyl, and the like, and acyloxy groups including: methoxycarbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like. Similarly, diphenylmethane and benzylcarbamates can be used as amine protecting groups. Suitable protecting groups and their respective uses are readily determined by one skilled in the art. For a general description of protecting groups and their use, see T. W. Greene, *Protective Groups in Organic Synthesis*, John Wiley & Sons, New York, 1991.

The compounds of the invention are intended to encompass racemic mixtures, specific stereoisomers and tautomeric forms of the compound. Another aspect of the invention is a salt form of the compound of the invention.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) are also the subject of the invention.

In addition to the neutral compounds of Formula (1), salt forms of the compounds are also active against endoparasites. The term "veterinary acceptable salt" is used throughout the specification to describe any salts of the compounds that are acceptable for administration for veterinary applications, and which provides the active compound upon administration.

In cases where compounds are sufficiently basic or acidic to form stable non-toxic acid or base salts, the compounds may be in the form of a veterinary or agriculturally acceptable salt. Veterinary acceptable salts include those derived from veterinary or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinary and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, a-ketoglutarate, and a-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

The compounds of Formula (1) may be prepared by processes adapted from those described in U.S. Pat. Nos. 5,514,773; 5,747,448; 5,874,530; 5,856,436; 6,033,879; 5,763,221; 6,329,338, 5,116,815; 6,468,966; 6,369,028; 5,777,075; and 5,646,244. In addition, various synthetic methods for cyclic depsipeptides have been reported in the chemical literature (see Luttenberg et al., *Tetrahedron* 68 (2012), 2068-2073; Byung H. Lee, *Tetrahedron Letters*, 1997, 38 (5), 757-760; Scherkenbeck et al., *Eur. J Org. Chem.*, 2012, 1546-1553; *Biosci. Biotech. Biochem.*, 1994, 58(6), 1193-1194; and Scherkenbeck et al., *Tetrahedron*, 1995, 51(31), 8459-8470) It will be understood by those skilled in the art that certain functional groups in the compounds and intermediates may be unprotected or protected by suitable protecting groups, as taught by Greene and Wuts, *Protective Groups in Organic Synthesis*, John Wiley and Sons, Inc., 4th edition 2006. Further, it will be apparent to those skilled in the art that the compounds and intermediates may be isolated by standard aqueous work-up conditions and optionally purified. For example, the compounds or intermediates may be purified by chromatographic methods or crystallized to yield the desired product in suitable purity.

One skilled in the art will recognize that, in some cases, after the introduction of a given reagent as it is depicted in the schemes, it may be necessary to perform additional routine synthetic Steps not described in detail to complete the synthesis of Formula (1) compounds.

The present invention includes all veterinary acceptable isotopically-labelled Formula (1) compounds wherein one or more atoms are replaced by atoms having the same atomic number, but an atomic mass or mass number different from the atomic mass or mass number usually found in nature. Examples of isotopes suitable for inclusion in the compounds of the present invention include isotopes of hydrogen, such as $^2H$ and $^3H$, carbon, such as $^{11}C$ $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{35}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (1) compounds are useful as antiparasitic agents, therefore, another aspect of the present invention is a veterinary composition comprising a therapeutically effective amount of a Formula (1) compound, stereoisomers thereof, and at least one veterinary acceptable excipient. The compounds of the present invention (including the compositions and processes used therein) may also be used in the manufacture of a medicament for the therapeutic applications described herein.

The compound of the present invention can be administered alone or in a formulation appropriate to the specific use envisaged, the particular species of host animal being treated and the parasite involved. Generally, it will be administered as a formulation in association with at least one veterinary acceptable excipient. The term "excipient" is used herein to describe any ingredient (e.g., carrier, diluents, and the like) other than the compound of the present invention or any additional veterinary (e.g., antiparasitic) agent. The choice of excipient will to a large extent depend on factors such as the particular mode of administration, the effect of the excipient on solubility and stability, and the nature of the dosage form. In addition to the excipient(s), the amount of the compound of the present invention that is administered and the dosage regimen for treating a condition or disorder with the compound depends on a variety of factors, including the age, weight, sex and medical condition of the animal, the severity of the disease, the route and frequency of administration, and thus may vary widely.

In another aspect, the veterinary composition comprises a Formula (1) compound with at least one veterinary acceptable excipient. The concentration range will vary depending on the composition (e.g., oral, topical, or injectable). For an oral dose, the range of active (i.e., compound of the present invention) is about 0.1 to 50 mg/kg, preferably from about 0.2 to 25 mg/kg, and even more preferably from about 0.25 to 10 mg/kg, and most preferably from about 0.5 to 7 mg/kg or 1-5 mg/kg. For a topical solution, the range of active is about 0.1 to 1000 mg/mL, and preferably from about 0.5 to 500 mg/mL, and more preferably from about 1 to 250 mg/mL, and even more preferably from about 2 to 200 mg/mL. Depending upon the final volumes of the topical solution(s), the concentration of the active can change from that described above. Generally, injectable doses tend to be, but not always, lower in concentration.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a Formula (1) compound with at least one veterinary acceptable excipient. Suitable excipients are well known to those skilled in the art and include materials such as carbohydrates, waxes, water soluble and/or swellable polymers, starches, hydrophilic or hydrophobic materials, gelatin, oils, solvents, water, and the like. The particular excipient(s) will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, flavoring agents and other known additives to provide an elegant presentation of the drug (i.e., a compound of the present invention or veterinary composition thereof) or aid in the manufacturing of the veterinary product (i.e., medicament). The compound of the present invention will typically be formulated into veterinary dosage forms to provide an easily controllable dosage form for administration.

The methods by which the compound of the present invention may be administered include oral, topical, and injectable (e.g., parenteral and subcutaneous) administration. The particular route selected by the practitioner depends upon factors such as the physicochemical properties of the therapeutic agent, the condition of the host and economics. In certain cases, it is convenient and efficient to administer veterinary medicines orally by placing the therapeutic agent in a solid or liquid matrix that is suitable for oral delivery. These methods include chewable drug-delivery formulations. The problem associated with administering oral formulations to animals is that the therapeutic agent often provides an unpleasant taste, aroma, or texture, which causes the animals to reject the composition. This is further exacerbated by compositions that are hard and difficult to swallow.

The compound of the present invention can be administered orally by capsule, bolus, tablet, powders, lozenges, chews, multi and nanoparticulates, gels, solid solution, films, sprays, or liquid form. This is a preferred method of administration and as such it is desirable to develop the compound for oral administration. Such formulations may be employed as fillers in soft or hard capsules, soft or hard palatable chews, which typically comprise at least one veterinary acceptable excipient, for example, water, ethanol, polyethylene glycol, N-methylpyrrolidone, propylene glycol, methylcellulose, or a suitable oil, and one or more emulsifying agents, flavorants, and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the compound of the present invention in a suitable medium (e.g. triethylene glycol, benzyl alcohol, and the like). The compound of the present invention can also be formulated with a food substance, e.g., a dietary admixture (food pellets or powder for birds).

The compound of the present invention can be administered topically to the skin or mucosa, that is dermally or transdermally. This is another preferred method of administration and as such it is desirable to develop the compound of the present invention to be suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical excipients include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid excipient such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the compound of the present invention has increased persistence of action and is more durable, for example it may be more water-fast. Topical formulations contemplated herein can comprise from about 0.1 mg/kg to 50 mg/kg of a compound of the present invention, and more preferably from about 1 mg/kg to 10 mg/kg of a compound of the present invention, and even more preferably, from 1 mg/kg to 5 mg/kg.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinary acceptable amount of a compound of the present invention alone, or with at least one veterinary acceptable excipient, and optionally an additional antiparasitic agent, or veterinary acceptable salts thereof. Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal. The volume of the applied composition can be from about 0.2 mL/kg to 5 mL/kg and preferably from about 1 mL/kg to 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

The compounds of the present invention can also be administered by injection. Injectable (e.g., subcutaneous and parenteral) formulations may be prepared in the form of a sterile solution, which may contain other substances, for example enough salts or glucose to make the solution isotonic with blood. Acceptable liquid excipients include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with at least one additional antiparasitic agent in the liquid excipient such that the final formulation contains from about 0.01 to 30% by weight of the active ingredients.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilization, may readily be accomplished using standard veterinary techniques well known to those skilled in the art. The solubility of a compound of the present invention used in the preparation of an injectable solution may be increased by the use of appropriate formulation techniques, such as the incorporation of solubility-enhancing agents.

Administration of the compound of the instant invention is contemplated to be once a month. However, an extended duration formulation may allow for dosing once every 2, 3, 4, 5, or 6 months.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

The composition of the present invention may be administered alone, as described above, or in combination with at least one other additional antiparasitic agent to form a multi-component parasiticide giving an even broader spectrum of veterinary utility. Thus, the present invention also envisions a combination veterinary composition comprising an effective amount of the compound of the present invention in combination with at least one other additional antiparasitic agent and can further comprise at least one veterinary acceptable excipient.

The following list of additional antiparasitic agents together with which the compound of the present invention can be used is intended to illustrate the possible combinations, but not to impose any limitation. Non-limiting examples of additional antiparasitic agents include: amitraz, aminoacetonitriles, albendazole, cambendazole, fenbendazole, flubendazole, thiabendazole, mebendazole, cyclic octadepsipeptides, oxfendazole, oxibendazole, paraherquamide, parbendazole, piperazines, praziquantel, thiabendazole, tetramisole, triclabendazole, levamisole, pyrantel (including the salt forms—pamoate, citrate, and tartrate), oxantel, morantel, abamectin, doramectin, emamectin, eprinomectin, ivermectin, moxidectin, selamectin, dimadectin, latidectin, lepimectin, milbemycin, milbemycin oxime, demiditraz, emodepside, fipronil, methoprene, diethylcarbamazine, hydroprene, kinoprene, lufenuron, metaflumizone, niclosamide, permethrin, pyrethrins, pyriproxyfen, closantel, clorsulon, novaluron, fluazuron, spinosad, sarolaner ((S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)-ethan-1-one), fluralaner (4-(5-(3,5-dichlorophenyl)-5-(trifluoromethyl)-4,5-dihydro-isoxazol-3-yl)-2-methyl-N-(2-oxo-2-((2,2,2-trifluoroethyl)amino)-ethyl)benzamide), afoxolaner (4-(5-(3-chloro-5-(trifluoromethyl)phenyl)-5-(trifluoromethyl)-4,5-dihydro-isoxazol-3-yl)-N-(2-oxo-2-((2,2,2-trifluoroethyl)amino)ethyl)-1-naphthamide), lotilaner (3-methyl-N-{2-oxo-2-[(2,2,2-trifluoroethyl)amino]ethyl}-5-[(5S)-5-(3,4,5-trichlorophenyl)-5-(trifluoromethyl)-4,5-dihydro-1,2-oxazol-3-yl]thiophene-2-carboxamide); and mixtures thereof. Preferred additional antiparasitic agents include moxidectin, doramectin, selamectin, abamectin, milbemycin, milbemycin oxime, pyrantel, praziquatel, sarolaner, afoxolaner, lotilaner, fluralaner, and levamisole.

The veterinary composition for application to an animal may be packaged in a variety of ways depending upon the method used for administering the compound of the present invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (1) compound and at least one veterinary acceptable excipient are useful as ectoparasiticides for the control and treatment of infections or infestations manifested by said ectoparasite in an animal. The compounds of the present invention have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish.

The compounds of the present invention are useful for the treatment of parasitic worms categorized as cestodes (tapeworms), nematodes (roundworms) and trematodes (flatworms or flukes). The gastrointestinal roundworms include, for example, *Ostertagia ostertagi* (including inhibited larvae), *O. lyrata, Haemonchus placei, H. similis, H. contortus, Toxocara canis, T. leonina, T. cati, Trichostrongylus axei, T. colubriformis, T. longispicularis, Cooperia oncophora, C. pectinata, C. punctata*, C. surnabada (syn. mcmasteri), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include: hookworms (e.g., *Ancylostoma caninum, A. tubaeforme, A. braziliense, Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the superfamily Filarioidea and the Onchocercidae Family. Non-limiting examples of filarial nematodes within the Onchocercidae Family include the genus *Brugia* spp. (i.e., *B. malayi, B. pahangi, B. timori*, and the like), *Wuchereria* spp. (i.e., *W. bancrofti*, and the like), *Dirofilaria* spp. (*D. immitis, D. repens, D. ursi, D. tenuis, D. spectans, D. lutrae*, and the like), Dipetalonema spp. (i.e., *D. reconditum, D. repens*, and the like), *Onchocerca* spp. (i.e., *O. gibsoni, O. gutturosa, O. volvulus*, and the like), *Elaeophora* spp. (*E. bohmi, E. elaphi, E. poeli, E. sagitta, E. schneideri*, and the like), *Mansonella* spp. (i.e., *M. ozzardi*, M. perstans, and the like), and *Loa* spp. (i.e., *L. loa*). In another aspect of the invention, the compound of the present invention is useful for treating endoparasiticidal infection from filarial nematodes within the genus *Dirofilaria* (i.e., *D. immitis, D. repens, D. ursi, D. tenuis*, and the like). The Formula (1) compounds are preferably endoparasitics.

The compounds of the present invention can also be used against ectoparasites, alone or in combination with at least one additional antiparasitic agent. Some non-limiting examples of ectoparasites include: ticks (e.g., *Ixodes* spp., (e.g., *I. ricinus, I. hexagonus*), *Rhipicephalus* spp., (e.g., *R. sanguineus*), *Boophilus* spp., *Amblyomma* spp. (e.g., *A. maculatum, A. triste, A. parvum, A. cajennense, A. ovale, A. oblongoguttatum, A. aureolatum, A. cajennense*), *Hyalomma* spp., *Haemaphysalis* spp., *Dermacentor* spp. (e.g., *D. variabilis, D. andersoni, D. marginatus*), *Ornithodorus* spp., and the like); mites (e.g., *Dermanyssus* spp., *Sarcoptes* spp., (e.g., *S. scabiei*), *Psoroptes* spp., (e.g., *P/bovis*), *Otodectes* spp., *Chorioptes* spp., *Demodex* spp., (e.g., *D. folliculorum, D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitos (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Hypoderma bovis, H. lineatum*); and copepods (e.g., sea lice within the Order Siphonostomatoida, including genera *Lepeophtheirus* and *Caligus*).

The compounds of the present invention and compositions comprising compounds of the present invention in conjunction with at least one other antiparasitic agent are of particular value in the control of ectoparasites and endoparasites which are injurious to, or spread or act as vectors of diseases in companion animals, livestock, birds, and fish. The ectoparasites and endoparasites which can be treated with a combination of a Formula (1) compound and an additional antiparasitic agent include those as herein before described.

Any of the compounds of the present invention, or a suitable combination of a compound of the present invention and optionally, with at least one additional antiparasitic agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (1) compound, stereoisomers thereof, veterinary acceptable salts thereof, and combinations with at least one additional antiparasitic agent, as described herein, are of value for the treatment and control of the various lifecycle stages of parasites including egg, nymph, larvae, juvenile and adult stages.

The present invention also relates to a method of administering a compound of the present invention alone or in combination with at least one additional antiparasitic agent to animals in good health comprising the application to said animal to reduce or eliminate the potential for human parasitic infection or infestation from parasites carried by the animal and to improve the environment in which the animals inhabit.

The present invention also relates to a method of administering a compound of the present invention alone or in combination with at least one additional antiparasitic agent, and optionally at least one veterinary acceptable excipient, to a human in good or poor health comprising the application to said human to reduce or eliminate the potential for human parasitic infection or infestation from parasites carried by the human and to improve the environment in which the human inhabits.

The present invention also relates to a method of administering a compound of the present invention alone or in combination with at least one additional antiparasitic agent, and optionally at least one veterinary acceptable excipient, to a plant or soil to prevent parasitic infection to the plant.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., J. Org. Chem. 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (e.g., high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance (1H NMR) spectra were determined using a Bruker spectrometer operating at a field strength of 400 megahertz (MHz). Chemical shifts are reported in parts per million (ppm) downfield from an internal tetramethylsilane standard. Mass spectra (MS) data were obtained using Agilent mass spectrometer with atmospheric pressure chemical ionization. Method: Acquity UPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Certain aspects of the present invention are illustrated by the following Examples. It is to be understood, however, that the aspects of the invention are not limited to the specific details of these Examples, as other variations thereof will be known, or apparent in light of the instant disclosure, to one of ordinary skill in the art.

Compounds of this invention can exist as one or more stereoisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers.

EXAMPLES

The following examples were prepared according to the Schemes and Preparations as presented herein.
PF1022a: (3S,6R,9S,12R,15S,18R,21S,24R)-6,18-dibenzyl-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone

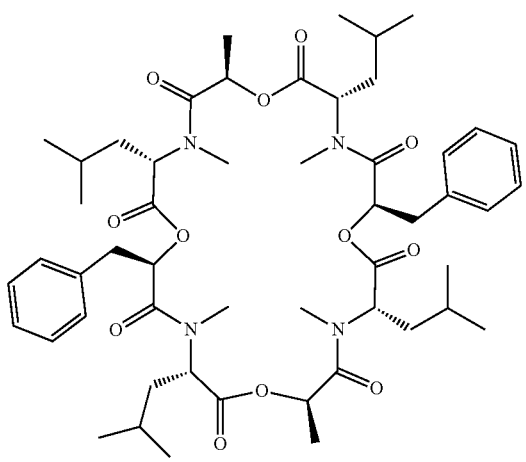 [SMILES: CC(C)C[C@H]1C(=O)O[C@H](Cc2ccccc2)C(=O)N(C)[C@@H](CC(C)C)C(=O)O[C@H](C)C(=O)N(C)[C@@H](CC(C)C)C(=O)O[C@H](Cc2ccccc2)C(=O)N(C)[C@@H](CC(C)C)C(=O)O[C@H](C)C(=O)N1C]

Emodepside: (3S,6R,9S,12R,15S,18R,21S,24R)-3,9,15,21-tetraisobutyl-4,6,10,16,18,22-hexamethyl-12,24-bis(4-morpholinobenzyl)-1,7,13,19-tetraoxa-4,10,16,22-tetraazacyclotetracosan-2,5,8,11,14,17,20,23-octaone

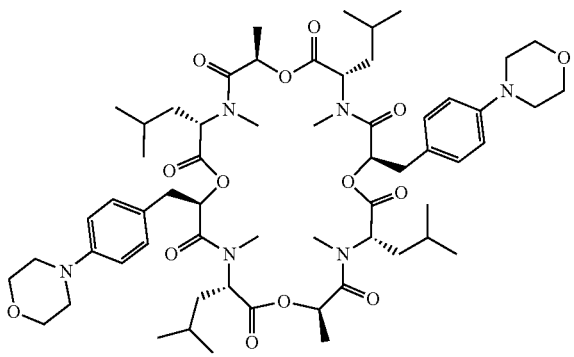 [SMILES: CC(C)C[C@H]1C(=O)O[C@H](Cc2ccc(N3CCOCC3)cc2)C(=O)N(C)[C@@H](CC(C)C)C(=O)O[C@H](C)C(=O)N(C)[C@@H](CC(C)C)C(=O)O[C@H](Cc2ccc(N3CCOCC3)cc2)C(=O)N(C)[C@@H](CC(C)C)C(=O)O[C@H](C)C(=O)N1C]

In the Schemes and Examples described below, the following catalysts/reactants and miscellaneous abbreviations include: room temperature (RT); dichloromethane (DCM); methanol (MeOH); dimethylformamide (DMF); ethyl acetate (EtOAc); propylphosphonic anhydride ($T_3P$); acetonitrile (MeCN or ACN); ethanol (EtOH); tributyltin hydride ($HSnBu_3$); tributylin chloride ($Bu_3SnCl$); sodium borohydride ($NaBH_4$); sodium nitrite ($NaNO_2$); sulfuric acid ($H_2SO_4$); zinc chloride ($ZnCl_2$); tetrahydrofuran (THF); cesium carbonate ($CsCO_3$); denatured alcohol or industrial methylated spirits (IMS); trifluoromethyltrimethylsilane ($CF_3TMS$); 4-dimethylaminopyridine (DMAP); t-butyloxycarbonyl (BOC, boc); palladium (Pd); N,N-diisopropylethylamine (DIPEA); 1-ethyl-3-(3-dimethylaminopropyl)carbodiimide (EDCl); methoxymethyl (MOM); sodium azide ($NaN_3$); tetra-n-butylammonium fluoride (TBAF); benzyl bromide (BnBr); tetrakis(triphenylphosphine)palladium (0) ($Pd(PPh_3)_4$); FurCat (succinimide-containing Pd catalyst: $Pd(N-succ)Br(P(2-Fu)_3)_2$)); isopropylmagnesium chloride lithium chloride (iPrMgCl—LiCl); hour (h, hr); minute(s) (min); bis(triphenylphosphine)palladium(II) dichloride ($PdCl_2(PPh_3)_2$), Ghosez Reagent (1-chloro-N,N,2-trimethyl-1-propenylamine; Dess-Martin (periodinane); iodomethane (MeI); saturated (sat); aqueous (aq); equivalents (eq or equiv); 1-ethyl-3(3-dimethylaminopropyl)carbodiimide (EDC); hydrochloric acid (HCl); dichloromethane (DCM); dichloroethane (DCE); N-methylmorpholine (NMM); palladium on carbon (Pd—C or Pd/C); triphenylphosphine (PPh₃); di-tert-butyl azodicarboxylate; trifluoroacetic acid (TFA); 1-[Bis(dimethylamino)methylene]-1H-1,2,3-triazolo[4,5-b]pyridinium 3-oxid hexafluorophosphate (HATU); hydrogen bromide (HBr); acetic acid (AcOH); p-toluenesulfonic acid (PTSA); triethylsilane (Et₃SiH); copper iodide (CuI); potassium iodide (KI); methylene chloride (CH₂Cl₂); triethanolamine (TEA); methyl tert-butyl ether (MTBE); tetramethylsilane (TMS); trimethylsilyl cyanide (TMSCN); diethylaminosulfur trifluoride (DAST); t-butyl nitrite (TBN or tBuONO); sodium hydride (NaH); tetrakis(triphenylphosphine)palladium (0) (Pd(TPP)₄); tetra-n-butylammonium fluoride (nBu₄F); di-tert-butyl azodicarboxylate (DBAD); and phosphorus tribromide (PBr₃).

Scheme 1: Synthetic Scheme for Preparation of Monomers M1, M2, M3 and M4.

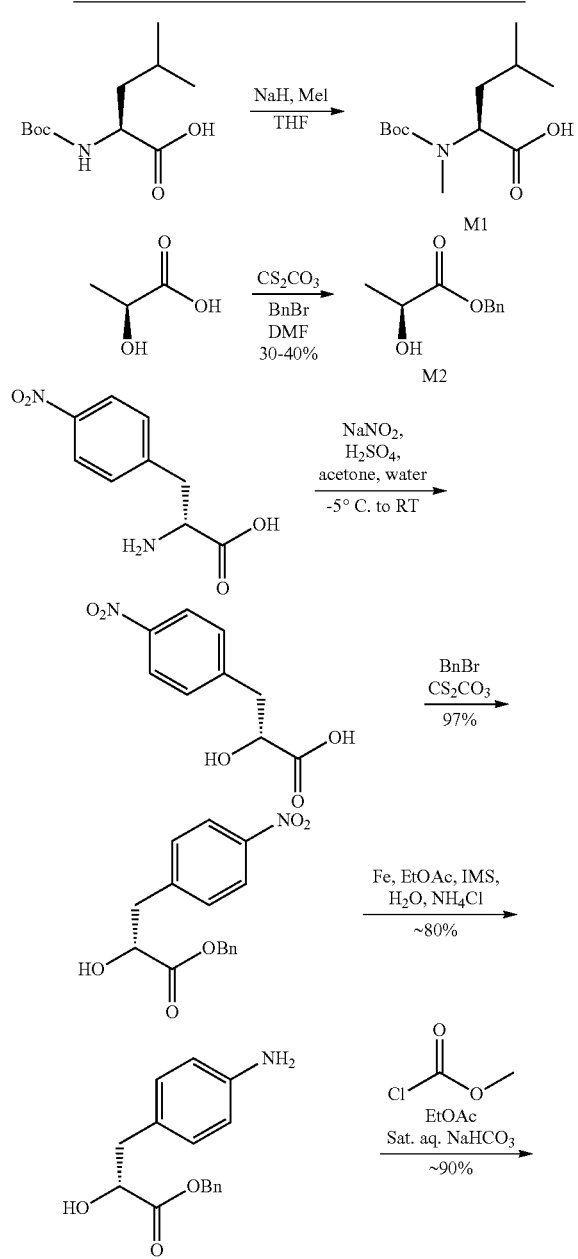

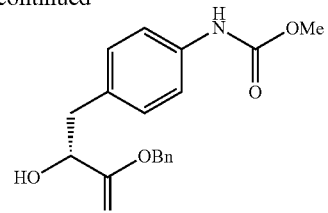

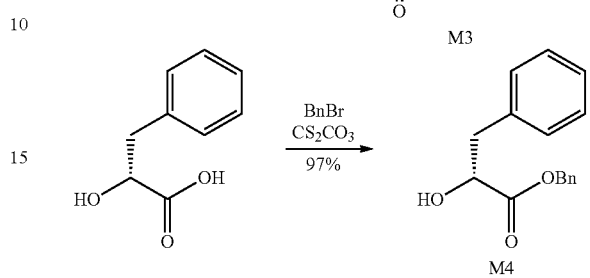

In Scheme 1, synthesis of monomers M1, M2, M3 and M4 was carried out by procedures well known in the literature. (Journal of Organic Chemistry, 79(17), 8491-8497; 2014; Organic Letters, 15(24), 6132-6135; 2013; ChemBioChem, 9(8), 1235-1242; 2008) These monomers were used in a stepwise synthesis of the PF1022a core as shown in subsequent schemes. In addition, the allyl protected monomers, allyl (S)-2-hydroxypropanoate and allyl (R)-2-hydroxy-3-(4-nitrophenyl)propanoate and allyl (R)-2-hydroxy-3-phenylpropanoate were also prepared according to the following literature procedures: Faming Zhuanli Shenqing, 101962323, 02 Feb. 2011 and Journal of Organic Chemistry, 67(4), 1061-1070; 2002). These allyl protected monomers were used in an alternative route which also provided Bis-Iodo PF1022a using the same coupling conditions described below and the requisite chemistry to remove the allyl protecting group as described in T. W. Greene, Protective Groups in Organic Synthesis, John Wiley & Sons, New York, 1991.

Synthesis of Boc-Methyl-L-Leucine (M1):

Sodium hydride (65.16 g, 1.63 mol) was added portionwise over 1.25 hours to a mixture of Boc-L-leucine (125 g, 0.50 mol) and iodomethane (160 mL, 2.50 mol) in THF (2 L) cooled to 0° C. The temperature was maintained below 5° C. during the addition and then allowed to warm up to room temperature and stirred for 2.5 days. The reaction mixture was cooled to 0° C. and quenched with water (2 L); the temperature was maintained below 5° C. during the addition and then allowed to warm up to room temperature. The aqueous layer was extracted with EtOAc (2×750 mL), then the aqueous was acidified to pH 5 with 10% aqueous citric acid solution, extracted with EtOAc (3×1 L), dried over MgSO₄, filtered and the solvent removed in vacuo (50° C.) and azeotroped with DCM. The two batches were combined to yield 236.09 g, M1, 94% yield. ¹H NMR (CDCl₃, 300 MHz): δ 4.85 (t, 0.5H), 4.61 (dd, 0.5H), 2.81 (s, 1.5H), 2.78 (s, 1.5H), 1.77-1.65 (m, 2H), 1.57-1.51 (m, 1H), 1.45 (s, 9H), 0.95-0.92 (m, 6H). Chiral analysis: 99.5% e.e. by GC.

Synthesis of Benzyl-L-Lactate (M2):

L-Lactic acid (467 g, 5.2 mol, anhydrous) was dissolved in DMF (1 L). Cesium carbonate (847 g, 2.6 mol, 0.5 eq) was added with stirring, followed by benzyl bromide (886 g, 5.18 mol, 0.99 eq) over about 45 minutes. The mixture was stirred at room temperature for 4 days, after which time analysis showed the reaction to be complete. Heteroneous mixture was filtered through Celite®; the filter cake was washed with ethyl acetate (2×500 mL). The filtrate was extracted with water (2×500 mL), saturated aqueous $Na_2CO_3$ (4×500 mL) and brine (2×500 mL), then concentrated in vacuo to yield a thick orange oil, M2, 775 g, 80%. This was purified by dry flash chromatography using EtOAc/heptane (0% to 10%) as eluent. Appropriate fractions were combined and concentrated in vacuo to yield benzyl-L-lactate, 385 g, 41%. $^1$H NMR ($CDCl_3$, 300 MHz): δ 7.40-7.35 (m, 5H), 5.21 (s, 2H), 4.37-4.27 (m, 1H), 2.79 (d, 1H), 1.43 (d, 3H).

Synthesis of benzyl (R)-2-hydroxy-3-(4-((methoxycarbonyl)amino)phenyl)propanoate (M3)

Step 1:

$NaNO_2$ (147.6 g, 2.13 mol) in water (600 mL) was added drop-wise to a mixture of 4-nitro-D-phenylalanine, (150 g, 0.71 mol) in 1M $H_2SO_4$ (aqueous, 900 mL), water (750 mL) and acetone (2.25 L) maintaining a temperature between −5° C. and −3° C. The mixture was stirred at −5° C. for 1.5 hours then allowed to warm to room temperature and stirred for 3 days. The mixture was concentrated in vacuo to remove the acetone and the mixture was extracted with EtOAc (5×~375 mL), the combined organics were dried over $MgSO_4$ filtered and the solvent removed in vacuo to yield a yellow solid that was recrystallised from isopropyl acetate (~2.5 volumes), to yield p-nitrophenyl-D-lactic acid (68.38 g, 45%) as a yellow solid; a second crop 6.25 g (combined yield 50%) was obtained from the residue by slurrying in DCM. $^1$H NMR ($CDCl_3$, 300 MHz): δ 8.18 (d, 2H), 7.45 (d, 2H), 4.59-4.54 (m, 1H), 3.31 (dd, 1H), 3.10 (dd, 1H). No chiral analysis was performed.

Step 2:

$Cs_2CO_3$ (123.3 g, 378 mmol) was added to a mixture of p-nitophenyl-d-lactic acid (156.75 g, 742 mmol) in DMF (700 mL) and stirred for 15 minutes, gas was evolved and the heterogenous solution cleared yielding a homogenous brown solution (a mild exotherm was observed). Benzyl bromide (124.39 g, 727 mmol) in DMF (140 mL) was added at room temperature over about 5 minutes; a precipitate formed and the mixture was stirred for about 20 hours at room temperature. The mixture was filtered through Celite® and the filter cake was washed with EtOAc (2×500 mL), the filtrate was washed with water (2×500 mL), saturated aqueous $NaHCO_3$ (3×500 mL), and then brine (500 mL). Heptane (about 1 L) was added to the organic layer and the resultant off white precipitate was filtered off, further crops were obtained from the mother liquors after concentration and trituration with heptanes. The batches were dried at 40° C. for about 18 hours and combined to yield an off white solid (197.6, 88% yield). $^1$H NMR ($CDCl_3$, 300 MHz): δ 8.04 (m, 2H), 7.45-7.25 (m, 7H), 5.20 (dd, 2H), 4.55-4.48 (m, 1H), 3.25-3.00 (dd, 2H), 2.86 (d, 1H). UPLC (CSH_C18, Short acid 2-95%): 0.73 min. No mass ion observed.

Step 3:

Iron powder (256 g, 4.59 mol) was added to a stirred mixture of (R)-benzyl 2-hydroxy-3-(4-nitrophenyl)propanoate (197.5 g, 0.66 mol), ammonium chloride (455 g, 8.52 mol), EtOAc (1 L), water (900 mL), IMS (100 mL) heated at 60° C. The reaction became darker in colour and was stirred for 18 hours at 50° C. The mixture was cooled, filtered through Celite® and the filter cake was washed with EtOAc (about 600 mL). The layers were separated, and the organic layer was washed with water (3×500 mL). The organic layer was extracted with aqueous 1 M HCl (4×250 mL); then the acidic extracts were basified with saturated aqueous $NaHCO_3$ until about pH 8-9. This was extracted into EtOAc (1 L, then 2×500 mL); the combined organic layers were concentrated in vacuo to yield a solid which was azeotroped with toluene, EtOAc, then DCM. The residue was dried at 50° C. to yield an off white solid (146.5 g, 82%). $^1$H NMR ($CDCl_3$, 300 MHz): δ 7.42-7.30 (m, 5H), 6.91 (d, 2H), 6.56 (d, 2H), 5.13 (s, 2H), 4.42 (t, 1H), 3.54 (s, br 1H), 3.08-2.80 (m, 2H). UPLC (CSH_C18, Short acid 2-95%): 0.32 min, 271.43 Da $[M+H]^+$.

Step 4:

Methyl chloroformate (24.5 mL, 316 mmol, 1.5 eq.), was added drop-wise to a stirred mixture of (R)-benzyl 3-(4-aminophenyl)-2-hydroxypropanoate (57.30 g, 211 mmol), EtOAc (375 mL) and saturated aqueous $NaHCO_3$ (300 mL, 5.2 vol) at room temperature over about 20 minutes (a mild exotherm to about 25° C. was observed along with gas evolution). The mixture was stirred for a further 10 minutes, the organic layer was removed and washed with brine (200 mL), dried over $Na_2SO_4$ filtered and concentrated in vacuo to yield M3 as a white solid (73.48 g, 99% yield) $^1$H NMR ($CDCl_3$, 300 MHz): δ 7.42-7.31 (m, 5H), 7.26-7.13 (m, 2H), 7.12-7.01 (m, 2H), 6.70 (s, 1H), 5.13-5.22 (m, 2H), 4.49-4.43 (m, 1H), 3.74 (s, 3H), 3.06 (dd, 1H), 2.93 (dd, 1H), 2.82 (d, 1H). UPLC (CSH_C18, Short acid 2-95%): 0.64 min, 330.4 Da $[M+H]^+$.

Synthesis of benzyl (R)-2-hydroxy-3-phenylpropanoate (M4)

$Cs_2CO_3$ (97.5, 300 mmol) was added to a mixture of (R)-2-hydroxy-3-phenylpropanoic acid (100 g, 602 mmol) in DMF (700 mL) and stirred for 15 minutes, gas was evolved and the heterogenous solution cleared yielding a homogenous brown solution (a mild exotherm was observed). Benzyl bromide (102.0 g, 602 mmol) in DMF (100 mL) was added at room temperature over about 5 minutes, a precipitate formed and the mixture was stirred for about 20 hours at room temperature. The mixture was filtered through Celite® and the filter cake was washed with EtOAc (2×400 mL), the filtrate was washed with water (2×400 mL), saturated aqueous $NaHCO_3$ (3×400 mL), and then brine (300 mL). Heptane (about 1 L) was added to the organic layer and the resultant off white precipitate was filtered off, further crops were obtained from the mother liquors after concentration and trituration with heptanes. The batches were dried at 40° C. for about 18 hours and combined to yield an off white solid (M4, 151 g, 89% yield). $^1$H NMR ($CDCl_3$, 300 MHz): δ 8.04 (m, 2H), 7.45-7.25 (m, 7H), 5.20 (dd, 2H), 4.55-4.48 (m, 1H), 3.25-3.00 (dd, 2H), 2.86 (d, 1H).

Scheme 2: Route for Stepwise Synthesis of Bis-Iodo PF1022a
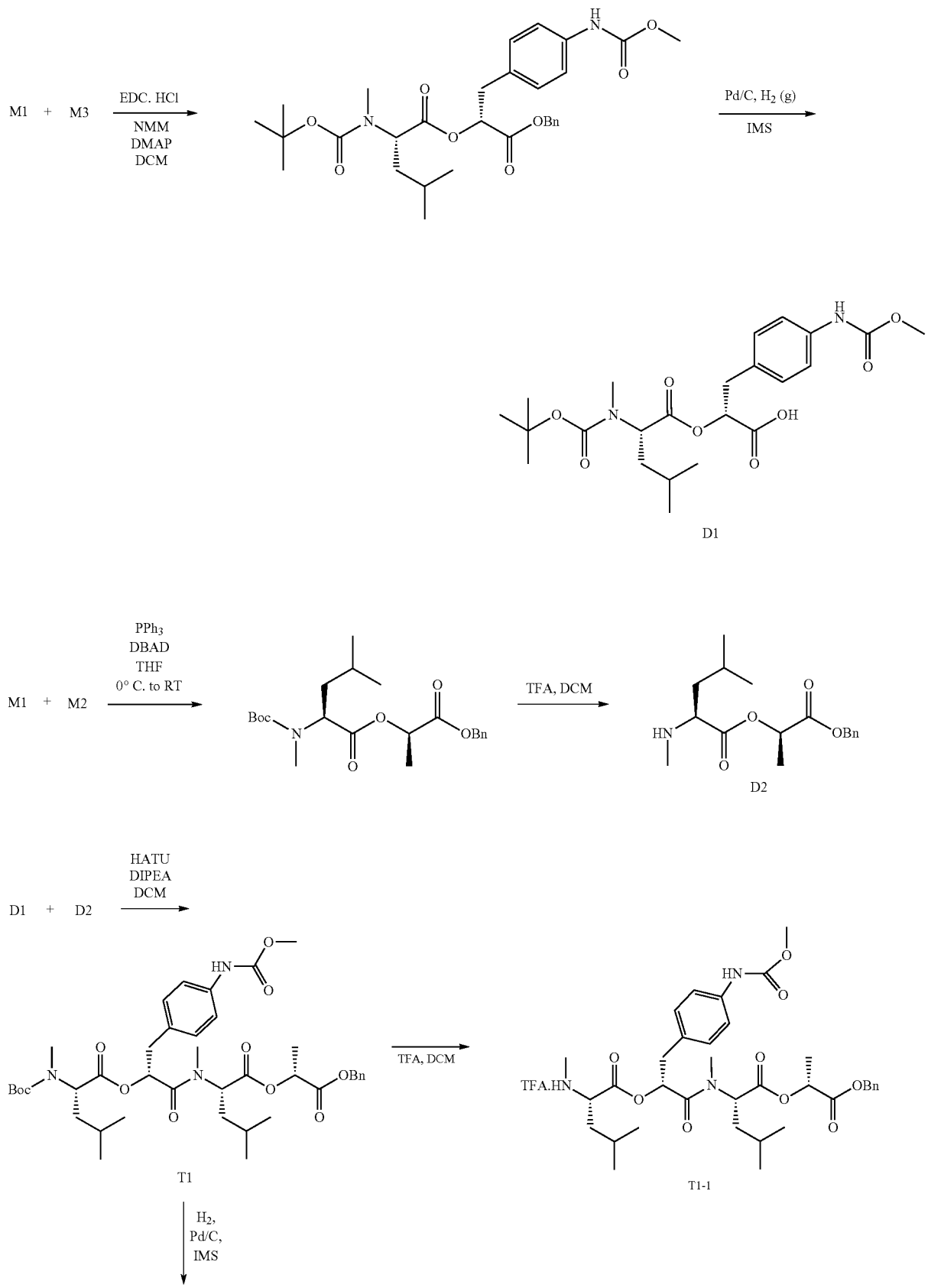

-continued
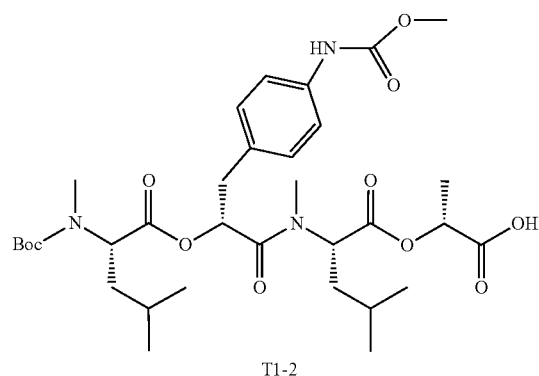
T1-2
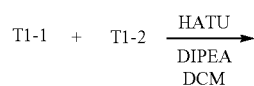
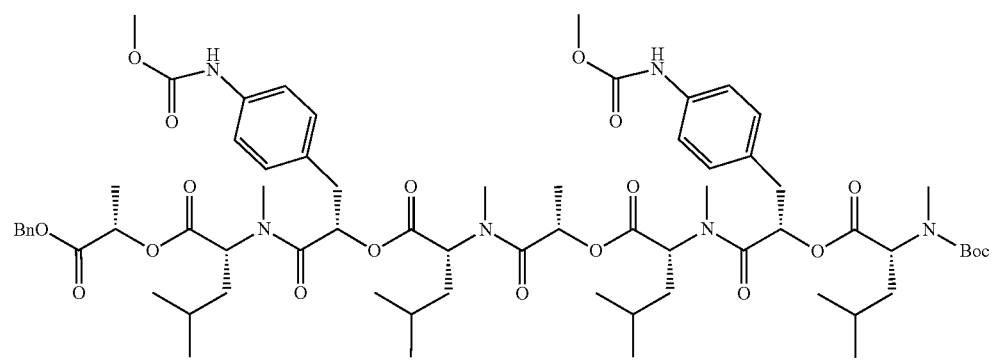
O1
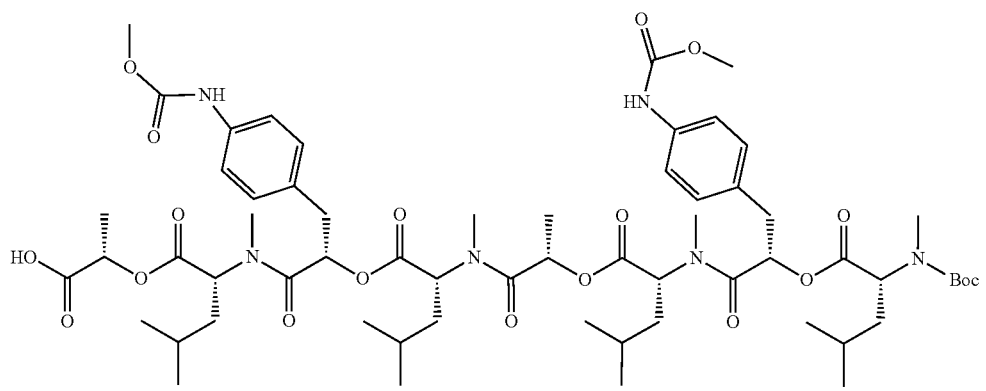
O1-1

-continued
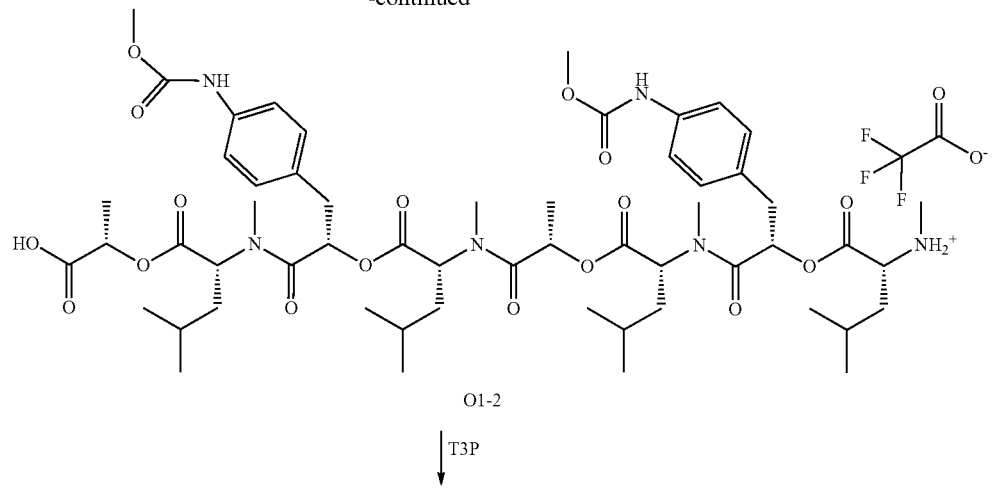
O1-2
↓ T3P
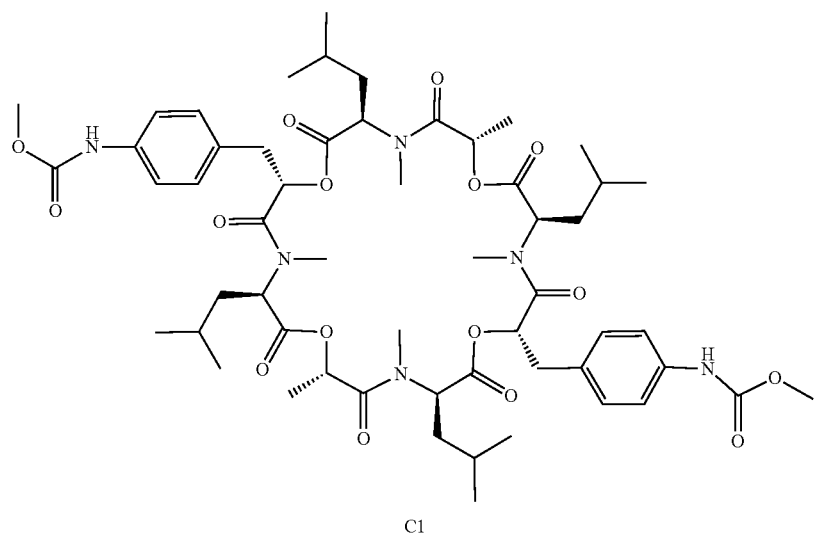
C1
↓ HBr/AcOH
35° C.
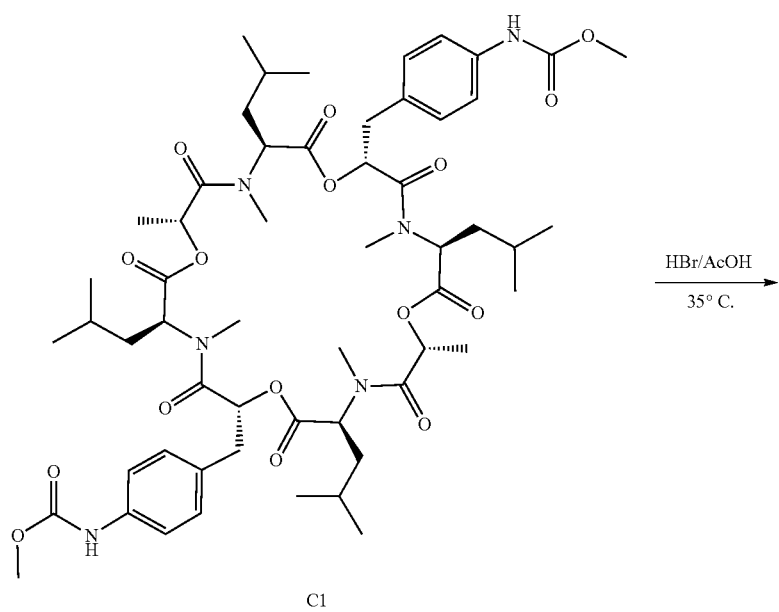
C1

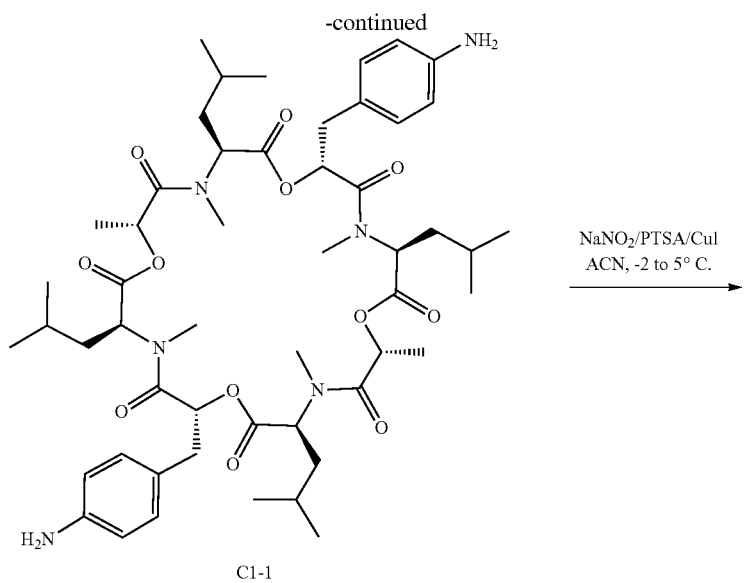

C1-1

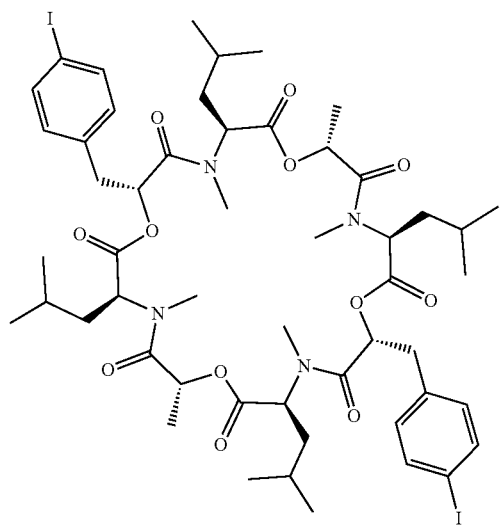

Bis-Iodo-PF1022a

As shown in Scheme 2, dimers D1 and D2 are prepared using standard amide bond forming methods and ester bond forming methods followed by standard protecting group removal steps. Tetramer T1, is formed from the reaction of D1 with D2 using routine amide bond forming methods. T1 is then selectively deprotected to provide either of two tetramers, T1-1 and T1-2, which when coupled together provide the corresponding linear octadepsipeptide, O1. Sequential deprotection and cyclization yielded the appropriately aryl functionalized cyclic octadepsipeptide, C1. Conversion to the advanced intermediate Bis-Iodo PF1022a was accomplished by performing a two-step sequence that included protecting group removal followed by routine sequence to convert the amino group to an iodo group. It will be appreciated by ones skilled in the art that mono-Iodo PF1022a may be readily obtained from the route shown in Scheme 2 through the appropriate use of M3 and M4.

Synthesis of (R)-1-(benzyloxy)-3-(4-((methoxycarbonyl)amino)phenyl)-1-oxopropan-2-yl N-(tert-butoxycarbonyl)-N-methyl-L-leucinate (D1)

Step 1:
EDC·HCl (134.8 g, 703 mmol), was added in one portion to a mixture of (R)-benzyl 2-hydroxy-3-(4-((methoxycarbonyl)amino)phenyl)propanoate (178.2 g, 541 mmol), Boc-Methyl-L-Leucine (146.0 g, 595 mmol), DMAP (6.60 g, 54 mmol), 4-methylmorpholine (154.6 mL, 406 mmol) and DCM (3.4 L). EDC·HCl slowly dissolves forming an orange solution; a mild exotherm was controlled by cooling after about 15 minutes. After 5 hours the reaction was washed with water (2×2 L), 10% aqueous citric acid solution (2×1 L), 5% aqueous citric acid solution (1×1 L), saturated aqueous NaHCO$_3$, water (1 L), dried over MgSO$_4$, filtered and the solvent removed in vacuo to yield an oil 296.1 g, 98%. $^1$H NMR (CDCl$_3$, 400 MHz): δ 7.44-6.95 (m, 9H), 6.67-6.45 (m, 1H), 5.36-4.64 (m, 4H), 4.14-3.63 (m, 3H), 3.22-2.92 (m, 2H), 2.74-2.50 (m, 3H), 1.69-1.32 (m, 12H), 1.01-0.79 (m, 6H). UPLC (CSH_C18, Short acid, 2-95%): 1.06 min, 457.6 Da, [M-Boc+H]$^+$.

Step 2:

Pd—C 10% w/w (20.7 g, 19 mmol) was washed into a solution of (R)-1-(benzyloxy)-3-(4-((methoxycarbonyl)amino)phenyl)-1-oxopropan-2-yl N-(tert-butoxycarbonyl)-N-methyl-L-leucinate (296 g, 532 mmol) in industrial methylated spirits (IMS, 3 L) with toluene (about 80 mL). The mixture was left to stir for about 18 hours under hydrogen (1 atm) for 2 days. The mixture filtered through Celite®, the filter cake was washed with IMS (about 500 mL) and the mixture concentrated in vacuo. The residue was purified by filtering through a plug of silica eluting with 40% EtOAc in heptanes and concentrated in vacuo to yield D1. (232.72 g, 91%). $^1$H NMR (CDCl$_3$, 300 MHz): δ 7.35-7.25 (m, 2H), 7.17-7.11 (m, 2H), 6.94 (s, br 1H), 5.27-5.18 (m, 1H), 4.73-4.67 (m, 1H), 3.76 (s, 3H), 3.20-3.05 (m, 2H), 2.80-2.70 (m, 3H), 1.76-1.40 (m, 11H), 0.95-0.85 (M, 6H), 96.72% pure w/w by HNMR with 0.34% DCM and 1.60% EtOAc, equivalent to 225.08 g, 90.6%. UPLC (CSH_C18, Short acid 2-95%): 0.86 min, 367.6 Da [M-Boc+H]$^+$.

Synthesis of Synthesis of (R)-1-(benzyloxy)-1-oxopropan-2-yl N-(tert-butoxycarbonyl)-N-methyl-L-leucinate (D2)

Step 1:

Triphenylphosphine (192 g, 732 mmol), Boc-Methyl-L-Leucine (165 g, 672.6 mmol), and benzyl-L-Lactate (120 g, 666 mmol) were dissolved in tetrahydrofuran (700 mL). The resulting solution was cooled to 0° C., then di-tertbutylazodicarboxylate (192 g, 834 mmol, 1.25 eq.) was added portionwise, maintaining internal temperature<5° C. Once addition complete, mixture was allowed to stir and warm to room temperature overnight, during which time an off-white precipitate had formed. Heptane (500 mL) was added, and the resulting mixture filtered through Celite®. The cake was washed with heptane (2×100 mL). The filtrate was concentrated in vacuo to yield a thick orange oil (602 g). Heptane (500 mL) was added, and the mixture was stirred vigorously for about 1 hour, resulting in further white precipitate forming. This was removed by filtration; the cake was washed with heptane (2×300 mL). The resulting filtrate was loaded directly onto silica (2 kg), and eluted with EtOAc/hetane (1% to 10%). First fraction (72.6 g) still contained triphenylphosphine oxide; this was recolumned (about 700 g silica, about 10% loading), using EtOAc/heptane (0% to 6%), to yield 68.2 g (25.1%) of Boc-MeLeu-DLac-OBn. The second fraction from the initial column was concentrated in vacuo to yield 100.1 g (combined=168.3 g, 62%) of (R)-1-(benzyloxy)-1-oxopropan-2-yl N-(tert-butoxycarbonyl)-N-methyl-L-leucinate as a straw coloured oil. $^1$H NMR (CDCl$_3$): δ 7.46-7.30 (m, 5H), 5.21-5.08 (m, 3H), 4.99-4.70 (ddd, 1H), 2.73 (d, 3H), 1.73-1.40 (m, 18H), 0.92 (t, 6H). UPLC (CSH_C18, Short acid 2-95%): 1.08 min, 308.5 Da [M-Boc+H]$^+$.

Step 2:

(R)-1-(benzyloxy)-1-oxopropan-2-yl N-(tert-butoxycarbonyl)-N-methyl-L-leucinate (100.1 g, 243 mmol) was dissolved in dichloromethane (575 mL, 5.75 vol), and subsequently cooled to 0° C. Trifluoroacetic acid (150 mL, 1.96 mol, 8 eq., 1.5 vol) was then introduced. UPLC data after 4 hours indicated that reaction was about 50% complete. Further portion of trifluoroacetic acid (75 mL, 980 mmol, 4 eq., 0.75 vol) was added. UPLC indicated not complete after 7 hours, so mixture was stirred overnight for about 16 hours. Toluene (300 mL) was added, and the mixture concentrated in vacuo to yield a thick orange oil, D2, $^1$H NMR shows residual toluene and trifluoroacetic acid. $^1$H NMR (CDCl$_3$, 300 Mhz): 9.67-9.15 (br s, 1H), 8.65-8.10 (br s, 1H), 7.47-7.26 (m, 5H), 5.29-5.09 (m, 3H), 3.97-3.85 (m, 1H), 1.92-1.78 (m, 1H), 1.77-1.66 (m, 2H), 1.59-1.54 (s, 3H), 0.98-0.90 (m, 6H). UPLC (CSH_C18, Short acid 2-95%): 0.43 min, 308.5 Da [M+H]$^+$.

Synthesis of (R)-1-(benzyloxy)-1-oxopropan-2-yl N—((R)-2-((N-(tert-butoxycarbonyl)-N-methyl-L-leucyl)oxy)-3-(4-((methoxycarbonyl)amino)phenyl)propanoyl)-N-methyl-L-leucinate (T1)

D1 (193 g, 458 mmol) and D2 (225 g, 482 mmol) were stirred in dichloromethane (2 L). HATU (250 g, 658 mmol, 1.36 eq.) was added, followed by diisopropylethylamine (375 mL, 2150 mmol) through a dropping funnel. Temperature of reaction was maintained with the use of an external ice-bath. The mixture was allowed to stir overnight at room temperature. The reaction mixture was washed with water (3×2 L), aqueous citric acid (10%, 2×1 L), saturated aqueous NaHCO$_3$ (2×1 L), and water (1 L). The organic phase was dried over MgSO$_4$, filtered and concentrated in vacuo to yield an orange oil. This was purified by dry flash chromatography using EtOAc/heptane as eluent (0% to 30%), to yield T1 (313 g, 83%).

$^1$H NMR (CDCl$_3$, 300 MHz): δ 7.41-7.26 (m, 7H), 7.20-7.10 (m, 2H), 6.59 (s, 1H), 5.42-4.60 (m, 6H), 3.82-3.71 (m, 3H), 3.10-2.96 (m, 2H), 2.93-2.71 (m, 6H), 1.77-1.36 (m, 18H), 1.01-0.83 (m, 12H). UPLC (CSH_C18, Short acid, 2-95%): 1.14 min, 656.9 Da [M-Boc+H]$^+$.

Synthesis of (R)-1-(benzyloxy)-1-oxopropan-2-yl N—((R)-3-(4-((methoxycarbonyl)amino)phenyl)-2-((methyl-L-leucyl)oxy)propanoyl)-N-methyl-L-leucinate (T1-1)

T1 (48.7 g, 64.4 mmol) was dissolved in dichloromethane (300 mL, 6 vol). The resulting solution was cooled to 0° C. with an external ice-bath. TFA (75 mL, 980 mmol, 1.5 vol) was added to the reaction mixture and the mixture stirred until complete. Toluene (300 mL) was added, and the mixture concentrated in vacuo yield a thick orange oil, 65.3 g, about 125% (containing ~16 g of TFA). Used without further purification. $^1$H NMR (CDCl$_3$, 300 MHz): δ 7.40-7.23 (m, 9H), 6.73 (s, 1H), 5.50-5.42 (m. 1H), 5.29-5.08 (m, 4H), 3.87-3.83 (m, 1H), 3.79-3.77 (m, 3H), 3.06 (d, 2H), 3.01-2.90 (m, 3H), 2.70-2.64 (m, 3H), 2.36 (m, 3H), 1.76-1.42 (m, 6H), 1.39-1.25 (m, 2H), 1.04-0.96 (m, 1H), 0.94-0.87 (m, 6H), 0.79-0.76 (m, 6H). UPLC (CSH_C18, Short acid 2-95%): 0.65 min, 656.91 Da [M+H]$^+$.

Synthesis of (6S,9R,12S,15R)-6,12-diisobutyl-9-(4-((methoxycarbonyl)amino)-benzyl)-2,2,5,11,15-pentamethyl-4,7,10,13-tetraoxo-3,8,14-trioxa-5,11-diazahexadecan-16-oic acid (T1-2)

Pd—C (10% w/w, 2.5 g, 2.3 mmol) was washed into a solution of T1 (48.3 g, 63.9 mmol) in IMS (500 mL) with toluene (about 20 mL) and stirred under hydrogen (1 atm)

for 4 hours, filtered and the solvent removed in vacuo and then azeotroped with DCM to yield Boc-MeLeu-DCbmPheLac-MeLeu-DLac-OH as an off-white foam 48.87 g, T1-2, 115% yield (used crude in subsequent reaction). $^1$H NMR (CDCl$_3$, 400 MHz): δ 7.05-7.29 (m, 4H), 5.70 (t, 1H), 4.65-5.45 (m, 5H), 3.75 (d, 3H), 2.68-3.19 (m, 8H), 2.30-2.34 (m, 1H), 1.38-1.74 (m, 17H), 1.10-1.29 (m, 1H), 0.83-0.99 (m, 13H). UPLC (CSH_C18, Short acid 2-95%): 0.97 min, 610.8 Da [M-$^t$Bu+H]$^+$, 664.8 Da [M–H]$^-$.

Synthesis of dimethyl ((((2S,5R,8S,11R,14S,17R, 20S,23R)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))dicarbamate (C1)

Step 1:

T1-1 (49.3 g, actual mass 65.3 g, contains ~16 g trifluoroacetic acid, 64.4 mmol) and T1-2 (42.5 g, actual mass 48.5 g, contains residual solvent from hydrogenation) were dissolved in dichloromethane (500 mL). The mixture was cooled with an external ice-bath. HATU (36.4 g, 95.7 mmol, 1.5 eq.) was added, followed by diisopropylethylamine (70 mL, 400 mmol, 6.3 eq.). The resulting mixture was stirred for 20 hours. Water (1 L) was added to the reaction mixture, and vigorously stirred for 0.83 hours. The layers were separated, and the organic phase washed with aq. citric acid (10%, 3×700 mL), saturated aqueous NaHCO$_3$ (1×700 mL), and brine (1×500 mL), then dried over MgSO$_4$, filtered and concentrated in vacuo directly onto Celite® (150 g) and silica gel (20 g). The material was dry loaded onto a column of silica (1 kg) and purified by dry flash chromatography using EtOAc/heptane (0-50%) as eluent. This afforded, after concentration in vacuo, O1, 85 g, 101% (some trace heptane observable in $^1$H NMR spectrum). $^1$H NMR (CDCl$_3$, 300 MHz): δ 7.06-7.34 (m, 13H), 6.61 (s, 1H), 4.58-5.46 (m, 10H), 3.73-3.76 (m, 6H), 2.66-3.16 (m, 15H), 1.16-1.69 (m, 28H), 0.83-0.98 (m, 24H). UPLC (CSH_C18, Long acid, 2-95%): retention time of 3.53 minutes, 1204.5 Da [M-Boc+H]$^+$.

Step 2:

O1 (199.5 g, 153 mmol) was dissolved in IMS (400 mL, 2 vol) and charged to the 2 L autoclave. 5% Pd/C (2 g) was added as a paste in toluene. The autoclave was sealed and charged to 150 psi hydrogen pressure. After stirring for 5 hours at room temperature, 16% starting material remained so the autoclave was recharged to 150 psi and allowed to stir at room temperature overnight. The reaction was complete by UPLC, so the autoclave was vented and the catalyst removed by filtration through Whatman GF/A media, washing with IMS (50 mL) and ethyl acetate (200 mL). The solvent was removed on the rotary to leave a white foam, O1-1 (175 g, 94% yield). $^1$H NMR (CDCl$_3$, 300 MHz): δ 7.06-7.34 (m, 8H), 4.58-5.46 (m, 10H), 3.73-3.76 (m, 6H), 2.66-3.16 (m, 15H), 1.16-1.69 (m, 28H), 0.83-0.98 (m, 24H). UPLC (Long acid, 2-95%): RT 3.36 min, 1113.5 Da, [M-Boc+H]$^+$.

Step 3:

O1-1 (245 g, 202 mmol) was dissolved in DCM (1.5 L, 6 vol) and cooled to <10° C. (ice/water bath). Trifluoroacetic acid (370 mL, 551 g, 1.5 vol) was added and the solution allowed to warm to room temperature and stirred overnight. The solvent was removed on the rotary and azeotroped with toluene (2×500 mL). The product was obtained as a thick orange oil O1-2 (359.5 g, overweight—estimated purity from NMR is 65%, giving calculated mass of 234 g, 94% yield).

$^1$H NMR (CDCl$_3$, 300 MHz): δ 11.91 (s, TFA), 7.1-7.35 (m, 8H), 4.6-5.65 (m, 8H), 3.79 (s, 6H), 2.6-3.2 (m, 18H), 1.1-1.9 (m, 16H), 0.65-1.07 (m, 28H).

Step 4:

A solution of O1-2 (359.5 g, 65% purity, 0.190 mol) in DCM (2.5 L) was added slowly over 1.5 hours to a solution of propylphosphonic anhydride (50% solution in EtOAc, 670 mL, 1.126 mol) and diisopropylethylamine (392 mL, 2.25 mol) in DCM (2.5 L), maintaining the temperature between 20 and 22° C. When the addition was complete, the solution was allowed to stir for a further 20 minutes and the reaction was checked for completion by UPLC. The solvent was removed on the rotary and replaced with EtOAc (5 L). The solution was washed with potassium hydrogen sulphate solution (1M, 2×1 L), 3% sodium carbonate solution (2×1.5 L) and brine (1 L). The organic layer was dried over MgSO$_4$ and filtered through Fisherbrand QL100 paper twice. The solvent was removed to leave a yellow foam (233 g). This was recrystallised from ethanol (660 mL) and water (130 mL) and the product was washed with ethanol/water (600 mL, 3:1). The product was dried on the filter bed and further dried on the rotary at 60° C. The product, C1, was obtained as a white solid (159.2 g, 77% yield). $^1$H NMR (CDCl$_3$, 300 MHz): δ 7.3 (m, 4H), 7.15 (m, 4H), 4.4-5.67 (m, 8H), 3.76 (s, 6H), 2.7-3.1 (m, 16H), 1.16-1.8 (m, 16H), 0.73-1.1 (m, 28H). UPLC (Short acid 2-95%): 1.08 min, 1095.5 Da [M+H]$^+$.

Synthesis of Bis-Iodo PF1022a

Step 1:

C1 (151.5 g, 0.138 mol) was added in portions to a 33% solution of HBr in acetic acid (750 mL) and stirred at 35° C. for 6.5 hours. The reaction mixture was cooled to 15° C. (ice/water bath) and ice/water (1.75 L) was added. A solution of 10% sodium carbonate was added carefully (about 2.5 L) to basify the mixture to pH 4-5. The mixture was extracted with ethyl acetate (2 L). The organic layer was separated and washed with saturated aqueous NaHCO$_3$ (2×1.5 L), and brine (1 L). The organic layer was dried over Na$_2$SO$_4$ and evaporated to a crisp foam (143 g). The foam was recrystallised from 2-propanol (600 mL) and dried to leave the product, C1-1, as a free flowing white powder (117.0 g, 87% yield). $^1$H NMR (CDCl$_3$, 300 MHz): δ 6.99 (m, 4H), 6.58 (m, 4H), 4.4-5.6 (m, 8H), 3.62 (br s, 4H), 2.7-3.1 (m, 16H), 1.16-1.9 (m, 14H), 0.73-1.1 (m, 28H). UPLC (Long acid 2-95%): 2.79 min, 980.3 Da [M+H]$^+$.

Step 2:

To a solution of C1-1 (10 g, 10.2 mmol) in CH$_3$CN (125 mL) and added pTSA (7.1 g, 40.8 mmol, 4.0 eq) at room temperature and then cooled to −2° C. using ice-salt bath. A 1.5M solution of NaNO$_2$ (1.70 g, 24.5 mmol, 2.4 eq) in water (15 mL) was slowly added over a period of 7 minutes while maintaining temperature around −1° C. After 15 minutes, CuI (8.7 g, 46.0 mmol, 4.5 eq) was added over 5 minutes and rinsed with water (20 ml). Resulting brown mixture was stirred at about −1° C. for 30 minutes, and then stirred at about −2 to 5° C. for 30 minutes without cooling. Reaction was cooled to 2° C. by adding ice into reaction and quenched with 25% sodium thiosulphate solution (100 mL). Organic layer was separated and aqueous layer extracted with ethyl acetate (2×75 ml). Combined organic solution was washed with water (100 mL) and saturated NaHCO$_3$ (75 mL), brine (100 mL), dried over Mg$_2$SO$_4$ and concentrated under vacuum to get solid 16 g. Obtained solid dissolved in DCM (30 mL), adsorbed on silica gel (60 g) and filter through silica gel bed (100 g) using 50% EtOAC/hexane.

Organic solution was concentrated under vacuum to a solid and dried under vacuum at 40° C. for overnight to get Bis-Iodo PF1022a, (7.5 g, 62%). 1H NMR (600 MHz, CDCl$_3$) δ: 0.68-0.98 (m, 29H), 1.24-1.7 (m, 13H), 2.67-3.07 (m, 16H), 4.36-4.43 (m, 1H), 4.96-5.63 (m, 7H), 6.98-7.05 (m, 4H), 7.60-7.69 (m, 4H). LC-MS (m/z): [M+]=1200

Scheme 3: Route for Preparation of Bis-CH$_2$Cl PF1022a:

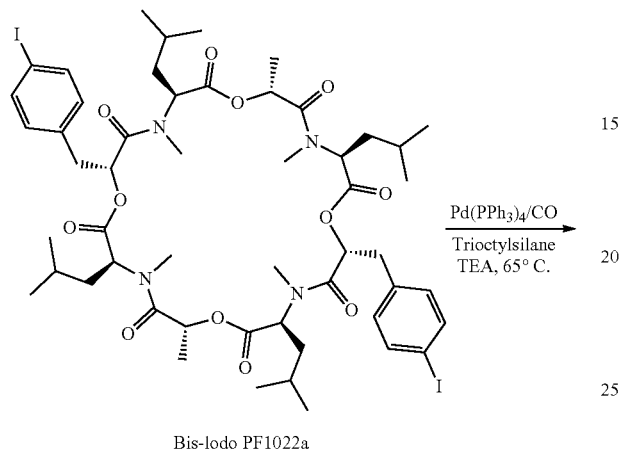

Bis-Iodo PF1022a

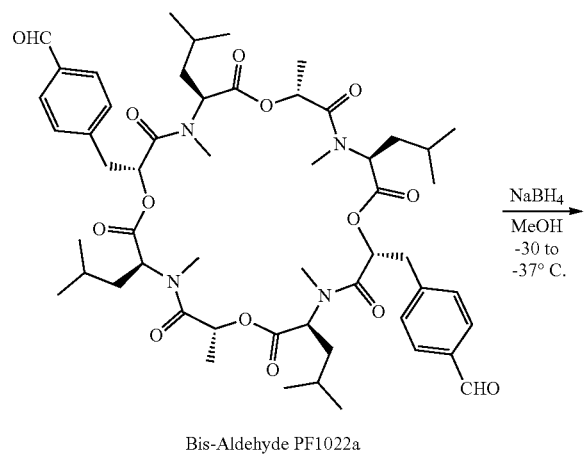

Bis-Aldehyde PF1022a

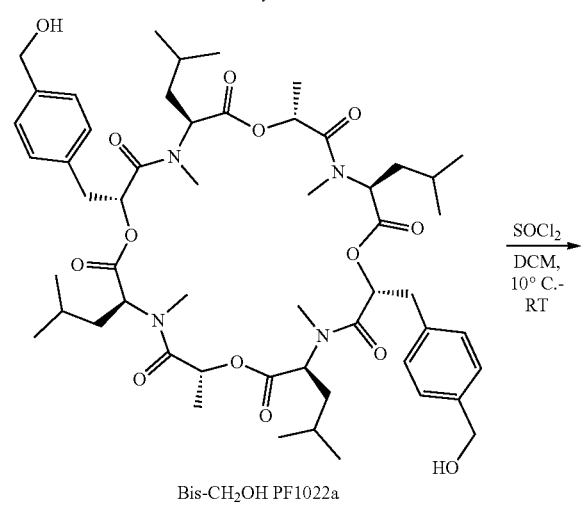

Bis-CH$_2$OH PF1022a

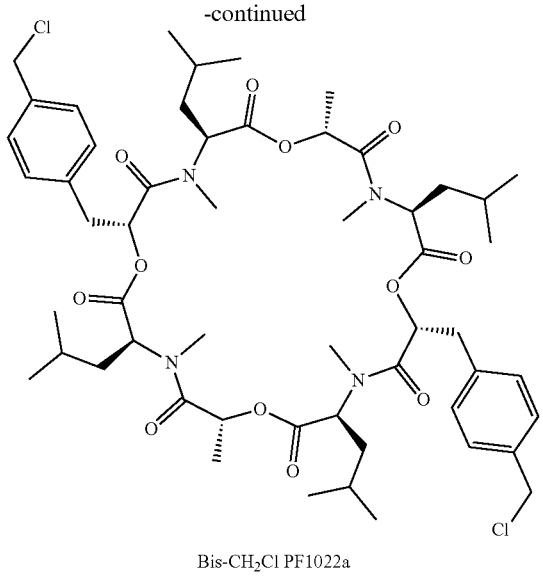

Bis-CH$_2$Cl PF1022a

As shown in Scheme 3, conversion of Bis-Iodo PF1022a to Bis-Aldehyde PF1022a is accomplished by a three step sequence. Palladium catalyzed carbonylation in an atmosphere of carbon monoxide to install the aldehyde that is then reduced with a hydride reagent to form Bis-CH$_2$OH PF1022a that is readily converted using standard functional group to the Bis-CH$_2$Cl PF1022a intermediate. In the preparation of Bis-Aldehyde PF1022a a small but appreciable amount (2%-20%) of 4-(((2R,5S,8R,11S,14R,17S,20R,23S)-14-benzyl-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosan-2-yl)methyl)benzaldehyde (Mono-Aldehyde PF1022a) is also formed. Mono-Aldehyde PF1022a may be separated from Bis-Aldehyde PF1022a using standard reverse phase HPLC methods. The mono-aldehyde PF1022a was also used as a starting material to prepare some of the compounds presented in Tables 1-4, according to Scheme 8

Synthetic Procedures for the Preparation of Bis-CH$_2$Cl PF1022a (Scheme 3)

Step 1:

A 2 L pressure reactor was charged with Bis-Iodo PF1022a (130.0 g, 101.7 mmol), HSi(octyl)$_3$ (225 g, 610.1 mmol), DMF (700 mL), TEA (131 mL, 938.8 mmol) and Pd(TPP)$_4$ (5.6 g, 4.8 mmol) and then purged with nitrogen and carbon monoxide. Reaction was heated to 65° C. under carbon monoxide (55 psi) and stirred for 2 hours. Reaction was cooled to 22° C., slowly diluted with ice-water (2.5 L). Solid was collected, washed with water (2×250 mL) hexane (2×200 mL) and dried under vacuum at 50° C. for overnight to get crude Bis-Aldehyde PF1022a as light brown solid (130 g).

Step 2:

A 3 L round bottom flask charged with crude Bis-Aldehyde PF1022a (130 g) and methanol (1100 mL) and then cooled to −35° C. using acetonitrile/dry-ice bath. To the mixture was slowly added NaBH$_4$ (5.0 g, 130 mmol) while maintaining temperature below −30° C. and stirred between −35 and −37° C. for 1 hour. Reaction was slowly quenched with saturated NH$_4$Cl (100 mL), brought to 10° C. and concentrated to approximately ¾ volume under vacuum at 40° C. Mixture was diluted with water (150 mL), extracted with ethyl acetate (3×150 mL). Organic solution was dried over MgSO$_4$, filtered and concentrated under vacuum at 45° C. to a dark brown solid. Solid was heated in 1:2 mixture of EtOAC/Hexane (200 ml) at 60° C. and stirred at room temperature for 4 hours. Solid was collected, washed with 25% ethyl acetate in hexane (2×50 mL), hexane (50 mL) and dried under vacuum to get Bis-CH$_2$OH PF1022a (103.5 g, 91% yield for 2 steps). 1H NMR (600 MHz, CDCl$_3$) δ: 0.75-1.17 (m, 26H), 1.23-1.96 (m, 16H), 2.70-2.92 (m, 9H), 3.01-3.23 (m, 7H), 4.45-4.53 (m, 1H), 4.65-4.74 (m, 4H), 5.03-5.14 (m, 1H), 5.19-5.72 (m, 6H) 7.20-7.36 (m, 8H). LC-MS (m/z): [M+H]=1009 and [(M+23]=1031

Step 3:

A 1 L 3 neck round bottom flask was charged with Bis-CH$_2$OH PF1022a (98 g, 90.30 mmol) and DCM (300 mL) and then cooled to 10° C. with external ice-water bath. Thionyl chloride (25 ml, 343.2 mmol) was added over 7 minutes, cooling bath removed and mixture stirred at room temperature. After 1 hour, reaction was concentrated under vacuum at 35° C. to a syrup, diluted with heptane (2×75 mL) and concentrated to a solid. Brown solid was dissolved in ethyl acetate (250 ml) washed with aqueous Na$_2$CO$_3$ (150 mL), 50 mL saturated Na$_3$CO$_3$ solution diluted with water (100 mL) to pH 7.8. Organic layer was separated and aqueous layer extracted with ethyl acetate (2×100 mL). Combined organic solution was dried over MgSO$_4$, and concentrated under vacuum to a brown solid. Crude product in ethyl acetate (300 ml) was stirred with activated carbon (12 g) for 4 hours at room temperature, filtered through celite bed and concentrated to solid. Obtained crude material in MTBE (110 mL) was heated to reflux, diluted with hexane (50 ml) and stirred at room temperature for overnight. Solid was collected, washed with 20% MTBE/hexane (50 mL), hexane (50 mL) and dried under vacuum at 50° C. to get BisCH$_2$Cl PF1022a as off-white solid (98 g, 98% yield). 1H NMR (600 MHz, CDCl3) δ: 0.75-1.17 (m, 26H), 1.25-1.95 (m, 16H), 2.70-2.90 (m, 9H), 3.04-3.26 (m, 7H), 4.44-4.57 (m, 1H), 4.54-4.62 (m, 4H), 5.05-5.13 (m, 1H), 5.24-5.74 (m, 6H) 7.20-7.39 (m, 8H). LC-MS (m/z): [M+H]=1045, [M+2]=1046, [M+3]=1047 and [M+4]=1047.

Scheme 4: Grignard Process

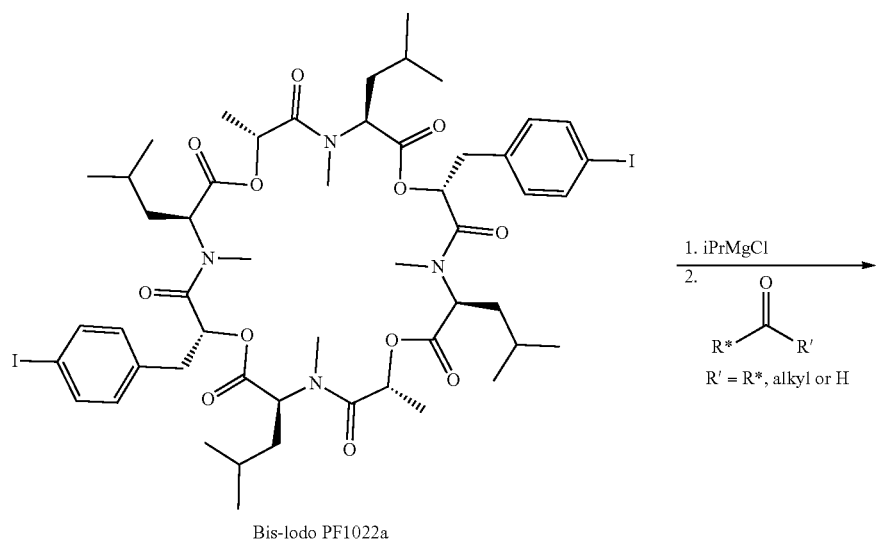

Bis-Iodo PF1022a

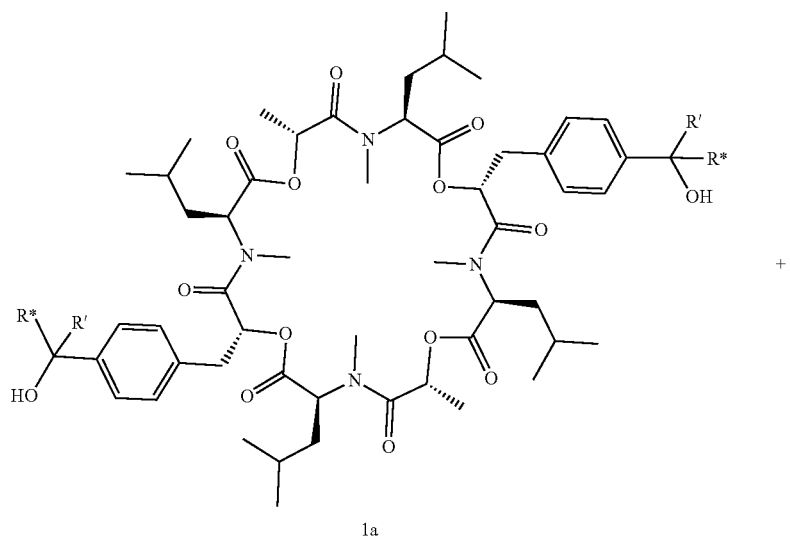

1a

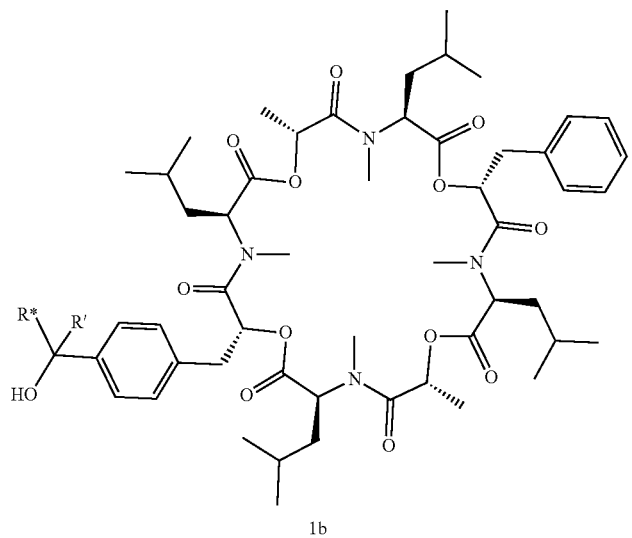
1b
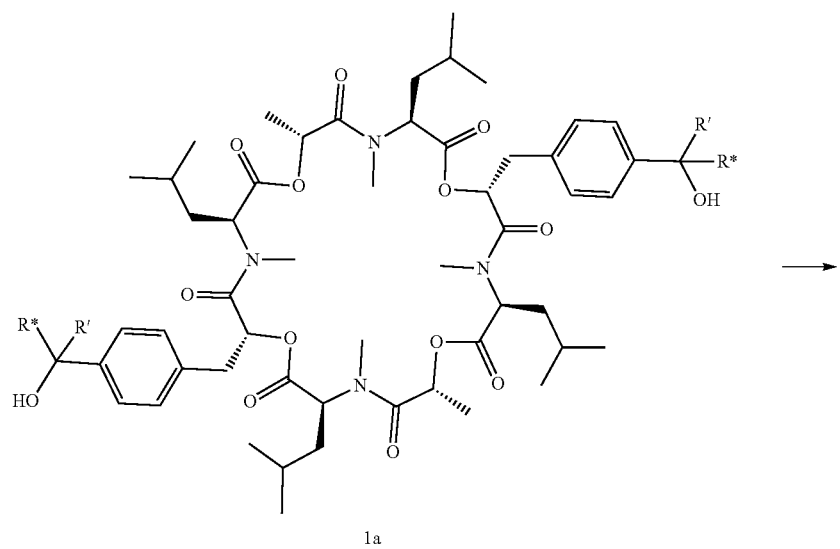
1a
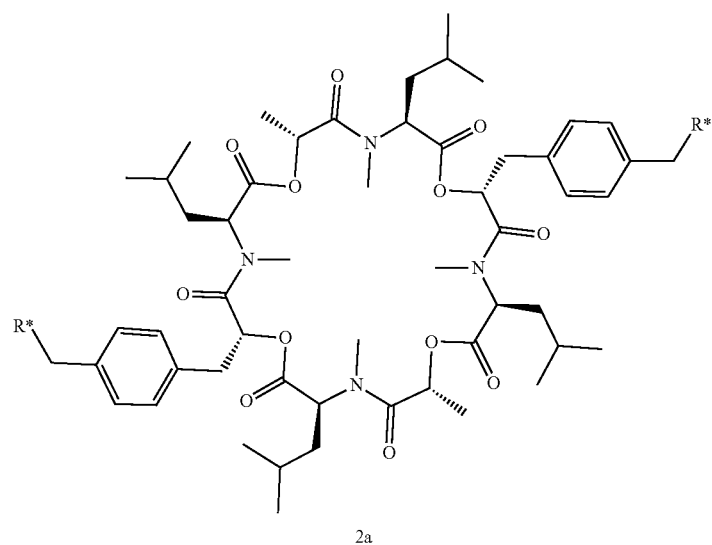
2a

-continued
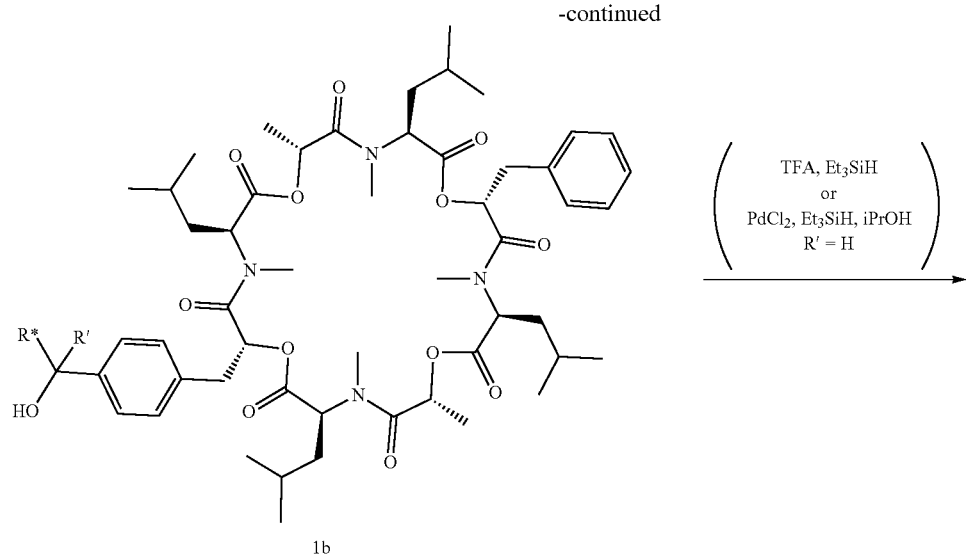
1b
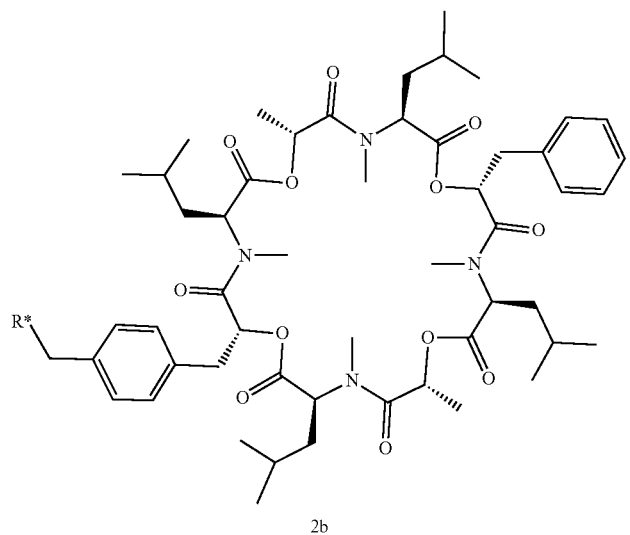
2b
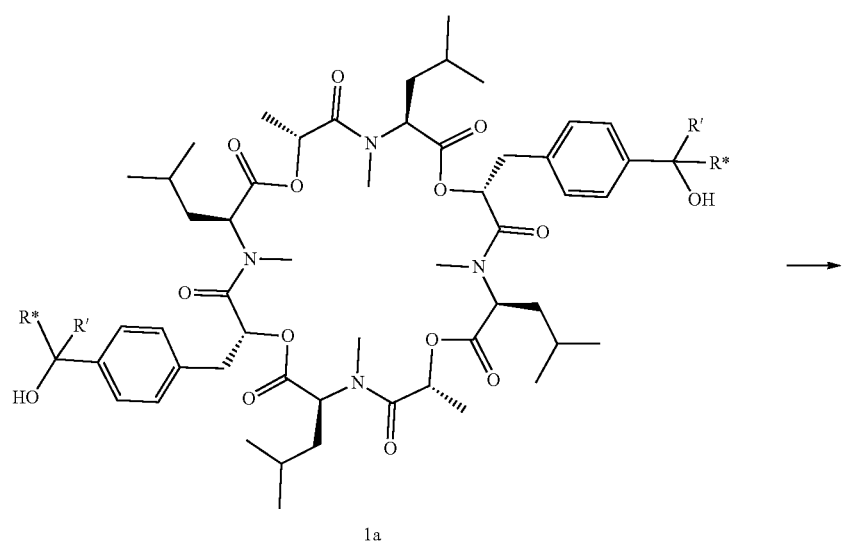
1a

-continued
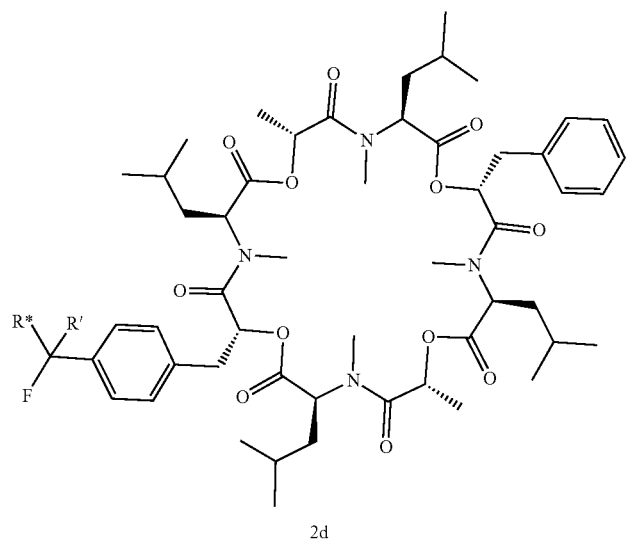
2d
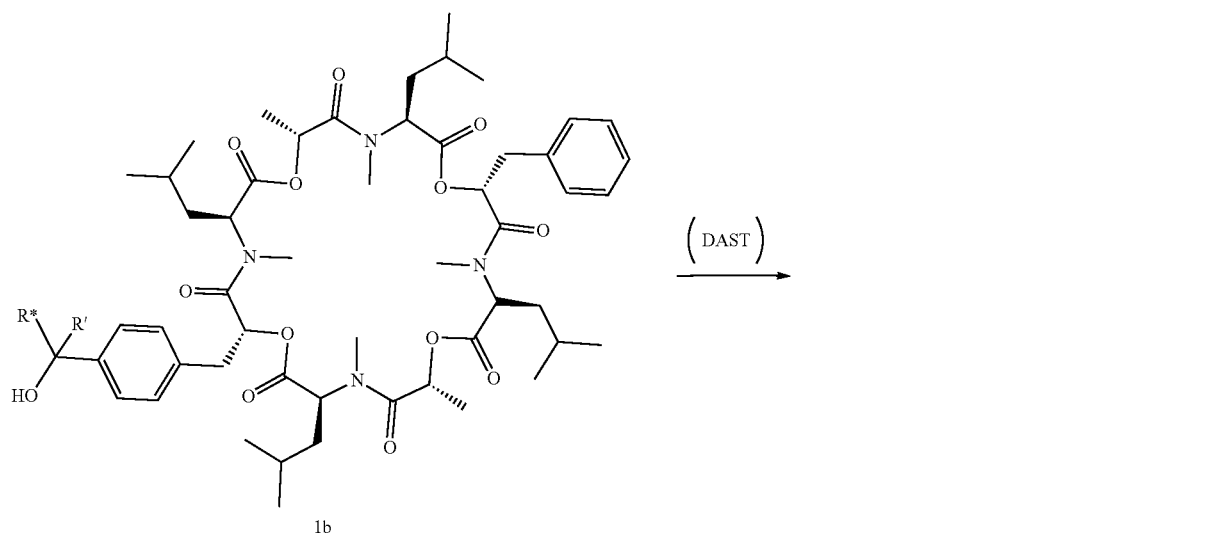
1b → (DAST)
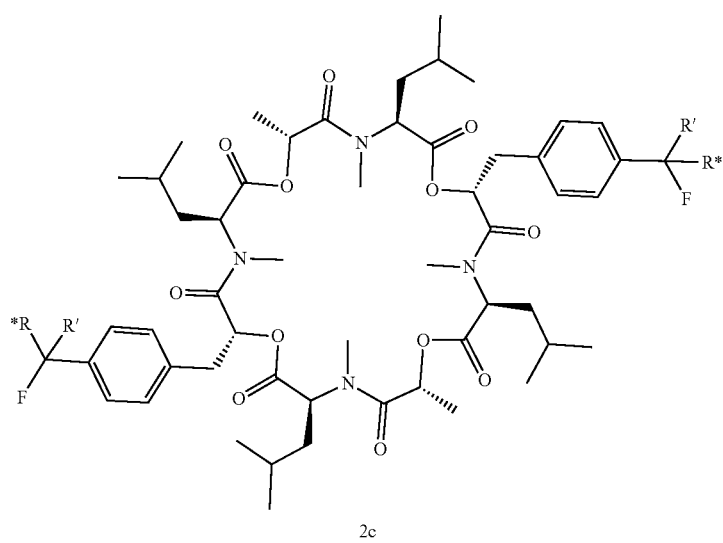
2c

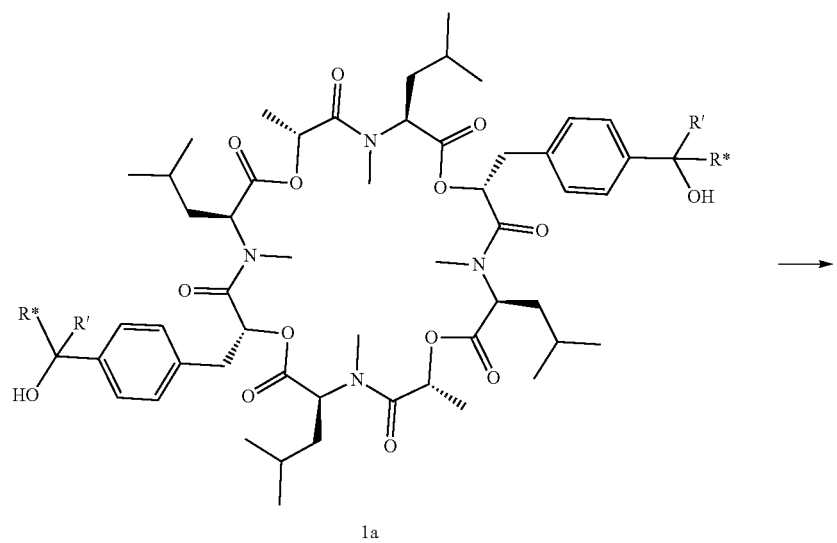
1a
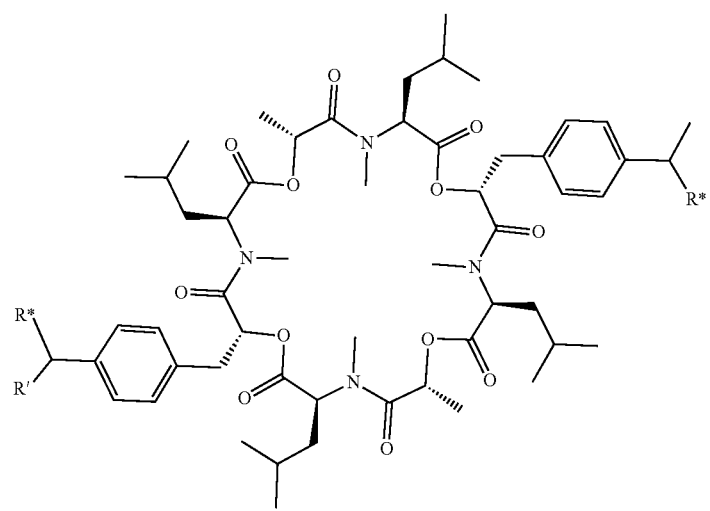
2e

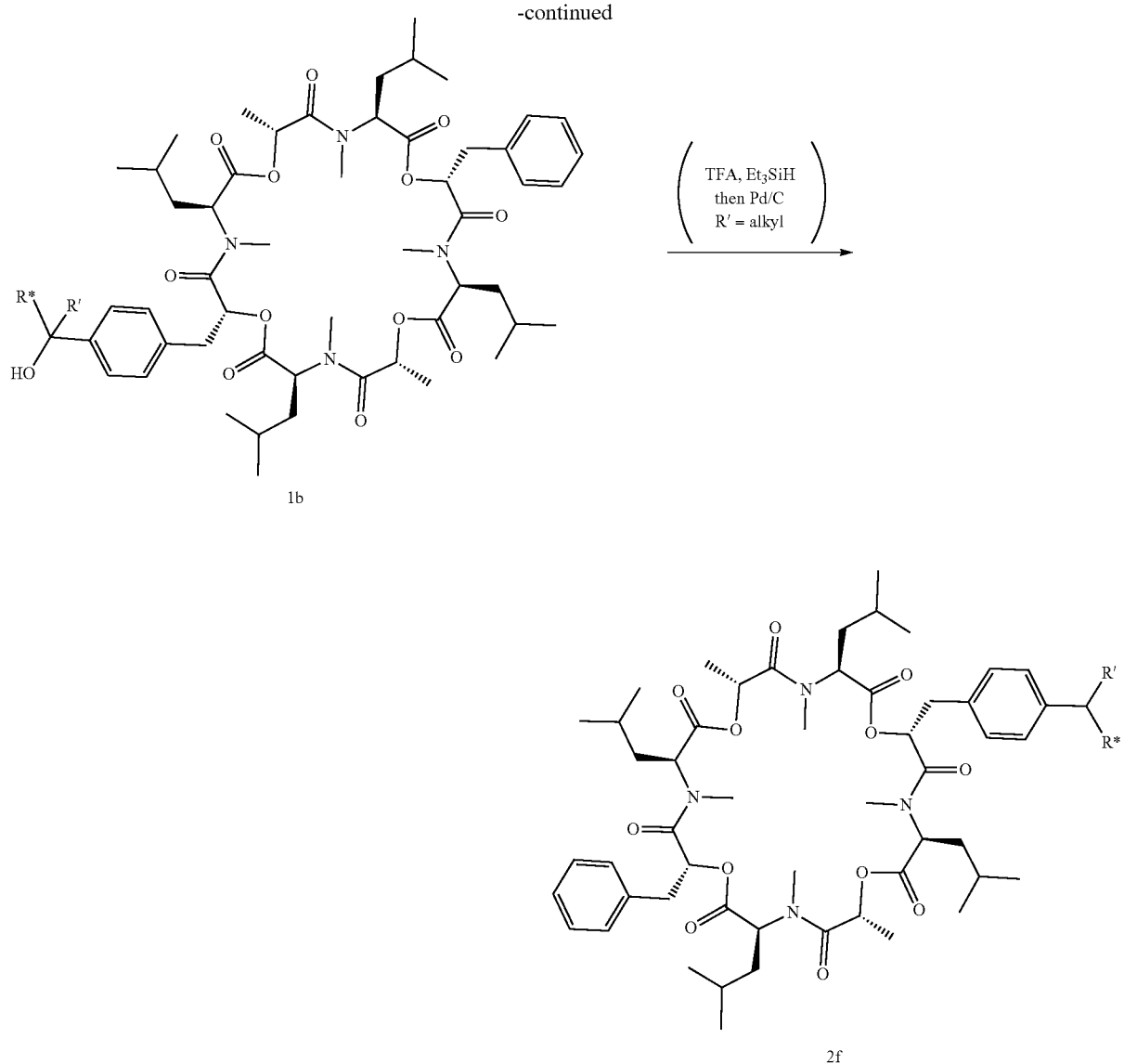

In Scheme 4, R* represents the $L_1$ and $L_2$ aryl, cycloalkyl, heteroaryl, and heterocycle moieties, each of which can be substituted as described herein; and R' can represent H or an alkyl group (e.g., methyl).

As shown in Scheme 4, Bis-Iodo PF1022a will undergo metal halogen exchange when treated with iPrMgCl—LiCl to give a depsipeptide Grignard reagent that can be reacted with a variety of electrophiles, such as aldehydes or ketones, to provide compounds 1a and 1b. The reaction yields the mono-substituted product, 1b, in minor amounts for most such reactions. Compounds 1a and 1b can be deoxygenated by treatment with triethylsilane in TFA or triethylsilane with $PdCl_2$ to give compounds of the type 2a and 2b. Compounds 1a and 1b can be separated by preparatory HPLC so as to prepare compounds 2a, 2d, and 2e from 1a; and 2b, 2c, and 2f from 1b; as shown in Scheme 4. Alternatively, a mixture of 1a and 1b can be reacted to provide mixtures of 2a and 2b, 2d and 2c, and 2e and 2f, respectively, which can then be separated by preparatory HPLC.

Preparation of Examples 3-7, 3-9, 4-6, and 4-8
(Scheme 4)

(3-7). (3S,6R,9S,12R,15S,18R,21S,24R)-6,18-bis(4-(hydroxy(6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone.

(3-9). (3S,6R,9S,12R,15S,18R,21S,24R)-6-benzyl-18-(4-(hydroxy(6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone.

(4-6). (3S,6R,9S,12R,15S,18R,21S,24R)-6-benzyl-18-(4-(hydroxy(6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone.

(4-8). (3S,6R,9S,12R,15S,18R,21S,24R)-6-benzyl-3,9,15,21-tetraisobutyl-18-(4-((6-methoxypyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone

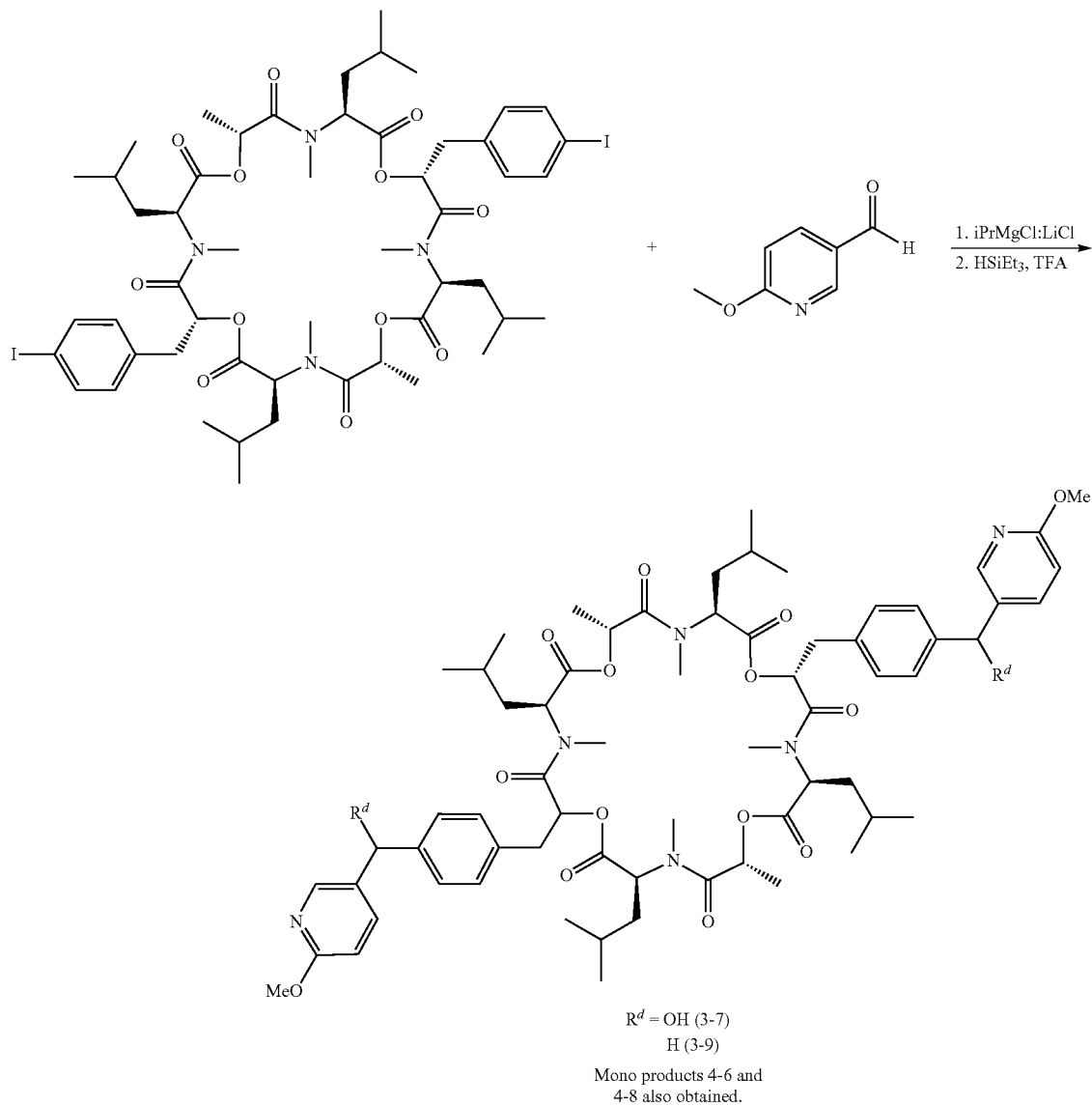

$R^d$ = OH (3-7)
H (3-9)

Mono products 4-6 and 4-8 also obtained.

Step 1:

Bis-Iodo PF1022a (200 mg, 0.16 mmol) was dissolved in THF (6 ml) in an atmosphere of nitrogen. The solution was cooled to −78° C. using a dry ice/iPrOH bath. An excess of Turbo Grignard (iPrMgCl—LiCl, 1.3M in THF, 0.90 mL, 1.17 mmol) was added and the mixture was stirred at −78° C. for 10 minutes. The dry ice bath was then replaced with an ice water bath (0° C.). The solution was allowed to stir at 0° C. for 20 minutes. A THF solution (2 ml) of 6-methoxynicotinaldehyde (137 mg, 1.0 mmol) that had been cooled to 0° C. was then added to the Grignard mixture. The solution was stirred for an additional 30 minutes at 0° C. before the reaction was quenched with AcOH (0.150 ml). The reaction mixture was added to EtOAc (25 ml) and the organic phase was washed with water (20 ml), dried over sodium sulfate and concentrated to give viscous oil which was dissolved in acetonitrile (3 ml) and purified by reverse phase HPLC to give the products: Example (3-7), 115 mg; and Example (4-6), 39 mg.

Step 2:

Example (3-7) (100 mg, 0.07 mmol) was dissolved in 1,2-DCE (4 ml). TFA (0.5 ml) and triethylsilane (0.5 ml, 4.3 mmol) were then added and the solution was heated at 90° C. in an atmosphere of nitrogen for 6 hours. The solution was concentrated and purified using reverse phase HPLC to give Example (3-9) (51 mg) product. From steps 1 and 2, a minor amount of Example (4-8); 13 mg is also obtained.

When compounds such as 1a and 1b contain an R' substituent, such as a methyl (Scheme 4.4), treatment with triethylsilane and TFA provide an intermediate alkene from alcohol dehydration. The crude intermediate can then be reduced to the alkanes 2e and 2f by further addition of Pd/C.

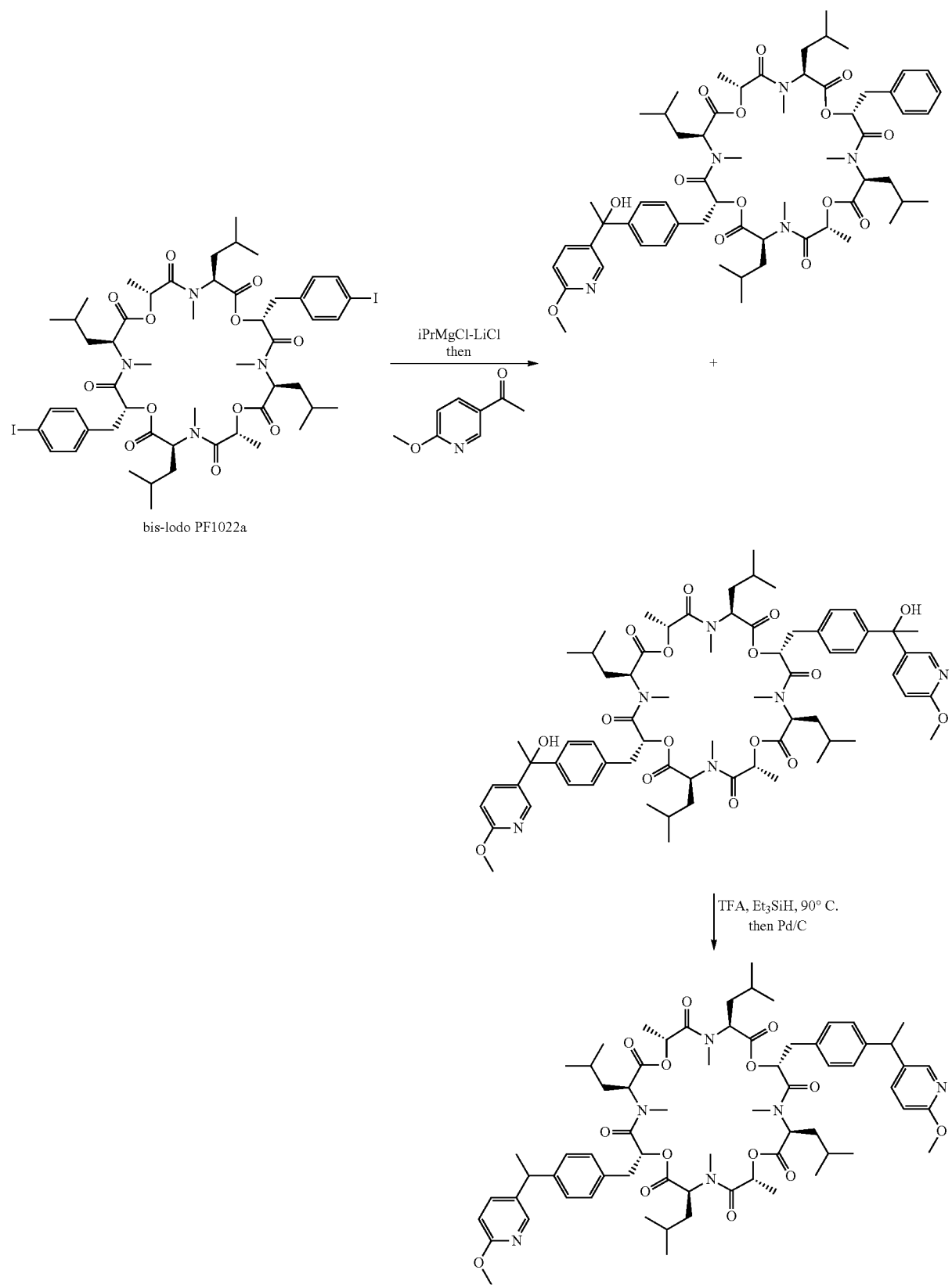

Preparation of Example (3-207)

To a solution of Bis-Iodo PF1022a (441.9 mg, 0.3679 mmol) in THF (26.5 mL) at −78° C. was added iPrMgCl·LiCl complex in THF (1.3 M, 2.8 mL) dropwise over 2 minutes and the mixture was allowed to stir for 5 minutes at this temperature. The solution was warmed at 0° C. in an ice bath and after 30 minutes a solution of 1-(6-methoxy-3-pyridyl)ethanone (1.0 g, 6.62 mmol) in THF (2.95 mL) was added all at once down the sides of the flask before the mixture was quickly warmed to rt. The reaction mixture was stirred at this temperature for 1 hour before being quenched with saturated aqueous NH$_4$Cl and extracted with EtOAC. The combined organics were washed with brine, dried, and concentrated. The residue was purified via reverse phase HPLC to provide 83 mg (18%) of the bis-substituted product and 92 mg (22%) of mono-substituted product.

To a solution of (3S,6R,9S,12R,15S,18R,21S,24R)-6,18-bis[[4-[1-hydroxy-1-(6-methoxy-3-pyridyl)ethyl]phenyl]methyl]-3,9,15,21-tetraisobutyl-4,10,12,16,22,24-hexamethyl-1,7,13,19-tetraoxa-4,10,16,22-tetrazacyclotetracosane-2,5,8,11,14,17,20,23-octaone (35.0 mg, 0.0280 mmol) in 1,2-dichloroethane (1.0 mL) was added TFA (0.3 mL, 4 mmol) followed by triethylsilane (0.3 mL, 2 mmol) in a MW vial. The reaction mixture was heated at 90° C. for 1 hour and then cooled to room temperature. To the cooled reaction mixture was added Pd/C (30 mg) and gas evolution proceeded. After 30 minutes the crude mixture was filtered through Celite and the cake washed with DCM. The combined filtrates were concentrated and by purified reverse phase HPLC to afford 18 mg (52%) of Example (3-207) as a white powder.

Compounds 1a and 1b can also undergo deoxyfluorination with reagents such as DAST to provide compounds such as 2c and 2d (Scheme 4.3).

Preparation of Example (3-252)

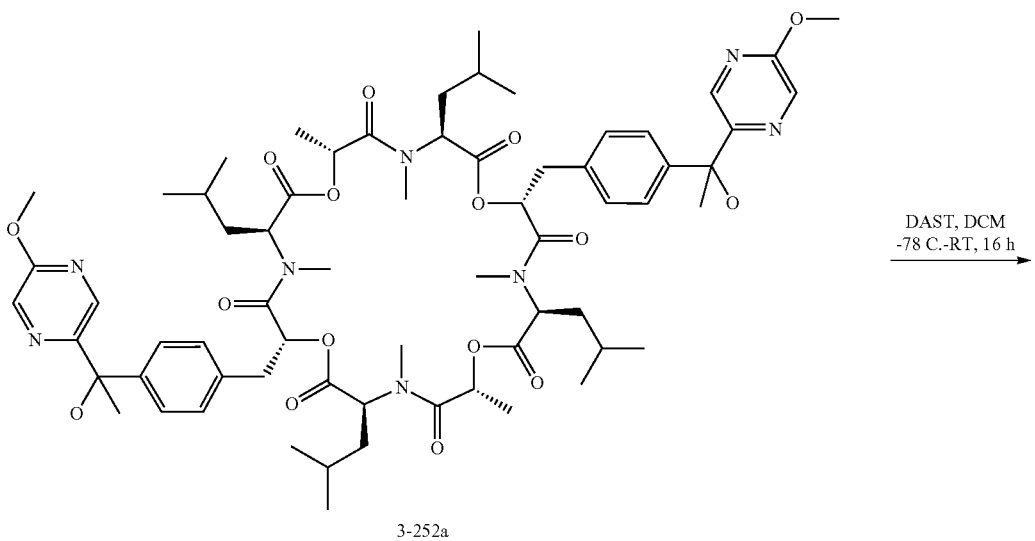

3-252a

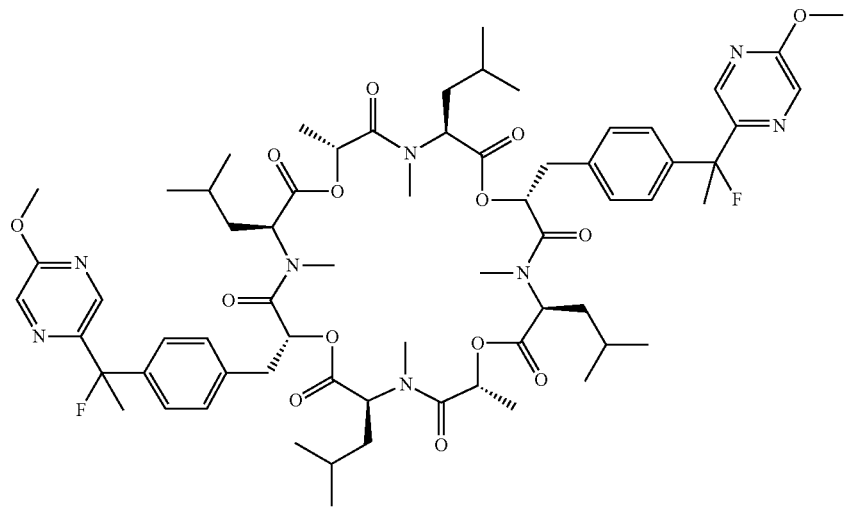

3-252

A solution of (3S,6R,9S,12R,15S,18R,21S,24R)-6,18-bis({4-[hydroxy(5-methoxypyrazin-2-yl)methyl]phenyl}methyl)-4,10,12,16,22,24-hexamethyl-3,9,15,21-tetrakis(2-methylpropyl)-1,7,13,19-tetraoxa-4,10,16,22-tetraazacyclotetracosan-2,5,8,11,14,17,20,23-octaone 2 (200 mg, 0.16 mmol) in DCM (10 mL) was cooled to −78° C. and a solution of DAST (0.32 mL, 2.39 mmol) in DCM (2 mL) was added slowly. The resulting mixture was warmed to room temperature and stirred for 16 hours. The reaction mixture was quenched with ice-water and extracted with 10% methanol in dichloromethane. The combined organic layer was washed with brine, dried over sodium sulphate, filtered and concentrated under reduced pressure. Crude material was purified by prep-HPLC to afford Example (3-252) (5 mg, 3%) as an off white solid.

Scheme 5: Reverse Grignard or Halogen-Metal Exchange Process

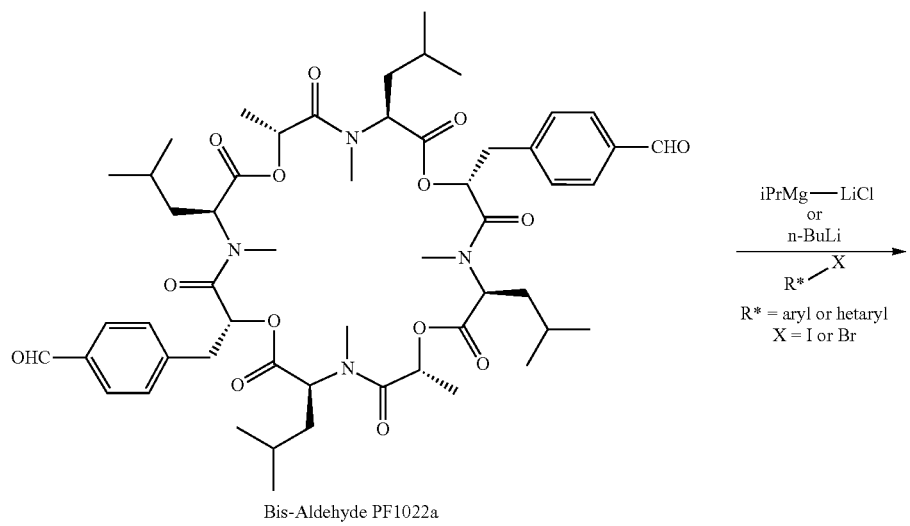

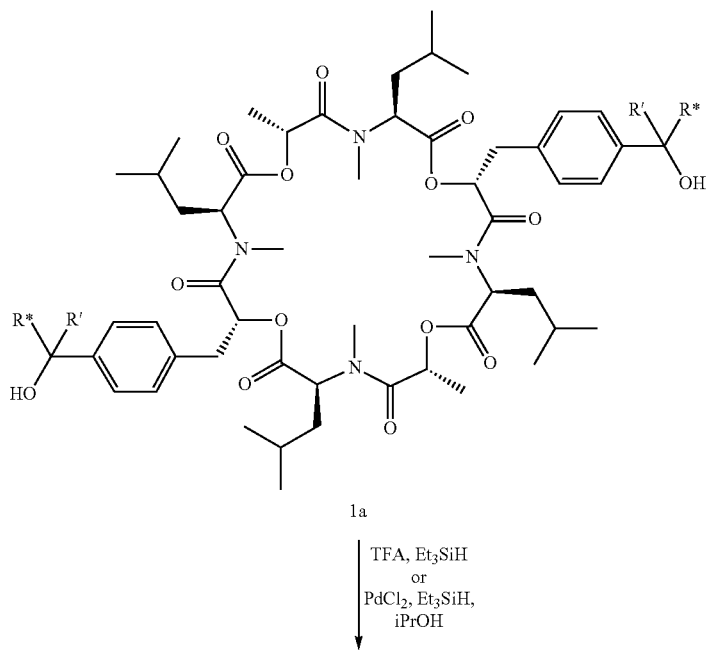

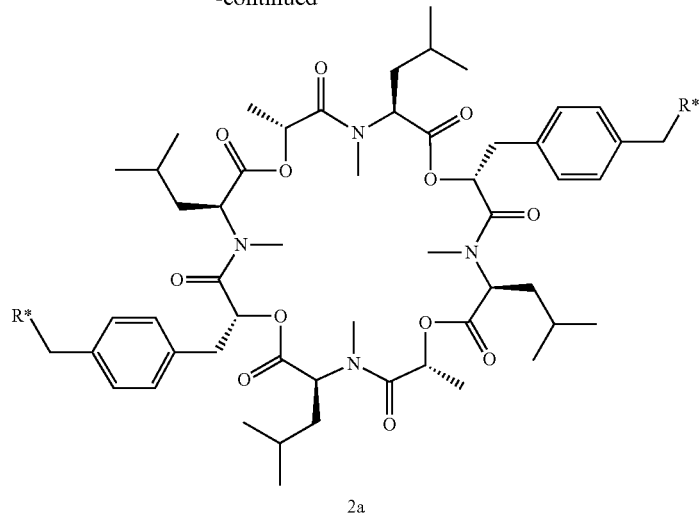

2a

In Scheme 5, R* represents the $L_1$ and $L_2$ aryl, cycloalkyl, heteroaryl, and heterocycle moieties, each of which can be substituted as described herein; and R' is H.

As shown in Scheme 5, an aryl, cycloalkyl, heterocycle, or heteroaryl halide (such as iodide or bromide) will undergo metal halogen exchange when treated with iPrMgCl—LiCl to give a Grignard reagent that can be reacted with Bis-Aldehyde PF1022a to provide compounds 1a and 1b (Scheme 4). The reaction yields the mono-substituted product, 1b, in minor amounts for most such reactions. Compounds 1a and 1b can be deoxygenated by treatment with triethylsilane in TFA or triethylsilane with $PdCl_2$ to give compounds of the type 2a and 2b (Scheme 4).

Preparation of (3S,6R,9S,12R,15S,18R,21S,24R)-6,18-Bis-[4-(5-cyclopropyl-[1,3,4]oxadiazol-2-ylmethyl)-benzyl]-3,9,15,21-tetraisobutyl-4,10,12,16,22,24-hexamethyl-1,7,13,19-tetraoxa-4,10,16,22-tetraaza-cyclotetracosan-2,5,8,11,14,17,20,23-octaone (3-330) in view of Scheme 5.

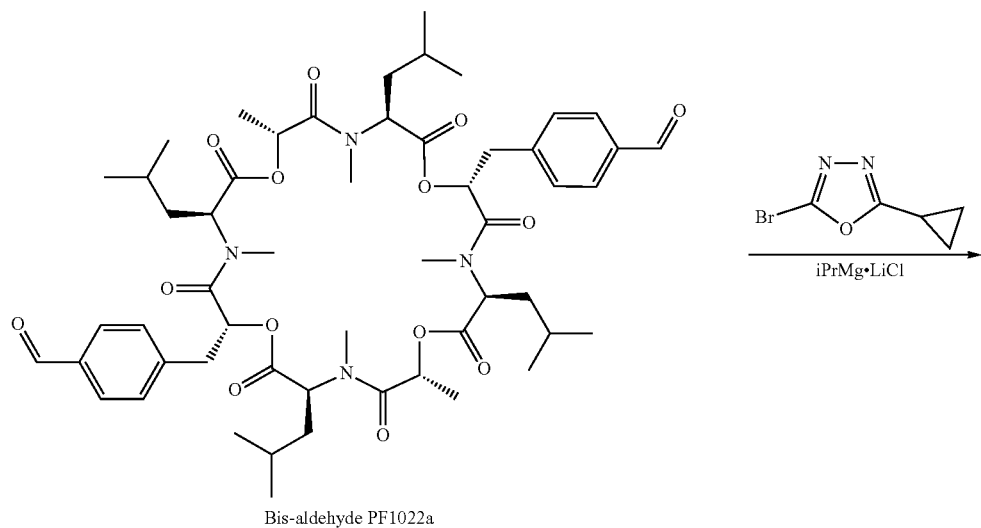

Bis-aldehyde PF1022a

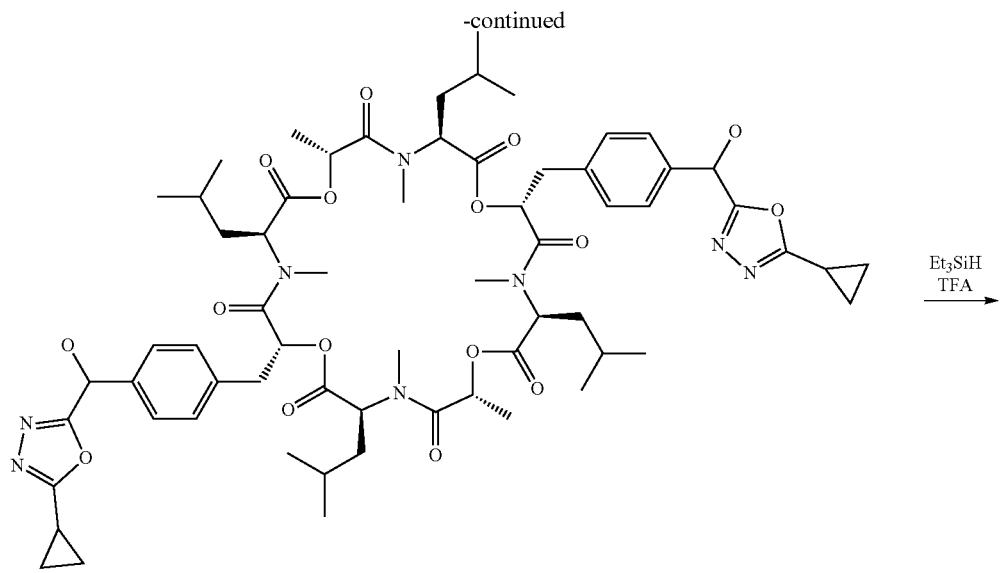

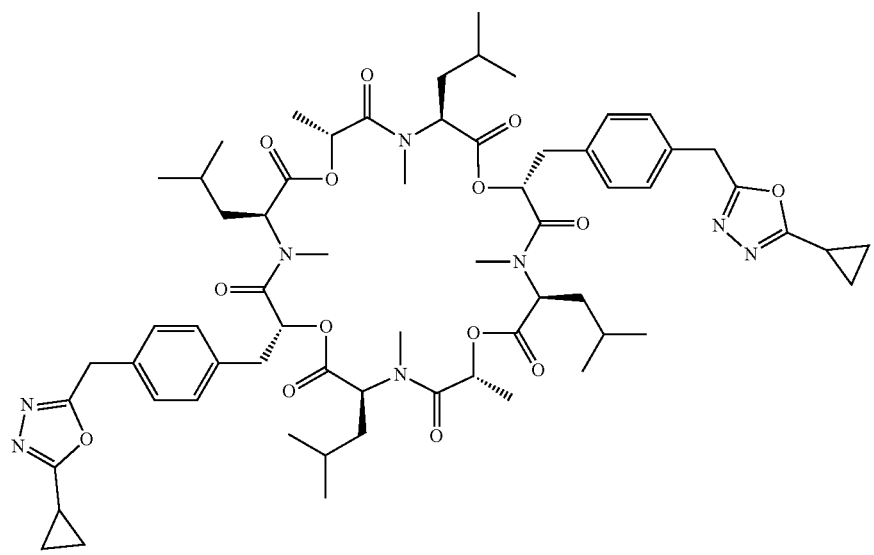

(3-330)

A stirred solution of 2-bromo-5-cyclopropyl-[1,3,4]oxadiazole (941 mg, 4.98 mmol) in dry THF (5 ml) was cooled to −78° C. and iPrMgCl LiCl (1.3M, 3 ml, 3.984 mmol) was added drop-wise. The reaction mixture was allowed to stir at −10° C. for 40 minutes. A solution of Bis-Aldehyde PF1022a (500 mg, 0.498 mmol) in dry THF (1 ml) was added to the mixture in one portion and allowed to stir at −10° C. for 1.5 hours followed by 2 hours at room temperature. The reaction mixture was quenched with saturated NH₄Cl solution and extracted with ethyl acetate (2×150 ml). The combined organic layer was washed with water, brine, dried over anhydrous Na₂SO₄ and concentrated under reduced pressure to afford crude (3S,6R,9S,12R,15S,18R,21S,24R)-6,18-Bis-{4-[(5-cyclopropyl-[1,3,4]oxadiazol-2-yl)-hydroxy-methyl]-benzyl}-3,9,15,21-tetraisobutyl-4,10,12,16,22,24-hexamethyl-1,7,13,19-tetraoxa-4,10,16,22-tetraaza-cyclotetracosan-2,5,8,11,14,17,20,23-octaone as a gum.

To a solution of the above intermediate (crude, 750 mg, 3.065 mmol) in DCE (5 ml) were added triethyl silane (5 ml) and TFA (5 ml) at 23° C. The resulting mixture was heated at 100° C. for 1 hour under microwave irradiation. The reaction mass was poured into saturated NaHCO₃ solution and extracted with DCM (2×100 ml). The combined organic layers were washed with water, brine, dried over anhydrous Na₂SO₄ and concentrated under reduced pressure to afford crude compound (3-330) (650 mg) as a gum. The crude material was purified by preparatory HPLC to afford the desired Example (3-330) (35 mg) as an off white solid.

Scheme 6. Stille and Suzuki Coupling Process

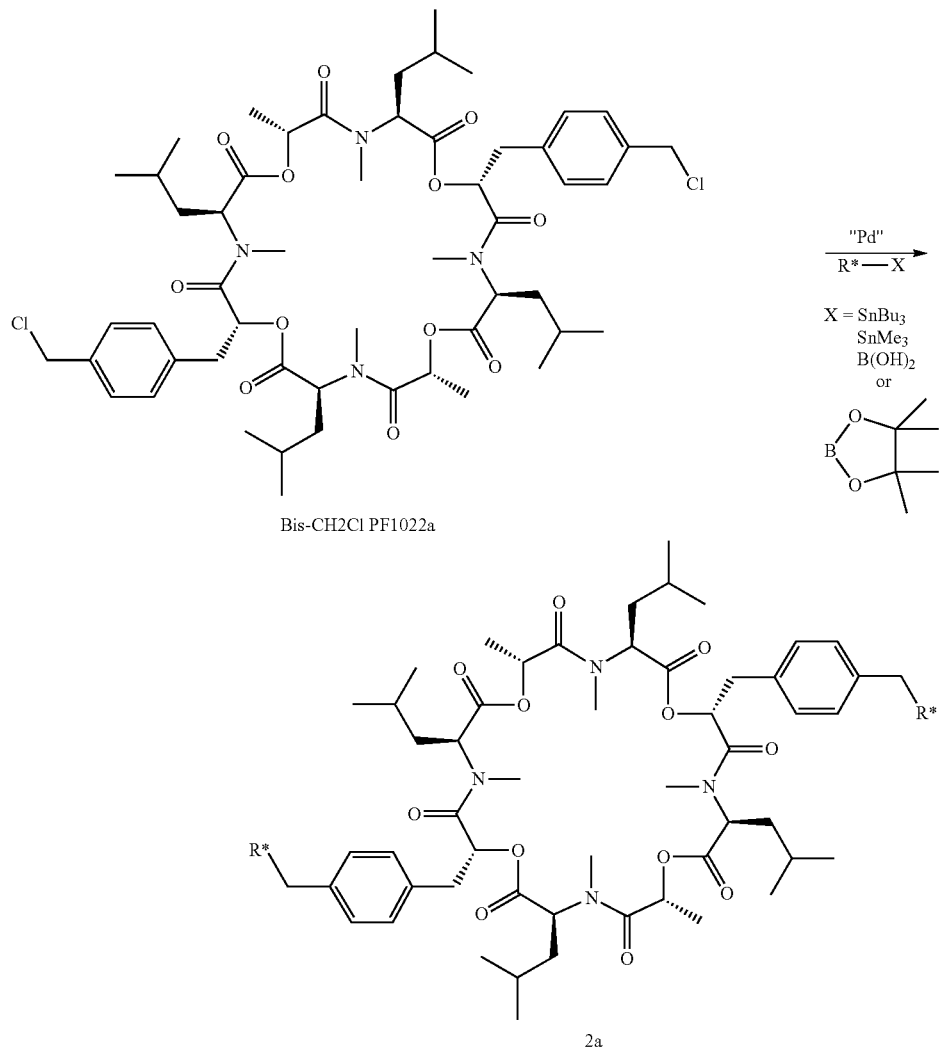

In Scheme 6, R* represents the $L_1$ and $L_2$ aryl, cycloalkyl, heterocycle, and heteroaryl, moieties, each of which can be substituted as described herein. "Pd" represents a palladium catalyst.

As shown in Scheme 6, compounds like 2a can be accessed directly from Bis-CH$_2$Cl PF1022a via palladium catalyzed cross coupling reactions such as in the Stille or Suzuki reaction. In this case, Bis-CH$_2$Cl PF1022a is treated with an organoboronic acid, organoboronate ester, or organnostannane in the presence of a palladium catalyst with or without base to provide the desired products after heating. The organostannane reagents and organoboronic acids/esters are either commercially available or prepared by standard methods found in the literature (European Journal of Organic Chemistry (2014), 24, 5153-5157; Journal of the American Chemical Society (2002), 12, 8001); Organic Letters (2012), 14(2), 502-505; Journal of Medicinal Chemistry (2005), 48(22), 7080-7083; and PCT Application publications WO2006/108591, WO2003/087102, and WO2012/177714; and from commercially available starting materials.

For Examples 3-50 and 4-40, to a stirred solution of TMP (137 mg, 0.967 mmol) in THF (1 ml), 2.3M n-BuLi in THF (0.37 mL, 0.86 mmol) was added at 0° C., then stirred for 30 minutes. Furan-3-carbonitrile (100 mg, 1.074 mmol) in THF (1 ml) was added at −78° C. and stirred at same temperature for 2 hours. Then Bu$_3$SnCl (0.321 ml, 1.182 mmol) in THF (1 mL) was added at −78° C. and the reaction mixture was allowed to stir at room temperature for 15 hours. The reaction was quenched with saturated NH$_4$Cl solution and extracted with DCM (2×15 ml), combined organic layer was washed with brine solution (5 ml), dried over Na$_2$SO$_4$ filtered and concentrated. Crude was purified by column chromatography used on silica gel eluting with 20 DCM-Hexane to afford crude stannane monomer, 2-(tributylstannyl)furan-3-carbonitrile, as a light yellow liquid.

For Example 3-209, to a stirred solution of 2-methoxy-4-methylthiazole (75 mg, 0.581 mmol) in THF (5 mL) at −78° C., n-BuLi (0.30 mL) was added and the reaction mixture was stirred for 1 hour at that temperature. Then tributyltin chloride (0.18 ml, 0.64 mmol) was added at −78° C. and the reaction mixture was stirred for 2 hours at room temperature. Water (10 mL) was added to the reaction mixture and extracted with ethyl acetate (2×20 mL). Total organic part was washed with brine solution, dried (Na₂SO4) and evaporated at 25° C. to afford the stannane monomer, 2-methoxy-4-methyl-5-(tributylstannyl)thiazole, as a dark brown liquid.

For Example 3-238, to a stirred solution of 3-bromo-2-(trifluoromethyl)pyridine (400 mg, 1.77 mmol) in THF (15 mL) at −78° C., n-BuLi (1.8 mL, 1.1 equiv) was added and the reaction mixture was stirred for 1 hour at that temperature. Then tributyltin chloride (0.52 ml, 1.947 mmol, 1.1 equiv) was added at −78° C. and the reaction mixture was allowed to stir for 1.5 hours at room temperature. Water (10 mL) was added to the reaction mixture and extracted with ethyl acetate (2×20 mL). Total organic part was washed with brine solution, dried (Na₂SO₄) and evaporated to afford the crude stannane monomer, 3-(tributylstannyl)-2-(trifluoromethyl)pyridine, as a dark liquid.

Preparation of (3S,6R,9S,12R,15S,18R,21S,24R)-3,9,15,21-tetraisobutyl-6,18-bis(4-((5-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone, Example (3-33) using the Stille process shown below. Similar compounds, as described in Tables 1-4, were also readily prepared using the Stille process.

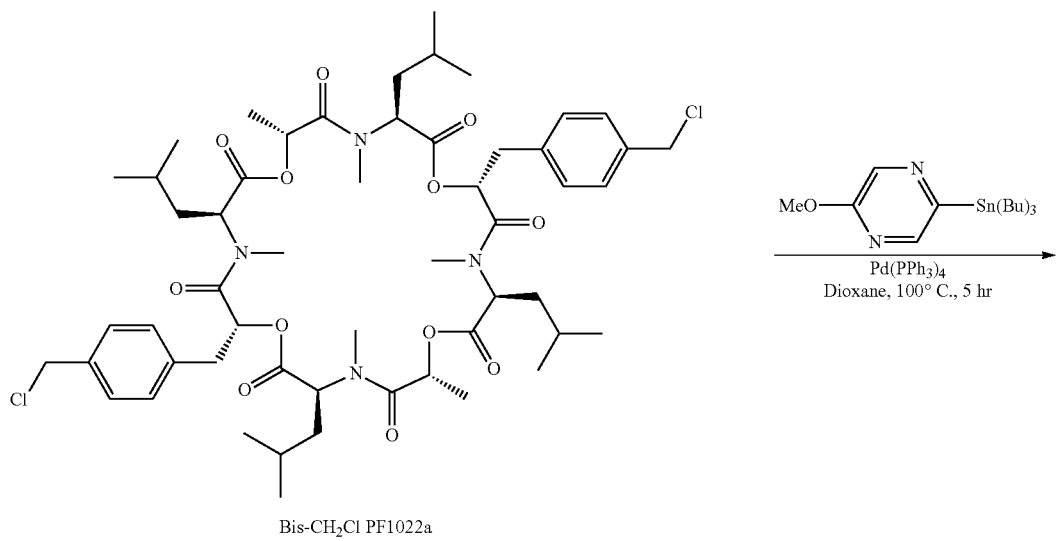

Bis-CH₂Cl PF1022a

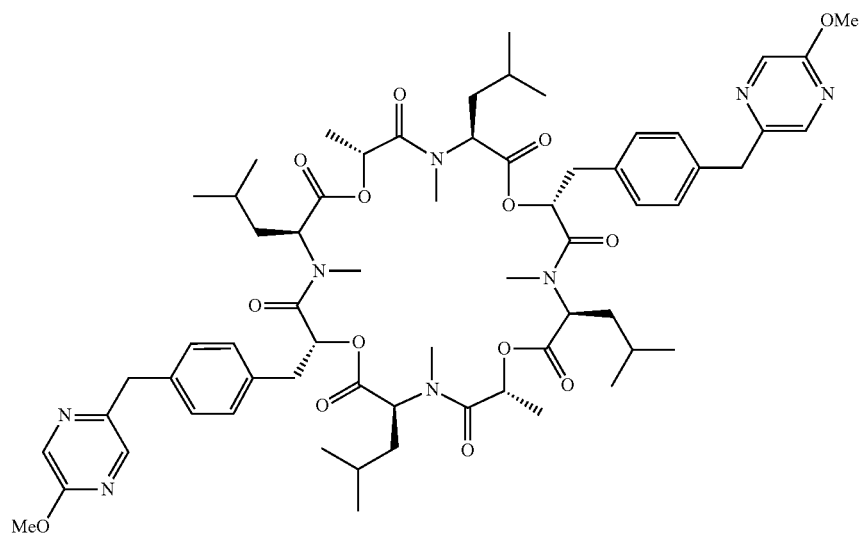

(3-33)

To a stirred solution of Bis-CH$_2$Cl PF1022a (150 mg, 0.14 mmol) and 2-methoxy-5-(tributylstannyl)pyrazine (0.40 g, 1.0 mmol) in p-dioxane (5 ml) was added Pd(PPh$_3$)$_4$ (75 mg, 0.065 mmol). The solution was heated at 100° C. in an atmosphere of N2 for 5 hours. The reaction mixture was cooled to room temperature and filtered through Celite. The filtrate was concentrated to a viscous black oil that was dissolved in a small volume of DMSO and purified by reverse phase HPLC to give Example (3-33).

Preparation of (3S,6R,9S,12R,15S,18R,21S,24R)-6,18-bis[[4-[[2-(difluoromethyl)-3-pyridyl]methyl]phenyl]methyl]-3,9,15,21-tetraisobutyl-4,10,12,16,22,24-hexamethyl-1,7,13,19-tetraoxa-4,10,16,22-tetrazacyclotetracosane-2,5,8,11,14,17,20,23-octaone, Example (3-290) using the Suzuki process shown below. Similar compounds, as described in Tables 1-4, were also readily prepared using the Suzuki process.

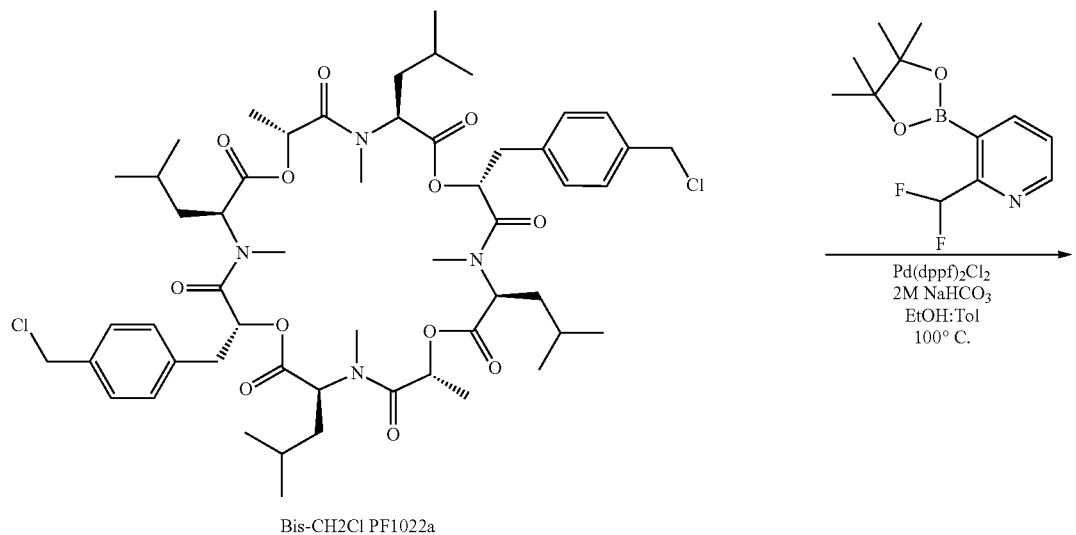

Bis-CH2Cl PF1022a

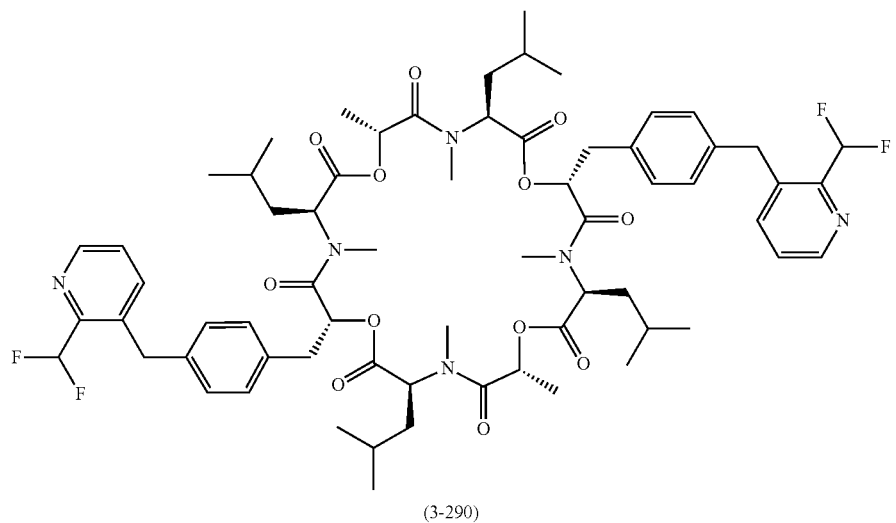

(3-290)

To a solution of Bis-CH$_2$Cl PF1022a (120 mg, 0.11 mmol) in EtOH:Toluene (4 mL, 1:1) was added 2-(difluoromethyl)-3-(4,4,5,5-tetramethyl-1,3,2-dioxaborolan-2-yl)pyridine (120 mg, 0.46 mmol), NaHCO$_3$ (1 mL of 2M sol.) and Pd(dppf)$_2$Cl$_2$ (15 mg, 0.014 mmol). The reaction mixture was purged with N2 and heated at 100° C. for 15 minutes in a microwave. After cooling at room temperature the reaction mixture was diluted with EtOAc/water and the organic phase was separated and concentrated under reduced pressure. The residue was purified by reverse phase chromatography to provide 88 mg (62%) of Example (3-290) as a white solid.

Scheme 7. Process for Preparing Compounds 2g and 2h

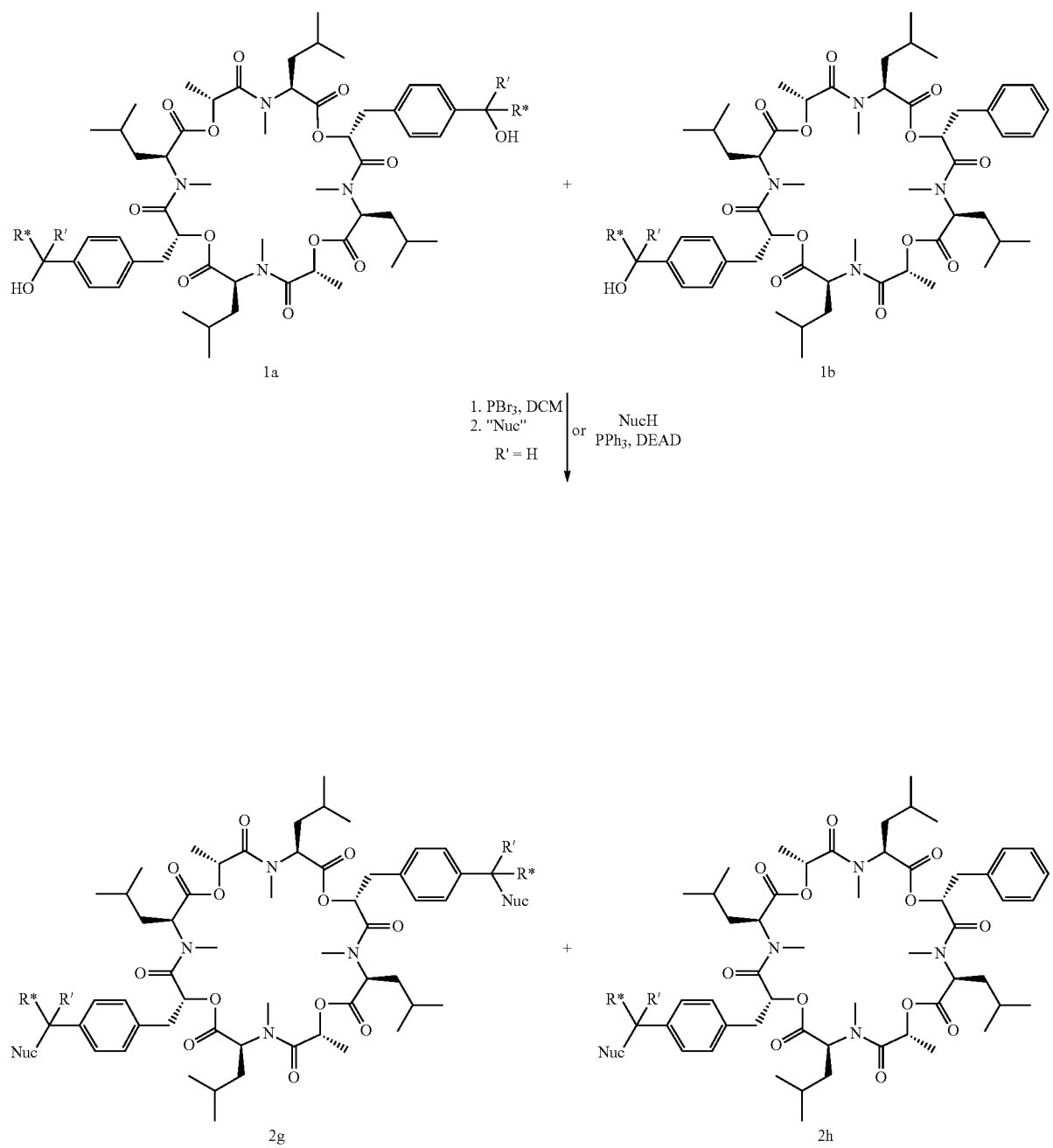

In Scheme 7, R* represents the $L_1$ and $L_2$ aryl, cycloalkyl, heteroaryl, and heterocycle moieties, each of which can be substituted as described herein; and R' is H. "Nuc" represents a nucleophilic functional group, e.g., alcohols, acyclic and cyclic amines, heterocycles (e.g., morpholine), heteroaryls (e.g., pyrazole), and any nucleophilic organometallic cycloalkyl, heterocycle, aryl, or heteroaryl group, such as organolithiums or Grignard reagents.

In Scheme 7, compounds 1a and 1b (Scheme 4) are treated individually with phosphorous tribromide to convert the hydroxyl group to a bromo group using conditions readily found in the literature. The bromo group is readily displaced by nucleophiles (Nuc) to form compounds of type 2g and 2h that are described in Tables 1-4.

Preparation of Compound (3S,6R,9S,12R,15S,18R, 21S,24R)-6-benzyl-18-(4-((3,4-difluorophenyl) (methoxy)methyl)benzyl)-3,9,15,21-tetraisobutyl-4, 10,12,16,22,24-hexamethyl-1,7,13,19-tetraoxa-4,10, 16,22-tetraazacyclotetracosan-2,5,8,11,14,17,20,23-octaone (2-37)

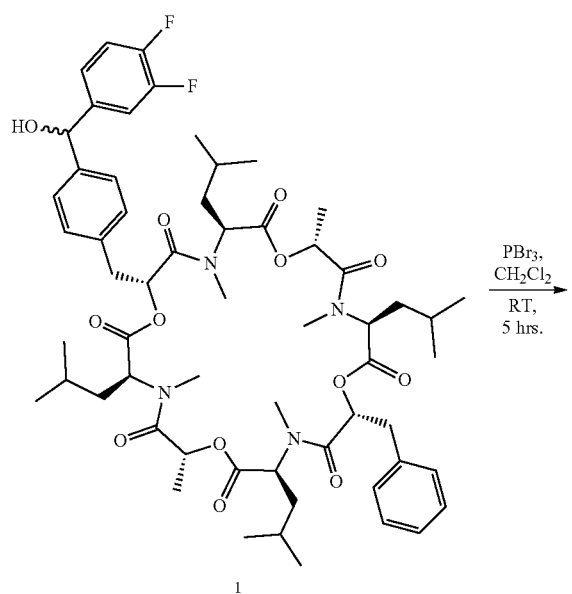

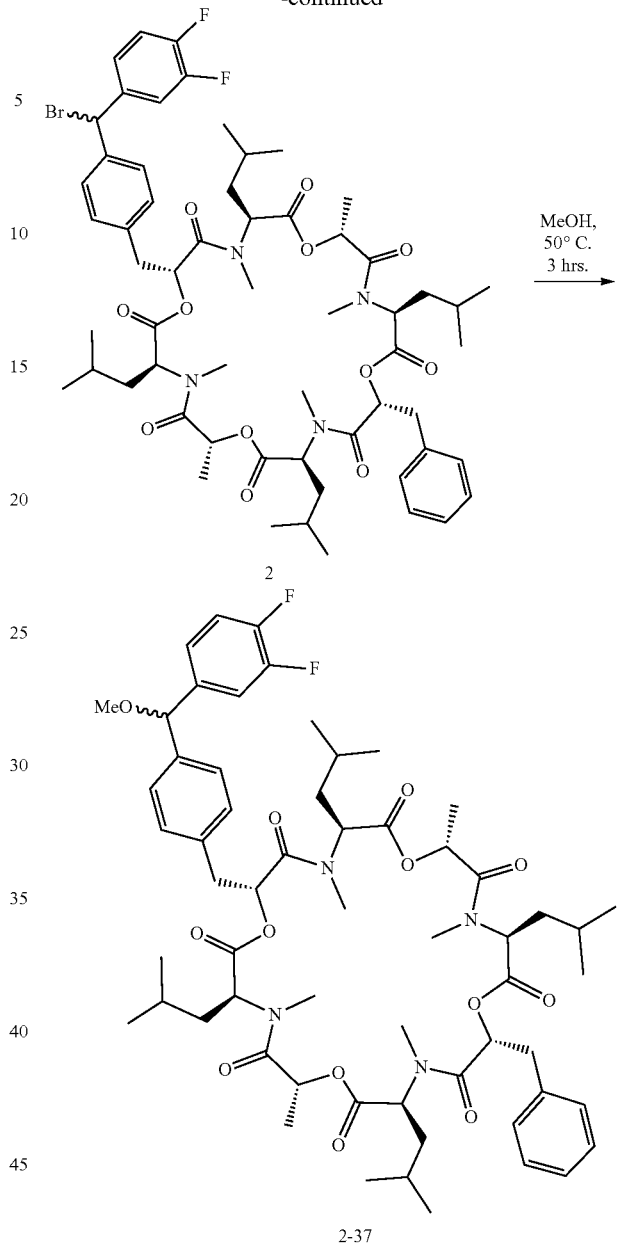

Step 1:
Compound 1 (300 mg, 0.275 mmol) was dissolved in DCM (5 ml) and the solution was cooled to 0° C. with an ice bath. PBr$_3$ (0.27 g, 1.0 mmol) was then added and the solution was allowed to stir 1 hour at 0° C. and for 2 hours at room temperature. The mixture was diluted with methylene chloride (25 ml) and ice water was added (20 ml). The layers were mixed then allowed to separate. The organic phase was collected, dried over sodium sulfate, then concentrated to give the crude product as an amber amorphous glassy solid. The solid was used as is in Step 2.

Step 2:
To the crude bromide, 2, (150 mg, 0.13 mmol) was added MeOH (2 ml) and the solution was stirred at 45° C. for 3 hours. The mixture was directly purified by reverse phase HPLC to give Example (2-37) (42 mg, 0.038 mmol) as a white solid after lyophilization.

Scheme 8: Organometallic Process for Preparing Compounds from Bis-Iodo PF1022a
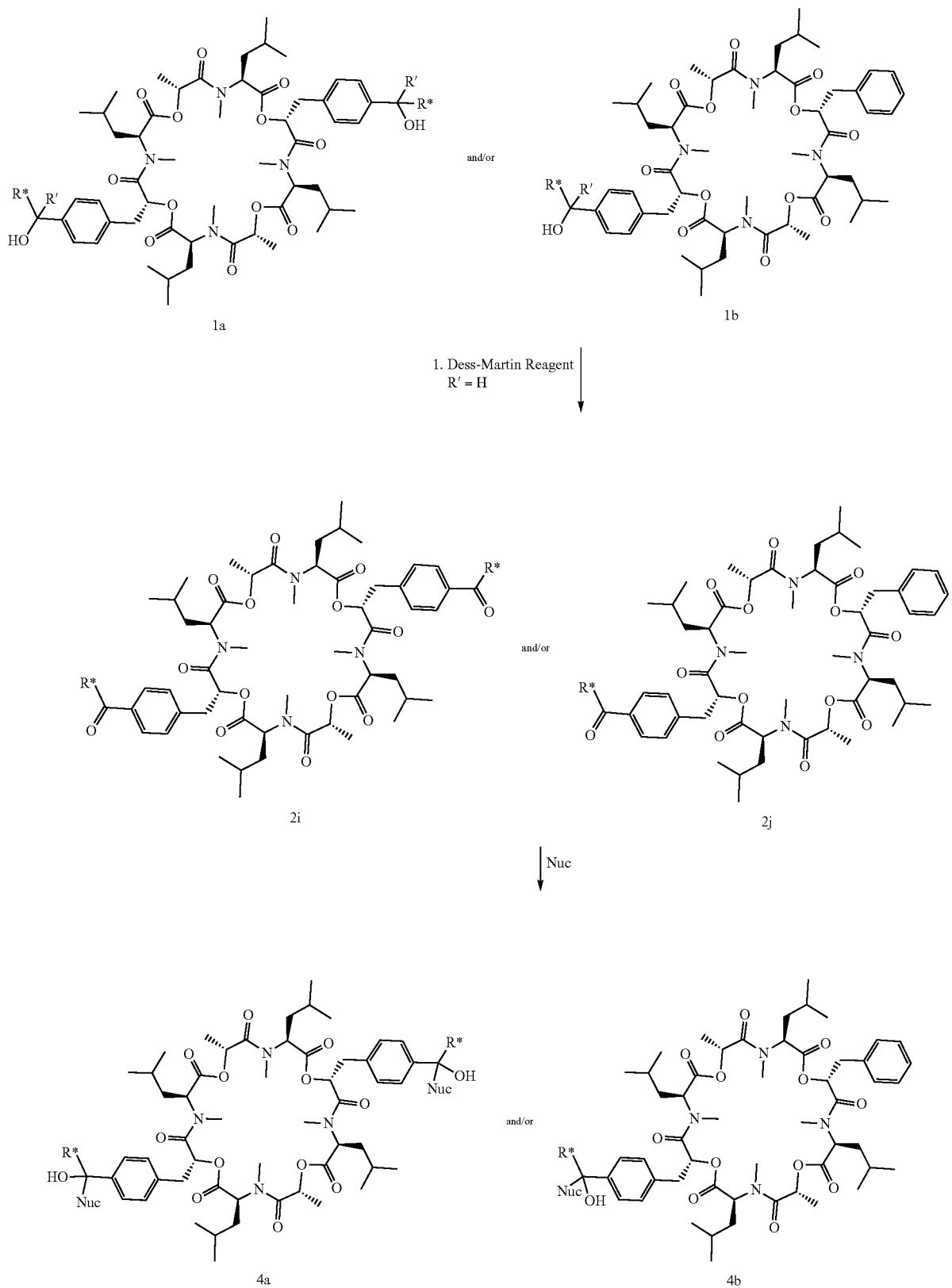

In Scheme 8, R* represents the $L_1$ and $L_2$ aryl, cycloalkyl, heteroaryl, and heterocycle moieties, each of which can be substituted as described herein. "Nuc" represents a nucleophilic functional group as defined above.

As shown in Scheme 8 compounds having the general structures 4a and 4b are prepared from 1a and 1b (when R'=H) via a two-step process. In the first step the alcohol 1a or 1b is treated with an oxidizing reagent, such as Dess-Martin periodinane, to yield a ketone (2i and 2j) that will react with a Grignard reagent to give compounds of the type 4a and 4b in the second step, e.g., Example (4-26) can be prepared.

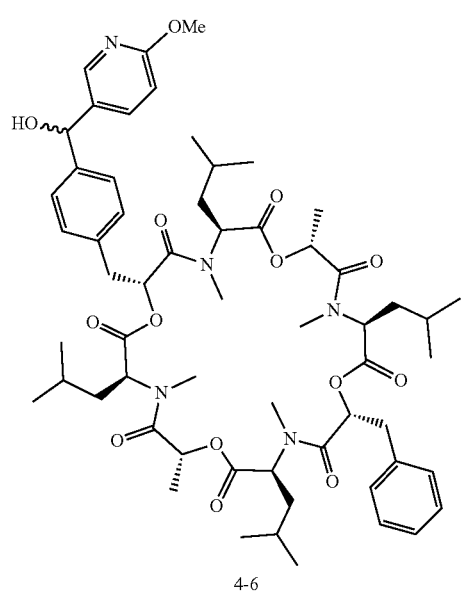

4-6

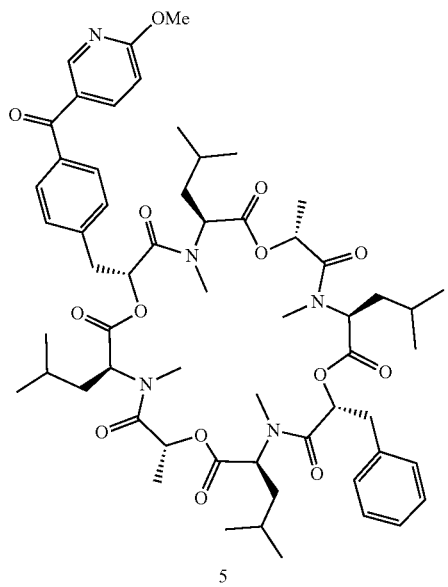

5

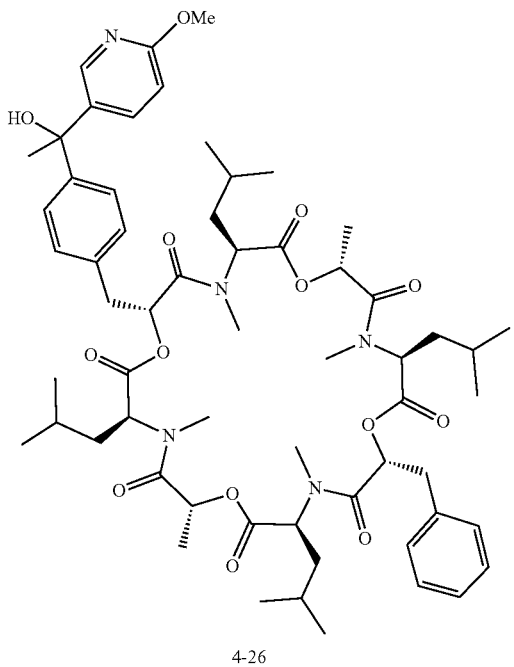

4-26

Step 1:

Compound 4-6 (50 mg, 0.046 mmol) was dissolved in DCM (3 ml) and Dess-Martin periodane (42 mg, 1 mmol) was added to the stirring solution. The solution was stirred at room temperature for 3 hours. The reaction mixture was diluted with DCM (10 ml) and cooled to 0° C. Then a 1 M aqueous solution of sodium bisulfite (2 ml) was added and the mixture was stirred at 0° C. for 0.5 hours. The organic phase was collected and washed with water (2×3 ml). The organic phase was dried with sodium sulfate then concentrated to give crude compound 5 that was used without further purification.

Step 2:

Compound 5 (39 mg, 0.035 mmol) was dissolved in anhydrous THF (5 ml) and the solution was cooled to 0° C. before MeMgBr (3 M in THF, 0.5 ml, 1.5 mmol) was added. The solution was then warmed to room temperature and stirred for 30 minutes. The solution was cooled again to 0° C. and quenched by the addition of AcOH (0.2 ml). The solution was then diluted with EtOAc (15 ml), washed with water (1×5 ml) and concentrated to provide crude Example (4-26). Purification was done using reverse phase HPLC to give Example (4-26) as a white solid after lyophilization.

Scheme 9: Process for Preparing Pyrrole Containing Compounds
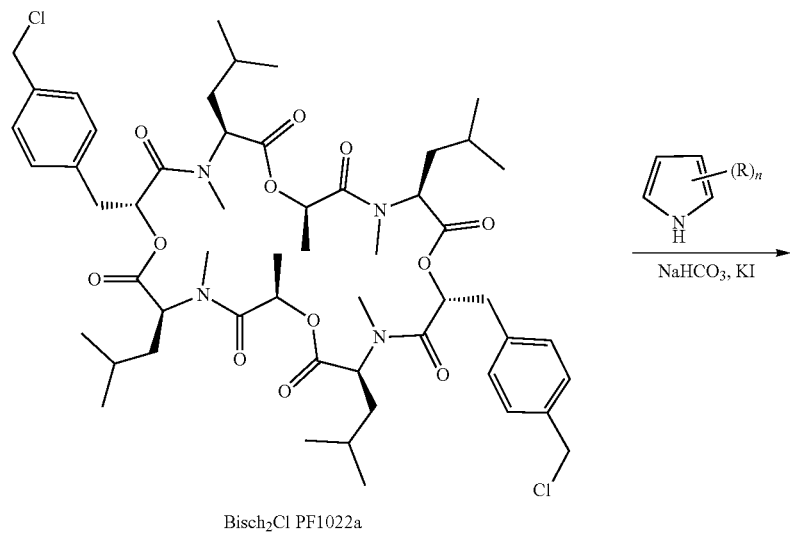
Bisch₂Cl PF1022a
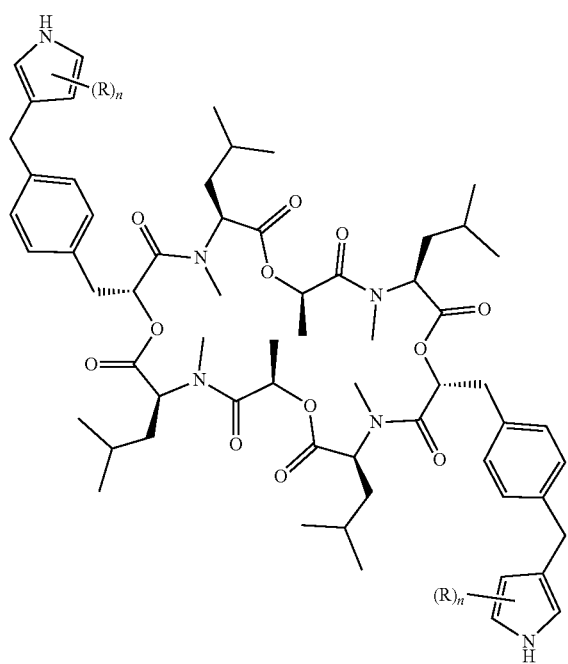

As shown in Scheme 9, pyrroles were reacted with BisCH₂Cl PF1022a under basic conditions to the give bis-C-linked pyrroles as products. (R)$_n$ is as defined herein. It will be understood that monoCH₂Cl PF1022a may be reacted similarly with pyrroles to give the mono-C-Linked pyrroles as products; e.g., Example (3-29) can be prepared using this scheme, as shown below.

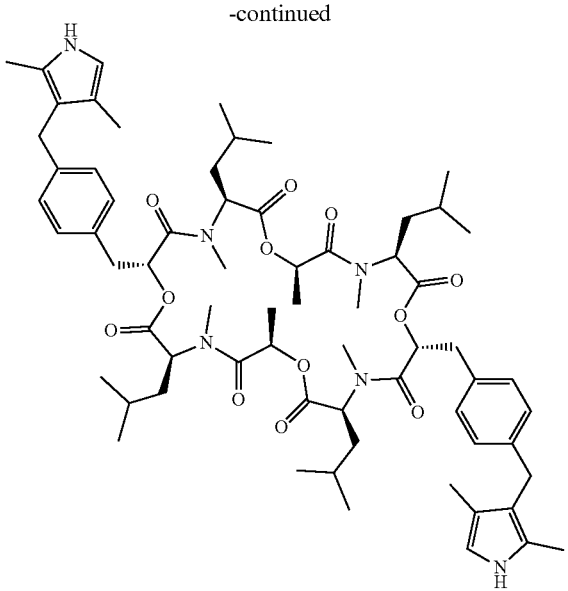

3-29

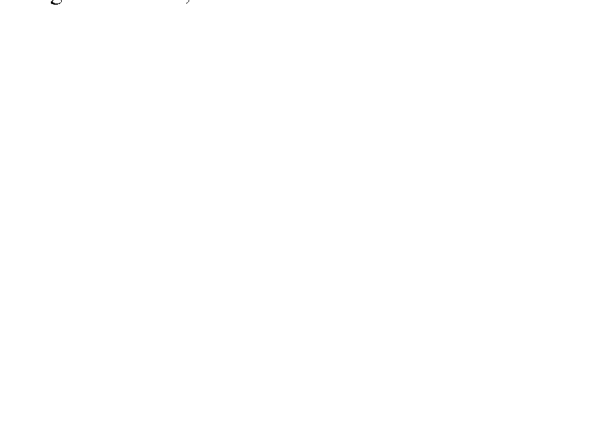

To (3S,6R,9S,12R,15S,18R,21S,24R)-6,18-bis[[4-(chloromethyl)phenyl]-methyl]-3,9,15,21-tetraisobutyl-4,10,12,16,22,24-hexamethyl-1,7,13,19-tetraoxa-4,10,16,22-tetrazacyclotetracosane-2,5,8,11,14,17,20,23-octaone (50.0 mg, 0.048 mmol) was added 2,4-dimethyl-1H-pyrrole (5.0 equiv., 0.24 mmol), potassium bicarbonate (24 mg), and potassium iodide (4.0 equiv, 0.191 mmol) followed by acetontrile (1.00 mL). The reaction mixture was then heated at 50° C. for 48 hours. The reaction was cooled and filtered through celite and washed with DCM. The crude material was absorbed onto celite and purified via reverse phase chromatography with a gradient of 60-95% acetonitrile in H₂O. Like fractions were combined and lyophilized overnight to provide the product, Example (3-29), (20 mg, 32%), a purplish solid.

In addition, other C-linked heterocyclic compounds, for Example (3-5) and (3-14), can be prepared using the following procedural Steps.

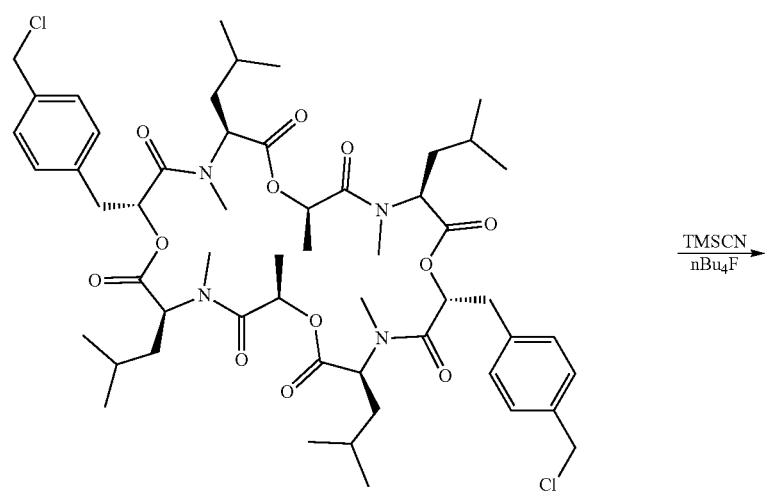

-continued
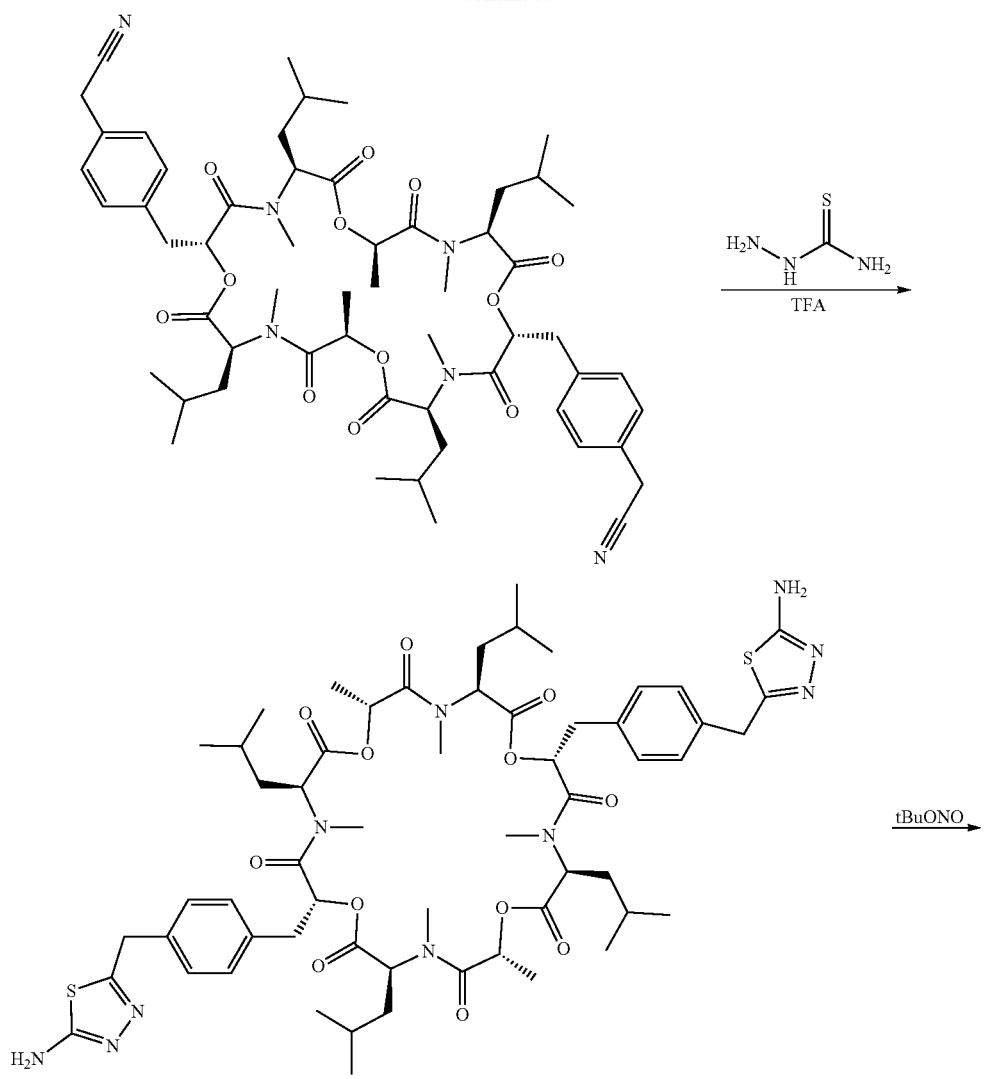
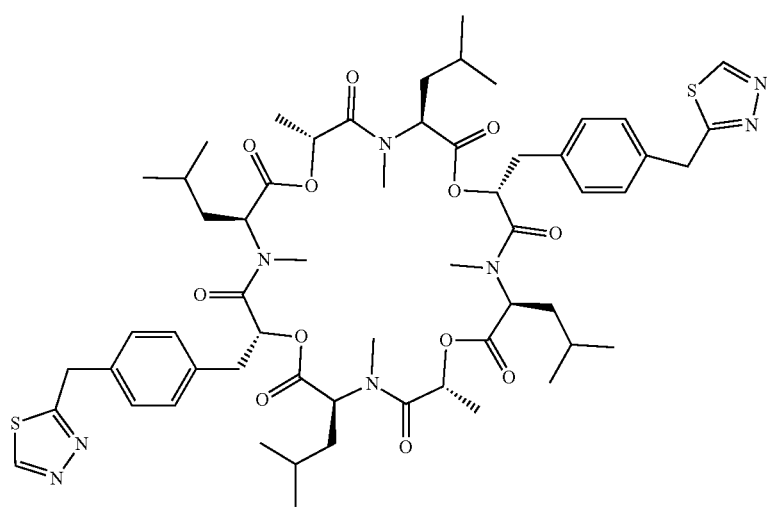

Step 1:
Pre-mixed tetrabutylammonium fluoride (4 eq) and TMSCN (4 eq) in acetonitrile were heated at 40° C. for 1 hour, after that addition of depsibenzylchloride (500 mg) was added at room temperature and stirred for 16 hours. After aqueous workup, the residue was purified by preparative HPLC to give the bis benzylnitrile.

Step 2:
A mixture of bis benzyl nitrile (40 mg), thiosemicarbazide (5 eq) and TFA was stirred at 90° C. for 16 hours. After cooling to room temperature, the mixture was given an aqueous work up and purified by preparatory HPLC to give the bis aminothiadiazole Example (3-5).

Step 3:
Aminothiadiazole (3-5; 23.5 mg), t-BuONO (10 eq), THF, 0° C. to room temperature, stirred for 16 hours. The solvent was evaporated and the residue purified by preparatory HPLC to give the bis thiadiazole Example (3-14). Similarly, the tetrazole Example (3-6) can be prepared.

Mass data ((ESI-MS m/z [M+H]$^+$), unless defined otherwise, is presented in each of Tables 1-4. The compounds described in the upper section of each of Tables 1-4 are compounds wherein the DiL4 data was ≤1 nM, the compounds in the lower section of each of Tables 1-4 had DiL4 data>1 nM. The upper and lower sections of Tables 1-4 are separated by the bold borders. Examples with an asterisk (*) have HcL3 MED values≤1 μM. Examples with a carrot (^) have HcL3 MED values>1 and ≤3.3 μM. Compounds were named using Perkin Elmer ChemBioDraw Ultra 2014, Version 14.0.0.117; CambridgeSoft Corporation.

The following Formula (1A1) compounds described in Table 1 were prepared in accordance with the schemes and examples described herein. Each tabulated Formula (1A1) compound is a bis-substitution; i.e., each of (R)$_n$ are the same; each of R$^c$ are the same, and each of R$^d$ are the same, and are as described in the Table.

TABLE 1

Formula (1A1) Compounds

| Ex# | R$^c$ | R$^d$ | n | R | Mass |
|---|---|---|---|---|---|
| 1-5 | H | H | 1 | 3-methoxy | 1190 |
| 1-11 | H | H | 1 | 2-methoxy | 1190 |
| 1-18 | H | 1H-pyrazol-1-yl | 2 | 3,4-difluoro | 1334 |
| 1-1 | H | H | 1 | 4-methoxy | 1190 |

TABLE 1-continued

Formula (1A1) Compounds

| Ex# | R$^c$ | R$^d$ | n | R | Mass |
|---|---|---|---|---|---|
| 1-2 | H | H | 1 | 4-F | 1165 |
| 1-3 | H | H | 1 | 4-Cl | 1198 |
| 1-4 | H | H | 1 | 4-CN | 1180 |
| 1-6 | H | H | 1 | 3-F | 1165 |
| 1-7 | H | H | 0 | — | 1129 |
| 1-8 | H | H | 2 | 2-methoxy; 4-F | 1198 |
| 1-9 | H | —OH | 1 | 4-methoxy | 1222 |
| 1-10 | H | —OH | 1 | 2-methoxy | 1222 |
| 1-12 | H | —OH | 2 | 3-F; 4-F | 1233 |
| 1-13 | H | H | 2 | 3-F; 4-F | 1201 |
| 1-14 | H | —OH | 1 | 4-F | 1197 |
| 1-15 | H | —OH | 1 | 4-(1H-pyrazol-1-yl) | 1294 |
| 1-16 | H | —OH | 1 | 4-(1H-imidazol-1-yl) | 1294 |
| 1-17 | H | H | 1 | 2-methylsulfonyl | 1286 |
| 1-19 | H | H | 1 | 4-(1H-pyrazol-1-yl) | 1262 |
| 1-20 | H | H | 1 | 4-(1H-imidazol-1-yl) | 1262 |
| 1-21 | H | H | 1 | 4-(1,2-dihydropyrimidin-5-yl) | 1290 |
| 1-22 | H | H | 1 | 4-(1,6-dihydropyrimidin-5-yl) | 1290 |
| 1-23 | —OH | —CF$_3$ | 1 | 3-isopropyl | 1382 |
| 1-24 | H | H | 1 | 4-(pyridin-4-yl) | 1284 |
| 1-25 | —OH | —CF$_3$ | 0 | — | 1297 |
| 1-26 | H | H | 2 | 3-fluoro; 4-methoxy | 1225 |
| 1-27 | H | H | 1 | 4-methoxy | 1175 |
| 1-28 | H | H | 1 | 4-methylsulfonyl | 1286 |
| 1-29 | H | —OH | 1 | 4-(pyrimidin-5-yl) | 1318 |
| 1-30 | H | —OH | 1 | 4-(pyrimidin-2-yl) | 1318 |

The following compound names and example #'s refer to the upper section compounds of Table 1.

(1-5). (3S,6R,9S,12R,15S,18R,21S,24R)-3,9,15,21-tetraisobutyl-6,18-bis(4-(3-methoxybenzyl)benzyl)-4,10,12,16,22,24-hexamethyl-1,7,13,19-tetraoxa-4,10,16,22-tetraazacyclotetracosan-2,5,8,11,14,17,20,23-octaone;

(1-11). (3S,6R,9S,12R,15S,18R,21S,24R)-3,9,15,21-tetraisobutyl-6,18-bis(4-(2-methoxybenzyl)benzyl)-4,10,12,16,22,24-hexamethyl-1,7,13,19-tetraoxa-4,10,16,22-tetraazacyclotetracosan-2,5,8,11,14,17,20,23-octaone; and (1-18). (3S,6R,9S,12R,15S,18R,21S,24R)-6,18-bis(4-((3,4-difluorophenyl)(1H-pyrazol-1-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone, stereoisomers thereof, and veterinary acceptable salts thereof.

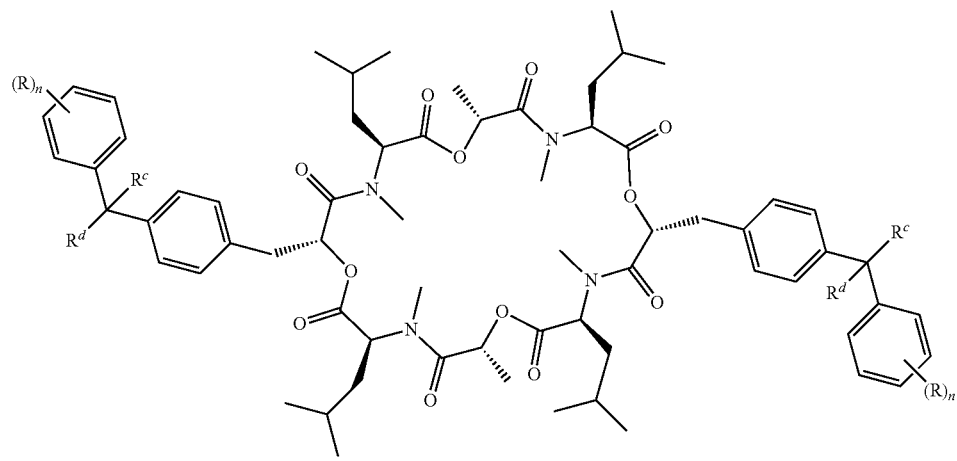

(1A1)

NMR data (1H NMR: 400 MHz, DMSO-d6, δ ppm) for the named Table 1 compounds are shown below:

(1-5). δ: 0.64-1.04 (m, 26H), 1.14-1.79 (m, 16H), 2.64-3.12 (m, 16H), 3.70 (s, 6H), 3.87 (s, 4H), 4.38-5.72 (m, 8H), 6.72-6.77 (m, 6H), 7.12-7.25 (m, 10H);

(1-11). δ: 0.63-0.98 (m, 26H) 1.09-1.78 (m, 16H) 2.66-3.07 (m, 20H) 3.75-3.77 (m, 3H) 3.85 (s, 3H) 4.37-4.45 (m, 1H) 4.99-5.72 (m, 7H) 6.80-7.23 (m, 16H); and (1-18). δ: 0.63-1.10 (m, 26H) 1.14-1.80 (m, 16H) 2.63-3.13 (m, 16H) 4.34-4.47 (m, 1H) 4.97-5.76 (m, 7H) 6.31 (s, 2H) 6.91-6.97 (m, 2H) 6.97-7.04 (m, 2H) 7.07-7.22 (m, 6H) 7.32 (br d, J=7.82 Hz, 4H) 7.37-7.49 (m, 2H) 7.55 (s, 2H) 7.67-7.79 (m, 2H).

The following Formula (2A1) compounds described in Table 2 were prepared in accordance with the schemes and examples described herein. Each of $(R)_n$, $R^c$, and $R^d$ are as described in the Table.

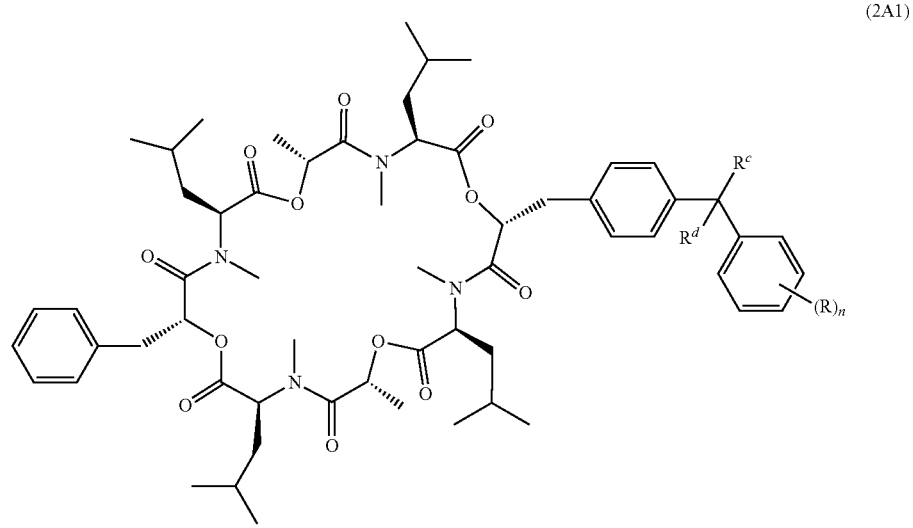

(2A1)

TABLE 2

Formula (2A1) Compounds

| Ex# | $R^c$ | $R^d$ | n | R | Mass |
|---|---|---|---|---|---|
| 2-1* | H | H | 0 | — | 1039 |
| 2-4^ | H | H | 1 | 4-F | 1057 |
| 2-36 | H | —N(CH$_2$CH$_3$)$_2$ | 2 | 3-F, 4-F | 1146 |
| 2-37^ | H | —OCH$_3$ | 2 | 3-F, 4-F | 1105 |
| 2-38* | H | —OCH$_2$CH$_3$ | 2 | 3-F, 4-F | 1119 |
| 2-42 | H | morpholine | 1 | 4-OCF$_3$ | 1208 |
| 2-2 | H | H | 1 | 4-methoxy | 1069 |
| 2-3 | H | —OH | 1 | 4-OCF$_3$ | 1139 |
| 2-5 | H | H | 1 | 4-Cl | 1074 |
| 2-6 | H | H | 1 | 4-CN | 1064 |
| 2-7 | H | H | 1 | 3-F | 1057 |
| 2-8 | H | H | 1 | 4-OCF$_3$ | 1123 |
| 2-9* | H | H | 2 | 2-methoxy; 4-F | 1087 |
| 2-10 | H | —OH | 1 | 4-methoxy | 1085 |
| 2-11 | H | —OH | 1 | 2-methoxy | 1085 |
| 2-12^ | H | H | 1 | 2-methoxy | 1069 |
| 2-13 | H | —OH | 1 | 4-OH | 1071 |
| 2-14 | H | H | 2 | 3-F, 4-F | 1075 |
| 2-15 | H | —OH | 1 | 3-OCF$_3$ | 1139 |
| 2-16 | H | —OH | 1 | 4-Cl | 1090 |
| 2-17 | H | —OH | 1 | 4-(1H-imidazol-1-yl) | 1121 |
| 2-18 | H | —OH | 1 | 4-F | 1073 |
| 2-19 | H | —OH | 1 | 4-(1H-pyrazol-1-yl) | 1121 |
| 2-20 | —OH | —CF$_3$ | 1 | 4-methoxy | 1153 |
| 2-21 | H | —OH | 1 | 3-(pyrimidin-5-yl) | 1133 |
| 2-22 | H | —OH | 1 | 3-(pyrimidin-2-yl) | 1133 |
| 2-23 | H | H | 1 | 4-(1H-pyrazol-1-yl) | 1105 |
| 2-24 | H | F | 1 | 4-Cl | 1092 |
| 2-25 | H | H | 1 | 4-(1H-imidazol-1-yl) | 1105 |
| 2-26 | —CH$_3$ | —OH | 1 | 4-OCF$_3$ | 1153 |
| 2-27 | H | H | 1 | 3-(1,6-dihydropyrimidin-2-yl) | 1119 |
| 2-28 | H | H | 1 | 3-(1,2-dihydropyrimidin-5-yl) | 1119 |
| 2-29 | —OH | —CF$_3$ | 1 | 3-isopropyl | 1165 |
| 2-30 | H | F | 1 | 4-F | 1075 |
| 2-31 | H | —OH | 1 | 3-(pyridin-4-yl) | 1132 |
| 2-32 | H | H | 1 | 3-(pyridin-4-yl) | 1116 |
| 2-33 | H | —OH | 1 | 3-OCF$_3$ | 1139 |
| 2-34 | H | —OH | 1 | 2-OCF$_3$ | 1139 |
| 2-35 | H | —OH | 1 | 4-OCF$_3$ | 1139 |
| 2-39 | —OH | —OF$_3$ | 0 | — | 1123 |
| 2-40 | H | H | 2 | 3-F, 4-methoxy | 1087 |
| 2-41 | H | imidazolyl | 1 | 4-OCF$_3$ | 1189 |
| 2-43 | H | pyrrolidin-1-yl | 2 | 3-F, 4-F | 1144 |

The following compound names and example #'s refer to the upper section compounds of Table 2.

(2-1). (3S,6R,9S,12R,15S,18R,21S,24R)-6-benzyl-18-(4-benzylbenzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(2-4). (3S,6R,9S,12R,15S,18R,21S,24R)-6-benzyl-18-(4-(4-fluorobenzyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(2-36). (3S,6R,9S,12R,15S,18R,21S,24R)-6-benzyl-18-(4-((diethylamino)(3,4-difluorophenyl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(2-37). (3S,6R,9S,12R,15S,18R,21S,24R)-6-benzyl-18-(4-((3,4-difluorophenyl)(methoxy)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(2-38). (3S,6R,9S,12R,15S,18R,21S,24R)-6-benzyl-18-(4-((3,4-difluorophenyl)(ethoxy)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone; and (2-42). (3S,6R,9S,12R,15S,18R,21S,24S)-6-benzyl-3,9,15,21-tetraisobutyl-4,10,12,16,22,24-hexamethyl-18-[[4-[(S)-morpholino-[4-(trifluoromethoxy)phenyl]methyl]phenyl]methyl]-1,7,13,19-tetraoxa-4,10,16,22-tetrazacyclotetracosane-2,5,8,11,14,17,20,23-octaone; stereoisomers thereof, and veterinary acceptable salts thereof.

NMR data (1H NMR: 400 MHz, DMSO-d6, δ ppm) for the named Table 2 compounds are shown below:

(2-1). Not available (2-4). Not available (2-36). δ: 0.64-1.79 (m, 48H) 2.58-3.22 (m, 21H) 4.32-4.51 (m, 1H) 4.96-5.82 (m, 7H) 7.18-7.90 (m, 12H);

(2-37). δ: 0.53-1.76 (m, 42H) 2.58-3.18 (m, 16H) 3.25 (s, 3H) 4.29-4.59 (m, 1H) 4.92-5.89 (m, 8H) 7.03-7.51 (m, 12H);

(2-38). δ: 0.65-1.82 (m, 45H) 2.63-3.14 (m, 16H) 3.35-3.47 (q, 3H) 4.35-4.47 (m, 1H) 4.98-5.79 (m, 8H) 7.14-7.42 (m, 12H); and (2-42). δ: 0.64-1.79 (m, 42H) 2.60-3.12 (m, 21H) 3.58-4.57 (br, 5H) 4.96-5.78 (m, 7H) 7.20-7.67 (m, 13H).

The following Formula (3A) compounds described in Table 3 were prepared in accordance with the schemes and examples described herein. Each tabulated Formula (3A) compound is a bis-substitution; i.e., Ring A is the same as Ring B, each of (R)$_n$ are the same; each of $R^c$ are the same, and each of $R^d$ are the same, and are as described in the Table.

TABLE 3

Formula (3A) Compounds

| Ex # | Rings A and B with (R)$_n$ | $R^c$ | $R^d$ | Mass |
|---|---|---|---|---|
| 3-4* | 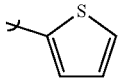 | H | H | 1142 |
| 3-8* | 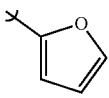 | H | H | 1109 |
| 3-12^ |  | H | H | 1144 |
| 3-17* | 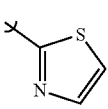 | H | H | 1144 |
| 3-18* | 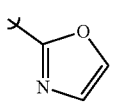 | H | H | 1111 |
| 3-21* | 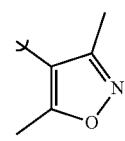 | H | H | 1168 |
| 3-24* | 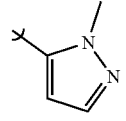 | H | H | 1137 |

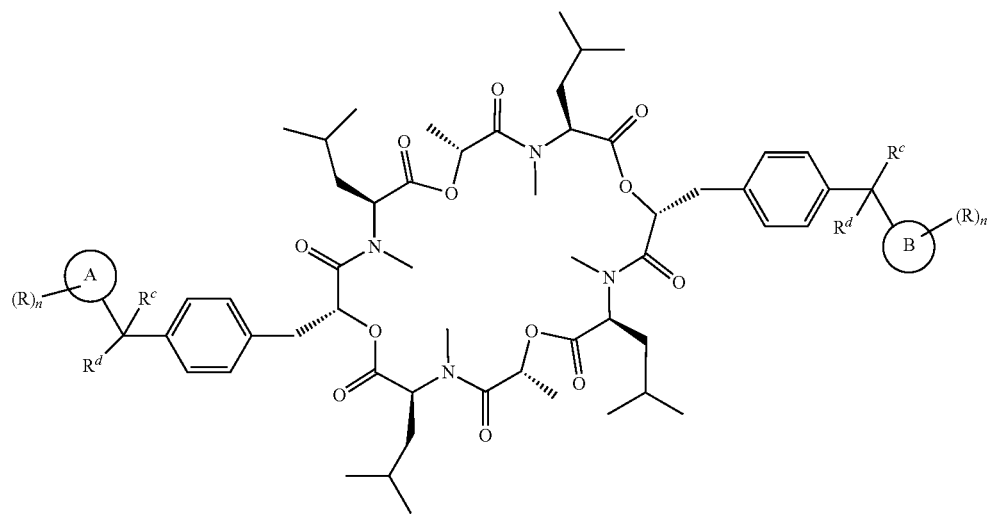

(3A)

TABLE 3-continued

Formula (3A) Compounds

| Ex # | Rings A and B with (R)n | R^c | R^d | Mass |
|---|---|---|---|---|
| 3-31^ | 3-pyridyl, 2-methoxy | H | H | 1191 |
| 3-44^ | 2-thienyl, 3-methyl | H | H | 1170 |
| 3-49^ | 1,3-dimethylpyrazol-5-yl | H | H | 1166 |
| 3-50* | 2-furyl, 3-CN | H | H | 1159 |
| 3-56* | 3-thienyl | H | H | 1142 |
| 3-57* | 4-oxazolyl | H | H | 1111 |
| 3-58* | 5-methylthiazol-4-yl | H | H | 1172 |
| 3-60 | 5-CN-furan-3-yl | H | H | 1159 |
| 3-69* | 6-methoxypyridin-2-yl | H | H | 1191 |
| 3-87* | 3-chlorothien-2-yl | H | H | 1210 |
| 3-110 | 4-methoxyisothiazol-5-yl | H | H | 1202 |
| 3-112* | 4-methylthiazol-5-yl | H | H | 1212 |
| 3-118 | 3-fluoro-2-methoxypyridin-5-yl | H | H | 1227 |
| 3-120* | 4-methyl-1,2,3-thiadiazol-5-yl | H | H | 1173 |
| 3-121^ | 2-methyl-6-methoxypyridin-3-yl | H | H | 1220 |
| 3-124* | 4-methylthien-2-yl | H | H | 1170 |
| 3-125 | 3-bromothien-2-yl | H | H | 1299 |
| 3-132 | 3-bromothien-2-yl | H | —OH | 1331 |
| 3-133 | 4-methyl-2-methoxypyridin-5-yl | H | H | 1220 |
| 3-148^ | 5-oxazolyl | H | H | 1111 |
| 3-155* | 4-methylthiazol-5-yl | H | H | 1172 |
| 3-156 | isothiazol-5-yl | H | H | 1143 |
| 3-157 | 5-methyl-2-furyl | H | H | 1137 |

TABLE 3-continued

Formula (3A) Compounds

| Ex # | Rings A and B with (R)$_n$ | R$^c$ | R$^d$ | Mass |
|---|---|---|---|---|
| 3-165 | 2-ethoxypyridin-3-yl | H | H | 1220 |
| 3-173^ | furan-3-yl | H | H | 1109 |
| 3-176^ | 2-(dimethylamino)pyridin-3-yl | H | H | 1218 |
| 3-178 | 2-morpholinopyrimidin-5-yl | H | H | 1304 |
| 3-193* | 4-methoxypyrimidin-3-yl | H | H | 1193 |
| 3-194 | 5-fluoropyridin-3-yl | H | H | 1167 |
| 3-207 | 6-methoxypyridin-3-yl | H | —CH$_3$ | 1220 |
| 3-209 | 2-methoxy-4-methylthiazol-5-yl | H | H | 1191 |
| 3-215* | 3-methoxypyridin-2-yl | H | H | 1192 |
| 3-217^ | 4-methoxypyrimidin-2-yl | H | H | 1193 |
| 3-218 | 5-methoxypyrimidin-2-yl | H | H | 1193 |
| 3-220 | 4-methoxypyridin-3-yl | F | —CH$_3$ | 1255 |
| 3-223 | 4-methylpyridin-3-yl | H | H | 1159 |
| 3-225 | 6-methoxypyridin-2-yl | —CH$_3$ | F | 1255 |
| 3-228 | 4-isopropyl-1,2,3-thiadiazol-5-yl | H | H | 1230 |
| 3-238 | 2-(trifluoromethyl)pyridin-3-yl | H | H | 1267 |
| 3-240 | 2,6-dimethylpyridin-3-yl | H | H | 1188 |
| 3-243 | 5-methyl-1H-pyrazol-4-yl | H | H | 1137 |
| 3-252 | 5-methoxypyrazin-2-yl | F | —CH$_3$ | 1257 |
| 3-253* | 1-ethyl-1H-pyrazol-5-yl | H | H | 1165 |
| 3-254 | isothiazol-4-yl | H | H | 1143 |
| 3-259^ | 6-hydroxypyridin-3-yl | H | —OCH$_3$ | 1223 |

TABLE 3-continued

Formula (3A) Compounds

| Ex # | Rings A and B with (R)$_n$ | R$^c$ | R$^d$ | Mass |
|---|---|---|---|---|
| 3-261 | 3-methoxypyridin-3-yl | H | —CH$_3$ | 1220 |
| 3-268* | 1-cyclopropyl-1H-pyrazol-5-yl | H | H | 1189 |
| 3-273* | 2-methylpyridin-3-yl | H | H | 1159 |
| 3-274* | 5-methoxypyrazin-2-yl | H | —CH$_3$ | 1201 |
| 3-275^ | 1-(cyclopropylmethyl)-1H-pyrazol-5-yl | H | H | — |
| 3-282 | 4-methoxypyridin-3-yl | H | H | 1191 |
| 3-283* | 4-isopropylpyrimidin-5-yl | H | H | 1218 |
| 3-284 | 3-cyclopropylisoxazol-5-yl | H | H | 1191 |
| 3-285 | thiazol-2-yl | H | F | 1179 |
| 3-286 | 1-(2-fluoroethyl)-1H-pyrazol-4-yl | H | H | 1201 |
| 3-287 | 2-(difluoromethyl)pyridin-5-yl | H | H | 1231 |
| 3-288* | 4-methylisothiazol-5-yl | H | H | 1172 |
| 3-289^ | 4-cyclopropylpyrimidin-5-yl | H | H | 1214 |
| 3-290* | 2-(difluoromethyl)pyridin-3-yl | H | H | 1231 |
| 3-291* | thiazol-2-yl | H | —CH$_3$ | 1172 |
| 3-292^ | 2-morpholinopyridin-4-yl | H | H | 1302 |
| 3-293 | 5-fluoro-2-methoxypyridin-3-yl | H | H | 1227 |
| 3-294* | 4-methylpyrimidin-5-yl | H | H | 1161 |
| 3-295^ | 4-(difluoromethyl)pyridin-3-yl | H | H | 1231 |
| 3-296^ | 2-cyclopropylpyridin-3-yl | H | H | 1212 |

TABLE 3-continued
Formula (3A) Compounds
| Ex # | Rings A and B with (R)$_n$ | R$^c$ | R$^d$ | Mass |
|---|---|---|---|---|
| 3-297 | 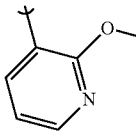 | H | H | 1263 |
| 3-307* | 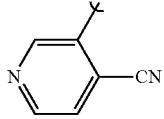 | H | H | 1181 |
| 3-308^ | 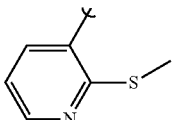 | H | H | 1223 |
| 3-309^ | 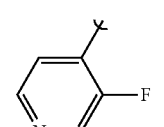 | H | H | 1167 |
| 3-310* | 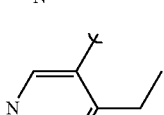 | H | H | 1189 |
| 3-313 | 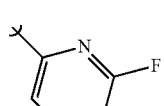 | H | H | 1167 |
| 3-318 | 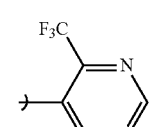 | H | H | 1269 |
| 3-319* | 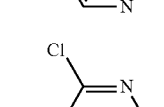 | H | H | 1199 |
| 3-321* | 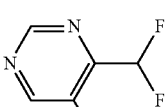 | H | H | 1233 |
| 3-322 | 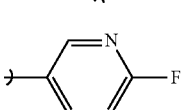 | H | H | 1195 |
| 3-323* | 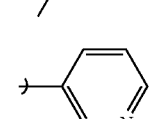 | H | H | 1167 |
| 3-324* | 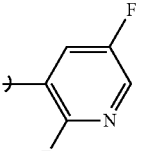 | H | H | 1195 |
| 3-326 | 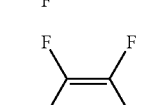 | H | H | 1203 |
| 3-329* | 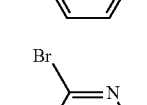 | H | H | 1286 |
| 3-332 | 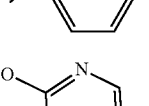 | H | H | 1260 |
| 3-333* | 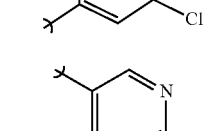 | H | H | 1267 |
| 3-334* | 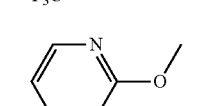 | H | H | 1252 |
| 3-1 | 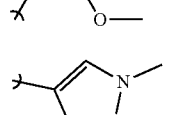 | H | H | 1166 |
| 3-2 | 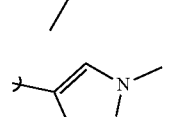 | H | H | 1137 |
| 3-3^ | 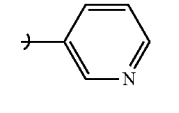 | H | H | 1131 |
| 3-5 | 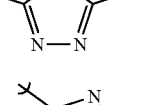 | H | H | 1176 |
| 3-6 | 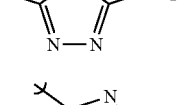 | H | H | 1113 |
| 3-7 | 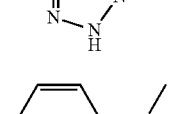 | H | —OH | 1224 |

TABLE 3-continued

Formula (3A) Compounds

| Ex # | Rings A and B with (R)$_n$ | R$^c$ | R$^d$ | Mass |
|---|---|---|---|---|
| 3-9 | 2-methoxypyridin-5-yl | H | H | 1192 |
| 3-10 | tetrahydropyran-4-yl | H | —OH | 1178 |
| 3-11 | cyclohexyl | H | —OH | 1210 |
| 3-13 | 1-methylimidazol-5-yl | H | H | 1139 |
| 3-14* | 1,3,4-thiadiazol-2-yl | H | H | 1146 |
| 3-15 | 5-chloropyridin-2-yl | H | —OH | 1232 |
| 3-16 | 1-(p-tolyl)pyrazol-4-yl | H | —OH | 1358 |
| 3-19 | 1-methyl-3-(trifluoromethyl)pyrazol-5-yl | H | H | 1273 |
| 3-20 | pyridin-2-yl | H | —OH | 1392 |
| 3-22 | 1-(p-tolyl)pyrazol-4-yl | H | H | 1290 |
| 3-23 | tetrahydropyran-4-yl | H | H | 1146 |
| 3-25 | 2-methoxythiazol-4-yl | H | H | 1204 |
| 3-26 | 4-methyloxazol-2-yl | H | H | 1139 |
| 3-27^ | pyridin-2-yl | H | H | 1131 |
| 3-28 | quinolin-8-yl | H | —OH | 1264 |
| 3-29 | 2,4-dimethyl-1H-pyrrol-3-yl | H | H | 1164 |
| 3-30 | benzofuran-3-yl | H | —OH | 1242 |
| 3-32 | 5-methyl-1,3,4-oxadiazol-2-yl | H | H | 1141 |
| 3-33 | 5-methoxypyrazin-2-yl | H | H | 1194 |
| 3-34 | thiophen-2-yl | —OH | —CF$_3$ | 1310 |
| 3-35 | 6-cyanopyridin-3-yl | H | H | 1181 |
| 3-36* | 4-phenylthiazol-2-yl | H | H | 1296 |
| 3-37 | 4,5-dimethylthiazol-2-yl | H | H | 1200 |
| 3-38^ | 4-methylthiazol-2-yl | H | H | 1172 |
| 3-39 | 5-methylthiazol-2-yl | H | H | 1172 |

TABLE 3-continued

Formula (3A) Compounds

| Ex # | Rings A and B with (R)ₙ | $R^c$ | $R^d$ | Mass |
|---|---|---|---|---|
| 3-40 | thiazole-phenyl | H | H | 1296 |
| 3-41 | thiazole-isopropyl | H | H | 1228 |
| 3-42 | benzothiazole | H | H | 1244 |
| 3-43 | thiophene-Cl | H | H | 1210 |
| 3-45* | thiazole | H | H | 1144 |
| 3-46 | thiophene-CN | H | H | 1192 |
| 3-47 | thiazole-OMe | H | H | 1204 |
| 3-48 | thiophene | H | —OH | 1174 |
| 3-51 | methyl-thiazole-phenyl | H | H | 1137 |
| 3-52* | dimethyl-thiazole | H | H | 1200 |
| 3-53 | oxazole | H | —OH | 1143 |
| 3-54 | thiazole | H | —OH | 1204 |
| 3-55 | dimethyl-thiazole | H | —OH | 1232 |
| 3-59 | methyl-isoxazole | H | H | 1139 |
| 3-61 | methyl-thiazole-phenyl | H | H | 1324 |
| 3-62 | thiophene-CF₃ | H | —OH | 1278 |
| 3-63 | furan | H | —OH | 1141 |
| 3-64 | methyl-isoxazole | H | —OH | 1171 |
| 3-65 | methyl-pyrazole-CF₃ | H | —OH | 1305 |
| 3-66 | methyl-thiazole | H | —OH | 1204 |
| 3-67 | tetrazole | H | H | 1113 |
| 3-68 | dimethoxy-pyridine | H | H | 1252 |
| 3-70 | methyl-thiazole | H | H | 1172 |
| 3-71 | ethyl-thiophene | H | H | 1198 |
| 3-72 | methyl-pyridine | H | —OH | 1191 |
| 3-73* | pyrimidine | H | H | 1133 |

TABLE 3-continued

Formula (3A) Compounds

| Ex # | Rings A and B with (R)$_n$ | R$^c$ | R$^d$ | Mass |
|---|---|---|---|---|
| 3-74 | 5-(2-isopropoxy)pyridyl | H | H | 1248 |
| 3-75 | 5-(2-trifluoromethyl)pyridyl | H | —OH | 1299 |
| 3-76^ | 2-methylthiazol-4-yl | H | H | 1172 |
| 3-77 | 5-(2-ethoxy)pyridyl | H | H | 1220 |
| 3-78 | 5-chloropyridin-3-yl | H | —OH | 1232 |
| 3-79 | 5-(2,3-dimethoxy)pyridyl | H | —OH | 1284 |
| 3-80 | 4-chlorothiazol-5-yl | H | —OH | 1244 |
| 3-81^ | 2,4-dimethyloxazol-5-yl | H | H | 1167 |
| 3-82 | 4-(trifluoromethyl)thiazol-2-yl | H | H | 1279 |
| 3-83 | 2,3-dihydrothieno[3,4-b][1,4]dioxin-5-yl | H | —OH | 1290 |
| 3-84 | 5-chlorothiazol-2-yl | H | —OH | 1244 |
| 3-85 | 5-phenylthiophen-2-yl | H | H | 1294 |
| 3-86 | 2-phenylthiazol-4-yl | H | —OH | 1328 |
| 3-88 | 5-phenylthiazol-2-yl | H | —OH | 1328 |
| 3-89 | 3-chlorothiophen-2-yl | H | —OH | 1242 |
| 3-90 | 2,5-dimethylthiophen-3-yl | H | H | 1198 |
| 3-91 | 2-(piperidin-1-yl)thiazol-5-yl | H | H | 1310 |
| 3-92 | 4,5-dimethylthiazol-2-yl | H | —OH | 1232 |
| 3-93 | 3-methoxythiophen-2-yl | H | —OH | 1234 |
| 3-94 | 5-methoxypyridin-3-yl | H | —OH | 1223 |
| 3-95 | 5-(2-trifluoromethyl)pyridyl | H | H | 1267 |
| 3-96 | 5-ethylthiophen-2-yl | H | —OH | 1230 |

TABLE 3-continued

Formula (3A) Compounds

| Ex # | Rings A and B with (R)$_n$ | R$^c$ | R$^d$ | Mass |
|---|---|---|---|---|
| 3-97 | 2-methyl-thiazol-5-yl | H | —OH | 1204 |
| 3-98 | 5-methoxy-2-phenyl-thiazol-4-yl | H | H | 1356 |
| 3-99 | 1-methyl-pyrrol-2-yl | H | —OH | 1167 |
| 3-100 | 2-(piperidin-1-yl)-thiazol-5-yl | H | —OH | 1342 |
| 3-101 | 2,4-dimethyl-oxazol-5-yl | H | —OH | 1199 |
| 3-102 | 5-chloro-thiophen-3-yl | H | H | 1210 |
| 3-103 | 5-methyl-thiazol-2-yl | H | —OH | 1204 |
| 3-104 | 1,2,3-thiadiazol-4-yl | H | —OH | 1177 |
| 3-105 | 5-chloro-thiophen-3-yl | H | —OH | 1242 |
| 3-106 | 5-methyl-furan-2-yl | H | —OH | 1169 |
| 3-107 | 6-(dimethylamino)-pyridin-3-yl | H | H | 1218 |
| 3-108 | 5-chloro-pyridin-3-yl | H | H | 1200 |
| 3-109 | 6-(morpholin-4-yl)-pyridin-3-yl | H | H | 1302 |
| 3-111 | 6-(diethylamino)-pyridin-3-yl | H | H | 1274 |
| 3-113 | 2,5-dimethyl-thiophen-3-yl | H | —OH | 1230 |
| 3-114 | 5-chloro-thiazol-2-yl | H | H | 1212 |
| 3-115^ | 5,6-dimethoxy-pyridin-3-yl | H | H | 1252 |
| 3-116 | 1-phenyl-pyrrol-3-yl | H | H | 1262 |
| 3-117 | 2-phenyl-thiazol-4-yl | H | H | 1296 |
| 3-119* | 1-(difluoromethyl)-pyrazol-4-yl | H | H | 1209 |
| 3-122 | 2-(diethylamino)-thiazol-5-yl | H | H | 1286 |
| 3-123 | 2-isopropyl-thiazol-5-yl | H | H | 1228 |
| 3-126* | 4-methyl-1,2,3-thiadiazol-5-yl | H | —OH | 1205 |
| 3-127 | 4-(trifluoromethyl)-thiazol-2-yl | H | —OH | 1311 |
| 3-128 | 5-(methoxymethyl)-furan-2-yl | H | —OH | 1229 |

TABLE 3-continued

Formula (3A) Compounds

| Ex # | Rings A and B with (R)$_n$ | R$^c$ | R$^d$ | Mass |
|---|---|---|---|---|
| 3-129 | (thiazole with isopropyl) | H | —OH | 1260 |
| 3-130 | (isoxazole with phenyl) | H | —OH | 1296 |
| 3-131 | (furan with phenyl) | H | —OH | 1294 |
| 3-134 | (pyridine with OMe and CF$_3$) | H | H | 1327 |
| 3-135 | (pyridine with OCH$_2$CF$_3$) | H | H | 1327 |
| 3-136 | (pyridine with SMe) | H | H | 1224 |
| 3-137 | (thiazole with morpholine) | H | H | 1314 |
| 3-138 | (pyridine with pyrrolidine) | H | H | 1270 |
| 3-139 | (thiazole with phenyl) | H | —OH | 1328 |
| 3-140 | (thiazole with CF$_3$) | H | H | 1279 |
| 3-141 | (pyrazole with cyclopropyl) | H | H | 1189 |
| 3-142 | (thiophene with OMe) | H | H | 1202 |
| 3-143 | (pyridinone with methyl) | H | H | 1220 |
| 3-144 | (pyridine with OMe) | H | H | 1191 |
| 3-145 | (N-methyl pyridinone) | H | —OH | 1223 |
| 3-146 | (isoxazole with methyl) | H | H | 1139 |
| 3-147 | (furan with methyl and phenyl) | H | H | 1290 |
| 3-149 | (isothiazole) | H | —OH | 1175 |
| 3-150 | (chromene-pyridine) | H | H | 1244 |
| 3-151 | (pyridine with OMe) | H | —OH | 1252 |
| 3-152 | (thiophene with SMe) | H | —OH | 1234 |
| 3-153 | (thiazole with NMe$_2$ and methyl) | H | H | 1258 |
| 3-154 | (oxazole with pyridyl) | H | H | 1265 |
| 3-158 | (thiophene with OMe) | H | H | 1202 |

TABLE 3-continued
Formula (3A) Compounds
| Ex # | Rings A and B with (R)$_n$ | R$^c$ | R$^d$ | Mass |
|---|---|---|---|---|
| 3-159^ | 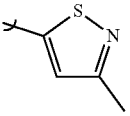 | H | H | 1172 |
| 3-160 | 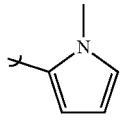 | H | H | 1135 |
| 3-161 | 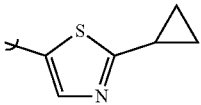 | H | H | 1224 |
| 3-162 | 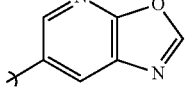 | H | H | 1213 |
| 3-163 | 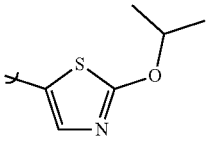 | H | H | 1260 |
| 3-164 | 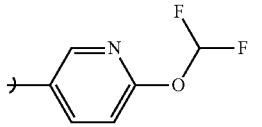 | H | H | 1263 |
| 3-166 | 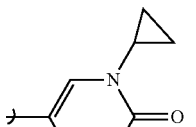 | H | H | 1244 |
| 3-167 | 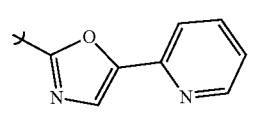 | H | H | 1265 |
| 3-168 | 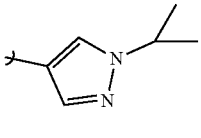 | H | H | 1194 |
| 3-169 | 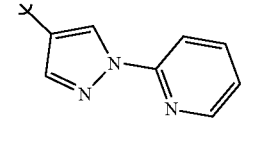 | H | H | 1264 |
| 3-170 | 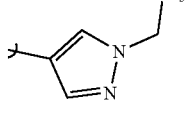 | H | H | 1273 |
| 3-171 | 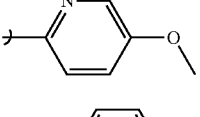 | H | H | 1191 |
| 3-172 | 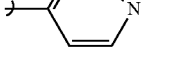 | H | H | 1131 |
| 3-174 | 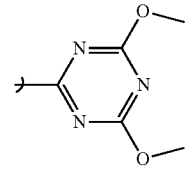 | H | H | 1255 |
| 3-175 | 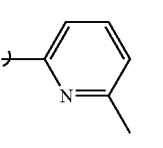 | H | H | 1159 |
| 3-177 | 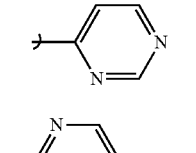 | H | H | 1133 |
| 3-179 | 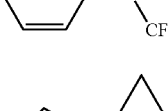 | H | H | 1299 |
| 3-180 | 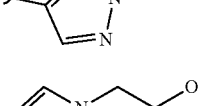 | H | H | 1189 |
| 3-181 | 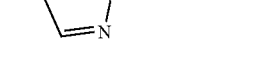 | H | H | 1226 |
| 3-182 | 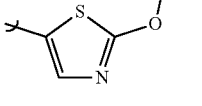 | H | H | 1232 |
| 3-183 | 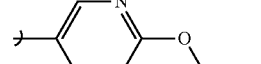 | H | H | 1221 |
| 3-184 | 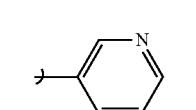 | H | H | 1159 |
| 3-185 | 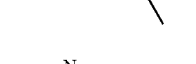 | H | H | 1272 |

TABLE 3-continued
Formula (3A) Compounds
| Ex # | Rings A and B with (R)n | R^c | R^d | Mass |
|---|---|---|---|---|
| 3-186 | 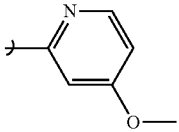 | H | H | 1191 |
| 3-187 | 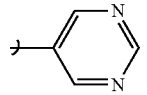 | H | H | 1133 |
| 3-188 | 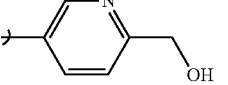 | H | H | 1191 |
| 3-189 | 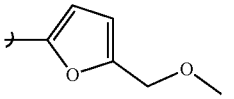 | H | H | 1197 |
| 3-190 | 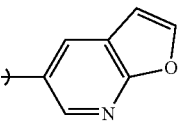 | H | H | 1211 |
| 3-191 | 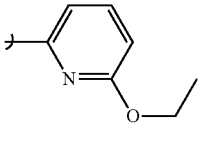 | H | H | 1220 |
| 3-192^ | 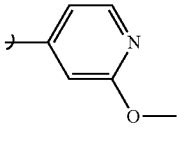 | H | H | 1191 |
| 3-195 | 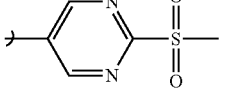 | H | H | 1290 |
| 3-196 | 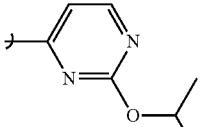 | H | H | 1250 |
| 3-197 | 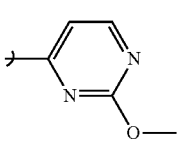 | H | H | 1193 |
| 3-198 | 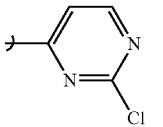 | H | H | 1202 |
| 3-199 | 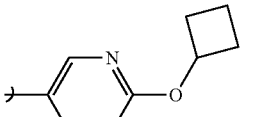 | H | H | 1272 |
| 3-200 | 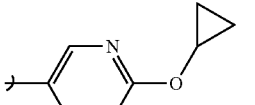 | H | H | 1244 |
| 3-201 | 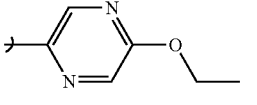 | H | H | 1221 |
| 3-202 | 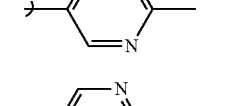 | H | H | 1159 |
| 3-203 | 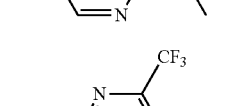 | H | H | 1193 |
| 3-204 | 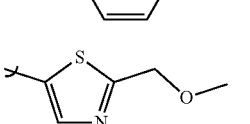 | H | H | 1267 |
| 3-205 | 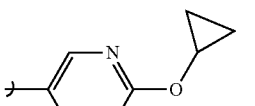 | H | H | 1232 |
| 3-206 | 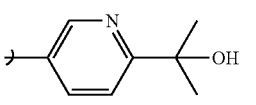 | H | H | 1246 |
| 3-208 | 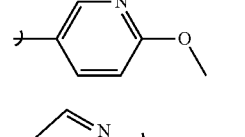 | H | H | 1248 |
| 3-210 | 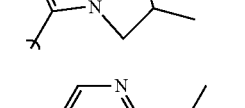 | H | H | 1177 |
| 3-211^ | 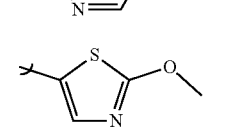 | H | H | 1221 |
| 3-212 |  | H | H | 1179 |
| 3-213 |  | H | H | 1189 |

TABLE 3-continued

Formula (3A) Compounds

| Ex # | Rings A and B with (R)$_n$ | R$^c$ | R$^d$ | Mass |
|---|---|---|---|---|
| 3-214 | 5-ethoxypyridin-3-yl | H | H | 1205 |
| 3-216 | 2-(dimethylamino)thiazol-4-yl | H | H | 1230 |
| 3-219 | 2,4-dimethoxypyrimidin-5-yl | H | H | 1253 |
| 3-221 | N,N-dimethylpicolinamide-5-yl | H | H | 1274 |
| 3-222 | pyridazin-3-yl | H | H | 1133 |
| 3-224 | 1,3-dimethyluracil-5-yl | H | H | 1253 |
| 3-226 | 5-methyl-1,3,4-thiadiazol-2-yl | H | H | 1173 |
| 3-227 | oxetan-3-yl | —CH$_3$ | F | 1181 |
| 3-229 | 2-isopropoxypyrimidin-5-yl | H | H | 1250 |
| 3-230 | pyrazolo[1,5-a]pyridin-5-yl | H | H | 1209 |
| 3-231 | 3-methyl-4H-1,2,4-triazol-5-yl | H | H | 1139 |
| 3-232 | 1-(2,2-difluoroethyl)-1H-pyrazol-4-yl | H | H | 1237 |
| 3-233 | 5-methyl-1H-pyrazol-3-yl | H | H | 1137 |
| 3-234 | 6-methylpyridazin-3-yl | H | H | 1161 |
| 3-235 | pyrazolo[1,5-a]pyrimidin-6-yl | H | H | 1211 |
| 3-236 | 1-isopropylazetidin-3-yl | H | H | 1172 |
| 3-237 | 3-cyclopropyl-1-methyl-1H-pyrazol-4-yl | H | H | 1218 |
| 3-239 | piperidin-4-yl | H | H | 1144 |
| 3-241 | 1,2,3-thiadiazol-4-yl | H | H | 1145 |
| 3-242 | 1-Boc-pyrrolidin-3-yl | H | H | 1316 |
| 3-244 | 6-(methylamino)pyridin-3-yl | H | H | 1189 |
| 3-245 | 1-isopropyl-1H-imidazol-2-yl | H | H | 1194 |
| 3-246 | 2-methyl-1H-imidazol-4-yl | H | H | 1137 |
| 3-247 | 1-Boc-piperidin-4-yl | H | H | 1344 |

TABLE 3-continued

Formula (3A) Compounds

| Ex # | Rings A and B with (R)$_n$ | $R^c$ | $R^d$ | Mass |
|---|---|---|---|---|
| 3-248 | (1-acetylpyrrolidin-3-yl) | H | H | 1200 |
| 3-249 | (1-methyl-1H-imidazol-2-yl) | H | H | 1137 |
| 3-250 | (2-fluoro-6-methylpyridin-3-yl) | H | H | 1195 |
| 3-251 | (5-cyclopropyl-1-methyl-1H-pyrazol-4-yl) | H | H | 1218 |
| 3-255 | (2-cyclopropylpyrimidin-5-yl) | H | H | 1214 |
| 3-256 | (6-(methylsulfonyl)pyridin-3-yl) | H | H | 1288 |
| 3-257 | (pyrrolidin-3-yl) | H | H | 1115 |
| 3-258 | (1-acetylpiperidin-4-yl) | H | H | 1228 |
| 3-260 | (2-ethoxypyrimidin-4-yl) | H | H | 1221 |
| 3-262 | (1-acetylazetidin-3-yl) | H | H | 1171 |
| 3-263 | (1-isobutyrylazetidin-3-yl) | H | H | 1228 |
| 3-264 | (1-methylazetidin-3-yl) | H | H | 1115 |
| 3-265 | (1-isopropyl-2-oxo-1,2-dihydropyridin-5-yl) | H | H | 1248 |
| 3-266 | (3-isopropoxypyridazin-6-yl) | H | H | 1248 |
| 3-267 | (6-hydroxypyridin-3-yl) | H | H | 1163 |
| 3-269 | (6-(N-methylacetamido)pyridin-3-yl) | H | H | 1274 |
| 3-270 | (3-methoxypyridin-4-yl) | H | H | 1191 |
| 3-271 | (5-cyclopropyl-1H-pyrazol-3-yl) | H | H | 1189 |
| 3-272 | (1-methyl-2-oxo-1,2-dihydropyridin-5-yl) | H | H | 1191 |
| 3-276 | (1-methyl-1H-pyrrolo[3,2-b]pyridin-5-yl) | H | H | 1238 |
| 3-277 | (6-(methoxymethyl)pyridin-3-yl) | H | H | 1220 |
| 3-278 | (1,5-dimethyl-1H-pyrazol-3-yl) | H | H | 1165 |
| 3-279 | (5-isopropyl-1H-pyrazol-4-yl) | H | H | 1193 |

TABLE 3-continued

Formula (3A) Compounds

| Ex # | Rings A and B with (R)$_n$ | R$^c$ | R$^d$ | Mass |
|---|---|---|---|---|
| 3-280 | (3-methyl-1H-pyrazol-5-yl) | H | H | 1137 |
| 3-281 | (1H-pyrrolo[3,2-b]pyridinyl) | H | H | 1209 |
| 3-298^ | (2-methyloxazol-5-yl) | H | H | 1139 |
| 3-299* | (4-methoxypyrimidin-2-yl) | H | H | 1229 |
| 3-300^ | (1-cyclobutyl-1H-pyrazol-5-yl) | H | H | 1217 |
| 3-301^ | (1H-pyrazol-3-yl) | H | H | 1109 |
| 3-302 | (3-methoxypyridin-2-yl) | H | F | 1227 |
| 3-303* | (1-propyl-1H-pyrazol-5-yl) | H | H | 1193 |
| 3-304 | (4-cyclopropyl-1H-pyrazol-3-yl) | H | H | 1189 |
| 3-305* | (1-isopropyl-1H-pyrazol-5-yl) | H | H | 1193 |
| 3-306* | (4-cyclopropylpyridin-3-yl) | H | H | 1211 |
| 3-311 | (2-(difluoromethyl)thiazol-5-yl) | H | H | 1243 |
| 3-312 | (2-cyanopyridin-4-yl) | H | H | 1181 |
| 3-314 | (2-(pyrrolidin-1-yl)pyridin-3-yl) | H | H | 1269 |
| 3-315 | (2-morpholinopyridin-3-yl) | H | H | 1301 |
| 3-316 | (5-cyclopropylpyridin-3-yl) | H | H | 1211 |
| 3-317 | (6-cyclopropylpyridin-3-yl) | H | H | 1211 |
| 3-320 | (5-(difluoromethyl)pyridin-3-yl) | H | H | 1231 |
| 3-325 | (2-fluoro-3-methylpyridin-5-yl) | H | H | 1195 |
| 3-327 | (5-methylpyridin-2-yl) | H | H | 1159 |
| 3-328 | (5-cyclopropylpyrazin-2-yl) | H | H | 1213 |
| 3-330 | (5-cyclopropyl-1,3,4-oxadiazol-2-yl) | H | —OH | 1204 |
| 3-331 | (2-chloropyridin-4-yl) | H | H | 1200 |

The following compound names and example #'s refer to the upper section compounds of Table 3.

(3-4). (3S,6R,9S,12R,15S,18R,21S,24R)-3,9,15,21-tetraisobutyl-4,6,10,16,18,22-hexamethyl-12,24-bis(4-

(thiophen-2-ylmethyl)benzyl)-1,7,13,19-tetraoxa-4,10,16,22-tetraazacyclotetracosan-2,5,8,11,14,17,20,23-octaone;

(3-8). (3S,6R,9S,12R,15S,18R,21S,24R)-6,18-bis(4-(furan-2-ylmethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-12). (3S,6R,9S,12R,15S,18R,21S,24R)-3,9,15,21-tetraisobutyl-4,6,10,16,18,22-hexamethyl-12,24-bis(4-(thiazol-5-ylmethyl)benzyl)-1,7,13,19-tetraoxa-4,10,16,22-tetraazacyclotetracosan-2,5,8,11,14,17,20,23-octaone;

(3-17). (3S,6R,9S,12R,15S,18R,21S,24R)-3,9,15,21-tetraisobutyl-4,6,10,16,18,22-hexamethyl-12,24-bis(4-(thiazol-2-ylmethyl)benzyl)-1,7,13,19-tetraoxa-4,10,16,22-tetraazacyclotetracosan-2,5,8,11,14,17,20,23-octaone;

(3-18). (3S,6R,9S,12R,15S,18R,21S,24R)-3,9,15,21-tetraisobutyl-4,6,10,16,18,22-hexamethyl-12,24-bis(4-(oxazol-2-ylmethyl)benzyl)-1,7,13,19-tetraoxa-4,10,16,22-tetraazacyclotetracosan-2,5,8,11,14,17,20,23-octaone;

(3-21). (3S,6R,9S,12R,15S,18R,21S,24R)-6,18-bis(4-((3,5-dimethylisoxazol-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-24). (3S,6R,9S,12R,15S,18R,21S,24R)-3,9,15,21-tetraisobutyl-4,6,10,16,18,22-hexamethyl-12,24-bis(4-((1-methyl-1H-pyrazol-5-yl)methyl)benzyl)-1,7,13,19-tetraoxa-4,10,16,22-tetraazacyclotetracosan-2,5,8,11,14,17,20,23-octaone;

(3-31). (3S,6R,9S,12R,15S,18R,21S,24R)-3,9,15,21-tetraisobutyl-6,18-bis(4-((2-methoxypyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-44). (3S,6R,9S,12R,15S,18R,21S,24R)-3,9,15,21-tetraisobutyl-4,6,10,16,18,22-hexamethyl-12,24-bis(4-((3-methylthiophen-2-yl)methyl)benzyl)-1,7,13,19-tetraoxa-4,10,16,22-tetraazacyclotetracosan-2,5,8,11,14,17,20,23-octaone;

(3-49). (3S,6R,9S,12R,15S,18R,21S,24R)-6,18-bis(4-((1,3-dimethyl-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-50). 2,2'-(((((2R,5S,8R,11 S,14R,17S,20R,23S)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))bis(methylene))bis(furan-3-carbonitrile);

(3-56). (3S,6R,9S,12R,15S,18R,21S,24R)-3,9,15,21-tetraisobutyl-4,6,10,16,18,22-hexamethyl-12,24-bis(4-(thiophen-3-ylmethyl)benzyl)-1,7,13,19-tetraoxa-4,10,16,22-tetraazacyclotetracosan-2,5,8,11,14,17,20,23-octaone;

(3-57). (3S,6R,9S,12R,15S,18R,21S,24R)-3,9,15,21-tetraisobutyl-4,6,10,16,18,22-hexamethyl-12,24-bis(4-(oxazol-4-ylmethyl)benzyl)-1,7,13,19-tetraoxa-4,10,16,22-tetraazacyclotetracosan-2,5,8,11,14,17,20,23-octaone;

(3-60). 4,4'-(((((2R,5S,8R,11 S,14R,17S,20R,23S)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))bis(methylene))bis(furan-2-carbonitrile);

(3-69). (3S,6R,9S,12R,15S,18R,21S,24R)-3,9,15,21-tetraisobutyl-6,18-bis(4-((6-methoxypyridin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-87). (3S,6R,9S,12R,15S,18R,21S,24R)-6,18-bis(4-((3-chlorothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-110). (3S,6R,9S,12R,15S,18R,21S,24R)-3,9,15,21-tetraisobutyl-6,18-bis(4-((3-methoxythiophen-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-112). (3S,6R,9S,12R,15S,18R,21S,24R)-6,18-bis(4-((4-chlorothiazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-118). (3S,6R,9S,12R,15S,18R,21S,24R)-6,18-bis(4-((5-fluoro-6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-120). (3S,6R,9S,12R,15S,18R,21S,24R)-3,9,15,21-tetraisobutyl-4,6,10,16,18,22-hexamethyl-12,24-bis(4-((4-methyl-1,2,3-thiadiazol-5-yl)methyl)benzyl)-1,7,13,19-tetraoxa-4,10,16,22-tetraazacyclotetracosan-2,5,8,11,14,17,20,23-octaone;

(3-121). (3S,6R,9S,12R,15S,18R,21S,24R)-3,9,15,21-tetraisobutyl-6,18-bis(4-((6-methoxy-2-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-124). (3S,6R,9S,12R,15S,18R,21S,24R)-3,9,15,21-tetraisobutyl-4,6,10,16,18,22-hexamethyl-12,24-bis(4-((4-methylthiophen-2-yl)methyl)benzyl)-1,7,13,19-tetraoxa-4,10,16,22-tetraazacyclotetracosan-2,5,8,11,14,17,20,23-octaone;

(3-125). (3S,6R,9S,12R,15S,18R,21S,24R)-6,18-bis(4-((3-bromothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-132). (3S,6R,9S,12R,15S,18R,21S,24R)-6-(4-((R)-(3-bromothiophen-2-yl)(hydroxy)methyl)benzyl)-18-(4-((S)-(3-bromothiophen-2-yl)(hydroxy)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-133). (3S,6R,9S,12R,15S,18R,21S,24R)-3,9,15,21-tetraisobutyl-6,18-bis(4-((6-methoxy-4-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-148). (3S,6R,9S,12R,15S,18R,21S,24R)-3,9,15,21-tetraisobutyl-4,6,10,16,18,22-hexamethyl-12,24-bis(4-(oxazol-5-ylmethyl)benzyl)-1,7,13,19-tetraoxa-4,10,16,22-tetraazacyclotetracosan-2,5,8,11,14,17,20,23-octaone;

(3-155). (3S,6R,9S,12R,15S,18R,21S,24R)-3,9,15,21-tetraisobutyl-4,6,10,16,18,22-hexamethyl-12,24-bis(4-((4-methylthiazol-5-yl)methyl)benzyl)-1,7,13,19-tetraoxa-4,10,16,22-tetraazacyclotetracosan-2,5,8,11,14,17,20,23-octaone;

(3-156). (3S,6R,9S,12R,15S,18R,21S,24R)-3,9,15,21-tetraisobutyl-6,18-bis(4-(isothiazol-5-ylmethyl)benzyl)-4,10,12,16,22,24-hexamethyl-1,7,13,19-tetraoxa-4,10,16,22-tetraazacyclotetracosan-2,5,8,11,14,17,20,23-octaone;

(3-157). (3S,6R,9S,12R,15S,18R,21S,24R)-3,9,15,21-tetraisobutyl-4,6,10,16,18,22-hexamethyl-12,24-bis(4-((5-methylfuran-2-yl)methyl)benzyl)-1,7,13,19-tetraoxa-4,10,16,22-tetraazacyclotetracosan-2,5,8,11,14,17,20,23-octaone;

(3-165). (3S,6R,9S,12R,15S,18R,21S,24R)-6,18-bis(4-((2-ethoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-173). (3S,6R,9S,12R,15S,18R,21S,24R)-6,18-bis(4-(furan-3-ylmethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-176). (3S,6R,9S,12R,15S,18R,21S,24R)-6,18-bis(4-((2-(dimethylamino)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-178). (3S,6R,9S,12R,15S,18R,21S,24R)-3,9,15,21-tetraisobutyl-4,6,10,16,18,22-hexamethyl-12,24-bis(4-((2-morpholinopyrimidin-5-yl)methyl)benzyl)-1,7,13,19-tetraoxa-4,10,16,22-tetraazacyclotetracosan-2,5,8,11,14,17,20,23-octaone;

(3-193). (3S,6R,9S,12R,15S,18R,21S,24R)-3,9,15,21-tetraisobutyl-6,18-bis(4-((3-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-194). (3S,6R,9S,12R,15S,18R,21S,24R)-6,18-bis(4-((5-fluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-207). (3S,6R,9S,12R,15S,18R,21S,24R)-3,9,15,21-tetraisobutyl-6,18-bis(4-(1-(6-methoxypyridin-3-yl)ethyl)benzyl)-4,10,12,16,22,24-hexamethyl-1,7,13,19-tetraoxa-4,10,16,22-tetraazacyclotetracosan-2,5,8,11,14,17,20,23-octaone;

(3-209). (3S,6R,9S,12R,15S,18R,21S,24R)-3,9,15,21-tetraisobutyl-6,18-bis(4-((2-methoxy-4-methylthiazol-5-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-215). 3S,6R,9S,12R,15S,18R,21S,24R)-3,9,15,21-tetraisobutyl-6,18-bis(4-((3-methoxypyridin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-217). (3S,6R,9S,12R,15S,18R,21S,24R)-3,9,15,21-tetraisobutyl-6,18-bis(4-((4-methoxypyrimidin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-218). (3S,6R,9S,12R,15S,18R,21S,24R)-3,9,15,21-tetraisobutyl-6,18-bis(4-((6-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-220). (3S,6R,9S,12R,15S,18R,21S,24R)-6,18-bis(4-(1-fluoro-1-(2-methoxypyridin-3-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-223). (3S,6R,9S,12R,15S,18R,21S,24R)-3,9,15,21-tetraisobutyl-4,6,10,16,18,22-hexamethyl-12,24-bis(4-((4-methylpyridin-3-yl)methyl)benzyl)-1,7,13,19-tetraoxa-4,10,16,22-tetraazacyclotetracosan-2,5,8,11,14,17,20,23-octaone;

(3-225). (3S,6R,9S,12R,15S,18R,21S,24R)-6,18-bis(4-(1-fluoro-1-(6-methoxypyridin-2-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-228). (3S,6R,9S,12R,15S,18R,21S,24R)-3,9,15,21-tetraisobutyl-6,18-bis(4-((4-isopropyl-1,2,3-thiadiazol-5-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-238). (3S,6R,9S,12R,15S,18R,21S,24R)-3,9,15,21-tetraisobutyl-4,6,10,16,18,22-hexamethyl-12,24-bis(4-((2-(trifluoromethyl)pyridin-3-yl)methyl)benzyl)-1,7,13,19-tetraoxa-4,10,16,22-tetraazacyclotetracosan-2,5,8,11,14,17,20,23-octaone;

(3-240). (3S,6R,9S,12R,15S,18R,21S,24R)-6,18-bis(4-((2,6-dimethylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-243). (3S,6R,9S,12R,15S,18R,21S,24R)-3,9,15,21-tetraisobutyl-4,6,10,16,18,22-hexamethyl-12,24-bis(4-((5-methyl-1H-pyrazol-4-yl)methyl)benzyl)-1,7,13,19-tetraoxa-4,10,16,22-tetraazacyclotetracosan-2,5,8,11,14,17,20,23-octaone;

(3-252). (3S,6R,9S,12R,15S,18R,21S,24R)-6,18-bis(4-(1-fluoro-1-(5-methoxypyrazin-2-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-253). (3S,6R,9S,12R,15S,18R,21S,24R)-6,18-bis(4-((1-ethyl-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-254). (3S,6R,9S,12R,15S,18R,21S,24R)-3,9,15,21-tetraisobutyl-6,18-bis(4-(isothiazol-4-ylmethyl)benzyl)-4,10,12,16,22,24-hexamethyl-1,7,13,19-tetraoxa-4,10,16,22-tetraazacyclotetracosan-2,5,8,11,14,17,20,23-octaone;

(3-259). (3S,6R,9S,12R,15S,18R,21S,24R)-6,18-bis(4-((6-hydroxypyridin-3-yl)(methoxy)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-261). (3S,6R,9S,12R,15S,18R,21S,24R)-3,9,15,21-tetraisobutyl-6,18-bis(4-(1-(2-methoxypyridin-3-yl)ethyl)benzyl)-4,10,12,16,22,24-hexamethyl-1,7,13,19-tetraoxa-4,10,16,22-tetraazacyclotetracosan-2,5,8,11,14,17,20,23-octaone;

(3-268). (3S,6R,9S,12R,15S,18R,21S,24R)-6,18-bis(4-((1-cyclopropyl-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-273). (3S,6R,9R,12R,15R,18R,21S,24S)-3,9,15,21-tetraisobutyl-4,6,10,16,18,22-hexamethyl-12,24-bis[[4-[(2-methyl-3-pyridyl)methyl]phenyl]methyl]-1,7,13,19-tetraoxa-4,10,16,22-tetrazacyclotetracosane-2,5,8,11,14,17,20,23-octaone;

(3-274). (3R,6R,9R,12R,15S,18S,21S,24R)-3,9,15,21-tetraisobutyl-6,18-bis(4-((5-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-275). (3S,6R,9S,12R,15S,18R,21S,24R)-6,18-bis(4-((1-(cyclopropylmethyl)-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-282). (3S,6R,9S,12R,15S,18R,21S,24R)-3,9,15,21-tetraisobutyl-6,18-bis(4-((4-methoxypyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-283). (3S,6R,9S,12R,15S,18R,21S,24R)-3,9,15,21-tetraisobutyl-6,18-bis(4-((4-isopropylpyrimidin-5-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3-284). (3S,6R,9S,12R,15S,18R,21S,24R)-6,18-bis(4-((3-cyclopropylisoxazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-285). (3S,6R,9S,12R,15S,18R,21S,24R)-6-(4-((R)-fluoro(thiazol-2-yl)methyl)benzyl)-18-(4-((S)-fluoro(thiazol-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-286). (3S,6R,9S,12R,15S,18R,21S,24R)-6,18-bis(4-((1-(2-fluoroethyl)-1H-pyrazol-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-287). (3S,6R,9S,12R,15S,18R,21S,24R)-6,18-bis(4-((6-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-288). (3S,6R,9S,12R,15S,18R,21S,24R)-3,9,15,21-tetraisobutyl-4,6,10,16,18,22-hexamethyl-12,24-bis(4-((4-methylisothiazol-5-yl)methyl)benzyl)-1,7,13,19-tetraoxa-4,10,16,22-tetraazacyclotetracosan-2,5,8,11,14,17,20,23-octaone;

(3-289). (3S,6R,9S,12R,15S,18R,21S,24R)-6,18-bis(4-((4-cyclopropylpyrimidin-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-290). (3S,6R,9S,12R,15S,18R,21S,24R)-6,18-bis(4-((2-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-291). (3S,6R,9S,12R,15S,18R,21S,24R)-3,9,15,21-tetraisobutyl-4,6,10,16,18,22-hexamethyl-12,24-bis(4-((R)-1-(thiazol-2-yl)ethyl)benzyl)-1,7,13,19-tetraoxa-4,10,16,22-tetraazacyclotetracosan-2,5,8,11,14,17,20,23-octaone;

(3-292). (3S,6R,9S,12R,15S,18R,21S,24R)-3,9,15,21-tetraisobutyl-4,6,10,16,18,22-hexamethyl-12,24-bis(4-((2-morpholinopyridin-4-yl)methyl)benzyl)-1,7,13,19-tetraoxa-4,10,16,22-tetraazacyclotetracosan-2,5,8,11,14,17,20,23-octaone;

(3-293). (3S,6R,9S,12R,15S,18R,21S,24R)-6,18-bis(4-((5-fluoro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-294). (3S,6R,9S,12R,15S,18R,21S,24R)-3,9,15,21-tetraisobutyl-4,6,10,16,18,22-hexamethyl-12,24-bis(4-((4-methylpyrimidin-5-yl)methyl)benzyl)-1,7,13,19-tetraoxa-4,10,16,22-tetraazacyclotetracosan-2,5,8,11,14,17,20,23-octaone;

(3-295). (3S,6R,9S,12R,15S,18R,21S,24R)-6,18-bis(4-((4-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-296). (3S,6R,9S,12R,15S,18R,21S,24R)-6,18-bis(4-((2-cyclopropylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone; and (3-297). (3S,6R,9S,12R,15S,18R,21S,24R)-6,18-bis(4-((2-(difluoromethoxy)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone, (3-307). 3,3'-(((((2R,5S,8R,11S,14R,17S,20R,23S)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))bis(methylene))diisonicotinonitrile;

(3-308). (3S,6R,9S,12R,15S,18R,21S,24R)-3,9,15,21-tetraisobutyl-4,6,10,16,18,22-hexamethyl-12,24-bis(4-((2-(methylthio)pyridin-3-yl)methyl)benzyl)-1,7,13,19-tetraoxa-4,10,16,22-tetraazacyclotetracosan-2,5,8,11,14,17,20,23-octaone;

(3-309). (3S,6R,9S,12R,15S,18R,21S,24R)-6-(4-((3-fluoropyridin-4-yl)methyl)benzyl)-3,9,15,21-tetraisobutyl-4,10,12,16,22,24-hexamethyl-18-(4-((3-methylpyridin-4-yl)methyl)benzyl)-1,7,13,19-tetraoxa-4,10,16,22-tetraazacyclotetracosan-2,5,8,11,14,17,20,23-octaone;

(3-310). (3S,6R,9S,12R,15S,18R,21S,24R)-6,18-bis(4-((4-ethylpyrimidin-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-313). (3S,6R,9S,12R,15S,18R,21S,24R)-6,18-bis(4-((6-fluoropyridin-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-318). (3S,6R,9S,12R,15S,18R,21S,24R)-3,9,15,21-tetraisobutyl-4,6,10,16,18,22-hexamethyl-12,24-bis(4-((4-(trifluoromethyl)pyrimidin-5-yl)methyl)benzyl)-1,7,13,19-tetraoxa-4,10,16,22-tetraazacyclotetracosan-2,5,8,11,14,17,20,23-octaone;

(3-319). (3S,6R,9S,12R,15S,18R,21S,24R)-6,18-bis(4-((2-chloropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-321). (3S,6R,9S,12R,15S,18R,21S,24R)-6,18-bis(4-((4-(difluoromethyl)pyrimidin-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-322). (3S,6R,9S,12R,15S,18R,21S,24R)-6,18-bis(4-((6-fluoro-4-methylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-323). (3S,6R,9S,12R,15S,18R,21S,24R)-6,18-bis(4-((2-fluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-324). (3S,6R,9S,12R,15S,18R,21S,24R)-6,18-bis(4-((2,5-difluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-326). (3S,6R,9S,12R,15S,18R,21S,24R)-6,18-bis(4-((2,3-difluoropyridin-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-329). (3S,6R,9S,12R,15S,18R,21S,24R)-6,18-bis(4-((2-bromopyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-332). (3S,6R,9S,12R,15S,18R,21S,24R)-6,18-bis(4-((5-chloro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3-333). (3S,6R,9S,12R,15S,18R,21S,24R)-3,9,15,21-tetraisobutyl-4,6,10,16,18,22-hexamethyl-12,24-bis(4-((4-(trifluoromethyl)pyridin-3-yl)methyl)benzyl)-1,7,13,19-tetraoxa-4,10,16,22-tetraazacyclotetracosan-2,5,8,11,14,17,20,23-octaone;

(3-334). (3S,6R,9S,12R,15S,18R,21S,24R)-6,18-bis(4-((2,3-dimethoxypyridin-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone, stereoisomers thereof, and veterinary acceptable salts thereof.

NMR data (1H NMR: 400 MHz, DMSO-d6, δ ppm) for the named Table 3 compounds are shown below:

(3-4). δ: 6.8-7.4 (m, 14H), 5.0-5.8 (m, 8H), (4.4 (m, 1H)), 4.1 (s, 4H), 2.6-3.2 (m, 16H), 1.1-1.8 (m, 13H), 0.6-1.0 (m, 30H);

(3-8). δ: 7.5 (s, 2H), 7.1-7.4 (m, 8H), 6.35 (s, 2H), 6.1 (s, 2H), 5.0-5.8 (m, 8H), 4.4 (m, 0.68H), 3.9 (s, 4H), 2.7-3.1 (m, 16H), 1.1-1.8 (m, 18H), 0.6-1.0 (m, 28H);

(3-12). δ: 0.68-0.94 (m, 26H), 1.23-1.70 (m, 16H), 2.66-3.06 (m, 16H), 4.17 (s, 4H), 4.40-4.42 (m, 1H), 5.02-5.71 (m, 7H), 7.18-7.26 (m, 8H), 7.70 (brs, 2H), 8.92 (s, 2H);

(3-17). δ: 0.70-0.94 (m, 26H), 1.23-1.70 (m, 16H), 2.67-3.04 (m, 16H), 4.30 (s, 4H), 4.40-4.42 (m, 1H), 5.02-5.71 (m, 7H), 7.26-7.28 (m, 8H), 7.57 (d, J=2.8 Hz, 2H), 7.70 (d, J=2.8 Hz, 2H);

(3-18). δ: 0.70-0.94 (m, 26H), 1.23-1.70 (m, 16H), 2.67-3.04 (m, 16H), 4.09 (s, 4H), 4.40-4.42 (m, 1H), 5.02-5.71 (m, 7H), 7.12 (brs, 2H), 7.18-7.28 (m, 8H), 7.98 (brs, 2H);

(3-21). δ: 0.68-0.94 (m, 26H), 1.23-1.70 (m, 16H), 1.99 (s, 6H), 2.31 (s, 6H), 2.66-3.02 (m, 16H), 3.65 (s, 4H), 4.40-4.42 (m, 1H), 5.02-5.69 (m, 7H), 7.06-7.23 (m, 8H);

(3-24). δ: 7.2-7.35 (m, 6H), 7.1-7.2 (m, 4H), 5.9-5.95 (m, 2H), 5.0-5.8 (m, 8H), 4.4 (m, 0.8H), 4.0 (s, 4H), 3.65 (s, 6H), 2.7-3.1 (m, 15H), 1.1-1.8 (m, 16H), 0.6-1.0 (m, 29H);

(3-31). δ: 0.62-1.79 (m, 42H) 2.65-3.10 (m, 16H) 3.80-3.90 (m, 10H) 4.36-4.46 (m, 1H) 4.99-5.74 (m, 7H) 6.84-6.96 (m, 2H) 7.09-7.17 (m, 4H) 7.18-7.27 (m, 4H) 7.37-7.47 (m, 2H) 7.96-8.06 (m, 2H);

(3-44). δ: 0.68-0.94 (m, 26H), 1.23-1.70 (m, 16H), 2.12 (s, 6H), 2.66-3.06 (m, 16H), 4.01 (s, 4H), 4.40-4.42 (m, 1H), 5.02-5.71 (m, 7H), 6.82-6.83 (m, 2H), 7.11-7.22 (m, 10H);

(3-49). δ: 0.68-0.94 (m, 26H), 1.23-1.70 (m, 16H), 2.04 (s, 6H), 2.66-3.06 (m, 16H), 3.56 (s, 6H), 3.90 (s, 4H), 4.40-4.42 (m, 1H), 5.02-5.71 (m, 9H), 7.11-7.25 (m, 8H);

(3-50). δ: 0.67-0.94 (m, 26H), 1.23-1.71 (m, 16H), 2.67-3.05 (m, 16H), 4.15 (s, 4H), 4.40-4.42 (m, 1H), 5.02-5.70 (m, 7H), 6.89 (brs, 2H), 7.15-7.18 (m, 4H), 7.27-7.30 (m, 4H), 7.78 (brs, 2H);

(3-56). δ: 0.68-0.95 (m, 26H), 1.23-1.69 (m, 16H), 2.67-3.05 (m, 16H), 3.90 (s, 4H), 4.40-4.42 (m, 1H), 5.03-5.70 (m, 7H), 6.91-7.43 (m, 14H);

(3-57). δ: 0.70-0.94 (m, 26H), 1.23-1.70 (m, 16H), 2.67-3.04 (m, 16H), 3.79 (s, 4H), 4.40-4.42 (m, 1H), 5.02-5.73 (m, 7H), 7.17-7.21 (m, 8H), 7.79-7.81 (m, 2H), 8.26 (s, 2H);

(3-58). δ: 0.68-0.94 (m, 26H), 1.23-1.70 (m, 16H), 2.39 (s, 6H), 2.66-3.06 (m, 16H), 3.99 (s, 4H), 4.40-4.42 (m, 1H), 5.02-5.69 (m, 7H), 7.11-7.21 (m, 8H), 8.78 (s, 2H);

(3-60). δ: 0.68-0.94 (m, 26H), 1.23-1.70 (m, 16H), 2.66-3.02 (m, 16H), 4.05 (s, 4H), 4.40-4.42 (m, 1H), 5.02-5.70 (m, 7H), 6.45 (brs, 2H), 7.17-7.36 (m, 8H), 7.52 (brs, 2H);

(3-69). δ: 0.61-0.99 (m, 27H), 1.15-1.76 (m, 15H), 2.64-2.94 (m, 12H), 2.96-3.11 (m, 3H), 3.82 (s, 6H), 3.95 (s, 4H), 4.36-4.48 (m, 1H), 4.99-5.54 (m, 6H), 5.63-5.75 (m, 2H), 6.61 (d, J=8.2 Hz, 2H) 6.73-6.82 (m, 2H), 7.13-7.30 (m, 1H), 7.23 (s, 7H), 7.54-7.64 (m, 2H);

(3-87). δ: 0.68-0.95 (m, 26H), 1.23-1.70 (m, 16H), 2.67-3.05 (m, 16H), 4.07 (s, 4H), 4.40-4.42 (m, 1H), 5.02-5.73 (m, 7H), 7.01 (d, J=5.2 Hz, 2H), 7.15-7.17 (m, 4H), 7.24-7.27 (m, 4H), 7.48-7.50 (m, 2H);

(3-110). δ: 0.67-0.94 (m, 27H), 1.23-1.68 (m, 15H), 2.67-3.10 (m, 16H), 3.77 (s, 6H), 3.91 (s, 4H), 4.39-4.4.42 (m, 1H), 5.01-5.70 (m, 7H), 6.96-6.99 (m, 2H), 7.10-7.25 (m, 10H);

(3-112). δ: 0.68-0.95 (m, 26H), 1.24-1.70 (m, 16H), 2.67-3.05 (m, 16H), 4.12 (s, 4H), 4.40-4.42 (m, 1H), 5.04-5.70 (m, 7H), 7.17-7.27 (m, 8H), 8.98 (s, 2H);

(3-118). δ: 0.68-0.95 (m, 26H), 1.24-1.69 (m, 16H), 2.67-3.05 (m, 16H), 3.87 (s, 4H), 3.89 (s, 6H), 4.40-4.42 (m, 1H), 5.04-5.70 (m, 7H), 7.17-7.24 (m, 8H), 7.46-7.50 (m, 2H), 7.88 (s, 2H);

(3-120). δ: 0.70-0.94 (m, 26H), 1.23-1.70 (m, 16H), 2.60 (s, 6H), 2.67-3.04 (m, 16H), 4.29 (s, 4H), 4.40-4.42 (m, 1H), 5.03-5.71 (m, 7H), 7.20-7.28 (m, 8H);

(3-121). δ: 0.68-0.94 (m, 26H), 1.23-1.70 (m, 16H), 2.26 (s, 6H), 2.66-3.02 (m, 16H), 3.76 (s, 6H), 3.84 (s, 4H), 4.40-4.42 (m, 1H), 5.02-5.70 (m, 7H), 6.54-6.56 (m, 2H), 7.02-7.20 (m, 8H), 7.38-7.40 (m, 2H);

(3-124). δ 0.65-0.94 (m, 27H), 1.02-1.80 (m, 15H), 2.12 (s, 6H), 2.67-3.10 (m, 16H), 4.03 (bs, 4H), 4.42-4.46 (m, 1H), 5.02-5.69 (m, 7H), 6.65 (s, 2H), 6.83-6.87 (m, 2H), 7.11-7.23 (m, 8H);

(3-125). δ 0.68-0.94 (m, 27H), 1.23-1.75 (m, 15H), 2.68-3.08 (m, 16H), 4.07 (s, 4H), 4.40-4.45 (m, 1H), 5.02-5.73 (m, 7H), 7.04-7.27 (m, 10H), 7.50-7.51 (m, 2H);

(3-132). δ 0.68-0.94 (m, 26H), 1.20-1.78 (m, 16H), 2.66-3.10 (m, 16H), 4.36-4.42 (m, 1H), 5.02-5.72 (m, 7H), 5.88-5.91 (m, 2H), 6.40-6.50 (m, 2H), 6.99 (d, J=5 Hz, 2H), 7.25-7.38 (m, 8H), 7.54-7.60 (m, 2H);

(3-133). δ: 0.68-0.94 (m, 26H), 1.23-1.70 (m, 16H), 2.08 (s, 6H), 2.66-3.02 (m, 16H), 3.79 (s, 6H), 3.86 (s, 4H), 4.40-4.42 (m, 1H), 5.02-5.70 (m, 7H), 6.61 (s, 2H), 7.04-7.22 (m, 8H), 7.89 (s, 2H);

(3-148). δ: 0.70-0.94 (m, 26H), 1.23-1.68 (m, 16H), 2.67-3.04 (m, 16H), 4.00 (s, 4H), 4.40-4.42 (m, 1H), 5.03-5.71 (m, 7H), 6.88 (s, 2H), 7.16-7.25 (m, 8H), 8.21 (s, 2H);

(3-155). δ: 8.76-8.95 (m, 2H), 7.02-7.35 (m, 8H), 4.95-5.81 (m, 10H), 4.36-4.45 (m, 1H), 4.02-4.12 (m, 4H), 2.59-3.19 (m, 16H), 2.26-2.42 (m, 6H), 1.10-1.80 (m, 16H), 0.62-1.01 (m, 26H);

(3-156). δ: 0.68-0.95 (m, 26H), 1.21-1.70 (m, 16H), 2.68-3.05 (m, 16H), 4.28 (s, 4H), 4.40-4.42 (m, 1H), 5.02-5.71 (m, 7H), 7.18-7.30 (m, 10H), 8.40-8.42 (m, 2H);

(3-157). δ: 0.68-0.94 (m, 26H), 1.23-1.70 (m, 16H), 2.17 (s, 6H), 2.66-3.06 (m, 16H), 3.85 (s, 4H), 4.40-4.42 (m, 1H), 5.02-5.69 (m, 7H), 5.91-5.93 (m, 4H), 7.12-7.23 (m, 8H);

(3-165). δ: 0.68-0.94 (m, 26H), 1.23-1.70 (m, 22H), 2.66-3.06 (m, 16H), 3.82 (s, 4H), 4.29 (q, J=7 Hz, 4H), 4.40-4.42 (m, 1H), 5.02-5.69 (m, 7H), 6.85-6.89 (m, 2H), 7.15-7.23 (m, 8H), 7.43-7.46 (m, 2H), 7.97-7.99 (m, 2H);

(3-173). δ: 0.68-0.94 (m, 26H), 1.23-1.70 (m, 16H), 2.66-3.06 (m, 16H), 3.69 (s, 4H), 4.40-4.42 (m, 1H), 5.02-5.71 (m, 7H), 6.28-6.29 (m, 2H), 7.11-7.24 (m, 8H), 7.43-7.44 (m, 2H), 7.55 (brs, 2H);

(3-176). δ: 0.68-0.95 (m, 26H), 1.24-1.69 (m, 16H), 2.67-3.05 (m, 28H), 3.95 (s, 4H), 4.40-4.42 (m, 1H), 5.04-5.72 (m, 7H), 6.83-6.87 (m, 2H), 7.08-7.10 (m, 4H), 7.19-7.31 (m, 6H), 8.08-8.09 (m, 2H);

(3-178). δ: 8.16-8.40 (m, 4H), 7.03-7.48 (m, 8H), 4.99-5.82 (m, 8H), 4.33-4.44 (m, 1H), 3.70-3.86 (m, 4H), 3.3-3.5 (m, 4H), 2.62-3.14 (m, 16H), 1.02-1.88 (m, 16H), 0.61-0.97 (m, 27H);

(3-193). δ: 0.68-0.94 (m, 26H), 1.23-1.70 (m, 16H), 2.66-3.06 (m, 16H), 3.89 (s, 6H), 4.04 (s, 4H), 4.40-4.42 (m, 1H), 5.02-5.71 (m, 7H), 7.13-7.21 (m, 8H), 8.07-8.09 (m, 4H);

(3-194). δ: 8.21-8.68 (m, 4H), 7.48-7.81 (m, 2H), 7.12-7.42 (m, 8H), 4.96-5.80 (m, 8H), 4.32-4.55 (m, 1H), 3.76-4.08 (m, 4H), 2.63-3.17 (m, 16H), 1.07-1.79 (m, 16H), 0.62-1.01 (m, 26H);

(3-207). δ: 0.61-1.01 (m, 26H), 1.13-1.77 (m, 16H), 2.64-3.10 (m, 16H), 3.75 (s, 6H), 4.12 (m, 2H), 4.37-4.46 (m, 1H), 4.98-5.74 (m, 8H), 6.72 (d, 2H), 7.15-7.28 (m, 8H), 7.54 (d, 2H), 8.02-8.11 (m, 2H);

(3-209). δ: 0.68-0.95 (m, 26H), 1.24-1.69 (m, 16H), 2.17 (s, 6H), 2.67-3.05 (m, 16H), 3.90 (s, 10H), 4.40-4.42 (m, 1H), 5.04-5.69 (m, 7H), 7.11-7.13 (m, 4H), 7.22-7.25 (m, 4H);

(3-215). δ: 0.69-0.94 (m, 26H), 1.23-1.68 (m, 16H), 2.67-3.05 (m, 16H), 3.76 (s, 6H), 4.00 (s, 4H), 4.40-4.42 (m, 1H), 5.02-5.68 (m, 7H), 7.08-7.21 (m, 10H), 7.32-7.35 (m, 2H), 8.00-8.02 (m, 2H);

(3-217). δ: 0.69-0.94 (m, 26H), 1.23-1.68 (m, 16H), 2.67-3.05 (m, 16H), 3.88 (s, 6H), 4.05 (s, 4H), 4.40-4.42 (m, 1H), 5.02-5.68 (m, 7H), 6.74-6.76 (m, 2H), 7.23-7.25 (m, 8H), 8.39-8.40 (m, 2H);

(3-218). δ: 0.69-0.94 (m, 26H), 1.23-1.70 (m, 16H), 2.67-3.05 (m, 16H), 3.87 (s, 6H), 4.00 (s, 4H), 4.40-4.42 (m, 1H), 5.02-5.70 (m, 7H), 7.23-7.25 (m, 8H), 8.09-8.12 (m, 4H);

(3-220). δ: 0.65-0.94 (m, 26H), 1.23-1.68 (16H), 2.01 (s, 3H), 2.07 (3H), 2.67-3.04 (m, 16H), 3.67 (s, 6H), 4.41-4.43 (m, 1H), 5.03-5.70 (m, 7H), 7.05-7.08 (m, 2H), 7.25-7.29 (m, 8H), 7.85-7.87 (m, 2H), 8.10-8.15 (m, 2H);

(3-223). δ: 0.69-0.94 (m, 26H), 1.23-1.68 (m, 16H), 2.16 (s, 6H), 2.67-3.05 (m, 16H), 3.96 (s, 4H), 4.40-4.42 (m, 1H), 5.02-5.68 (m, 7H), 7.06-7.24 (m, 10H), 8.28-8.30 (m, 4H);

(3-225). δ: 0.63-0.92 (m, 26H), 1.23-1.69 (m, 16H), 1.98 (s, 3H), 2.04 (s, 3H), 2.67-3.04 (m, 16H), 3.83 (s, 6H), 4.38-4.43 (m, 1H), 5.01-5.73 (m, 7H), 6.72 (d, J=8.2 Hz, 2H), 7.09 (d, J=7.0 Hz, 2H), 7.30-7.31 (m, 4H), 7.40-7.42 (m, 4H), 7.71 (t, J=7.8 Hz, 2H);

(3-228). δ: 7.15-7.45 (m, 8H), 4.94-5.77 (m, 8H), 4.37-4.53 (m, 1H), 4.24-4.35 (m, 4H), 3.24-3.49 (m, 2H), 2.60-3.12 (m, 15H), 1.14-1.84 (m, 28H), 0.61-1.07 (m, 26H);

(3-238). δ: 0.69-0.94 (m, 26H), 1.23-1.68 (m, 16H), 2.67-3.05 (m, 16H), 4.15 (s, 4H), 4.40-4.42 (m, 1H), 5.02-5.70 (m, 7H), 7.07-7.26 (m, 8H), 7.65-7.67 (m, 2H), 7.80-7.82 (m, 2H), 8.60-8.61 (m, 2H);

(3-240). δ: 0.69-0.95 (m, 26H), 1.20-1.74 (m, 16H), 2.60-3.07 (m, 28H), 4.10 (s, 4H), 4.39-5.72 (m, 8H), 7.14 (d, 4H), 7.28 (d, 4H), 7.69 (d, 2H), 8.17 (d, 2H);

(3-243). δ: 0.69-0.94 (m, 26H), 1.23-1.68 (m, 16H), 2.05 (s, 6H), 2.67-3.05 (m, 16H), 3.66 (s, 4H), 4.40-4.42 (m, 1H), 5.02-5.70 (m, 7H), 7.07-7.20 (m, 10H), 12.25 (brs, 2H);

(3-252). δ: 0.64-0.92 (m, 26H), 1.19-1.57 (m, 16H), 2.00 (s, 3H), 2.06 (s, 3H), 2.67-3.05 (m, 16H), 3.90 (s, 6H), 4.42-4.48 (m, 1H), 5.02-5.72 (m, 7H), 7.31-7.33 (m, 8H), 8.28-7.32 (m, 4H);

(3-253). δ: 0.64-0.99 (m, 27H), 1.09-1.77 (m, 21H) 2.64-2.94 (m, 13H), 3.03 (br d, 3H), 3.93-4.05 (m, 8H), 4.99-5.77 (m, 7H), 5.60-5.76 (m, 1H), 5.90-5.98 (m, 2H), 7.06-7.19 (m, 4H), 7.24-7.36 (m, 6H);

(3-254). δ: 0.69-0.94 (m, 26H), 1.23-1.68 (m, 16H), 2.67-3.05 (m, 16H), 4.01 (s, 4H), 4.40-4.42 (m, 1H), 5.02-5.70 (m, 7H), 7.18-7.25 (m, 8H), 8.42 (s, 2H), 8.67 (s, 2H);

(3-259). Not available (3-261). δ: 0.67-0.93 (m, 26H), 1.23-1.68 (22H), 2.67-2.88 (s, 12H), 2.99-3.02 (m, 4H), 3.81 (s, 6H), 4.30-4.42 (m, 3H), 5.03-5.67 (m, 7H), 6.91-6.94 (m, 2H), 7.12-7.21 (m, 8H), 7.51-7.54 (m, 2H), 7.99-8.01 (m, 2H);

(3-268). δ: 0.67-1.01 (m, 34H), 1.20-1.75 (m, 16H), 2.68-3.08 (m, 16H), 3.35-3.40 (m, 2H), 4.07 (s, 4H), 4.39-5.71 (m, 8H), 5.91 (s, 2H), 7.16 (d, 4H), 7.23-7.28 (m, 6H);

(3-273). δ: 0.69-0.94 (m, 26H), 1.23-1.68 (m, 16H), 2.36 (s, 6H), 2.67-3.05 (m, 16H), 3.94 (s, 4H), 4.40-4.42 (m, 1H), 5.02-5.70 (m, 7H), 7.06-7.25 (m, 10H), 7.43-7.45 (m, 2H), 8.28-8.29 (m, 2H);

(3-274). δ: 0.67-0.92 (m, 26H), 1.23-1.66 (m, 22H), 2.67-3.00 (m, 16H), 3.85 (s, 6H), 4.26-4.28 (m, 2H), 4.37-4.43 (m, 1H), 5.02-5.69 (m, 7H), 7.22 (brs, 8H), 8.11 (brs, 2H), 8.23 (s, 2H);

(3-275). δ: 0.22-0.28 (m, 4H), 0.38-0.44 (m, 4H), 0.69-1.01 (m, 26H), 1.06-1.15 (m, 2H), 1.21-1.76 (m, 16H), 2.68-3.07 (m, 16H), 3.86 (d, 4H), 4.00 (s, 4H), 4.40-5.70 (m, 8H), 5.88-5.91 (m, 2H), 7.14 (d, 4H), 7.24-7.28 (d, 4H), 7.30-7.33 (m, 2H);

(3-282). Not available (3-283). δ: 0.69-1.08 (m, 38H), 1.18-1.74 (m, 16H), 2.66-3.07 (m, 16H), 3.19-3.27 (m, 2H), 4.02 (s, 4H), 4.38-5.69 (m, 8H), 7.11 (d, 4H), 7.23-7.28 (m, 4H), 8.56 (s, 2H), 9.00 (s, 2H);

(3-284). δ: 0.61-0.97 (m, 34H), 1.23-1.93 (m, 18H), 2.67-3.05 (m, 16H), 4.01 (s, 4H), 4.40-4.42 (m, 1H), 5.08-5.70 (m, 7H), 5.91-5.93 (m, 2H), 7.18-7.27 (m, 8H);

(3-285). δ: 0.69-0.94 (m, 26H), 1.23-1.68 (m, 16H), 2.67-3.05 (m, 16H), 4.40-4.42 (m, 1H), 5.02-5.70 (m, 7H), 6.95 (d, J=44 Hz, 2H), 7.41 (brs, 8H), 7.86 (brs, 4H);

(3-286). δ: 0.67-0.96 (m, 26H), 1.18-1.76 (m, 16H), 2.68-3.07 (m, 16H), 3.72 (s, 4H), 4.28-5.72 (m, 16H), 7.14 (d, 4H), 7.19-7.27 (m, 6H), 7.50 (s, 2H);

(3-287). δ: 0.66-0.94 (m, 26H), 1.15-1.76 (m, 16H), 2.67-3.07 (m, 16H), 4.02 (s, 4H), 4.39-5.73 (m, 8H), 6.90 (t, 2H), 7.19-7.28 (m, 8H), 7.61 (d, 2H), 7.80 (d, 2H), 8.58 (s, 2H);

(3-288). δ: 0.69-0.94 (m, 26H), 1.23-1.68 (m, 16H), 2.17 (s, 6H), 2.67-3.05 (m, 16H), 4.15 (s, 4H), 4.40-4.42 (m, 1H), 5.02-5.70 (m, 7H), 7.18-7.29 (m, 8H), 8.30 (s, 2H);

(3-289). δ: 0.66-1.05 (m, 34H), 1.18-1.73 (m, 16H), 2.19-2.26 (m, 2H), 2.68-3.06 (m, 16H), 4.11 (s, 4H), 4.39-5.70 (m, 8H), 7.16 (d, 4H), 7.23-7.28 (m, 4H), 8.45-8.48 (m, 2H), 8.84 (s, 2H);

(3-290). δ: 0.67-0.97 (m, 26H), 1.17-1.76 (m, 16H), 2.68-3.07 (m, 16H), 4.16 (s, 4H), 4.39-5.71 (m, 8H), 6.96-7.28 (m, 10H), 7.49-7.53 (m, 2H), 7.69 (d, 2H), 8.52-8.54 (m, 2H)

(3-291). δ: 0.69-0.94 (m, 26H), 1.23-1.68 (m, 22H), 2.67-3.05 (m, 16H), 4.40-4.42 (m, 1H), 4.51-4.53 (m, 2H), 5.02-5.70 (m, 7H), 7.27 (brs, 8H), 7.54-7.56 (m, 2H), 7.69-7.71 (m, 2H);

(3-292). δ: 0.69-0.94 (m, 26H), 1.23-1.68 (m, 16H), 2.67-3.05 (m, 16H), 3.37-3.39 (m, 8H), 3.65-3.68 (m, 8H), 3.81 (s, 4H), 4.40-4.42 (m, 1H), 5.07-5.70 (m, 7H), 6.47-6.48 (m, 2H), 6.73 (s, 2H), 7.16-7.23 (m, 8H), 7.97-7.98 (m, 2H);

(3-293). δ: 0.67-0.95 (m, 26H), 1.19-1.76 (m, 16H), 2.68-3.06 (m, 16H), 3.83-3.86 (m, 10H), 4.39-5.72 (m, 8H), 7.16-7.26 (m, 8H), 7.38-7.43 (m, 2H), 7.98-8.00 (m, 2H);

(3-294). δ: 0.68-1.01 (m, 26H), 1.18-1.74 (m, 16H), 2.36 (s, 6H), 2.68-3.07 (m, 16H), 3.98 (s, 4H), 4.39-5.71 (m, 8H), 7.12 (d, 4H), 7.24-7.28 (m, 4H), 8.49-8.52 (m, 2H), 8.90 (s, 2H);

(3-295). δ: 0.68-1.00 (m, 26H), 1.18-1.73 (m, 16H), 2.67-3.07 (m, 16H), 4.14 (s, 4H), 4.38-5.71 (m, 8H), 7.13-7.40 (m, 10H), 7.56 (d, 2H), 8.53 (s, 2H), 8.62 (d, 2H);

(3-296). δ: 0.68-1.06 (m, 34H), 1.18-1.74 (m, 16H), 2.21-2.30 (m, 2H), 2.68-3.07 (m, 16H), 4.18 (s, 4H), 4.39-5.71 (m, 8H), 7.15 (d, 4H), 7.24-7.39 (m, 6H), 7.73-7.80 (m, 2H), 8.37 (d, 2H);

(3-297). δ: 0.67-0.96 (m, 26H), 1.18-1.76 (m, 16H), 2.68-3.07 (m, 16H), 3.90 (s, 4H), 4.39-5.71 (m, 8H), 7.14-7.27 (m, 10H), 7.52-7.89 (m, 4H), 8.09-8.13 (m, 2H);

(3-307). δ: 0.64-1.01 (m, 27H), 1.15-1.74 (m, 15H), 2.60-2.97 (m, 13H), 2.97-3.10 (m, 3H), 3.86-4.24 (m, 4H), 4.31-4.49 (m, 1H), 4.95-5.80 (m, 9H), 7.13-7.36 (m, 8H), 7.76-7.96 (m, 2H), 8.48-9.01 (m, 2H), 8.56-8.86 (m, 2H);

(3-308). δ: 0.64-1.03 (m, 27H), 1.17-1.74 (m, 15H), 2.51-2.56 (m, 3H), 2.60-2.96 (m, 13H), 2.96-3.12 (m, 3H), 3.90 (s, 4H), 4.41 (br dd, 1H), 4.96-5.77 (m, 8H), 7.01-7.16 (m, 6H), 7.16-7.28 (m, 4H), 7.35-7.45 (m, 2H), 8.30-8.40 (m, 2H);

(3-309). δ: 0.65-1.01 (m, 27H), 1.12-1.74 (m, 15H), 2.63-2.98 (m, 13H), 2.98-3.09 (m, 3H), 3.92-4.10 (m, 4H), 4.34-4.49 (m, 1H), 4.95-5.76 (m, 7H), 7.18 (br d, 4H), 7.26 (br d, 4H), 7.34 (t, 2H), 8.28-8.41 (m, 2H), 8.44-8.57 (m, 2H);

(3-310). δ: 0.62-1.03 (m, 28H), 1.04-1.14 (m, 6H), 1.17-1.80 (m, 16H), 2.59-2.96 (m, 17H), 2.96-3.11 (m, 3H), 3.89-4.06 (m, 4H), 4.33-4.48 (m, 1H), 4.98-5.75 (m, 7H), 7.03-7.19 (m, 4H), 7.19-7.33 (m, 4H), 8.48-8.57 (m, 2H), 8.91-9.01 (m, 2H);

(3-313). δ: 0.41-1.00 (m, 27H), 1.06-1.80 (m, 15H), 2.52-3.17 (m, 1H), 2.58-2.96 (m, 12H), 2.96-3.14 (m, 3H), 4.00 (s, 4H), 4.36-4.48 (m, 1H), 4.98-5.77 (m, 7H), 6.87-7.04 (m, 2H), 7.11-7.50 (m, 10H), 7.82-7.96 (m, 2H);

(3-318). δ: 0.51-1.02 (m, 27H), 1.09-1.77 (m, 15H), 2.59-3.14 (m, 15H), 4.07-4.24 (m, 4H), 4.34-4.48 (m, 1H), 4.99-5.76 (m, 8H), 7.12 (br d, 4H), 7.20-7.36 (m, 4H), 8.96-9.08 (m, 2H), 9.25-9.37 (m, 2H);

(3-319). δ: 0.61-1.02 (m, 27H), 1.15-1.79 (m, 15H), 2.61-3.12 (m, 16H), 4.32-4.52 (m, 1H), 4.96-5.77 (m, 7H), 7.07-7.30 (m, 8H), 7.31-7.45 (m, 2H), 7.66-7.82 (m, 2H), 8.21-8.34 (m, 2H);

(3-321). δ: 0.67-1.01 (m, 27H), 1.16-1.74 (m, 15H), 2.62-3.09 (m, 16H), 4.34-4.48 (m, 1H), 4.98-5.75 (m, 8H), 7.00-7.36 (m, 10H), 8.80-8.92 (m, 2H), 9.12-9.26 (m, 2H);

(3-322). δ: 0.64-0.97 (m, 27H), 1.16-1.75 (m, 15H), 2.20 (s, 6H), 2.63-3.09 (m, 16H), 3.95 (s, 4H), 4.36-5.71 (m, 8H), 6.99 (s, 2H), 7.05-7.11 (m, 4H), 7.18-7.30 (m, 4H), 7.94-7.80 (m, 2H);

(3-323). δ: 0.63-0.97 (m, 27H), 1.14-1.75 (m, 15H), 2.65-3.10 (m, 16H), 3.94 (s, 4H), 4.37-5.74 (m, 8H), 7.12-7.18 (m, 4H), 7.21-7.27 (m, 4H), 7.27-7.33 (m, 2H), 7.77-7.86 (m, 2H), 8.05-8.11 (m, 2H);

(3-324). δ: 0.62-0.98 (m, 27H), 1.13-1.76 (m, 15H), 2.24 (s, 6H), 2.64-3.10 (m, 16H), 3.89 (s, 4H), 4.37-5.74 (m, 8H), 7.10-7.18 (m, 4H), 7.21-7.28 (m, 4H), 7.61-7.68 (m, 2H), 7.88 (s, 2H);

(3-326). δ: 0.62-0.97 (m, 27H), 1.13-1.76 (m, 15H), 2.64-3.13 (m, 16H), 4.07 (s, 4H), 4.37-5.75 (m, 8H), 7.17-7.24 (m, 4H), 7.24-7.32 (m, 6H), 7.92-7.98 (m, 2H);

(3-329). δ: 0.69-0.94 (m, 26H), 1.23-1.68 (m, 16H), 2.67-3.04 (m, 16H), 4.03 (s, 4H), 4.40-4.42 (m, 1H), 5.02-5.70 (m, 7H), 7.13-7.15 (m, 4H), 7.24-7.27 (m, 4H), 7.39-7.42 (m, 2H), 7.67-7.69 (m, 2H), 8.24-8.26 (m, 2H);

(3-332). δ: 0.64-0.99 (m, 27H) 1.16-1.77 (m, 15H) 2.66-2.95 (m, 13H) 2.98-3.11 (m, 3H) 3.79-3.91 (m, 10H) 4.34-4.47 (m, 1H) 5.00-5.75 (m, 7H) 7.13-7.30 (m, 8H) 7.49 (br s, 2H) 8.02-8.12 (m, 2H)

(3-333). δ: 0.60-1.05 (m, 27H) 1.16-1.74 (m, 15H) 2.64-2.96 (m, 13H) 2.97-3.15 (m, 3H) 4.11-4.22 (m, 4H) 4.48 (s, 1H) 4.95-5.76 (m, 7H) 7.09 (m, 4H) 7.20-7.34 (m, 4H) 7.72 (m, 2H) 8.62-8.79 (m, 4H); and (3-334). δ: 0.67-0.97 (m, 27H), 1.13-1.76 (m, 15H), 2.64-3.09 (m, 16H), 3.61-3.71 (m, 6H), 3.80-3.95 (m, 10H), 4.34-4.49 (m, 1H), 4.98-5.74 (m, 7H), 6.69-6.80 (m, 2H), 7.08-7.28 (m, 8H), 7.71-7.81 (m, 2H).

The following Formula (4A) compounds described in Table 4 were prepared in accordance with the schemes and examples described herein. Each of $(R)_n$, $R^c$ and $R^d$ are as described in the Table.

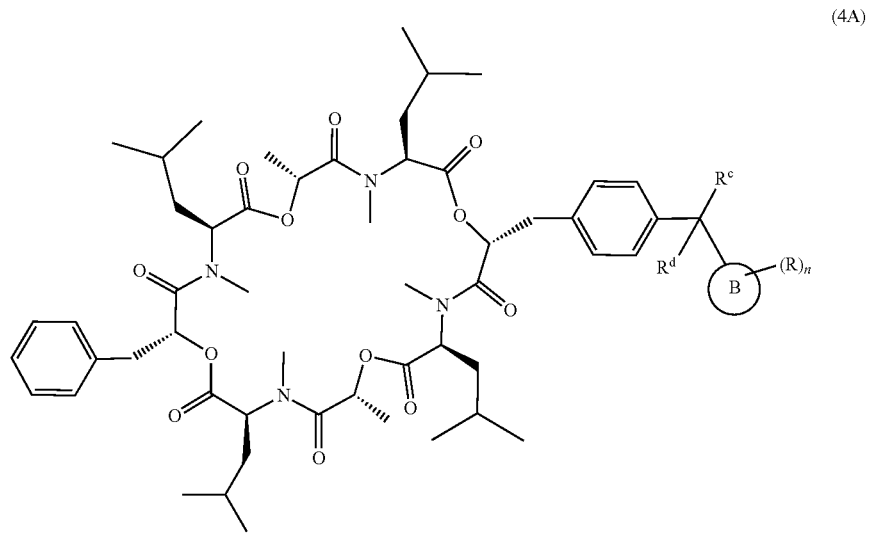
(4A)
TABLE 4
Formula (4A) Compounds
| Ex# | Ring B with (R)$_n$ | R$^c$ | R$^d$ | Mass |
|---|---|---|---|---|
| 4-18 | 6-indazolyl | H | H | 1079 |
| 4-19 | 2,4-dimethylpyrrolyl | H | H | 1056 |
| 4-21 | 3-benzofuranyl | H | —OH | 1095 |
| 4-30* | 2-oxazolyl | H | H | 1030 |
| 4-32* | 2-furanyl | H | H | 1029 |
| 4-34* | 3-methylthien-2-yl | H | H | 1059 |

TABLE 4-continued

Formula (4A) Compounds

| Ex# | Ring B with (R)$_n$ | R$^c$ | R$^d$ | Mass |
|---|---|---|---|---|
| 4-40* | 2-furyl, 3-CN | H | H | 1054 |
| 4-50^ | 3-thienyl | H | H | 1045 |
| 4-63* | 1-methyl-pyrazol-5-yl | H | H | 1043 |
| 4-75* | 3-chloro-isothiazol-5-yl | H | H | 1080 |
| 4-105* | 3-methoxy-thien-2-yl | H | H | 1075 |
| 4-107* | 4-chloro-thiazol-5-yl | H | H | 1081 |
| 4-109* | 4-chloro-thiazol-5-yl | H | H | 1058 |
| 4-118* | 6-methoxy-2-methyl-pyridin-3-yl | H | H | 1084 |
| 4-126^ | 2-methoxy-4-methyl-pyridin-5-yl | H | H | 1084 |
| 4-139* | 2-methyl-pyridin-3-yl | H | H | 1054 |
| 4-141^ | 4-methyl-isothiazol-5-yl | H | H | |

TABLE 4-continued

Formula (4A) Compounds

| Ex# | Ring B with (R)ₙ | $R^c$ | $R^d$ | Mass |
|---|---|---|---|---|
| 4-1 | 1-methylpyrazol-4-yl | H | —OH | 1059 |
| 4-2 | pyridin-3-yl | H | —OH | 1056 |
| 4-3^ | 1,3-dimethylpyrazol-4-yl | H | H | 1057 |
| 4-4 | 1-methylpyrazol-4-yl | H | H | 1043 |
| 4-5^ | thiophen-2-yl | H | H | 1045 |
| 4-6 | 6-methoxypyridin-3-yl | H | —OH | 1086 |
| 4-7 | 2H-tetrazol-5-yl | H | H | 1031 |
| 4-8 | 6-methoxypyridin-3-yl | H | H | 1070 |
| 4-9 | tetrahydropyran-4-yl | H | —OH | 1063 |
| 4-10 | cyclohexyl | H | —OH | 1061 |
| 4-11 | 5-chloropyridin-2-yl | H | Cl | 1091 |
| 4-12 | 1-(p-tolyl)pyrazol-4-yl | H | —OH | 1135 |
| 4-13 | pyridin-2-yl | H | —OH | 1170 |

TABLE 4-continued
Formula (4A) Compounds
| Ex# | Ring B with (R)$_n$ | R$^c$ | R$^d$ | Mass |
|---|---|---|---|---|
| 4-14 | 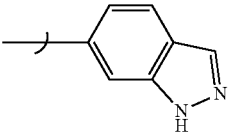 | H | —OH | 1095 |
| 4-15 | 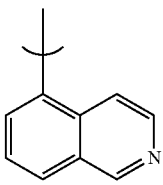 | H | —OH | 1106 |
| 4-16 | 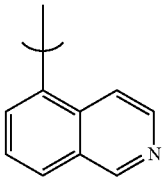 | H | H | 1090 |
| 4-17 | 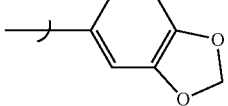 | H | H | 1083 |
| 4-20 | 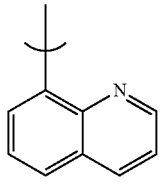 | H | —OH | 1106 |
| 4-22^ | 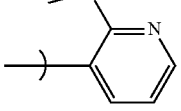 | H | H | 1070 |
| 4-23 | 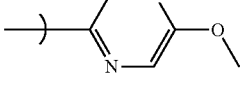 | H | H | 1071 |
| 4-24 |  | —OH | —CF$_3$ | 1129 |
| 4-25 | 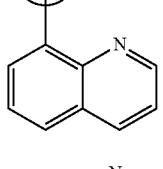 | H | H | 1090 |
| 4-26 | 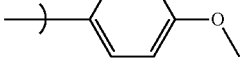 | —OH | —CH$_3$ | 1100 |

TABLE 4-continued

Formula (4A) Compounds

| Ex# | Ring B with (R)$_n$ | R$^c$ | R$^d$ | Mass |
|---|---|---|---|---|
| 4-27 | 5-(6-methoxypyridin-3-yl) | —OH | —CH$_2$CH$_3$ | 1114 |
| 4-28 | 5-(6-methoxypyridin-3-yl) | —CH(CH$_3$)$_2$ | —OH | 1128 |
| 4-29 | 5-(6-methoxypyridin-3-yl) | cyclopropyl | —OH | 1126 |
| 4-31* | thiazol-2-yl | H | H | 1046 |
| 4-33 | 5-chlorothiophen-2-yl | H | H | 1080 |
| 4-35^ | thiazol-5-yl | H | H | 1046 |
| 4-36^ | isothiazol-3-yl | H | H | 1046 |
| 4-37 | 5-cyanothiophen-2-yl | H | H | 1070 |
| 4-38 | 2-methoxythiazol-5-yl | H | H | 1076 |
| 4-39 | 2-methoxythiazol-4-yl | H | H | 1076 |
| 4-41 | thiophen-3-yl | H | —OH | 1061 |
| 4-42^ | 1,3-dimethyl-1H-pyrazol-5-yl | H | H | 1057 |
| 4-43 | 5-cyanothiophen-3-yl | H | H | 1054 |

TABLE 4-continued

Formula (4A) Compounds

| Ex# | Ring B with (R)$_n$ | R$^c$ | R$^d$ | Mass |
|---|---|---|---|---|
| 4-44 | (2,5-dimethylthiazol-4-yl) | H | H | 1074 |
| 4-45 | (5-phenylthiophen-2-yl) | H | —OH | 1137 |
| 4-46 | (5-methylthiophen-2-yl) | H | —OH | 1075 |
| 4-47 | (oxazol-4-yl) | H | —OH | 1046 |
| 4-48 | (furan-3-yl) | H | —OH | 1045 |
| 4-49 | (2,4-dimethylthiazol-5-yl) | H | —OH | 1090 |
| 4-51 | (5-methylthiophen-2-yl) | H | H | 1059 |
| 4-52* | (oxazol-4-yl) | H | H | 1030 |
| 4-53^ | (4-methylisothiazol-3-yl) | H | —OH | 1060 |
| 4-54 | (3-methylisoxazol-5-yl) | H | H | 1044 |
| 4-55 | (5-trifluoromethylthiophen-2-yl) | H | H | 1113 |
| 4-56^ | (5-methylthiazol-4-yl) | H | —OH | 1076 |

TABLE 4-continued
Formula (4A) Compounds
| Ex# | Ring B with (R)$_n$ | R$^c$ | R$^d$ | Mass |
|---|---|---|---|---|
| 4-57 | 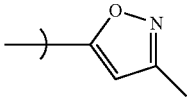 | H | H | 1060 |
| 4-58 | 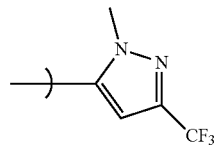 | H | —OH | 1127 |
| 4-59 | 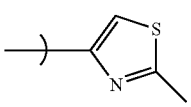 | H | —OH | 1076 |
| 4-60 | 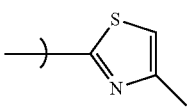 | H | —OH | 1076 |
| 4-61 | 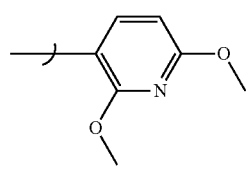 | H | H | 1100 |
| 4-62 | 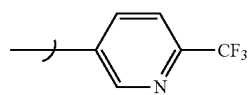 | H | H | 1108 |
| 4-64 | 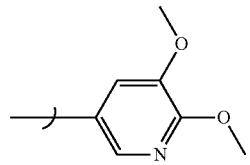 | H | H | 1100 |
| 4-65 | 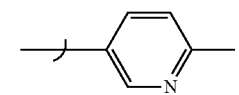 | H | —OH | 1070 |
| 4-66^ | 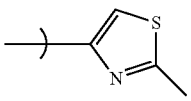 | H | H | 1060 |
| 4-67 | 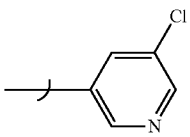 | H | —OH | 1091 |
| 4-68 | 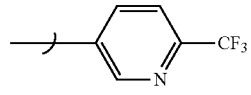 | H | —OH | 1124 |

TABLE 4-continued

Formula (4A) Compounds

| Ex# | Ring B with (R)$_n$ | R$^c$ | R$^d$ | Mass |
|---|---|---|---|---|
| 4-69 | piperidinyl-thiazole | H | —OH | 1145 |
| 4-70 | 5-chlorothiazole | H | —OH | 1097 |
| 4-71 | 5-(methoxymethyl)furan | H | —OH | 1089 |
| 4-72 | 5-phenylthiophene | H | H | 1121 |
| 4-73 | 1-methyl-3-(trifluoromethyl)pyrazole | H | H | 1111 |
| 4-74 | 5-methoxy-2-phenylthiazole | H | H | 1152 |
| 4-76 | 4-phenylthiazole | H | —OH | 1138 |
| 4-77 | 3-chlorothiophene | H | —OH | 1096 |
| 4-78 | 2-phenylthiazole | H | H | 1122 |
| 4-79 | 2,5-dimethylthiophene | H | H | 1073 |

TABLE 4-continued

Formula (4A) Compounds

| Ex# | Ring B with (R)$_n$ | R$^c$ | R$^d$ | Mass |
|---|---|---|---|---|
| 4-80 | (4,5-dimethyl-thiazol-2-yl) | H | —OH | 1090 |
| 4-81 | (4-morpholino-thiazol-2-yl) | H | H | 1131 |
| 4-82 | (3-methoxy-thiophen-2-yl) | H | —OH | 1091 |
| 4-83^ | (2-methyl-oxazol-4-yl) | H | H | 1044 |
| 4-84 | (2-morpholino-thiazol-5-yl) | H | —OH | 1147 |
| 4-85 | (4-chloro-thiazol-5-yl) | H | —OH | 1097 |
| 4-86 | (4-phenyl-thiazol-2-yl) | H | H | 1122 |
| 4-87 | (2,3-dihydrothieno[3,4-b][1,4]dioxin-5-yl) | H | —OH | 1119 |
| 4-88 | (1-methyl-pyrrol-2-yl) | H | —OH | 1058 |
| 4-89 | (2-phenyl-oxazol-4-yl) | H | H | 1106 |

TABLE 4-continued
Formula (4A) Compounds
| Ex# | Ring B with (R)$_n$ | R$^c$ | R$^d$ | Mass |
|---|---|---|---|---|
| 4-90^ | 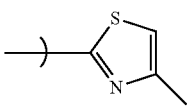 | H | H | 1060 |
| 4-91^ | 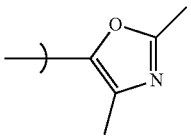 | H | H | 1058 |
| 4-92 | 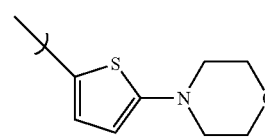 | H | H | 1130 |
| 4-93 | 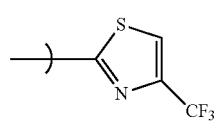 | H | H | 1114 |
| 4-94^ | 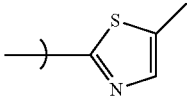 | H | H | 1060 |
| 4-95 | 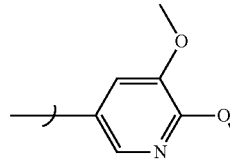 | H | —OH | 1116 |
| 4-96 | 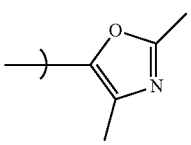 | H | —OH | 1074 |
| 4-97 | 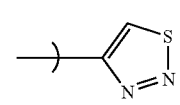 | H | —OH | 1063 |
| 4-98 | 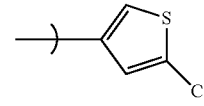 | H | H | 1080 |
| 4-99 | 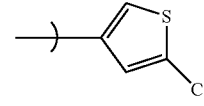 | H | —OH | 1096 |
| 4-100 | 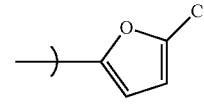 | H | —OH | 1080 |
| 4-101^ | 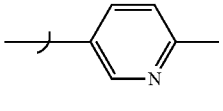 | H | H | 1054 |

TABLE 4-continued
Formula (4A) Compounds
| Ex# | Ring B with (R)$_n$ | R$^c$ | R$^d$ | Mass |
|---|---|---|---|---|
| 4-102 | 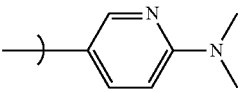 | H | H | 1083 |
| 4-103 | 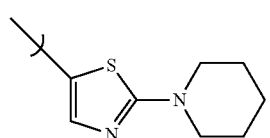 | H | H | 1129 |
| 4-104 | 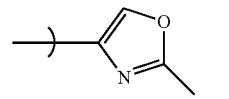 | H | —OH | 1060 |
| 4-106 | 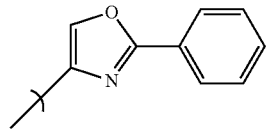 | H | —OH | 1122 |
| 4-108 | 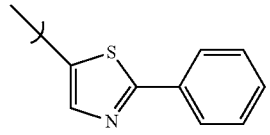 | H | —OH | 1138 |
| 4-110 | 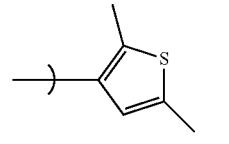 | H | —OH | 1089 |
| 4-111^ | 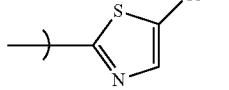 | H | H | 1081 |
| 4-112 | 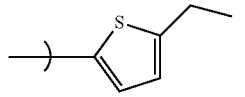 | H | —OH | 1089 |
| 4-113 | 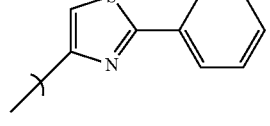 | H | H | 1122 |
| 4-114 | 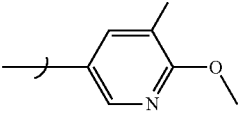 | H | H | 1088 |
| 4-115^ | 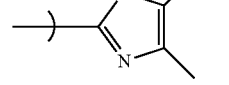 | H | H | 1074 |

TABLE 4-continued

Formula (4A) Compounds

| Ex# | Ring B with (R)$_n$ | R$^c$ | R$^d$ | Mass |
|---|---|---|---|---|
| 4-116^ | 4-methyl-1,2,3-thiadiazol-5-yl | H | H | 1061 |
| 4-117 | 1-phenyl-1H-pyrazol-5-yl | H | H | 1105 |
| 4-119 | 2-(diethylamino)thiazol-5-yl | H | H | 1117 |
| 4-120 | 2-isopropylthiazol-5-yl | H | H | 1088 |
| 4-121 | 5-phenylfuran-2-yl | H | H | 1105 |
| 4-122 | 4-methyl-1,2,3-thiadiazol-5-yl | H | —OH | 1077 |
| 4-123 | 4-(trifluoromethyl)thiazol-2-yl | H | —OH | 1130 |
| 4-124 | 5-phenylfuran-2-yl | H | —OH | 1121 |
| 4-125 | 2-methylthiazol-5-yl | H | H | 1060 |
| 4-127 | 6-methoxy-5-(trifluoromethyl)pyridin-3-yl | H | H | 1138 |

TABLE 4-continued
Formula (4A) Compounds
| Ex# | Ring B with (R)ₙ | $R^c$ | $R^d$ | Mass |
|---|---|---|---|---|
| 4-128 | 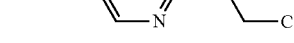 | H | H | 1138 |
| 4-129 | 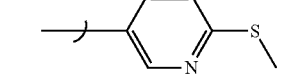 | H | H | 1086 |
| 4-130 |  | H | H | 1109 |
| 4-131 |  | H | H | 1084 |
| 4-132 |  | H | H | 1075 |
| 4-133 | 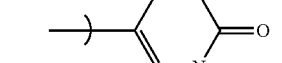 | H | H | 1044 |
| 4-134 |  | H | H | 1119 |
| 4-135^ | 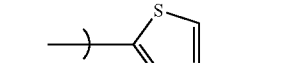 | H | H | 1030 |
| 4-136 |  | H | H | 1125 |
| 4-137 | 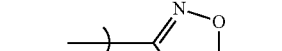 | H | —OH | 1062 |
| 4-138 |  | H | H | 1103 |
| 4-140 | 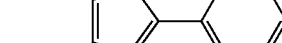 | H | H | 1106 |

TABLE 4-continued

Formula (4A) Compounds

| Ex# | Ring B with (R)$_n$ | R$^c$ | R$^d$ | Mass |
|---|---|---|---|---|
| 4-142 | [fused pyrazole-cyclohexene structure] | H | H | 1069 |
| 4-143 | [fused pyrazole-cyclohexadiene structure] | H | H | 1067 |

The following compound names and example #'s refer to the upper section compounds of Table 4.

(4-18). (3S,6R,9S,12R,15S,18R,21S,24R)-6-(4-((1H-indazol-6-yl)methyl)benzyl)-18-benzyl-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-19). (3S,6R,9S,12R,15S,18R,21S,24R)-6-benzyl-18-(4-((2,4-dimethyl-1H-pyrrol-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-21). (3S,6R,9S,12R,15S,18R,21S,24R)-6-(4-(benzofuran-3-yl(hydroxy)methyl)benzyl)-18-benzyl-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-30). (3S,6R,9S,12R,15S,18R,21S,24R)-6-benzyl-3,9,15,21-tetraisobutyl-4,10,12,16,22,24-hexamethyl-18-(4-(oxazol-2-ylmethyl)benzyl)-1,7,13,19-tetraoxa-4,10,16,22-tetraazacyclotetracosan-2,5,8,11,14,17,20,23-octaone;

(4-32). (3S,6R,9S,12R,15S,18R,21S,24R)-6-benzyl-18-(4-(furan-2-ylmethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-34). (3S,6R,9S,12R,15S,18R,21S,24R)-6-benzyl-3,9,15,21-tetraisobutyl-4,10,12,16,22,24-hexamethyl-18-(4-((3-methylthiophen-2-yl)methyl)benzyl)-1,7,13,19-tetraoxa-4,10,16,22-tetraazacyclotetracosan-2,5,8,11,14,17,20,23-octaone;

(4-40). 2-(4-(((2R,5S,8R,11S,14R,17S,20R,23S)-14-benzyl-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosan-2-yl)methyl)benzyl)furan-3-carbonitrile;

(4-50). (3S,6R,9S,12R,15S,18R,21S,24R)-6-benzyl-3,9,15,21-tetraisobutyl-4,10,12,16,22,24-hexamethyl-18-(4-(thiophen-3-ylmethyl)benzyl)-1,7,13,19-tetraoxa-4,10,16,22-tetraazacyclotetracosan-2,5,8,11,14,17,20,23-octaone;

(4-63). (3S,6R,9S,12R,15S,18R,21S,24R)-6-benzyl-3,9,15,21-tetraisobutyl-4,10,12,16,22,24-hexamethyl-18-(4-((1-methyl-1H-pyrazol-5-yl)methyl)benzyl)-1,7,13,19-tetraoxa-4,10,16,22-tetraazacyclotetracosan-2,5,8,11,14,17,20,23-octaone;

(4-75). (3S,6R,9S,12R,15S,18R,21S,24R)-6-benzyl-18-(4-((3-chlorothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-105). (3S,6R,9S,12R,15S,18R,21S,24R)-6-benzyl-3,9,15,21-tetraisobutyl-18-(4-((3-methoxythiophen-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(4-107). (3S,6R,9S,12R,15S,18R,21S,24R)-6-benzyl-18-(4-((4-chlorothiazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-109). (3S,6R,9S,12R,15S,18R,21S,24R)-6-benzyl-18-(4-((3,5-dimethylisoxazol-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(4-118). (3S,6R,9S,12R,15S,18R,21S,24R)-6-benzyl-3,9,15,21-tetraisobutyl-18-(4-((6-methoxy-2-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(4-126). (3S,6R,9S,12R,15S,18R,21S,24R)-6-benzyl-3,9,15,21-tetraisobutyl-18-(4-((6-methoxy-4-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(4-139). (3S,6R,9S,12R,15S,18R,21S,24R)-3,9,15,21-tetraisobutyl-4,6,10,16,18,22-hexamethyl-12,24-bis(4-((2-methylpyridin-3-yl)methyl)benzyl)-1,7,13,19-tetraoxa-4,10,16,22-tetraazacyclotetracosan-2,5,8,11,14,17,20,23-octaone; and (4-141). (3S,6R,9S,12R,15S,18R,21S,24R)-3,9,15,21-tetraisobutyl-4,6,10,16,18,22-hexamethyl-12,24-bis(4-((4-methylisothiazol-5-yl)methyl)benzyl)-1,7,13,19-tetraoxa-4,10,16,22-tetraazacyclotetracosan-2,5,8,11,14,17,20,23-octaone; stereoisomers thereof, and veterinary acceptable salts thereof.

NMR data (1H NMR: 400 MHz, DMSO-d6, δ ppm) for the named Table 4 compounds are shown below:

(4-18). δ: 0.56-1.85 (m, 42H) 2.62-3.19 (m, 16H) 4.05 (s, 2H) 3.94-4.44 (m, 1H) 4.97-5.83 (m, 9H) 6.97 (m, 1H) 7.15-7.39 (m, 10H) 7.65 (m, 1H) 7.99 (s, 1H);

(4-19). δ: 0.62-1.02 (m, 26H), 1.13-1.78 (m, 16H), 1.81-1.91 (m, 3H), 2.00-2.13 (m, 3H), 2.63-3.18 (m, 16H), 3.70 (s, 2H), 4.42 (m, 1H), 4.95-5.82 (m, 7H), 7.02-7.41 (m, 10H), 9.93-10.06 (m, 1H);

(4-21). δ: 0.65-0.99 (m, 27H), 1.14-1.80 (m, 15H), 2.47-2.62-2.99 (m, 13H), 2.99-3.15 (m, 3H), 4.38-4.46 (m, 2H), 4.98-5.77 (m, 8H), 5.88-5.93 (m, 1H), 7.07-7.17 (m, 1H), 7.17-7.35 (m, 9H), 7.37-7.44 (m, 2H), 7.51 (d, J=8.31 Hz, 1H), 7.78-7.83 (m, 1H);

(4-30). δ: 0.68-0.94 (m, 26H), 1.23-1.70 (m, 16H), 2.66-3.02 (m, 16H), 4.09 (s, 2H), 4.40-4.42 (m, 1H), 5.02-5.70 (m, 7H), 7.12-7.31 (m, 10H), 7.98-7.99 9m, 1H);

(4-32). δ: 0.70-0.94 (m, 26H), 1.23-1.70 (m, 16H), 2.67-3.04 (m, 16H), 3.93 (s, 2H), 4.40-4.42 (m, 1H), 5.02-5.71 (m, 7H), 6.07 (brs, 1H), 6.34-6.35 (m, 1H), 7.13-7.16 (m, 2H), 7.22-7.31 (m, 7H), 7.50 (brs, 1H);

(4-34). δ: 0.68-0.94 (m, 26H), 1.23-1.70 (m, 16H), 2.12 (s, 3H), 2.66-3.06 (m, 16H), 4.01 (s, 2H), 4.40-4.42 (m, 1H), 5.02-5.71 (m, 7H), 6.82-6.83 (m, 1H), 7.11-7.31 (m, 10H);

(4-40). δ: 0.70-0.94 (m, 26H), 1.23-1.71 (m, 16H), 2.67-3.05 (m, 16H), 4.15 (s, 2H), 4.40-4.42 (m, 1H), 5.04-5.70 (m, 7H), 6.87 (s, 1H), 7.16-7.30 (m, 9H), 7.79 (s, 1H);

(4-50). δ: 0.68-0.95 (m, 26H), 1.23-1.69 (m, 16H), 2.67-3.05 (m, 16H), 3.90 (s, 2H), 4.40-4.42 (m, 1H), 5.03-5.70 (m, 7H), 6.91-7.43 (m, 12H);

(4-63). δ: 0.68-0.94 (m, 26H), 1.23-1.70 (m, 16H), 2.66-3.06 (m, 16H), 3.65 (s, 3H), 3.98 (s, 2H), 4.40-4.42 (m, 1H), 5.02-5.70 (m, 7H), 5.92 (brs, 1H), 7.11-7.31 (m, 10H);

(4-75). δ: 0.68-0.95 (m, 26H), 1.23-1.70 (m, 16H), 2.67-3.05 (m, 16H), 4.07 (s, 2H), 4.40-4.42 (m, 1H), 5.02-5.73 (m, 7H), 7.01-7.50 (m, 11H);

(4-105). δ: 0.68-0.94 (m, 27H), 1.20-1.80 (m, 15H), 2.66-3.10 (m, 16H), 3.77 (s, 3H), 3.91 (s, 2H), 4.38-4.44 (m, 1H), 5.02-5.75 (m, 7H), 6.97-7.31 (m, 11H);

(4-107). δ: 0.68-0.95 (m, 26H), 1.24-1.70 (m, 16H), 2.67-3.05 (m, 16H), 4.12 (s, 2H), 4.40-4.42 (m, 1H), 5.04-5.70 (m, 7H), 7.17-7.30 (m, 9H), 8.98 (s, 1H);

(4-109). δ: 0.68-0.94 (m, 26H), 1.23-1.70 (m, 16H), 1.99 (s, 3H), 2.30 (s, 3H), 2.67-3.05 (m, 16H), 3.65 (s, 2H), 4.40-4.42 (m, 1H), 5.09-5.67 (m, 7H), 7.06-7.08 (m, 2H), 7.22-7.31 (m, 7H);

(4-118). δ: 0.68-0.94 (m, 26H), 1.23-1.70 (m, 16H), 2.26 (s, 3H), 2.66-3.02 (m, 16H), 3.76 (s, 3H), 3.84 (s, 2H), 4.40-4.42 (m, 1H), 5.02-5.70 (m, 7H), 6.54-6.56 (m, 1H), 7.02-7.40 (m, 10H);

(4-126). δ: 0.68-0.94 (m, 26H), 1.23-1.70 (m, 16H), 2.08 (s, 3H), 2.66-3.02 (m, 16H), 3.79 (s, 3H), 3.86 (s, 2H), 4.40-4.42 (m, 1H), 5.02-5.70 (m, 7H), 6.61 (s, 1H), 7.04-7.31 (m, 9H), 7.89 (s, 1H);

(4-139). δ: 0.68-0.95 (m, 26H), 1.23-1.72 (m, 16H), 2.37 (s, 3H), 2.66-3.06 (m, 18H), 3.94 (s, 4H), 4.40-4.42 (m, 1H), 5.02-5.71 (m, 7H), 7.06-7.31 (m, 10H), 7.43-7.46 (m, 1H), 8.28-8.29 (m, 1H); and (4-141). δ: 0.69-0.94 (m, 26H), 1.23-1.68 (m, 16H), 2.17 (s, 3H), 2.67-3.05 (m, 16H), 4.15 (s, 2H), 4.40-4.42 (m, 1H), 5.02-5.70 (m, 7H), 7.18-7.31 (m, 9H), 8.30 (s, 1H).

Biological

Heartworm infection, caused by the endoparasite *Dirofilaria immitis* (*D. immitis*), can be a severe and life-threatening disease in animals such as dogs and cats. Heartworm has a complicated life cycle involving several life stages before they mature into adults that will eventually infect the pulmonary artery of the host animal. Heartworm transmission also requires the mosquito to act as an intermediate host to complete this life cycle. For example, the beginning of the heartworm life cycle and transmission process involves a mosquito biting a previously infected dog and ingesting blood containing heartworm microfilariae (larva stage 1). Within the mosquito, the microfilariae will molt into infective larva stage 3 (L3) worms over a two week period. Once the mosquito bites another dog, infective L3 worms will move through the bite wound to enter the host and migrate into the tissues where they will begin molting into larva stage 4 (L4) worms, usually within 1 to 3 days post infection. Subsequently, L4 worms will continue their migration through tissues and molt into sexually immature or "adolescent" adults (larva stage 5, immature adult), approximately 50-70 days post infection. Sexually mature worms will eventually migrate to the heart and lungs of the dog, as early as 70 days post infection. Approximately 6-7 months post infection *D. immitis* adults reach maturity and sexually reproduce in the pulmonary artery leading to microfilaria (MF) production and circulation in the blood of the dog, thus completing the heartworm life cycle.

The most commonly used heartworm preventatives are the macrocyclic lactones (MLs) such as ivermectin, moxidectin and selamectin. These agents are administered on a monthly basis whereby they kill *D. immitis* L3 and L4 worms acquired by the host within the previous 30 days. Their primary action is to disrupt the heartworm life cycle by killing L3 and L4 worms thus preventing adult formation and subsequent disease. While very effective at preventing heartworm disease, owners are advised to test dogs for existing heartworm infections (i.e. heartworm positive dogs) prior to starting treatment with MLs due to their potential to kill circulating microfilariae. A rapid decrease in the numbers of microfilariae in the blood can lead to hypersensitivity-type reactions and circulatory shock (e.g. anaphylaxis), presumably due to dead or dying microfilariae. These potential adverse effects can be life-threatening to the dog and as such are presented as caution statements on many ML product labels. Therefore, the discovery of a novel heartworm preventative that would selectively target L3 and L4 stage worms versus microfilariae would offer a potential safety advantage. By not killing circulating microfilariae in heartworm positive dogs, a targeted treatment would prevent the adverse effects known to occur with other heartworm preventatives that lack *D. immitis* stage selectivity.

To identify novel heartworm preventatives, compounds were screened for nematocidal activity using in vitro motility assays. The compounds described herein have demonstrated nematocidal activity against either *Dirofilaria immitis* (Larva stage 4 (DiL4)) and/or *Dirofilaria immitis* microfilaria (DiMF)) as determined by reductions in nematode motility either by paralysis or death. Active and selective (DiL4 vs. DiMF potency) example compounds were subsequently evaluated in heartworm positive dog studies to correlate the in vitro selectivity profile with in vivo effects on circulating microfilariae.

The in vitro (DiL4 and DiMF) and in vivo (heartworm positive dog studies) biological activity against *Dirofilaria immitis* of the compounds of the invention can be measured using the test methods described below.

*Dirofilaria immitis*, Microfilaria (DiMf) In Vitro Assay

Compounds were dissolved and serially diluted in DMSO. Aliquots were spotted to the empty wells of assay plates. Media and microfilariae of *Dirofilaria immitis* were added to each well to dilute the test compounds to the desired concentrations. Assay plates were incubated for approximately 72 hours, and the larvae in each well were observed microscopically for drug effect. Microfilariae in each well were assessed subjectively for survival or paralysis, and results were reported as Minimum Effective Dose (MED).

*Dirofilaria immitis*, L4 Stage (DiL4) In Vitro Assay

Compounds were initially dissolved in DMSO. The stock concentration was subsequently diluted in basal media and serially diluted to give a concentration response curve starting at 100 µM (11 total concentrations). Following the serial dilution, compound solution was transferred to an assay plate (384-well) where *D. immitis* L4 larvae (10/well) that have been molted from L3 larvae in vitro were subsequently added. Assay plates were observed at 72 hours for drug effect. Each compound was evaluated for decrease in L4 motility by subjective visual assessment and endpoint data were recorded as minimally effective concentration (MEC) in µM following the incubation period. Examples with DiL4 MED data≤1 nM are presented in Tables 1-4 (i.e., upper sections). Examples with data>1 nM are also presented in Tables 1-4 (i.e., lower sections).

Heartworm Positive Dog Studies

Dogs with pre-existing heartworm infections, via surgical transplantation were used for these studies. To confirm that the dogs had circulating microfilariae, blood samples were taken from each dog and examined for microfilariae by using the modified Knott's method. All dog cohorts included in the studies exhibited average microfilariae counts of at least 15,000 MF/mL of the blood (pre-dose). On approximately Day −7, dogs were randomly allocated to treatments (based on Day −7 MF counts) and pens according to a randomized complete block design with one-way structure. Dogs were fasted overnight prior to dosing and fed immediately following dosing of the test articles. Compounds were administered by point dosing in oral liquid-filled capsules on Day 0 (3 dogs/treatment group). Blood samples were collected to measure MF counts on Days 0 (pre-dose and 2 hours post-dose), 1, 7, 21 and 28. Clinical observations were conducted by a suitably experienced Veterinarian on days −7, 0 (immediately prior to treatment, 1-2 hours post-treatment), 1 and 2 whereby any abnormal clinical signs were documented using standard veterinary medical terminology. Additionally, general health observations were conducted throughout the study including (but not limited to) general physical appearance and behavior, abnormalities of food and water consumption, vomiting/regurgitation, appearance of urine and feces and any sign of MF anaphylaxis.

The reference depsipeptide, emodepside, has equivalent in vitro potency against DiL4 (30 nM) and DiMF (30 nM) when assessed in the nematode motility assays and therefore represents a non-selective compound. As such, emodepside was evaluated for effects against circulating microfilariae in a heartworm positive dog study. At a dose of 1 mg/kg (po), emodepside demonstrated a rapid killing of circulating microfilariae, reducing the average MF counts from 61,000 MF/mL of blood pre-dose to 8,300 MF/mL of blood at 2 hours post-dose (87% decrease; Table 5). Moreover, all treated dogs exhibited adverse effects consistent with dead or dying circulating microfilariae (e.g. lethargy, tremors, ataxia, hyper-salivation) within 2 hours of emodepside administration. All dogs were treated with dexamethasone, epinephrine and valium such that they were able to recover from their symptoms.

In contrast to emodepside, the compounds described herein demonstrate larval stage selectivity (i.e. DiL4 vs. DiMF potency) as shown in Table 5. Emodepside (1 mg/kg) and Example (3-9; 3 mg/kg) were progressed into a heartworm positive dog study to correlate the in vitro selectivity profile with in vivo effects on circulating microfilariae. Both compounds were administered orally. Selectivity is shown as a ratio of Dimf/DiL4. The Dimf and DiL4 MED for emodepside 10 nM. There was no selectivity (1×) between these larval stages with emodepside. In contrast, For Example (3-9), the Dimf and DiL4 MED was 60 nM and 3 nM, respectively; thereby providing a 20× larval selectivity ratio. Additionally, there were no adverse effects observed following the administration of Example (3-9), consistent with a lack of microfilariae kill in the blood. Average mean MF counts were 18,000 MF/mL of blood pre-dose and remained elevated throughout the study where it averaged 24,000 MF/mL of blood on day 21 of the dog study. Moreover, there were no adverse clinical observations noted throughout the study, consistent with a lack of potency against circulating MF in the dogs. These data highlight the importance of generating larval stage selective compounds as novel heartworm preventatives. Specifically targeting the L4 stage versus the MF stage *D. immitis* worms provides an improved safety profile when administering preventatives to dogs with an already active adult heartworm infection. Indeed, the compounds described herein exhibit improved selectivity ratios whereby they also offer improved safety profiles over older preventatives and reference depsipeptides such as emodepside.

TABLE 5

Heartworm positive dog studies evaluating effects on circulating microfilariae (MF) following compound administration.

| Compound | | Day 0 Pre-dose | Day 0, Post-dose, 2 hours | Day 1 | Day 7 | Day 14 | Day 21 |
| --- | --- | --- | --- | --- | --- | --- | --- |
| Emodepside | Mean MF/mL | 61,000 | 8,300 | 4,500 | 8,800 | N.D. | N.D. |
|  | % Reduction |  | 87% | 93% | 86% | N.D. | N.D. |
| Example 3-9 | Mean MF/mL | 18,000 | 20,000 | 23,000 | 25,000 | 22,000 | 24,000 |
|  | % Reduction |  | −11% | −28% | −50% | −22% | −33% |

N.D. = Not Determined;

Microfilariae raw counts are shown as mean MF/mL (3 dogs/treatment) of blood. Percent reductions were calculated from counts on day of assessment compared back with pre-dose (day 0) levels. Negative percent reductions are a reflection of natural variability across time due to active adult heartworm infection and continued microfilariae production.

*Haemonchus contortus*, Larvae Stage 3 (HcL3) In Vitro Assay

The *Haemonchus contortus* L3 strain was obtained from the University of Georgia and is a relatively recent multiple-resistant field isolate (International Journal for Parasitology 37 (2007) 795-804). Compounds were dissolved and serially diluted in DMSO. Aliquots were spotted to the empty wells of assay plates. Media and third stage larvae of *Haemonchus* contortus were added to each well to dilute the test compounds to the desired concentrations. Assay plates were incubated for approximately 96 hours, and the larvae in each well were observed microscopically for drug effect. Larvae in each well were assessed subjectively for survival or paralysis, and results were reported as Minimum Effective Dose (MED). Examples with HcL3 MED data≤1 µM (Ex #*) and data 1>x≤3.3 µM (Ex #^) are presented in Tables 1-4.

Summary worm data is presented in Table 6 for those compounds with a DiL4 MED (nM) value of <1 nM. In addition, DiMf MED (nM), HcL3 MED (µM) data, and DiMf//DiL4 specificity is also shown.

TABLE 6

DiL4, Dimf, Dimf/DiL4, and HcL3 data

| Ex.# | DiL4 (nM) | DiMf (nM) | DiMf/DiL4 | HcL3 (µM) |
|---|---|---|---|---|
| (1-5) | 1 | 500 | 500 | >100 |
| (1-11) | 1 | 300 | 300 | >10 |
| (1-18) | <0.1 | 3 | >30 | >100 |
| (2-1) | 1 | 20 | 20 | 0.65 |
| (2-4) | 0.7 | 50 | 71.4 | 3.3 |
| (2-36) | 0.2 | 30 | 150 | 1 |
| (2-37) | 1 | 20 | 20 | 3.3 |
| (2-38) | 0.6 | 30 | 50 | 0.5 |
| (2-42) | 0.3 | 300 | 1000 | >10 |
| (3-4) | 0.1 | 20 | 200 | 0.5 |
| (3-8) | 0.3 | 10 | 33.3 | 1 |
| (3-12) | 1 | 0.7 | 0.7 | 3.3 |
| (3-17) | 0.3 | 0.3 | 1 | 0.5 |
| (3-18) | 0.1 | 0.2 | 2 | 1 |
| (3-21) | <0.03 | 0.1 | >3.3 | 0.3 |
| (3-24) | 0.03 | 0.1 | 3.3 | 1 |
| (3-31) | 0.2 | 5 | 25 | 2.4 |
| (3-44) | 0.1 | 100 | 1000 | 1.8 |
| (3-49) | 1 | 5 | 5 | 3.3 |
| (3-50) | 0.1 | 1 | 10 | 0.3 |
| (3-56) | 0.5 | 100 | 200 | 0.5 |
| (3-57) | 0.3 | 0.3 | 1 | 1 |
| (3-58) | 0.2 | 5 | 25 | 1 |
| (3-60) | 1 | 50 | 50 | >10 |
| (3-69) | 0.7 | 30 | 42.9 | 0.5 |
| (3-87) | 0.3 | 100 | 333 | 0.3 |
| (3-110) | 0.1 | 30 | 300 | >100 |
| (3-112) | 0.03 | 1 | 33.3 | 1 |
| (3-118) | 1 | 100 | 100 | >100 |
| (3-120) | 0.1 | 0.4 | 4 | 1 |
| (3-121) | 0.05 | 3 | 60 | 1.8 |
| (3-124) | 1 | 100 | 100 | 0.3 |
| (3-125) | <0.2 | 30 | >150 | >100 |
| (3-132) | 0.4 | 10 | 25 | >10 |
| (3-133) | 0.3 | 20 | 66.7 | 57 |
| (3-148) | 0.3 | 1 | 3.3 | 3 |
| (3-155) | 0.02 | 0.1 | 5 | 0.5 |
| (3-156) | 0.1 | 0.5 | 5 | 5.6 |
| (3-157) | 1 | 100 | 100 | >100 |
| (3-165) | 1 | 200 | 200 | >100 |
| (3-173) | <0.1 | 3 | >30 | 3.3 |
| (3-176) | 0.3 | 4 | 13.3 | 1.2 |
| (3-178) | 1 | 1 | 1 | >100 |
| (3-193) | 0.4 | 2 | 5 | 1 |
| (3-194) | 1 | 1 | 1 | >100 |
| (3-207) | 1 | 50 | 50 | >100 |
| (3-209) | 0.5 | 10 | 20 | >100 |
| (3-215) | <0.2 | 0.7 | >3.5 | 1 |
| (3-217) | <0.7 | 3 | >4.3 | 3.3 |
| (3-218) | 0.8 | 10 | 12.5 | >23 |
| (3-220) | 0.7 | 5 | 7.1 | >100 |
| (3-223) | 0.7 | 5 | 7.1 | 5.7 |
| (3-225) | 0.7 | 300 | 429 | >100 |
| (3-228) | 0.5 | 10 | 20 | >100 |
| (3-238) | 0.1 | 2 | 20 | >5 |
| (3-240) | 1 | 20 | 20 | 5.7 |
| (3-243) | 1 | 1 | 1 | 7.5 |
| (3-252) | 0.7 | 20 | 28.6 | >42 |
| (3-253) | 1 | 0.3 | 0.3 | 1 |

TABLE 6-continued

DiL4, Dimf, Dimf/DiL4, and HcL3 data

| Ex.# | DiL4 (nM) | DiMf (nM) | DiMf/DiL4 | HcL3 (µM) |
|---|---|---|---|---|
| (3-254) | 1 | 3 | 3 | 10 |
| (3-259) | 0.5 | 10 | 20 | 3.3 |
| (3-261) | <0.1 | 30 | >300 | >100 |
| (3-268) | 0.5 | 2 | 4 | 1 |
| (3-273) | 0.3 | 2 | 6.7 | 1 |
| (3-274) | 0.3 | 10 | 33.3 | 1 |
| (3-275) | 1 | 10 | 10 | 1.8 |
| (3-282) | 1 | 5 | 5 | 30 |
| (3-283) | 0.5 | 3 | 6 | 1 |
| (3-284) | 0.5 | 100 | 200 | >10 |
| (3-285) | 0.5 | 3 | 6 | 5.7 |
| (3-286) | 0.5 | 30 | 60 | >10 |
| (3-287) | 0.5 | 50 | 100 | >10 |
| (3-288) | 0.1 | 3 | 30 | 0.2 |
| (3-289) | 0.5 | 3 | 6 | 3.3 |
| (3-290) | 0.1 | 0.3 | 3 | 0.2 |
| (3-291) | 0.1 | 0.3 | 3 | 0.3 |
| (3-268) | 0.5 | 2 | 4 | 1 |
| (3-273) | 0.3 | 2 | 6.7 | 1 |
| (3-274) | 0.3 | 10 | 33.3 | 1 |
| (3-275) | 1 | 10 | 10 | 1.8 |
| (3-282) | 1 | 5 | 5 | 30 |
| (3-283) | 0.5 | 3 | 6 | 1 |
| (3-284) | 0.5 | 100 | 200 | >10 |
| (3-285) | 0.5 | 3 | 6 | 5.7 |
| (3-286) | 0.5 | 30 | 60 | >10 |
| (3-287) | 0.5 | 50 | 100 | >10 |
| (3-288) | 0.1 | 3 | 30 | 0.2 |
| (3-289) | 0.5 | 3 | 6 | 3.3 |
| (3-290) | 0.1 | 0.3 | 3 | 0.2 |
| (3-291) | 0.1 | 0.3 | 3 | 0.3 |
| (3-292) | 0.3 | 1 | 3.3 | 1.8 |
| (3-293) | 0.3 | 50 | 167 | 5.7 |
| (3-294) | 0.1 | 0.1 | 1 | 1 |
| (3-295) | 0.3 | 5 | 16.7 | 1.8 |
| (3-296) | 0.5 | 30 | 60 | 1.8 |
| (3-297) | 1 | 30 | 30 | >10 |
| (3-307) | 0.1 | 0.3 | 3 | 1 |
| (3-308) | 1 | 10 | 10 | 3.3 |
| (3-309) | 0.55 | 3 | 5.5 | 3.3 |
| (3-310) | 1 | 0.3 | 0.3 | 1 |
| (3-313) | 0.55 | 3 | 5.5 | 0.55 |
| (3-318) | 0.03 | 0.3 | 10 | 0.55 |
| (3-319) | 0.055 | 1.73 | 31.5 | 0.55 |
| (3-321) | 0.02 | 0.05 | 2.5 | 0.3 |
| (3-322) | 0.3 | 10 | 33.3 | 10 |
| (3-323) | 0.1 | 1 | 10 | 0.3 |
| (3-324) | 0.1 | 10 | 100 | 1 |
| (3-326) | 0.3 | 30 | 100 | 10 |
| (3-329) | 0.1 | 1 | 10 | — |
| (3-332) | 0.5 | 300 | 548 | — |
| (3-333) | 0.2 | 3 | 17 | — |
| (3-334) | 0.3 | 3 | 10 | 0.1 |
| (4-18) | 1 | 50 | 50 | >10 |
| (4-19) | 1 | 100 | 100 | >10 |
| (4-21) | 1 | 50 | 50 | >10 |
| (4-30) | 1 | 1 | 1 | 1 |
| (4-32) | 1 | 3 | 3 | 1 |
| (4-34) | 0.3 | 10 | 33.3 | 0.5 |
| (4-40) | 0.2 | 0.5 | 2.5 | 0.5 |
| (4-50) | 1 | 10 | 10 | 1.8 |
| (4-63) | 1 | 1 | 1 | 1 |
| (4-75) | 0.5 | 10 | 20 | 1 |
| (4-105) | 0.2 | 5 | 25 | 0.3 |
| (4-107) | 0.2 | 3 | 15 | 0.3 |
| (4-109) | 0.4 | 1 | 2.5 | 1 |
| (4-118) | 0.1 | 1 | 10 | 0.3 |
| (4-126) | 0.2 | 3 | 15 | 1.8 |
| (4-139) | 0.4 | 1 | 2.5 | 1 |
| (4-141) | 1 | 3 | 3 | 1.8 |

We claim:
1. A compound of Formula (3A)

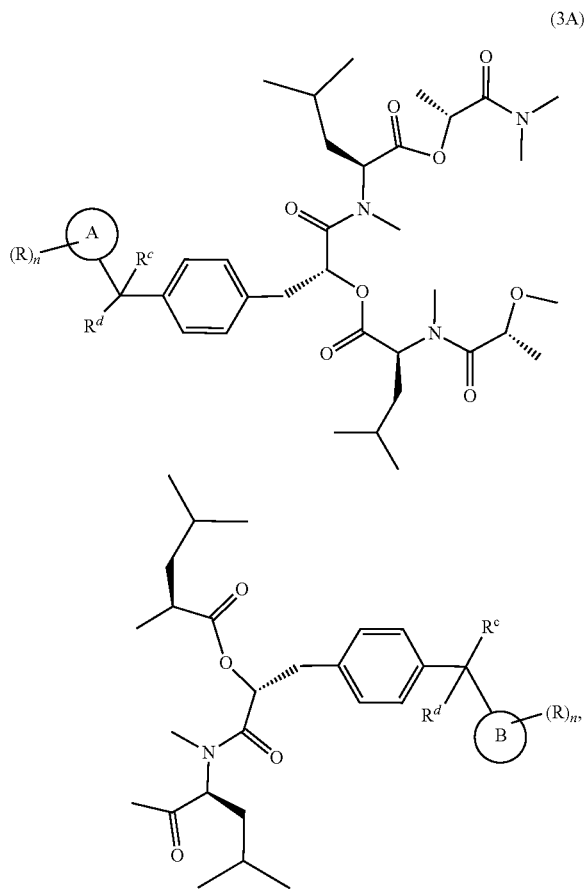

(3A)

wherein Ring A and Ring B are the same and are selected from the group consisting of cyclopropyl, cyclobutyl, cyclopentyl, cyclohexyl, oxetanyl, azetidinyl, piperidinyl, pyrrolidinyl, morpholinyl, tetrahydropyranyl, tetrahydropyrimidinyl, tetrahydropyridinyl, tetrahydropyranyl, thiophenyl, furanyl, thiazolyl, oxazolyl, pyrrolyl, pyrazolyl, imidazolyl, pyridinyl, thiadiazolyl, isothiazolyl, triazinyl, pyrimidinyl, pyrazinyl, pyridazinyl, isoxazolyl, tetrazolyl, oxadiazolyl, 1,2-dihydropyridinyl, triazolyl, quinolinyl, isoquinolinyl, benzofuranyl, 2,3-dihydrothieno[3,4-b][1,4]dioxine, 3,4-dihydro-2H-pyrano[2,3-b]pyridinyl, oxazolo[5,4-b]pyridinyl, pyrazolo[1,5-a]pyridinyl, pyrazolo[1,5-a]pyrimidine, 4,5,6,7-tetrahydropyrazolo[1,5-a]pyridinyl, 4,5-tetrahydropyrazolo[1,5-a]pyrimidine, 1H-pyrrolo[3,2-b]pyridinyl, indazolyl, furo[2,3-b]pyridinyl, and benzo[d][1,3]dioxole; each $(R)_n$ is the same and each R in $(R)_n$ is independently selected from the group consisting of $C_1$-$C_6$alkyl optionally substituted with at least one substituent selected from hydroxyl, $C_3$-$C_6$cycloalkyl and —$OR^a$; halo, oxo, cyano, hydroxyl, —$OR^5$, —$NR^aR^b$, $C_1$-$C_4$haloalkyl, $C_1$-$C_4$haloalkoxy, —$S(O)_pR^a$, $C_1$-$C_6$alkoxy, $C_3$-$C_6$cycloalkyl, —$C(O)NR^aR^b$, —$C(O)R^a$, —$C(O)OR^a$, —$NR^aC(O)R^b$, pyrazolyl, imidazolyl, pyridinyl, pyrimidinyl, piperidinyl, morpholinyl, pyrrolidinyl, dihydropyrimidinyl; and phenyl optionally substituted with at least one substituent selected from $C_1$-$C_3$alkyl, —$CF_3$, halo, and hydroxyl; n is 0, 1, 2, or 3;

$R^a$ and $R^b$ are each independently selected from H or $C_1$-$C_6$alkyl;

$R^c$ and $R^d$ are each independently selected from the group consisting of H, hydroxyl, —$CF_3$, F, methyl, ethyl, methoxy, ethoxy and —$N(CH_2CH_3)_2$; and wherein each $R^c$ is the same and each $R^d$ is the same;

$R^5$ is $C_3$-$C_6$cycloalkyl or $C_1$-$C_3$alkyl$C_3$-$C_6$cycloalkyl; and p is 0, 1, or 2;

stereoisomers thereof, and veterinary acceptable salts thereof.

2. The compound of claim 1, wherein Ring A and Ring B are selected from the group consisting of thiophenyl, furanyl, thiazolyl, oxazolyl, pyrazolyl, pyridinyl, thiadiazolyl, isothiazolyl, triazinyl, pyrimidinyl, pyrazinyl, pyridazinyl, isoxazolyl, benzofuranyl, indazolyl, and tetrahydropyranyl; stereoisomers thereof, and veterinary acceptable salts thereof.

3. The compound of claim 2, wherein Ring A and Ring B are selected from the group consisting of pyrazolyl, isothiazolyl, thiazolyl, pyridinyl, pyrimidinyl, pyrazinyl, and pyridazinyl; each $(R)_n$ is the same and each R in $(R)_n$ is independently selected from the group consisting of methyl, ethyl, isopropyl, propyl, isobutyl, fluoro, chloro, bromo, cyano, hydroxyl, —$NH_2$, —$NHCH_3$, —$N(CH_3)_2$, —$N(CH_2CH_3)_2$, —$NHC(O)CH_3$, methoxy, ethoxy, isopropoxy, oxo, —$CF_3$, —$CHF_2$, —$CH_2CH_2F$, —$CH_2CF_3$, cyclopropyl, cyclobutyl, —$CH_2$cyclopropyl, —$OCHF_2$, —$OCF_3$, —$OCH_2CF_3$, —O-cyclopropyl, —O-cyclobutyl, —O—$CH_2$-cyclopropyl, —$CH_2$—O—$CH_3$; —$CH_2$—$CH_2$—O—$CH_3$, —$CH_2OH$, —$CH(CH_3)_2OH$, —$C(O)CH_3$, —$SCH_3$, —$S(O)_2CH_3$, —$C(O)N(CH_3)_2$, —$C(O)OC(CH_3)_3$, —$C(O)CH(CH_3)_2$, pyrazolyl, imidazolyl, pyrimidinyl, pyridinyl, dihydropyrimidinyl, piperidinyl, pyrrolidinyl, morpholinyl; and phenyl optionally substituted with methyl; stereoisomers thereof, and veterinary acceptable salts thereof.

4. The compound of claim 3, wherein each $(R)_n$ is the same and each R in $(R)_n$ is independently selected from the group consisting of methyl, ethyl, isopropyl, fluoro, chloro, bromo, cyano, hydroxyl, —$N(CH_3)_2$, methoxy, ethoxy, isopropoxy, —$CHF_2$, —$CH_2CH_2F$, —$CF_3$, cyclopropyl, —$CH_2$cyclopropyl, —$OCHF_2$, —$OCF_3$, —$C(O)CH_3$, —$SCH_3$, and morpholinyl; and wherein $R^c$ and $R^d$ are each independently selected from the group consisting of H, hydroxyl, methyl, methoxy, and F; and wherein each $R^c$ is the same and each $R^d$ is the same; stereoisomers thereof, and veterinary acceptable salts thereof.

5. A composition comprising a compound of claim 1, stereoisomers thereof, and veterinary acceptable salts thereof, and a veterinary acceptable excipient.

6. The composition of claim 5, wherein the composition further comprises an additional antiparasitic agent selected from the group consisting of moxidectin, doramectin, selamectin, abamectin, milbemycin, milbemycin oxime, pyrantel, praziquantel, sarolaner, afoxolaner, lotilaner, fluralaner, and levamisole.

7. A method of treating a parasitic infection in an animal in need thereof, wherein the method comprises administering to said animal a therapeutically effective amount of a compound of claim 1, stereoisomers thereof, and veterinary acceptable salts thereof.

8. The method of claim 7, wherein the parasitic infection is an endoparasitic infection and the animal is a companion animal or livestock; and wherein the compound is administered orally, topically, or parenterally.

9. The method of claim 7, wherein an additional antiparasitic agent is administered to said animal, and wherein the additional antiparasitic agent is selected from the group consisting of moxidectin, doramectin, selamectin, abamectin, milbemycin, milbemycin oxime, pyrantel, praziquantel, sarolaner, afoxolaner, lotilaner, fluralaner, and levamisole.

10. A compound selected from the group consisting of:
(3S,6R,9S,12R,15S,18R,21 S,24R)-3,9,15,21-tetraisobutyl-4,6,10,16,18,22-hexamethyl-12,24-bis(4-(thiophen-2-ylmethyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-(furan-2-ylmethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-(thiazol-5-ylmethyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-(thiazol-2-ylmethyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-(oxazol-2-ylmethyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-((3,5-dimethylisoxazol-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-((1-methyl-1H-pyrazol-5-yl)methyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-6,18-bis(4-((2-methoxypyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-((3-methylthiophen-2-yl)methyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-((1,3-dimethyl-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
2,2'-(((((2R,5S,8R,11S,14R,17S,20R,23S)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))bis(methylene))bis(furan-3-carbonitrile);
(3S,6R,9S,12R,15S,18R,21 S,24R)-3,9,15,21-tetraisobutyl-4,6,10,16,18,22-hexamethyl-12,24-bis(4-(thiophen-3-ylmethyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-(oxazol-4-ylmethyl)benzyl)-1,7,13,19-tetraoxa-4,10,16,22-tetraazacyclotetracosan-2,5,8,11,14,17,20,23-octaone;
4,4'-(((((2R,5S,8R,11S,14R,17S,20R,23S)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))bis(methylene))bis(furan-2-carbonitrile);
(3S,6R,9S,12R,15S,18R,21 S,24R)-3,9,15,21-tetraisobutyl-6,18-bis(4-((6-methoxypyridin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-((3-chlorothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-6,18-bis(4-((3-methoxythiophen-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-((4-chlorothiazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-((5-fluoro-6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-((4-methyl-1,2,3-thiadiazol-5-yl)methyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-6,18-bis(4-((6-methoxy-2-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-4,6,10,16,18,22-hexamethyl-12,24-bis(4-((4-methylthiophen-2-yl)methyl)benzyl)-1,7,13,19-tetraoxa-4,10,16,22-tetraazacyclotetracosan-2,5,8,11,14,17,20,23-octaone;
(3S,6R,9S,12R,15S,18R,21 S,24R)-6,18-bis(4-((3-bromothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-6-(4-((R)-(3-bromothiophen-2-yl)(hydroxy)methyl)benzyl)-18-(4-((S)-(3-bromothiophen-2-yl)(hydroxy)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;
(3S,6R,9S,12R,15S,18R,21 S,24R)-3,9,15,21-tetraisobutyl-6,18-bis(4-((6-methoxy-4-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-(oxazol-5-ylmethyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((4-methylthiazol-5-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-(isothiazol-5-ylmethyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((5-methylfuran-2-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2-ethoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-(furan-3-ylmethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2-(dimethylamino)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((2-morpholinopyrimidin-5-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((3-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((5-fluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-(1-(6-methoxypyridin-3-yl)ethyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((2-methoxy-4-methylthiazol-5-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

13S,6R,9S,12R,15S,18R,21S,24R)-3,9,15,21-tetraisobutyl-6,18-bis(4-((3-methoxypyridin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((4-methoxypyrimidin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((6-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-(1-fluoro-1-(2-methoxypyridin-3-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((4-methylpyridin-3-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-(1-fluoro-1-(6-methoxypyridin-2-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((4-isopropyl-1,2,3-thiadiazol-5-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((2-(trifluoromethyl)pyridin-3-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2,6-dimethylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((5-methyl-1H-pyrazol-4-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-(1-fluoro-1-(5-methoxypyrazin-2-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((1-ethyl-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-(isothiazol-4-ylmethyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((6-hydroxypyridin-3-yl)(methoxy)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-(1-(2-methoxypyridin-3-yl)

ethyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((1-cyclopropyl-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9R,12R,15R,18R,21 S,24S)-3,9,15,21-tetraisobutyl-4,6,10,16,18,22-hexamethyl-12,24-bis[[4-[(2-methyl-3-pyridyl)methyl]phenyl]methyl]-1,7,13,19-tetraoxa-4,10,16,22-tetrazacyclotetracosane-2,5,8,11,14,17,20,23-octaone;

(3R,6R,9R,12R,15S,18S,21 S,24R)-3,9,15,21-tetraisobutyl-6,18-bis(4-((5-methoxypyrazin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((1-(cyclopropylmethyl)-1H-pyrazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-6,18-bis(4-((4-methoxypyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-6,18-bis(4-((4-isopropylpyrimidin-5-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((3-cyclopropylisoxazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6-(4-((R)-fluoro(thiazol-2-yl)methyl)benzyl)-18-(4-((S)-fluoro(thiazol-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((1-(2-fluoroethyl)-1H-pyrazol-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((6-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-4,6,10,16,18,22-hexamethyl-12,24-bis(4-((4-methylisothiazol-5-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((4-cyclopropylpyrimidin-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((2-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-4,6,10,16,18,22-hexamethyl-12,24-bis(4-((R)-1-(thiazol-2-yl)ethyl)benzyl)-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-4,6,10,16,18,22-hexamethyl-12,24-bis(4-((2-morpholinopyridin-4-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((5-fluoro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-4,6,10,16,18,22-hexamethyl-12,24-bis(4-((4-methylpyrimidin-5-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((4-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((2-cyclopropylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((2-(difluoromethoxy)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

3,3'-(((((2R,5S,8R,11S,14R,17S,20R,23S)-5,11,17,23-tetraisobutyl-4,8,10,16,20,22-hexamethyl-3,6,9,12,15,18,21,24-octaoxo-1,7,13,19-tetraoxa-4,10,16,22-tetraazacyclotetracosane-2,14-diyl)bis(methylene))bis(4,1-phenylene))bis(methylene))diisonicotinonitrile;

(3S,6R,9S,12R,15S,18R,21 S,24R)-3,9,15,21-tetraisobutyl-4,6,10,16,18,22-hexamethyl-12,24-bis(4-((2-(methylthio)pyridin-3-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21 S,24R)-6-(4-((3-fluoropyridin-4-yl)methyl)benzyl)-3,9,15,21-tetraisobutyl-4,10,12,16,22,24-hexamethyl-18-(4-((3-methylpyridin-4-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((4-ethylpyrimidin-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((6-fluoropyridin-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-4,6,10,16,18,22-hexamethyl-12,24-bis(4-((4-(trifluoromethyl)pyrimidin-5-yl)methyl)benzyl)-1, 7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2-chloropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((4-(difluoromethyl)pyrimidin-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((6-fluoro-4-methylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2-fluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2,5-difluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2,3-difluoropyridin-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2-bromopyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((5-chloro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((4-(trifluoromethyl)pyridin-3-yl)methyl)benzyl)-1,7,13,19-tetraoxa-4,10,16,22-tetraazacyclotetracosan-2,5,8,11,14,17,20,23-octaone; and (3S,6R,9S,12R,15S,18R,21S,24R)-6,18-bis(4-((2,3-dimethoxypyridin-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone, stereoisomers thereof, and veterinary acceptable salts thereof.

11. The compound of claim 10, wherein the compound is selected from the group consisting of:

(3S,6R,9S,12R,15S,18R,21S,24R)-3,9,15,21-tetraisobutyl-4,6,10,16,18,22-hexamethyl-12,24-bis(4-(thiophen-2-ylmethyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((3-methylthiophen-2-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-(thiophen-3-ylmethyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((6-methoxypyridin-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((3-chlorothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((3-methoxythiophen-2-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((5-fluoro-6-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((6-methoxy-2-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((4-methylthiophen-2-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((3-bromothiophen-2-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-((6-methoxy-4-methylpyridin-3-yl)methyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-4,6,10,16,18,22-hexamethyl-12,24-bis(4-((5-methylfuran-2-yl)methyl)benzyl)-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-((2-ethoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-(furan-3-ylmethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-3,9,15,21-tetraisobutyl-6,18-bis(4-(1-(6-methoxypyridin-3-yl)ethyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21S,24R)-6,18-bis(4-(1-fluoro-1-(6-methoxypyridin-2-yl)ethyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-3,9,15,21-tetraisobutyl-6,18-bis(4-(1-(2-methoxypyridin-3-yl)ethyl)benzyl)-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((3-cyclopropylisoxazol-5-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((1-(2-fluoroethyl)-1H-pyrazol-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((6-(difluoromethyl)pyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((5-fluoro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((2-cyclopropylpyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((2,5-difluoropyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone;

(3S,6R,9S,12R,15S,18R,21 S,24R)-6,18-bis(4-((2,3-difluoropyridin-4-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone; and (3S,6R,9S,12R,15S,18R,21 S,24R)-6,18-bis(4-((5-chloro-2-methoxypyridin-3-yl)methyl)benzyl)-3,9,15,21-tetraisobutyl-4,10,12,16,22,24-hexamethyl-1,7,13,19-tetraoxa-4,10,16,22-tetraazacyclotetracosan-2,5,8,11,14,17,20,23-octaone, stereoisomers thereof, and veterinary acceptable salts thereof.

12. A composition comprising a compound of claim 10, stereoisomers thereof, and veterinary acceptable salts thereof, and a veterinary acceptable excipient.

13. A method of treating a parasitic infection in an animal in need thereof, wherein the method comprises administering to said animal a therapeutically effective amount of a compound of claim 10, stereoisomers thereof, and veterinary acceptable salts thereof.

\* \* \* \* \*